US009249454B2

(12) United States Patent
Woolf et al.

(10) Patent No.: US 9,249,454 B2
(45) Date of Patent: Feb. 2, 2016

(54) SCREENING METHODS OF BMP/GDF SIGNALING MODULATORS USING DRG11-RESPONSIVE (DRAGON) PROTEINS

(71) Applicant: The General Hospital Corporation, Boston, MA (US)

(72) Inventors: Clifford J. Woolf, Newton, MA (US); Tarek A. Samad, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/206,950

(22) Filed: Mar. 12, 2014

(65) Prior Publication Data

US 2014/0336066 A1    Nov. 13, 2014

Related U.S. Application Data

(63) Continuation of application No. 13/655,941, filed on Oct. 19, 2012, now abandoned, which is a continuation of application No. 13/171,429, filed on Jun. 28, 2011, now Pat. No. 8,309,524, which is a continuation of application No. 12/489,212, filed on Jun. 22, 2009, now Pat. No. 7,968,520, which is a continuation of application No. 11/195,205, filed on Aug. 2, 2005, now abandoned.

(60) Provisional application No. 60/598,380, filed on Aug. 2, 2004.

(51) Int. Cl.
*G01N 33/53*   (2006.01)
*G01N 33/566*  (2006.01)
*C12Q 1/68*    (2006.01)
*G01N 33/74*   (2006.01)
*G01N 33/68*   (2006.01)

(52) U.S. Cl.
CPC ........ *C12Q 1/68* (2013.01); *G01N 33/53* (2013.01); *G01N 33/6893* (2013.01); *G01N 33/74* (2013.01); *G01N 2333/495* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 5,116,964 A | 5/1992 | Capon et al. | |
| 5,399,346 A | 3/1995 | Anderson et al. | |
| 5,571,714 A | 11/1996 | Dasch et al. | |
| 5,595,760 A | 1/1997 | Cherif-Cheikh | |
| 5,672,659 A | 9/1997 | Shalaby et al. | |
| 5,719,120 A | 2/1998 | Letarte et al. | |
| 5,830,847 A | 11/1998 | Letarte et al. | |
| 6,015,693 A | 1/2000 | Letarte et al. | |
| 2003/0153519 A1 | 8/2003 | Kay et al. | |
| 2003/0157030 A1 | 8/2003 | Davis et al. | |
| 2003/0170891 A1 | 9/2003 | McSwiggen | |
| 2003/0180756 A1 | 9/2003 | Shi et al. | |

FOREIGN PATENT DOCUMENTS

| | | |
|---|---|---|
| CN | 1284380 A | 2/2001 |
| WO | 9424314 A1 | 10/1994 |
| WO | 9512608 A1 | 5/1995 |
| WO | 0177350 A2 | 10/2001 |
| WO | 02051438 A2 | 7/2002 |
| WO | 02098444 A2 | 12/2002 |
| WO | 03004615 A2 | 1/2003 |
| WO | 03089608 A2 | 10/2003 |
| WO | 2004003150 A2 | 1/2004 |
| WO | 2004004750 A2 | 1/2004 |
| WO | 2004016606 A1 | 2/2004 |
| WO | 2005028517 A2 | 3/2005 |

OTHER PUBLICATIONS

Kondoh et al. "Suppression of macho-1-directed muscle fate by FGF and BMP is required for formation of posterior endoderm in ascidian embryos." Development 130.14 (2003): 3205-3216.
Shimasaki et al. "The bone morphogenetic protein system in mammalian reproduction." Endocrine Reviews 25.1 (2004): 72-101.
Soderstrom et al. "Expression of serine/threonine kinase receptors including the bone morphogenetic factor type II receptor in the developing and adult rat brain." Cell and tissue research 286.2 (1996): 269-279.
Souchelnytskyi et al., "Physical and functional interaction of murine and Xenopus Smad7 with bone morphogenetic protein receptors and transforming growth factor-β receptors", J. Biol. Chem., 273(39):25364-25370 (1998).
Storm et al., "Joint patterning defects caused by single and double mutations in members of the bone morphogenetic protein (BMP) family." Development 122.12 (1996): 3969-3979.
Tang et al., "Transforming growth factor-β 1 is a new form of tumor suppressor with true haploid insufficiency", Nat. Med., 4(7):802-807 (1998).
Ten Dijke et al., "Controlling cell fate by bone morphogenetic protein receptors", Mol. Cell. Endocrinol., 211:105-113 (2003).
Villanueva et al., "Disruption of the antiproliferative TGF-β signaling pathways in human pancreatic cancer cells", Oncogene, 17:1969-1978 (1998).
Von Bubnoff et al., "Intracellular BMP Signaling Regulation in Vertebrates: Pathway or Network?", Dev. Biol., 239:1-14 (2001).
Wells, J. A., "Additivity of Mutational Effects in Proteins", Biochem., 29(37):8509-8517 (1990).
Welt et al., "Activins, Inhibins, and Follistatins: From Endocrinology to Signaling. A Paradigm for the New Milennium", Exp. Biol. Med. 227:724-752 (2002).

(Continued)

*Primary Examiner* — Christine J Saoud
*Assistant Examiner* — Jon M Lockard
(74) *Attorney, Agent, or Firm* — Lathrop & Gage LLP

(57) ABSTRACT

This invention features methods and compositions useful for treating and diseases caused by a dysregulation of the BMP/GDF branch of the TGF-β signaling pathway. Also disclosed are methods for identifying compounds useful for such therapy.

14 Claims, 56 Drawing Sheets

(56) References Cited

OTHER PUBLICATIONS

Wiater et al., "Inhibin Is an Antagonist of Bone Morphogenetic Protein Signaling", J. Biol. Chem., 278(10):7934-7941 (2003).

Winnier et al., "Bone morphogenetic protein-4 is required for mesoderm formation and patterning in the mouse", Genes Dev., 9(17):2105-2116 (1995).

Wozney et al., "Novel Regulators of Bone Formation: Molecular Clones and Activities", Science, 242:1528-1534 (1988).

Xia et al., "Localization and Action of Dragon (Repulsive Guidance Molecule b), a Novel Bone Morphogenetic Protein Coreceptor, throughout the Reproductive Axis", Endocrinol., 146(8):3614-3621 (2005).

Xia et al., "Overexpression of Follislalin-Like 3 in Gonads Causes Defects in Gonadal Development and Function in Transgenic Mice", Mol. Endocrinol., 18(4):979-994 (2004).

Xia et al., "Repulsive Guidance Molecule RGMa Alters Utilization of Bone Morphogenetic Protein (BMP) Type II Receptors by BMP2 and BMP4", J. Biol., Chem., 282(25):18129-18140 (2007).

Yamaguchi et al., "Negative regulation of transforming growth factor-$\beta$ by the proteoglycan decorin", Nature, 346:281-284 (1990).

Ying et al., "Cooperation of Endoderm-Derived BMP2 and Extraembryonic Ectoderm-Derived BMP4 in Primordial Germ Cell Generation in the Mouse", Dev. Biol., 232(2):484-492 (2001).

Zhang et al., "Regulation of Smad degradation and activity by Smurf2, an E3 ubiquitin ligase", Proc. Natl. Acad. Sci. U.S.A., 98(3):974-979 (2001).

Zhao et al., "Bone morphogenetic protein 8A plays a role in the maintenance of spermatogenesis and the integrity of the epididymis." Development 125.6 (1998): 1103-1112.

Zhao et al., "The gene encoding bone morphogenetic protein 8B is required for the initiation and maintenance of spermatogenesis in the mouse", Genes Dev., 10:1657-1669 (1996).

Zhao, G. 0., "Consequences of Knocking Out BMP Signaling in the Mouse", Genesis, 35:43-56 (2003).

Zhu et al., "A SMAD ubiquitin ligase targets the BMP pathway and affects embryonic pattern formation", Nature, 400:687-693 (1999).

Zimmerman et al., "The Spemann Organizer Signal noggin Binds and Inactivates Bone Morphogenetic Protein 4", Cell, 86:599-606 (1996).

Weinstein et al., "Inappropriate expression of Hepcidin is associated with iron refractory anemia: implications for the anemia of chronic disease", Blood (2002), 100(10): 3776-3781.

Korchynskyi et al., "Identification and functional characterization of distinct critically important bone morphogenetic protein-specific response elements in the ld1 promoter", J. Biol. Chem., 277(7):4883-4891 (2002).

Krijt et al., "Expression of Rgmc, the murine ortholog of hemojuvelin gene, is modulated by development and inflammation, but not by iron status or erythropoietin", Blood (2004), 104(13), pp. 4308-4310.

Langenfeld et al., "The mature bone morphogenetic protein-2 is aberrantly expressed in non-small cell lung carcinomas and stimulates tumor growth of A549 cells", Carcinogenesis, 24(9):1445-1454 (2003).

Lawson et al., "Bmp4 is required for the generation of primordial germ cells in the mouse embryo", Genes Dev., 13 (4):424-436 (1999).

Lin et al., "Kielin/chordin-like protein, a novel enhancer of BMP signaling, attenuates renal fibrotic disease", Nat. Med., 11(4):387-393 (2005).

Lopez-Casillas et al., "Betaglycan presents ligand to the TGF$\beta$ signaling receptor", Cell, 73:1435-1444 (1993).

Lopez-Rovira et al., "Direct Binding of Smad1 and Smad4 to Two Distinct Motifs Mediates Bone Morphogenetic Protein-specific Transcriptional Activation of ld1 Gene", J. Biol. Chem., 277(5):3176-3185 (2002).

Lu et al., "The Bone Morphogenic Protein Antagonist Gremlin Regulates Proximal-Distal Patterning of the Lung", Dev. Dyn. 222(4):667-680 (2001).

Lu et al., "From fertilization to gastrulation: axis formation in the mouse embryo", Curr. Opin. Genet. Dev., 11 (4):384-392 (2001).

Macias-Silva et al., "MADR2 Is a Substrate of the TGF-$\beta$ Receptor and Its Phosphorylation Is Required for Nuclear Accumulation and Signaling", Cell, 87:1215-1224 (1996).

Macias-Silva et al., "Specific activation of Smad1 signaling pathways by the BMP7 type I receptor, ALK2", J. Biol. Chem., 273:25628-25636 (1998).

Martinez et al., "Hepatic and extrahepatic expression of the new iron regulatory protein hemojuvelin", Haematologica, 89:1441-1445 (2004).

Massague et al., "Controlling TGF-$\beta$ signaling", Genes Dev., 14:627-644 (2000).

Massague et al., "TGF-$\beta$ Signal Transduction", Annu. Rev. Biochem., 67:753-791 (1998).

Massague, J., "How Cells Read TGF-$\beta$ Signals", Nat. Rev. Mol. Cell Biol., 200(1):169-178 (2000).

Masuda et al., "Expression of Bone Morphogenetic Protein-7 (BMP-7) in Human Prostate", Prostate, 59:101-106 (2004).

Matsunaga et al., "RGM and its receptor neogenin regulate neuronal survival", Nat. Cell Biol., 6(8):749-755 (2004).

McMahon et al., "Noggin-mediated antagonism of BMP signaling is required for growth and patterning of the neural tube and somite", Genes Dev., 12:1438-1452 (1998).

Merino et al., "Expression and Function of Gdf-5 during Digit Skeletogenesis in the Embryonic Chick Leg Bud", Dev. Biol., 206:33-45 (1999).

Mishina et al., "Bmpr encodes a type I bone morphogenetic", Genes Dev., 9(24):3027-3037 (1995).

Miyazono et al., "Id: A Target of BMP Signaling", Sci. stke, 151:PE40 (2002).

Moen, R. C., "Directions in Gene Therapy", Blood Cells, 17:407-416 (1991).

Monnier et al., "RGM is a repulsive guidance molecule for retinal axons", Nature, 419:392-395 (2002).

Nakao et al., "Identification of Smad7, a TGF-$\beta$-inducible antagonist of TGF-$\beta$ signalling", Nature, 389:631-635 (1997).

NCBI GenBank Accession No. CAA48885.1, saporin [Saponaria officinalis] protein [online], [Retrieved on May 4, 2012]. Retrieved from http://www.ncbi.nih.gov/protein/CAA4885.

NCBI GenBank Accession No. CAB98207.1, hypothetical protein [Homo sapiens] [online], [Retrieved on May 4, 2012]. Retrieved from http://www.ncbi.nih.gov/protein/CAB98207.

NCBI Reference Sequence No. NM_177740.5, Mus musculus RGM domain family, member A (Rgma), mRNA organism [online], [Retrieved on May 4, 2012]. Retrieved from http://www.ncbi.nih.gov/nuccore/NM_177740.

NCBI Reference Sequence No. XP_002416009.1,Shk1 kinase-binding protein (Skb1), putative [Ixodes scapularis] [online], [Retrieved on May 4, 2012]. Retrieved from http://www.ncbi.nih.gov/protein/XP_002416009.

NCBI UniProtKB/Swiss-Prot: Q95XN8, Hypothetical protein [online], [Retrieved on May 4, 2012]. Retrieved from http://www.ncbi.nih.gov/protein/Q95XN8.

Nemeth et al., "Hepcidin is decreased in TRF2 hemochromatosis", Blood (2005), 105(4): 1803-1806.

Ngo et al., "Computational Complexity, Protein Structure Prediction, and the Levinthal Paradox", in The Protein Folding Problem and Tertiary Structure Prediction, Ch. 14, Merz and LeGrand Eds., Birkhauser, Boston, pp. 491-495 (1994).

Niederkofter et al., "Repulsive Guidance Molecule (RGM) Gene Function Is Required for Neural Tube Closure But Not Retinal Topography in the Mouse Visual System", J. Neurosci., 24(4):808-818 (2004).

Nishi et al., "Establishment and Characterization of a Steroidogenic Human Granulosa-Like Tumor Cell Line, KGN, That Expresses Functional Follicle-Stimulating Hormone Receptor", Endocrinology, 142(1):437-445 (2001).

Oldekamp et al.. "Expression pattern of the repulsive guidance molecules RGM A, Band C during mouse development", Gene Expr. Patterns, 4:283-288 (2004).

Onichtchouk et al., "Silencing ofTGF-$\beta$ signalling by the pseudoreceptor BAMBI", Nature, 401:480-485 (1999).

(56) References Cited

OTHER PUBLICATIONS

Otsuka et al., "A Novel Function of Bone Morphogenetic Protein-15 in the Pituitary: Selective Synthesis and Secretion of FSH by Gonadotropes", Endocrinol., 143(12):4938-4941 (2002).
Paez-Pereda et al., "Involvement of bone morphogenetic protein 4 (BMP-4) in pituitary prolactinoma pathogenesis through a Smad/estrogen receptor crosstalk", Proc. Natl. Acad. Sci U.S.A., 100(3):1034-1039 (2003).
Papanikolaou et al., "Mutations in HFE2 cause iron overload in chromosome 1q-linked juvenile hemochromatosis", Nat. Genet., 36(1):77-82 (2004).
Pellegrini et al., "Developmental expression of BMP4/ALK3/SMAD5 signaling pathway in the mouse testis: a potential role of BMP4 in spermatogonia differentiation", J. Cell Science, 116:3363-3372 (2003).
Piscione et al., "BMP7 controls collecting tubule cell proliferation and apoptosis via Smad1-dependent and-independent pathways", Am. J. Physiol. Renal Physiol, 280:F19-F33 (2001).
Puglisi et al., "Regulatory role of BMP2 and BMP7 in spermatogonia and Sertoli cell proliferation in the immature mouse", Eur. J. Endocrinol., 151:511-520 (2004).
Rajagopalan et al., "Neogenin mediates the action of repulsive guidance molecule", Nat. Cell Biol., 6(8):756-762 (2004).
Roetto et al, "Mutant antimicrobial peptide hepcidin is associated with severe juvenile hemochromatosis", Nature Genetics (2003), 33(1):21-22.
Samad et al., "DRAGON, a Bone Morphogenetic Protein Co-receptor", J. Biol. Chem., 280(14):14122-14129 (2005).
Samad et al., "DRAGON: A Member of the Repulsive Guidance Molecule-Related Family of Neuronal- and Muscle-Expressed Membrane Proteins Is Regulated by DRG11 and has neuronal Adhesive Properties", J. Neurosci., 24 (8):2027-2036 (2004).
Schmidtmer et al., "Isolation and expression pattern of three mouse homologues of chick Rgm", Gene Expr. Patterns, 4:105-110 (2004).
Sharp, P. A., "RNA interference—2001", Genes Dev., 15:485-490 (2000).
Shen et al., "The EGF-CFC gene family in vertebrate development", Trends Genet., 16(7):303-309 (2000).
Shi et al., "Mechanisms of TGF-.beta. Signaling from Cell Membrane to the Nucleus", Cell, 113:685-700 (2003).
Shimasaki et al., "A functional bone morphogenetic protein system in the ovary", Proc. Natl. Acad. Sci. U.S.A., 96:7282-7287 (1999).
ATCC Global Biological Resource Center, Accession No. CL-101, sus scrofa organism (designation LLC-PK1) [online], [Retrieved on May 4, 2012]. Retrieved from http://www.atcc.org.
ATCC Global Biological Resource Center, Accession No. CRL-1573, *Homo sapiens* organism (designation 293 [HEK-293]) [online], [Retrieved on May 4, 2012]. Retrieved from http://www.atcc.org.
Augsburger et al., "BMPs as Mediators of Roof Plate Repulsion of Commissural Neurons", Neuron., 24:127-141 (1999).
Babitt et al., "Bone morphogenetic protein signaling by hemojuvelin regulates hepcidin expression", Nat. Genet., 38 (5):531-539 (2006).
Babitt et al., "Repulsive Guidance Molecule (RGMa), a DRAGON Homologue, Is a Bone Morphogenetic Protein Co-receptor", J. Biol. Chem., 280(33):29820-29827 (2005).
Balemans et al., "Extracellular Regulation of BMP Signaling in Vertebrates: A Cocktail of Modulators", Dev. Biol. 250:231-250 (2002).
Barcellos-Hoff et al., "Transforming growth factor-β and breast cancer: Mammary gland development", Breast Cancer Res., 2:92-99 (2000).
Barthelemy et al., "The Expression of Saporin, a Ribosome-inactivating Protein from the Plant Saponaria officinalis, in *Escherichia coli*", J. Biol. Chem., 268(9):6541-6548 (1993).
Brinks et al., "The Repulsive Guidance Molecule RGMa Is Involved in the Formation of Afferent Connections in the Dentate Gyrus", J. Neurosci., 24(15):3862-3869 (2004).
Brown et al., "Requirement of Type III TGF-β Receptor for Endocardial Cell Transformation in the Heart", Science, 283:2080-2082 (1999).
Brunet et al., "Noggin, Cartilage Morphogenesis, and Joint Formation in the Mammalian Skeleton", Science, 280:1455-1457 (1998).
Chappuis-Fiament et al., "Multiple cadherin extracellular repeats mediate hemophilic binding and adhesion", J. Cell Biol., 154(1):231-243 (2001).
Chen et al., "Differential Roles for Bone Morphogenetic Protein (BMP) Receptor Type IB and IAin Differentiation and Specification of Mesenchymal Precursor Cells to Osteoblast and Adipocyte Lineages", J. Cell Bio., 142(1):295-305 (1998).
Cheng et al., "EGF-CFC proteins are essential coreceptors for the TFG-β signals Vg1 and GDF1", Genes Dev., 17:31-36 (2003).
Clarke et al., "Mullerian Inhibiting Substance Signaling Uses a Bone Morphogenetic Protein (BMP)-Like Pathway Mediated by ALK2 and Induces Smad6 expression", Mol. Endocrinol., 15:946-959 (2001).
Costigan et al., "Heat Shock Protein 27: Developmental Regulation and Expression after Peripheral Nerve Injury", J. Neurosci., 18(15):5891-5900 (1998).
Dagerlind et al., "Sensitive mRNA detection using unfixed tissue: combined radioactive and non-radioactive in situ hybridization histochemistry", Histochemistry, 98:39-49 (1992).
Deangelis et al., "The acid-stress response in Lactobacillus sanfranciscensis CB1", Microbiol., 147:1863-1873 (2001).
Del Re et al., "In the Absence of Type III Receptor, the Transforming Growth Factor (TGF)-β Type 11-B Receptor Requires the Type I Receptor to Bind TGF-β2", J. Biol. Chem., 279(21):22765-22772 (2004).
Dennler et al., "Direct binding of Smad3 and Smad4 to critical TGF-β-inducible elements in the promoter of human plasminogen activator inhibitor-type 1 gene", EMBO J., 17(11):3091-3100 (1998).
Derynck et al., "Smad-dependent and Smad-independent pathways in TGF-β family signalling", Nature, 425:577-584 (2003).
Dewulf et al., "Distinct Spatial and Temporal Expression Patterns of Two Type I Receptors for Bone Morphogenetic Proteins during Mouse Embryogenesis", Endocrinol., 136(6):2652-2663 (1995).
Edwards et al., "Bone Morphogenetic Proteins in the Development and Healing of Synovial Joints", Semin. Arthritis Rheum., 31(1):33-42 (2001).
Elbashir et al., "Duplexes of 21-nucleotide RNAs mediate RNA interference in cultured mammalian cells", Nature, 411:494-498 (2001).
Erickson et al., "Analysis of spatial and temporal expression patterns of bone morphogenetic protein family members in the rat uterus over the estrous cycle", J. Endocrinol., 182:203-217 (2004).
European Examination Report, Application No. EP 06735151.0, Mail Date: Apr. 16, 2010.
Faber et al., "Bmp signaling is required for development of primary lens fiber cells", Dev., 129:15:3727-3737 (2002).
Fabre et al., "The Booroola mutation in sheep is associated with an alteration of the bone morphogenetic protein receptor-IS functionality", J. Endocrinol., 177:435-444 (2003).
Feng et al., "Generation and in Vitro Differentiation of a Spermatogonial Cell Line", Science, 297:392-395 (2002).
Friedmann, T., "Progress Toward Human Gene Therapy", Science, 244:1275-1281 (1989).
Frolik et al., "Characterization of a Membrane Receptor for Transforming Growth Factor-β in Normal Rat Kidney Fibroblasts", J. Biol. Chem., 259(17):10995-11000 (1984).
Gallaway et al., "Mutations in an oocyte-derived growth factor gene (BMP15) cause increased ovulation rate and infertility in a dosage-sensitive manner", Nat. Genet., 25:279-283 (2000).
Ge et al., "RNA interference of influenza virus production by directly targeting mRNA for degradation and indirectly inhibiting all viral RNA transcription", Proc. Natl. Acad. Sci. U.S.A., 100(5):2718-2723 (2003).
Goggins et al., "Genetic Alterations of the Transforming Growth Factor β Receptor Genes in Pancreatic and Biliary Adenocarcinomas", Cancer Res., 58:5329-5332 (1998).

(56) References Cited

OTHER PUBLICATIONS

Gong et al., "Heterozygous mutations in the gene encoding noggin affect human joint morphogenesis", Nat. Genet., 21:302-304 (1999).

Grady et al., "Mutational Inactivation of Transforming Growth Factor β Receptor Type II in Microsatellite Stable Colon Cancers", Cancer Res., 59:320-324 (1999).

Gray et al., "Criplo forms a complex with activin and type II activin receptors and can block activin signaling", Proc. Nail. Acad. Sci. U.S.A., 100(9):5193-5198 (2003).

Groppe et al., "Structural basis of BMP signalling inhibition by the cystine knot protein Noggin", Nature, 420:636-642 (2002).

Hannon, G. J., "RNA interference", Nature, 418:244-251 (2002).

Hata et al., "Smad6 inhibits BMP/Smad1 signaling by specifically competing with the Smad4 tumor suppressor", Genes Dev., 12:186-197 (1998).

Hogan, B. L., "Bone morphogenetic proteins: multifunctional regulators of vertebrate development", Genes Dev., 10:1580-1594 (1996).

Hollnagel et al., "Id Genes Are Direct Targets of Bone Morphogenetic Protein Induction in Embryonic Stem Cells", J. Bioi. Chern., 274(28):19838-19845 (1999).

Hoodless et al., "MADR1, a MAD-Related Protein That Functions in BMP2 Signaling Pathways", Cell, 85:489-500 (1996).

Hsu et al., "The Xenopus Dorsalizing Factor Gremlin Identifies a Novel Family of Secreted Proteins that Antagonize BMP Activities", Mol. Cell, 1:673-683 (1998).

Huang et al., "A Novel Role for Bone Morphogenetic Proteins in the Synthesis of Follicle-Stimulating Hormone", Endocrinology, 142(6):2275-2283 (2001).

Imamura et al., "Smad6 inhibits signalling by the TGF-β superfamily", Nature, 389:622-626 (1997).

Kavsak et al., "Smad7 Binds to Smurf2 to Form an E3 Ubiquitin Ligase that Targets the TGF-β Receptor for Degradation", Mol. Cell, 6:1365-1375 (2000).

Kawabata et al., "Signal Transduction by Bone Morphogenetic Proteins", Cytokine Growth Factor Rev., 9(1):49-61 (1998).

Keutmann et al., "The Role of Follistatin Domains in Follistatin Biological Action", Mol. Endocrinol., 18(1):228-240 (2004).

Klahr, S., "The bone morphogenetic proteins (BMPs). Their role in renal fibrosis and renal function", J. Nephrol., 16:179-185 (2003).

d

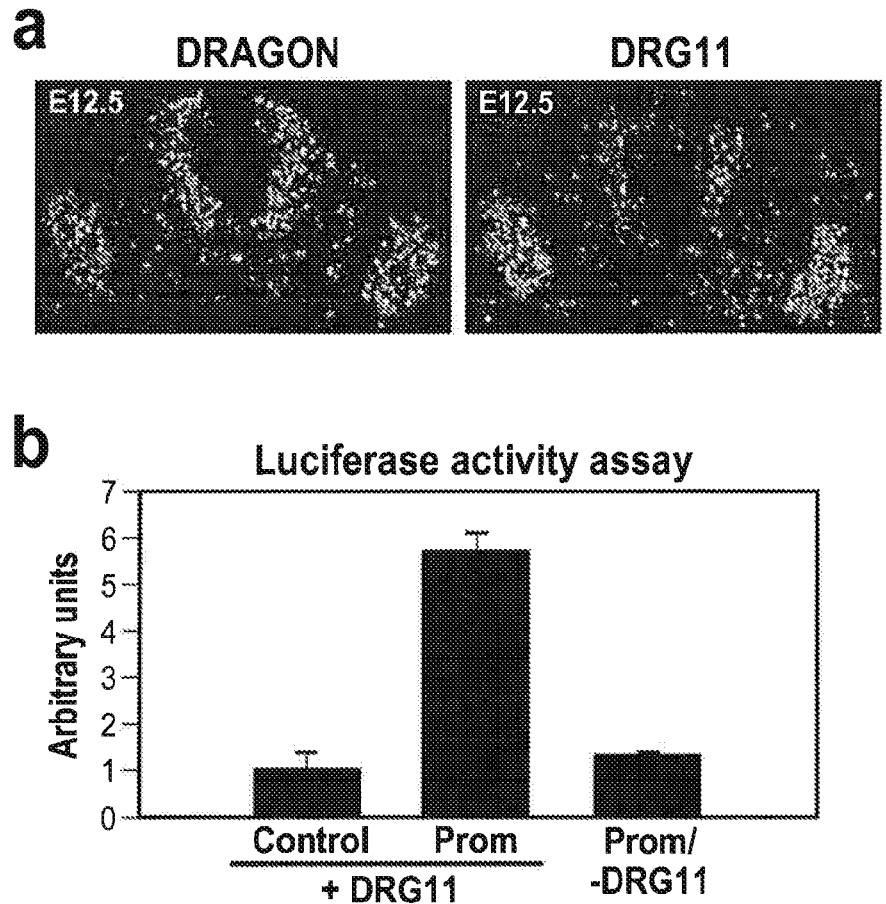
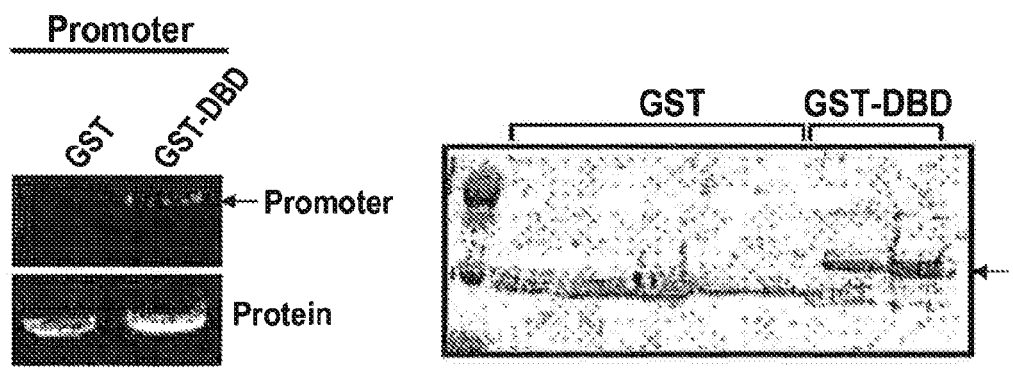
Figures 5a-5c

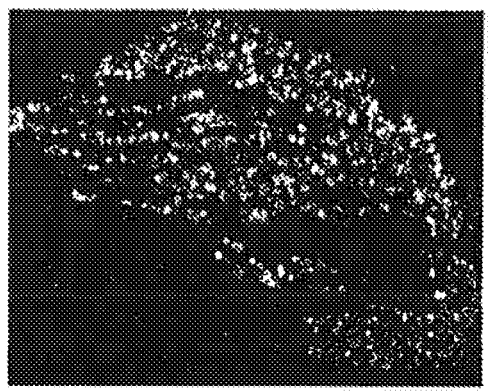
DRAGON (mRNA) Adult rat DRG
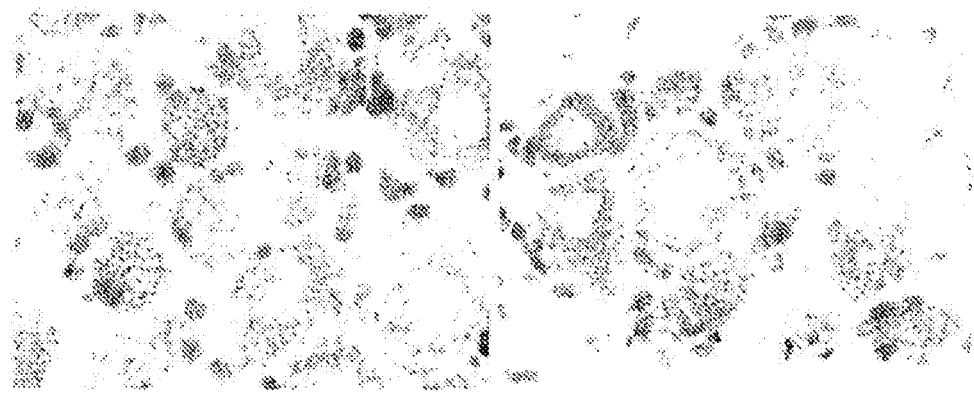
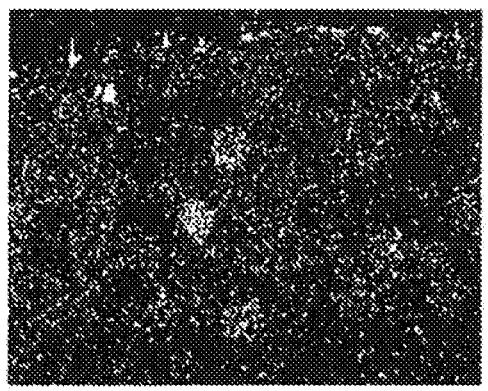
Figure 6

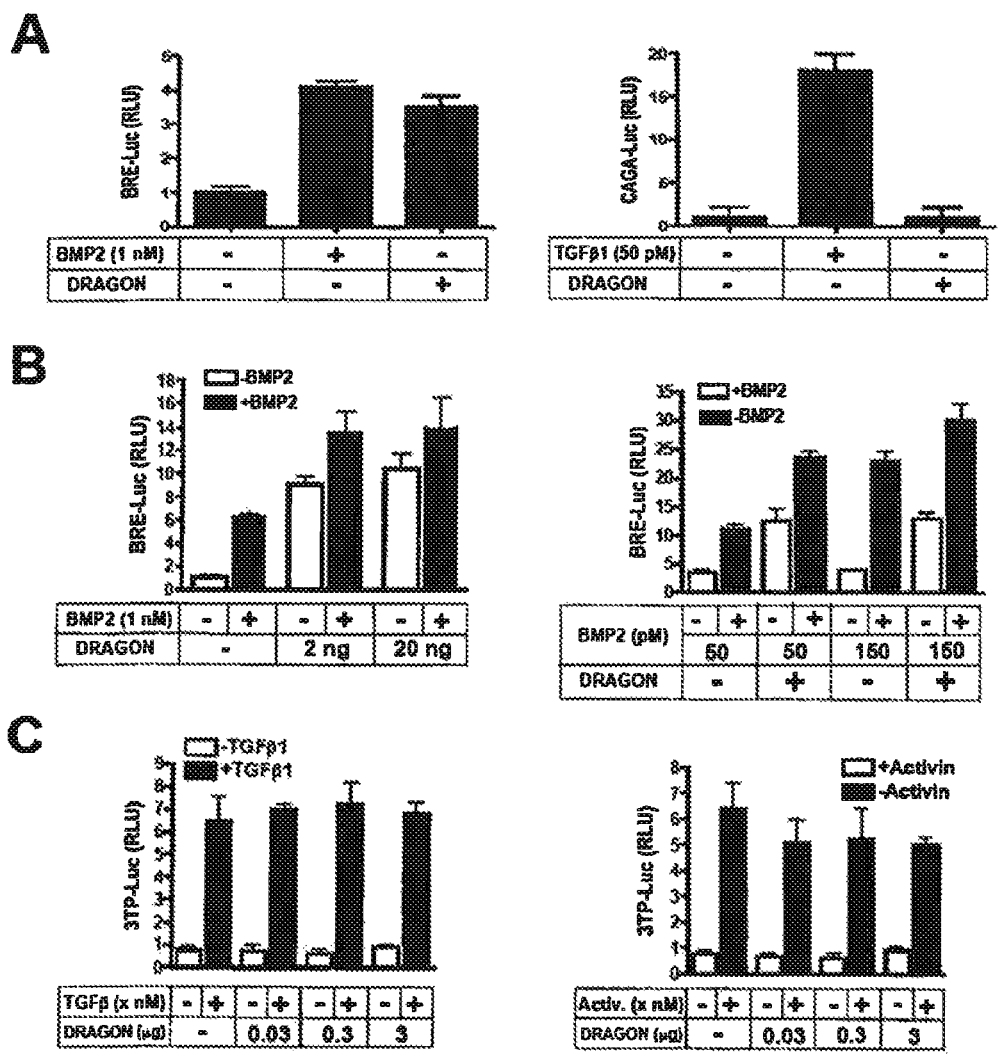
Figures 9A-C

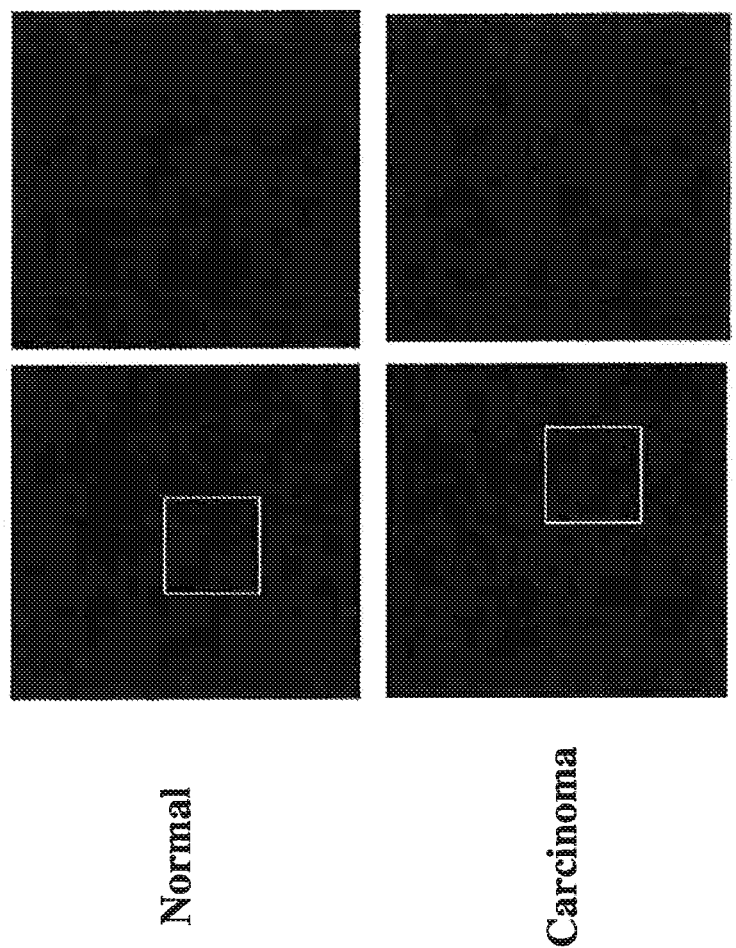

Figure 24 A

SEQ ID NO: 1 - murine DRAGON protein

```
MGVRAAPSCA AAPAAAGAEQ SRRPGLWPPS PPPPLLLLLL LSLGLLHAGD  50
CQQPTQCRIQ KCTTDFVALT AHLNSAADGF DSEFCKALRA YAGCTQRTSK 100
ACRGNLVYHS AVLGISDLMS QRNCSKDGPT SSTNPEVTHD PCNYHSHGGV 150
REHGGGDQRP PNYLFCGLFG DPHLRTFKDH FQTCKVEGAW PLIDNNYLSV 200
QVTNVPVVPG SSATATNKVT IIFKAQHECT DQKVYQAVTD DLPAAFVDGT 250
TSGGDGDVKS LHIVEKESGR YVEMHARYIG TTVFVRQLGR YLTLAIRMPE 300
DLAMSYEESQ DLQLCVNGCP MSECIDDGQG QVSAILGHSL PHTTSVQAWP 350
GYTLETASTQ CHEKMPVKDI YFQSCVFDLL TTGDANFTAA AHSALEDVEA 400
LHPRKERWHI FPSSCGGCRD LPVGLGLTCL ILIMFL               436
```

SEQ ID NO: 2 - human DRAGON protein

```
MGLRAAPSSA AAAAAEVEQR RRPGLCPPPL ELLLLLLFSL GLLHAGDCQQ  50
PAQCRIQKCT TDFVSLTSHL NSAVDGFDSF FCKALRAYAG CTQRTSKACR 100
GNLVYHSAVL GISDLMSQRN CSKDGPTSST NPEVTHDPCN YHSHAGAREH 150
RRGDQNPPSY LFCGLFGDPH LRTFKDNFQT CKVEGAWPLI DNNYLSVQVT 200
NVPVVPGSSA TATNKITIIF KAHHECTDQK VYQAVTDDLP AAFVDGTTSG 250
GDSDAKSLRI VERESGHYVE MHARYIGTTV FVRQVGRYLT LAIRMPEDLA 300
MSYEESQDLQ LCVNGCPLSE RIDDGQGQVS AILGHSLPRT SLVQAWPGYT 350
LETANTQCHE KMPVKDIYFQ SCVFDLLTTG DANFTAAAHS ALEDVEALHP 400
RKERWHIFPS SGNGTPRGGS DLSVSLGLTC LILIVFL              437
```

SEQ ID NO: 3 - C. elegans DRAGON protein

```
MRRHWKEFEC EKWESCNDNS HVKRKHVNTG HICGGKFELS EKNLAAKFKY SGDTVWRGRP
NFLKSLCYFN PPPSNRKLKY CSLFGDPHLI MFNGSVQTCS EEGARPLVDN RYFLQVTNR
NVRGEALTTT VTKVTVLVRK HNCTASLRYE ASSDEEGLPR GFVDGTTFQM TSKHSVEVLW
QDDNYVEIAL HFIHSSIHIR RQGPYLSVSV RAPTIVLETG GDVARELCWS GCRKSSRIPA
ELAVEMTKKF AECYRRRVHV PKKVAEETTF LSEQKVLPIY DRCKDIGNIG VFFDASARKI
LNFRVSGSQV TSLQNCKARR GLRRGQAIIL ERYFSAPKPK KFHLCTATGG QVTALQSFEA
RRGLRRGQAT TVERCISAPR DPTDLKIFAL TDNCEETKKY WNFFRYDILC DTHSQNFLLP
```

SEQ ID NO: 4 - Zebrafish DRAGON Protein

```
MGMGRAGSYY PGAERLISPV LHLLVLCTLS SLTPIGESQV QTPQCRIQKC
TTDFVSLTSH LNPSLDGFDT EFCKALRAYS ACTQRTAKSC RGNLVFHSAM
LGITDLMSQR NCSKDGPTSS THPVIPIEPC NYHSRHHHHV SRFGTGVPEH
PRLMYLFCGL FGDPHLRTFK DQFQTCKVEG AWPLIDNNYL SVQVTNPVVV
YGSSATATNK ITIIFKPYQE CTDQKVYQAV TDDLPAAFVD GTISGGDSET
RSIWILEKSP GRHVEIHAAY IGVTIIIRQQ GRYLTLAVRM PEELAMAFDE
TQDLQLCMNG CPTSERIDQE GHLQLPVGLG LQQAGFQQQQQ PRVEAQRGVF
TLESASRRCR DQLEVKDIYF HSCVFDLLTT GDANFTTAAY NALKDMETLH
PKKERWQIFP NSASRLSPFS LLLTALLSSF LIAVLL
```

Figure 24 B

SEQ ID NO: 5 - murine DRAGON cDNA

```
acgagacctg catggacggg catgggcgtg agagcagcac cttcctgcgc cgccgccccc
gccgccgccg gggctgagca gtcccgccgc cccgggctct ggccgccgtc gccccgccg
ccgctgttgc tgctgctgct gctcagcctt gggctgctcc acgcaggtga ttgccaacag
cctactcaat gccgaatcca gaaatgtacc acagacttcg tggccctgac tgcacacctg
aactctgccg ctgatgggtt tgactctgag ttttgcaagg cacttcgcgc ctatgctggc
tgcacccagc gaacttcaaa ggcctgccga ggcaacctgg tgtaccattc tgctgtgtta
ggcatcagtg atctcatgag ccagaggaac tgttccaagg atggacccac atcttccacc
aatccggaag tgacccatga ccctgtaac taccacagcc acggggagt cagagaacat
gggggagggg accagagacc tcccaattac ctttctgtg gcttgtttgg agaccctcac
cttcgaactt tcaaggatca cttccagaca tgcaaagtgg aagggcctg gccactcata
gacaacaatt acctttcggt tcaagtgacg aacgtgcctg tggtccccgg gtccagtgca
actgctacaa acaaggtcac gattatcttc aaagcacagc acgagtgcac ggatcagaag
gtgtaccaag ctgtgacaga tgacctgccg gccgcctttg tagatggcac caccagtggg
ggggacggtg acgtgaagag tcttcacatc gtggagaagg agagtggccg ctacgtagag
atgcatgccc gctacatagg caccacagtg tttgtgcgac agctgggtcg ctacctaacc
ctcgctatcc ggatgcccga agacttggcc atgtcctatg aggaaagcca ggacttgcag
ctgtgtgtga atggctgccc catgagtgaa tgcattgatg atggacaagg ccaggtgtct
gctatcctgg ggcacagcct gcctcacacc acctcagtgc aggcctggcc tggctacaca
ctggagactg ccagcaccca atgccacgag aagatgccgg tgaaggacat ctatttccaa
tcgtgtgtct tcgacctgct caccactggt gatgccaact ttactgctgc agcccacagt
gccttggagg atgtggaagc gctgcaccca agaaaggaac gctggcacat cttcccccagc
agctgtgggg gatgtaggga tttgcctgtt ggtcttggac tcacatgctt gatccttatt
atgtttttgt ag
```

SEQ ID NO: 6 - human DRAGON cDNA

```
acgacacctg catggacggg catgggcttg agagcagcac cttccagcgc cgccgctgcc
gccgccgagg ttgagcagcg ccgccgcccc gggctctgcc cccgccgct ggagctgctg
ctgctgctgc tgttcagcct cgggctgctc cacgcaggtg actgccaaca gccagcccaa
tgtcgaatcc agaaatgcac cacggacttc gtgtccctga ttctcacct gaactctgcc
gttgacggct tgactctga gttttgcaag gccttgcgtg cctatgctgg ctgcacccag
cgaacttcaa aagcctgccg tggcaacctg gtataccatt ctgccgtgtt gggtatcagt
gacctcatga gccagaggaa ttgttccaag gatggaccca tcctctac caacccgaa
gtgacccatg atccttgcaa ctatcacagc cacgctggag ccagggaaca caggagaggg
gaccagaacc ctccagtta ccttttttgt ggcttgtttg gagatcctca cctcagaact
ttcaaggata acttccaaac atgcaaagta gaagggcct ggccactcat agataataat
tatctttcag ttcaagtgac aaacgtacct gtggtccctg gatccagtgc tactgctaca
aataaggtca ctattatctt caaagcccac catgagtgta cagatcagaa agtctaccaa
gctgtgacag atgacctgcc ggccgccttt gtggatggca ccaccagtgg tgggacagc
gatgccaaga gcctgcgtat cgtggaaagg gagagtggcc actatgtgga gatgcacgcc
cgctatatag gaccacagt gtttgtgcgg caggtgggtc gctacctgac ccttgccatc
cgtatgcctg aagacctggc catgtcctac gaggagagcc aggacctgca gctgtgcgtg
aacggctgcc ccctgagtga acgcatcgat gacgggcagg gccaggtgtc tgccatcctg
ggacacagcc tgcctcgcac ctccttggtg caggcctggc ctggctacac actggagact
gccaacactc aatgccatga gaagatgcca gtgaaggaca tctatttcca gtcctgtgtc
```

Figure 24 C

```
ttcgacctgc tcaccactgg tgatgccaac tttactgccg cagcccacag tgccttggag
gatgtggagg ccctgcaccc aaggaaggaa cgctggcaca ttttccccag cagtggcaat
gggactcccc gtggaggcag tgatttgtct gtcagtctag gactcacctg cttgatcctt
atcgtgtttt tgtaggggtt gtcttttgtt ttggtttttt attttttgtc tataacaaaa
ttttaaaata tatattgtca taatatattg agtaaaagag tatatatgta tataccatgt
atatgacagg atgtttgtcc tgggacaccc accagattgt acatactgtg tttggctgtt
ttcacatatg ttggatgtag tgttctttga ttgtatcaat tttgttttgc agttctgtga
aatgttttat aatgtccctg cccagggacc tgttagaaag cactttattt tttatatatt
aaatatttat gtgtgtgctt ggttgatatg tatagtacat atacacagac atccatatgc
agcgtttcct ttgaaggtga ccagttgttt gtagctattc ttggctgtac cttcctgccc
tttcccattg ctactgattt gccacggtgt gcagctttta ctcgccacct tccggtggag
ctgcctcgtt cctttgaact atgccctcac ccttctgccc tcacttgatt tgaaagggtc
gttaactctc ccttacaggt gctttgactc ttaaacgctg atcttaagaa gctctcttca
tctaagagct gttactttt cagaaggggg ggtattattg gtattctgat tactctcaat
tctaattgtt atatatttga gcccatacag tgtattaggt tgaaccatag aaactgctat
tctcgtaggt caaaagggtc tagtgatgga agttttgtag ataagtacca ggcatctcag
taactcctag acttttctc atcccatgcc ccgttttaaa ttgtcagttt tccctctgac
tcttctgtgt taaaacatga aactataaat ttagtaatta tcatgccttg ctctttttaa
tctatatgac tgatgcaagc ccctcttctt aaccgtttct tggctttgag cccagaaaca
cagctctccc tgtctccaac tccagtaagc cctcctcagc ctcaccttac gaatccaaag
aactggggtt tgttaggttc tttctctaat gtagaggccc agatcccatc acaaagtttt
tcattcttcc ttgtccacca tgatcttcat cacagtcttt gatatgtctg catgcaaagt
ggaacagagt tgggcggcaa tgacagaaga gcttccttgg cctgactcgg tgtgcggcca
cttcggcact gcttaatcca gatattcttg ttaactaagc attgtgcttc ccaggtggtc
tgaagtcagg tactctctct ctcaacacct gtagttgaat atgatttggt cagttgctcg
ttgtaacttg gagaaattcc tataaagtaa gatctccttg cctcttccat ccattgttgg
cacccccttg caaaaggaaa agaacagcaa aagtcaggag cagtaatctg agaaagttaa
ctccaggata ggtaggtttc tattgttata gctagatgta aatctttagt tccaagaagt
gatagagttt ctgctttaat aatttgttga taagtttaca taaacagaaa taaaagatac
tatctttacc gtagtagttc aggccaagat tatgcttagt tttagttctc caggtagtta
cttttgccat gtcctattga tcagtgacac tgccagaggc ccataccggc aagaggaaga
ggacgtcatt ttgtaaagtt taacttctta gcgaactgat gtgccaccca gtcacagagt
ggagttgtga attcatgtag aggtggcaaa cctctacctt gtgttgatga gagaataatc
ttgggcagtc tgggaaaata aggaaggcat ctccttctta ctcatggaga ttcaactata
gagagttgaa acctaaaccc gccttccttt tatagaagct ggactagaga cggactgacc
atcagctctg aactgtggct ttttttgttc acctatgatg ccatgtacca aattcagaag
ctatcgttaa taatttgttt tataattgag tagtacaagc gaggaaaaaa tacggaggat
aaccactatt tttgtgcaaa tagtatgaaa gtgaagtaaa agcaatagaa gaaatttcta
taggatctgg gtttagagtg tgtatcatta ataaatatac ctttgctctt ttcagggaaa
ataacaacca cccttactga tagttgggaa aagaagattg ggttattttg ccatatcatt
tagctgaag tgacatttaa aagcaccctg catcactagt aatagtgtat tttgctattc
tgccttgta atcggtgtcc ctgtaaaaca atccccacag attactttca gaaatagatg
tatttctcta cgtaagggcc aggtttattt tctccttttt tgagatttct agaaaaaatg
ctgcttgcac atgttggttc ttgaaaccct agctagaaga atttcaggtc ataccaacat
gtggataggc tatagctgtt cagaggtctc ctgggggagc ttaaaacggg ggaaacactg
gttttcacag atgctccaca tggctgtctt taaaagactc aaaacttttt tttgtcctct
ttgttatgct tggaagctcc ccccccccca acagtgtgtc gagtct
```

Figure 24 D

SEQ ID NO: 7 - Zebrafish DRAGON cDNA

```
atgggtatgg ggagagcagg atcttactac cccggggctg agcgcctcat
ctctccggta ctacatctac tagtgctgtg caccctctcc tccctcactc
ccataggtga gagtcaggtt cagactcctc agtgccgcat ccagaagtgc
actaccgact tcgtttctct gacgtcccat ctgaacccat cactggatgg
ctttgatacg gagttctgca aggcgctgcg agcctattcg gcctgtacgc
agcgtacagc caagagctgc aggggggaacc tggtcttcca ctccgccatg
ctgggcatca ctgaccttat gagccagagg aactgctcca agacgggcc
cacgtcctcc acccatcccg tcatccctat cgagccttgc aactatcaca
gccggcatca ccaccacgtg tgcggttcg gacgggggt gcccgaacac
cctcgtctga tgtacctgtt ctgtggcctg ttcggggacc ctcatcttag
gacttttaaa gaccagtttc aaacgtgtaa agttgaaggg gcttggcctc
tcattgataa caactacctg tcagtgcagg tcactaatgt tccagtggtt
tatggatcca gtgccacagc taccaataag atcacaataa tcttcaaacc
ataccaagaa tgcacagacc agaaggtcta ccaggccgtg acagacgacc
ttccagccgc cttcgtagac ggcaccatca gcggaggtga cagtgagacc
cgcagcatct ggatcctgga gaaatctccc ggtcggcatg tagaaatcca
cgctgcgtac atcggggtca ccatcatcat cgccagcag ggccgttacc
tgacactagc tgtgcgaatg cctgaggaac tggccatggc ctttgatgaa
acgcaggacc tgcagctgtg catgaacggc tgccccacat cagagcgcat
tgaccaggag ggacacctcc agctgcccgt gcttggcctc cagcaggctg
gctttcagca gcagcagcag cccagggtgg aagcccagag aggcgtcttc
actcttgaaa gtgcctccag gaggtgcagg gaccaactgg aggtgaagga
catctatttc cactcctgtg tgtttgacct gctcactaca ggagatgcca
acttcaccac tgccgcctac aatgccctga aagacatgga gacactgcat
cccaaaaagg agcgctggca gattttcccc aactcggctt ccaggctgag
tccttttca ttgcttctca ctgcactgct gagcagcttc cttatcgctg
tgcttttata a
``` human DL-N protein

```
MQPPRERLVV TGRAGWMGMG RGAGRSALGF WPTLAFLLCS FPAATSPCKI  50
LKCNSEFWSA TSGSHAPASD DTPEFCAALR SYALCTRRTA RTCRGDLAYH 100
SAVHGIEDLM SQHNCSKDGP TSQPRLRTLP PAGDSQERSD SPEICHYEKS 150
FHKHSATPNY THCGLFGDPH LRTFTDRFQT CKVQGAWPLI DNNYLNVQVT 200
NTPVLPGSAA TATSKLTIIF KNFQECVDQK VYQAEMDELP AAFVDGSKNG 250
GDKHGANSLK ITEKVSGQHV EIQAKYIGTT IVVRQVGRYL TFAVRMPEEV 300
VNAVEDWDSQ GLYLCLRGCP LNQQIDFQAF HTNAEGTGAR RLAAASPAPT 350
APETFPYETA VAKCKEKLPV EDLYYQACVF DLLTTGDVNF TLAAYYALED 400
VKMLHSNKDK LHLYERTRDL PGRAAAGLPL APRPLLGALV PLLALLPVFC 500
```

Figure 24 E human DL-M protein

```
MGEPGQSPSP RSSHGSPPTL STLTLLLLLC GLAHSQCKIL RCNAEYVSST  50
LSLRGGGSSG ALRGGGGGGR GGGVGSGGLC RALRSYALCT RRTARTCRGD 100
LAFHSAVHGI EDLMIQHNCS RQGPTAPPPP RGPALPGAGS GLPAPDPCDY 150
EGRFSRLHGR PPGFLHCASF GDPHVRSFHH HFHTCRVQGA WPLLDNDFLF 200
VQATSSPMAL GANATATRKL TIIFKNMQEC IDQKVYQAEV DNLPVAFEDG 250
SINGGDRPGG SSLSIQTANP GNHVEIQAAY IGTTIIIRQT AGQLSFSIKV 300
AEDVAMAFSA EQDLQLCVGG CPPSQRLSRS ERNRRGAITI DTARRLCKEG 350
LPVEDAYFHS CVFDVLISGD PNFTVAAQAA LEDARAFLPD LEKLHLFPSD 400
AGVPLSSATL LAPLLSGLFV LWLCIQ                          426
```

Human DL-M cDNA

```
Attgcagccagtccgggggatcggggacagacatggagaaggagatggaggaccccctggctggagcaga
ccaacagaataggcaactatggctggagaaccgggtatcagagtaatgcttgacctcgggaaacaccaaa
tttcttcttccgatcgcagaagtagtactcggcgaaattcactaggtaggaggctcctcatctgggaaga
accggtgcctggggggacctggctggataggtatggggatcgaggccggtccctagtctccggtcccc
ccatggcagtcctccaactctaagcaccctcactctcctgctgctcctctgtggacaggctcactcccag
tgcaagatcctccgctgcaatgccgagtacgtctcgttcactctgagccttcggggaggggctcaccgg
acacgccacgtggaggcggccgtggtgggccggcctcaggtggcttgtgtcgcgccctgcgctcctacgc
tctctgcacgcggcgcaccgcccgcacctgccgcggggacctcgcttccactccgcggtgcatggcata
gaggacctgatgatccagcacaactgctcacgccaggtccccacggcctcgccccggcccggggtcctg
ccctgcccggggccggccagcgcccctgaccccagatccctgtgactatgaagcccggttttccaggct
gcacggtcgaacccgggttttcttgcattgtgcttcctttggagaccccatgtgcgcagcttccacaat
cacttttcacacatgccgcgtccaaggagcttggcccctactagataacgacttcctctttgtccaagcca
ccagctccccggtagcatcgggagccaacgctaccaccatccggaagatcactatcatatttaaaaacat
gcaggaatgcattgaccagaaagtctaccaggctgaggtagacaatcttcctgcagcctttgaagatggt
tctgtcaatgggggcgaccgacctggggctcgagtttgtccattcaaactgctaaccttgggagccacg
tggagattcgagctgcctacattggaacaactataatcgttcgtcagacagctggacagctctccttctc
catcagggtagcggaggatgtggcacgggcctctctgctgagcaggatctacagctgtgtgttggggga
tgccctccgagccagcgactctctcgctcagagcgcaatcgccgtggggcgatagccatagatactgcca
gaaggttgtgtaaggaagggcttccggttgaagatgcctacttccaatcctgcgtctttgatgtttcagt
ctccggtgacccaactttactgtggcagctcagtcagctctggacgatgcccgagtcttcttgaccgat
ttggagaacttgcaccttttcccagtagatgcggggcctcccctctctccagccacctgcctagtccggc
ttctttcggtcctctttgttctgtggttttgcattcagtaaggtaggccagcaacccgtgactagtttgga
aacggtttgaggagagaggttgatgtgagaaaacacaaagatgtgccaaaggaaacagtggggacaggag
acaacgaccttactcaatcacacgaggttgcagtccagggctgaaatgaccctagaataaagattctgag
acagggttttgcactccagaccttggtatgggctccccatgtatttccccattagtgatttcccacttgt
agtgaaattctactctctgtacacctgatatcactcctgcaaggctagagattgtgagagcgctaagggc
cagcaaaacattaaaggctgagatatcttaaaggcagaaactagaaaaggggaaaccatgattatctat
aagaaaatcaaagaggggtttgggaatttagctcagtggtagagcacttgcctagcaagcgcaaggccc
tgggttcggtcccagctcctaaaaagaaaaaaaatcaaagagaaaaaactaattaaggcaagctt
tttggttcagaaatgaagtgggcattgtctggcagaggaagtcagcttttggagactggcaccaacatct
ccaccttcctactctgttattaaagtgacgaattccccatcctg
```

Figure 24 F

Human DL-N cDNA

```
agttgtctccgagcgctggctgcgccgcccgagccgctgggccggggaagcactggccgttcgctcccg
ggccggccccgccaggcgctcgcaggcatgcagcccgggagcaggaggcgctccccgggccgctgctgag
ccggccggggcggcggggaccagcgccagcggagcccctcccaccttgccccggggcagacgagcggcgc
cccgacacccctcttctcccgcagcccgccagcgccaccccccgcgggccgcagggctcatgcagcc
gccaagggagaggctagtggtaacaggccgagctggatggatgggtatggggagaggggcaggacgttca
gccctgggattctggccgaccctcgccttcctctctgcagcttccccgcagccacctccccgtgcaaga
tcctcaagtgcaactctgagttctggagcgccacgtcgggcagccacgcccagcctcagacgacacccc
cgagttctgtgcagccttgcgcagctacgccctgtgcacgcggcggacggcccgcacctgccggggtgac
ctggcctaccactcggccgtccatggcatagaggacctcatgagccagcacaactgctccaaggatggcc
ccacctcgcagccacgcctgcgcacgctcccaccggccggagacagccaggagcgctcggacagccccga
gatctgccattacgagaagagctttcacaagcactcggccaccccaactacacgcactgtggcctcttc
ggggacccacacctcaggactttcaccgaccgcttccagacctgcaaggtgcagggcgcctggccgctca
tcgacaataattacctgaacgtgcaggccaccaacacgcctgtgctgcccggctcagcggccactgccac
cagcaagctcaccatcatcttcaagaacttccaggagtgtgtggaccagaaggtgtaccaggctgagatg
gacgagctcccggccgccttcgtggatggctctaagaacggtggggacaagcacggggccaacagcctga
agatcactgagaaggtgtcaggccagcacgtggagatccaggccaagtacatcggcaccaccatcgtggt
gcgccaggtgggccgctacctgacctttgccgtccgcatgccagaggaagtggtcaatgctgtggaggac
tgggacagccagggtctctacctctgcctgcggggctgccccctcaaccagcagatcgacttccaggcct
tccacaccaatgctgagggcaccggtgcccgcaggctggcgccgcccagccctgcacccacagccccga
gaccttcccatacgacagccgtggccaagtgcaaggagaagctgccggtggaggacctgtactaccag
gcctgcgtcttcgacctcctcaccacgggcgacgtgaacttcacactggccgcctactacgcgttggagg
atgtcaagatgctccactccaacaaagacaaactgcacctgtatgagaggactcgggacctgccaggcag
ggcggctgcggggctgcccctggccccggcccctcctgggcgccctcgtcccgctcctggccctgctc
cctgtgttctgctagacgcgtagatgtggagggaggcgcgggctccgtcctctcggcttcccatgtgtg
ggctgggaccgcccacggggtgcagatctcctggcgtgtccaccatggcccgcagaacgccagggaccg
cctgctgccaagggctcaggcatggaccctccccttctagtgcacgtgacaaggttgtggtgactggtg
ccgtgatgtttgacagtagagctgtgtgagagggagagcagctcccctcgccccgccctgcagtgtgaa
tgtgtgaaacatcccctcaggctgaagcccccaccccaccagagacacactgggaaccgtcagagtca
gctccttccccctcgcaatgcactgaaaggcccggccgactgctgctcgctgatccgtggggcccctgt
gcccgccacacgcacgcacacactcttacacgagagcacactcgatcccctaggccagcggggacaccc
cagccacacagggaggcatccttggggcttggccccaggcagggcaacccggggcgctgcttggcacct
tagcagactgctggaacctttggccagtaggtcgtgcccgcctggtgccttctggcctgtggcctccct
gcccatgttcacctggctgctgtgggtaccagtgcaggtcccggttttcaggcacctgctcagctgccg
tctctggcctgggcccctgccccttccaccctgtgcttagaaagtcgaagtgcttggttctaaatgtcta
aacagagaagagatccttgacttctgttcctctccctcctgcagatgcaagagctcctgggcaggggtgc
ctgggccccagggtgtggcaggagacccagtggatggggccagctggcctgccctgatcctctgcttcct
cctcacaacccaagagccccagccggtccatccacgtctggagtctggggagaggagcagggtctta
ggactctcagctctgagcatccctggcagggtcttcaacctctaatctcttcccttaagccctgtggcca
cacagccaggagagacttgccgctggctcccgcctcatttcagcccagggtgctcatccaggggcccaga
acagtccacctgtgctgctatgcccacagcacaaagccaggcttcactcccaaagtgcagccaggccc
tggagggtgatcctgccagcagccctacagctccacacccctacccacccatcggcagcctctctgctgtt
ccccagggacctctcatacactggccaggaggctgcagaacgtgtgtctcccctccctccaagaggtcc
tgctccctctgccagaaccgtgtgtggcgggtgggagggcgctcggggccggccctccctctccctg
ctggttttagttggtccctatgttggaagtaaaaagtgaagcactttattttggttgtgtttgctcacgt
tctgcttggaagtggggacccctcactgcgtccacgtgtctgcgacctgtgtggagtgtcaccgcgtgta
catactgtaaattatttattaatggctaaatgcaagtaaagtttggttttttttgttatttttcttt
```

Figure 24 G

Human RGMa protein

```
  1 mqpprerlvv tgragwmgmg rgagrsalgf wptlafllcs fpaatspcki lkcnsefwsa
 61 tsgshapasd dtpefcaalr syalctrrta rtcrgdlayh savhgiedlm sqhncskdgp
121 tsqprlrtlp pagdsqersd speichyeks fhkhsatpny thcglfgdph lrtftdrfqt
181 ckvqgawpli dnnylnvqat ntpvlpgsaa tatskltiif knfqecvdqk vyqaemdelp
241 aafvdgskng gdkhganslk itekvsgqhv eiqakyigtt ivvrqvgryl tfavrmpeev
301 vnavedwdsq glylclrgcp lnqqidfqaf htnaegtgar rlaaaspapt apetfpyeta
361 vakckeklpv edlyyqacvf dllttgdvnf tlaayyaled vkmlhsnkdk lhlyertrdl
421 pgraaaglpl aprpllgalv pllallpvfc
```

Figure 24 H

Human RGMa mRNA sequence

```
   1 agttgtctcc cgagcgctgg ctgcgccgcc cgagccgctg ggccggggaa gcactggccg
  61 ttcgctcccg ggccggcccc gccaggcgct cgcaggcatg cagcccggga gcaggaggcg
 121 ctccccgggc cgctgctgag ccggccgggg cggcggggac cagcgccagc ggagcccctc
 181 ccaccttgcc ccggggcaga cgagcggcgc cccgacaccc cctcttctcc cgcagccccg
 241 ccagcgccac ccccgcggg ccgcaggggc tcatgcagcc gccaagggag aggctagtgg
 301 taacaggccg agctggatgg atgggtatgg ggagaggggc aggacgttca gccctgggat
 361 tctggccgac cctcgccttc cttctctgca gcttccccgc agccacctcc ccgtgcaaga
 421 tcctcaagtg caactctgag ttctggagcg ccacgtcggg cagccacgcc ccagcctcag
 481 acgacacccc cgagttctgt gcagccttgc gcagctacgc cctgtgcacg cggcggacgg
 541 cccgcacctg ccggggtgac ctggcctacc actcggccgt ccatggcata gaggacctca
 601 tgagccagca caactgctcc aaggatggcc ccacctcgca gccacgcctg cgcacgctcc
 661 caccggccgg agacagccag gagcgctcgg acagcccga gatctgccat tacgagaaga
 721 gctttcacaa gcactcggcc accccaact acacgcactg tggcctcttc ggggacccac
 781 acctcaggac tttcaccgac cgcttccaga cctgcaaggt gcagggcgcc tggccgctca
 841 tcgacaataa ttacctgaac gtgcaggcca ccaacacgcc tgtgctgccc ggctcagcgg
 901 ccactgccac cagcaagctc accatcatct tcaagaactt ccaggagtgt gtggaccaga
 961 aggtgtacca ggctgagatg gacgagctcc cggccgcctt cgtggatggc tctaagaacg
1021 gtggggacaa gcacgggtcc aacagcctga agatcactga gaaggtgtca ggccagcacg
1081 tggagatcca ggccaagtac atcggccacca ccatcgtggt gcgccaggtg ggccgctacc
1141 tgacctttgc cgtccgcatg ccagaggaag tggtcaatgc tgtggaggac tgggacagcc
1201 agggtctcta cctctgcctg cggggctgcc ccctcaacca gcagatcgac ttccaggcct
1261 tccacaccaa tgctgagggc accggtgccc gcaggctggc agccgccagc cctgcaccca
1321 cagccccga gaccttccca tacgagacag ccgtggccaa gtgcaaggag aagctgccgg
1381 tggaggacct gtactaccag gcctgcgtct tcgacctcct caccacgggc gacgtgaact
1441 tcacactggc cgcctactac gcgttggagg atgtcaagat gctccactcc aacaaagaca
1501 aactgcacct gtatgagagg actcgggacc tgccaggcag ggcggctgcg gggctgcccc
1561 tggcccccg gcccctcctg ggcgccctcg tccgctcct ggccctgctc cctgtgttct
1621 gctagaccg tagatgtgga gggagccgcg ggctccgtcc tctcggcttc cccatgtgtg
1681 ggctgggacc gcccacgggg tgcagatctc ctggcgtgtc caccatggcc ccgcagaacg
1741 ccaggacccg cctgctgcca agggctcagg catggacccc tcccttcta gtgcacgtga
1801 caaggttgtg gtgactggtg ccgtgatgtt tgacagtaga gctgtgtgag agggagagca
1861 gctcccctcg ccccgcccct gcagtgtgaa tgtgtgaaac atcccctcag gctgaagccc
1921 cccacccca ccagagacac actgggaacc gtcagagtca gtccttccc cctcgcaatg
1981 cactgaaagg cccggccgac tgctgctcgc tgatccgtgg ggcccctgt gccgccaca
2041 cgcacgcaca cactcttaca cgagagcaca ctcgatcccc ctaggccagc ggggacaccc
2101 cagccacaca gggaggcatc cttggggctt ggccccaggc agggcaaccc cggggcgctg
2161 cttggcacct tagcagactg ctggaacctt ttggccagta ggtcgtgccc gcctggtgcc
2221 ttctggcctg tggcctccct gcccatgttc acctggctgc tgtgggtacc agtgcaggtc
2281 ccggttttca ggcacctgct cagctgcccg tctctggcct gggcccctgc cccttccacc
2341 ctgtgcttag aaagtcgaag tgcttggttc taaatgtcta aacagagaag agatccttga
2401 cttctgttcc tctccctcct gcagatgcaa gagctcctgg gcagggtgc ctgggcccca
2461 gggtgtggca ggagaccag tggatggggc cagctggcct gccctgatcc tctgcttcct
2521 cctcacaacc ccaagagccc ccagcccggt ccatccacgt ctggagtctg gggagaggag
2581 cagggtctta ggactctcag ctctgagcat ccctggcagg gtcttcaacc tctaatctct
2641 tcccttaagc cctgtggcca cacagccagg agagacttgc cgctggctcc cgcctcattt
2701 cagcccaggg tgctcatcca ggggcccaga acagtcccac ctgtgctgct atgcccacag
2761 cacaaagcca ggcttcactc ccaaaagtgc agccaggccc tggagggtga tcctgccagc
2821 agccctacag ctccacaccc tacccaccca tcggcagcct ctctgctgtt ccccagggac
2881 ctctcataca ctggccagga ggctgcagaa cgtgtgtctc ccctccctc caagaggtcc
2941 tgctccctct gccagaaccg tgtgtgggcg ggtgggaggg cgctcggggc cggccccttc
3001 cctctccctg ctggtttag ttggtcccta tgttggaagt aaaaagtgaa gcactttatt
3061 ttggttgtgt ttgctcacgt tctgcttgga agtggggacc cctcactgcg tccacgtgtc
3121 tgcgacctgt gtggagtgtc accgcgtgta catactgtaa attatttatt aatggctaaa
3181 tgcaagtaaa gtttggtttt tttgttattt tcttttt
```

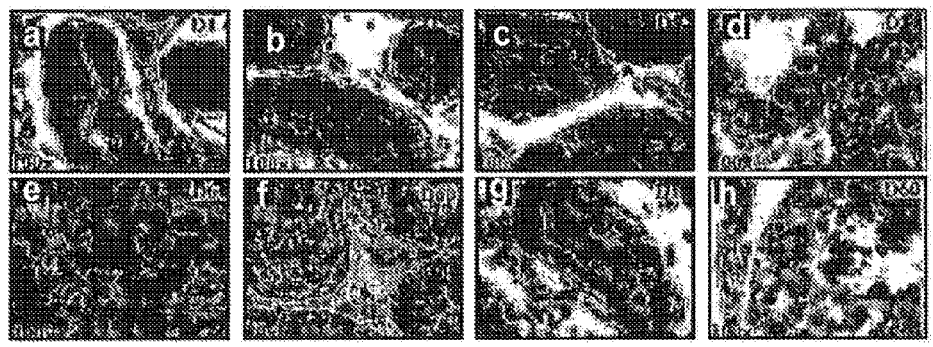
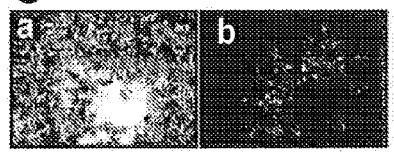
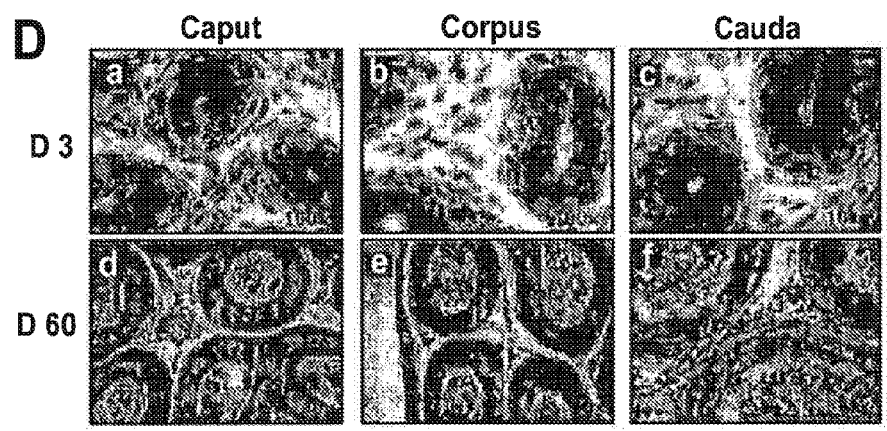
Figures 26A(a-h), 26B(a-b), 26C, and 26D(a-f)

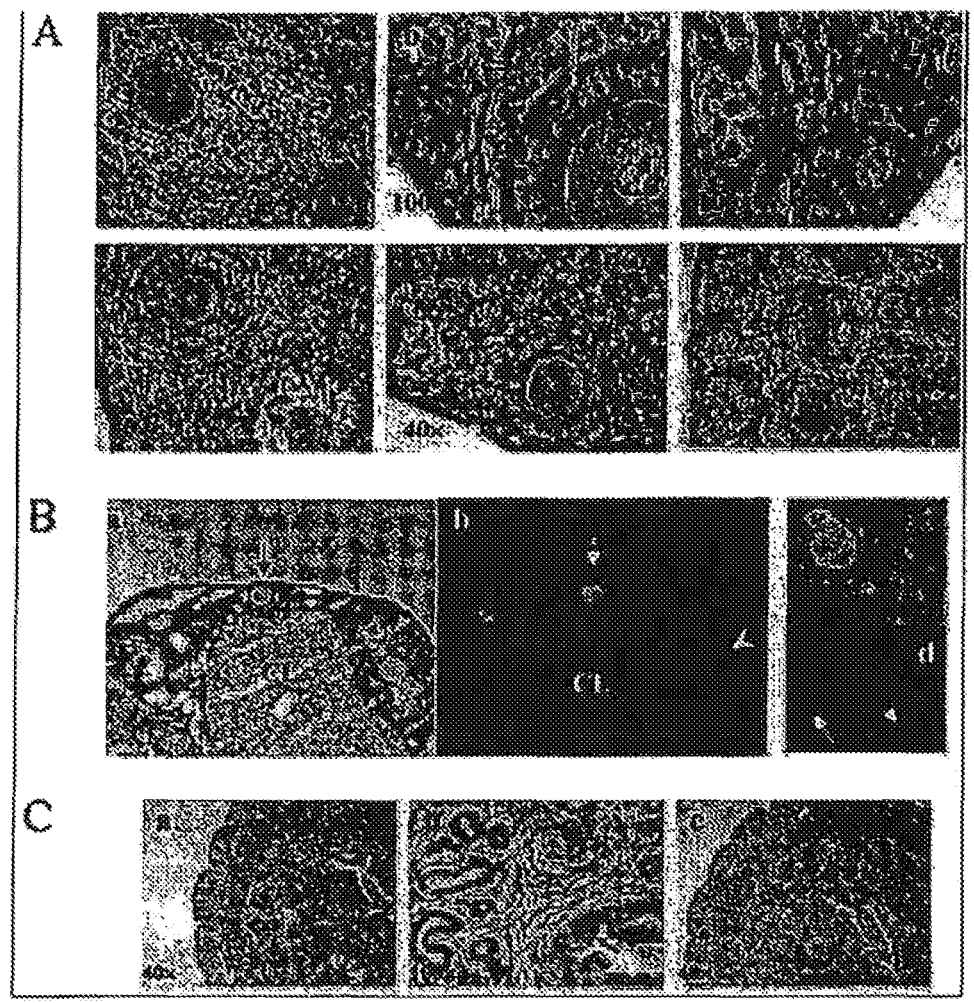
Figures 27A(a-f), 27B(a-d), and 27C(a-c)

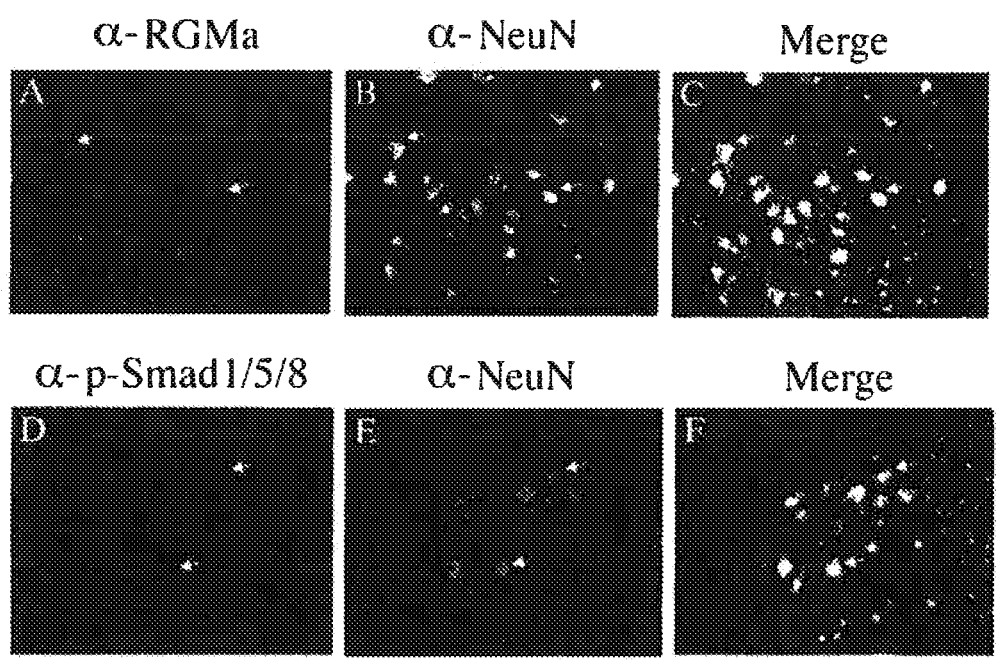
Figures 38 A-F

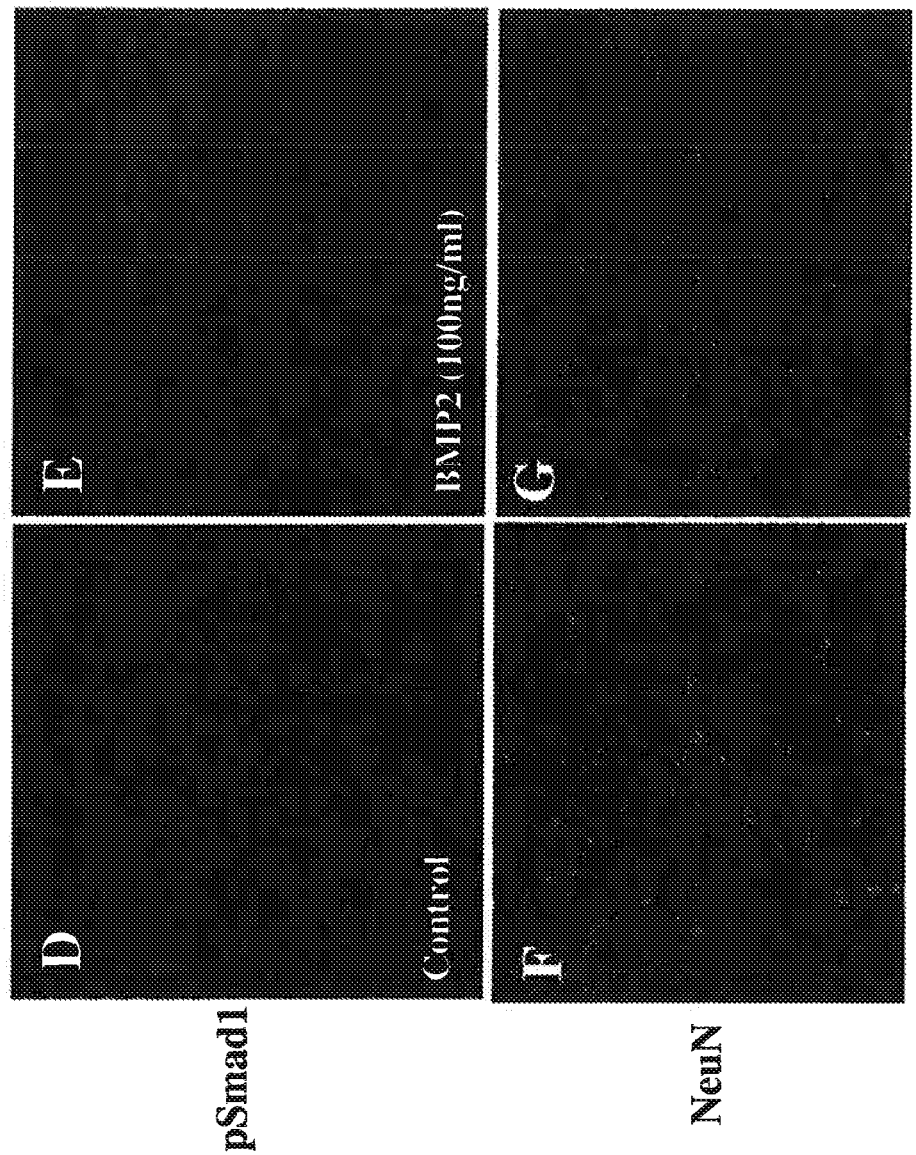
Figures 41D-G

SCREENING METHODS OF BMP/GDF SIGNALING MODULATORS USING DRG11-RESPONSIVE (DRAGON) PROTEINS

CROSS REFERENCE TO RELATED APPLICATIONS

This application is a continuation of U.S. patent application Ser. No. 13/655,941, filed Oct. 19, 2012, which is a continuation of U.S. patent application Ser. No. 13/171,429, filed Jun. 28, 2011, issued as U.S. Pat. No. 8,309,524, on Nov. 13, 2012, which is a continuation of U.S. patent application Ser. No. 12/489,212, filed Jun. 22, 2009, issued as U.S. Pat. No. 7,968,520, on Jun. 28, 2011, which is a continuation of U.S. patent application Ser. No. 11/195,205, filed on Aug. 2, 2005, which claims priority under 35 U.S.C. §119 to of U.S. Provisional Application Ser. No. 60/598,380, filed Aug. 2, 2004, the disclosure of which is incorporated herein by reference in its entirety.

STATEMENT AS TO FEDERALLY SPONSORED RESEARCH

The present research was supported by grants from the National Institutes of Health (Nos. HD039777, DK055838, HD038533, NS038253, GM075267, DK071837, and DK069533). The U.S. Government may therefore have certain rights to this invention.

FIELD OF THE INVENTION

This invention relates to the treatment and diagnosis of diseases that are modulated by a TGF-β-dependent signaling pathway.

BACKGROUND OF THE INVENTION

Developmentally regulated transcription factors drive developmental gene programs that result in embryo formation and the birth, proliferation, growth, migration, and differentiation of the cells that eventually make up the different tissues of the body. This involves the expression and repression of many genes including those whose protein products act as regulators of this process as signal molecules. Some of these signal molecules may be re-expressed in the adult after injury, or the failure of such re-expression may relate to the failure of replacement cells to survive, grow, or regenerate after injury. Some of the signal molecules may act in pathological situations to either promote or suppress abnormal growth or function. These signal molecules, acting on specific transmembrane receptors, may serve as cell fate determinants, survival factors, growth factors, guidance cues, or differentiation factors, and many may have potential therapeutic roles as biological agents beyond their specific involvement in development. Such factors can have biological activity both in vivo and for maintaining cultured cells in vitro, or for converting pluripotent stem cells into specific neuronal or non-neuronal subtypes. Similarly, mimicking the action of these signal molecules by activating their membrane bound receptors or the intracellular signal transduction pathways coupled to their receptors, may also have therapeutic potential.

The transforming growth factor beta (TGF-β) superfamily ligands are central to many signal transduction pathways that control the growth and differentiation of mammalian cells. These ligands and pathways have been implicated in the control of a variety of cellular processes ranging from early vertebrate development to carcinogenesis where specific TGF-β ligands are involved in cell specification, differentiation, proliferation, patterning, and migration.

The TGF-β signaling pathways may be subdivided along two major branches—the TGF-β/Activin/Nodal pathways and the BMP/GDF pathways. The TGF-β/activin/nodal subfamily of ligands contribute to the specification of endoderm and mesoderm in pregastrula embryos and at gastrula stages, to dorsal mesoderm formation and anterior-posterior patterning. Later, they influence the body axis and dorsal-ventral patterning of the nervous system. Bone morphogenetic proteins (BMPs), the second major subfamily of TGF-β ligands contribute to the ventralization of germ layers in the early embryo, suppressing the default neural cell fate of the ectoderm. Neural induction follows formation of the organizer in the dorsal mesoderm which generates inhibitory signals that interrupt BMP signaling in the ectoderm leading to a separation of neural from epidermal territories. BMPs also participate later in development in the formation and patterning of the neural crest, heart, blood, kidney, limb, muscle, and skeletal system.

SUMMARY OF THE INVENTION

We have discovered that DRAGON (DRG11-Responsive Axonal Guidance and Outgrowth of Neurite) proteins, including RGMa and RGMb, the prototypical members of a novel gene family (WO 03/089608), function as co-receptors for both BMP ligands and BMP ligand receptors and facilitate enhanced BMP signaling. Homologous DRAGON proteins have been identified in each of the mouse, zebrafish, and human (WO 03/089608). A partial sequence of an ortholog has also been identified in *C. elegans*.

Accordingly, the invention features a method for identifying a compound that modulates a TGF-β signaling pathway, preferably a BMP/GDF pathway, by (a) providing a sample containing DRAGON protein and a TGF-β signaling pathway member, (b) contacting the sample with a candidate compound, and (c) assessing the binding of the DRAGON protein to the TGF-β signaling pathway member in the sample in the presence of the candidate compound relative to binding in the absence of the candidate compound, wherein a compound that modulates binding of the DRAGON protein to the TGF-β signaling pathway member is identified as a compound that modulates a TGF-β signaling pathway. Preferably, the TGF-β signaling pathway member is a BMP (e.g., BMP-2 and BMP-4), GDF5, a type I BMP receptor (e.g., ALK2, ALK3, and ALK6), or a type II BMP receptor (e.g., BMPRII, ActRIIA, and ActRIIB). More preferably, the TGF-β signaling pathway member is labeled with a radioisotope (e.g., [$^{125}$I]-BMP-2 and [$^{125}$I]-BMP-4) in order to facilitate the assessing step (c). In another embodiment, the assessing step (c) uses an antibody specific for DRAGON (i.e., an anti-DRAGON antibody) or an antibody specific for the TGF-β signaling pathway member.

The invention also features a second method for identifying a compound that modulates a TGF-β signaling pathway, preferably a BMP/GDF pathway, by (a) providing a cell that expresses, naturally or recombinantly, a type I BMP receptor, a type II BMP receptor, and an intracellular TGF-β signaling pathway member, (b) contacting the cell with DRAGON and a candidate compound, and (c) assessing the level of activation of the TGF-β signaling pathway by assessing the activation of the intracellular TGF-β signaling pathway member relative to the level of activation in the absence of the candidate compound, wherein a compound that modulates the activation of the intracellular TGF-β signaling pathway member is identified as a compound that modulates a TGF-β signaling pathway. Preferably, the type I BMP receptor is ALK2, ALK3, or ALK6, and the type II BMP receptor is BMPRII, ActRIIA, or ActRIIB. Preferably, the intracellular TGF-β signaling pathway member is an R-Smad (e.g., Smad1, Smad5, and Smad8). Preferably, step (c) assesses the phosphorylation state of the intracellular TGF-β signaling pathway member or the binding of the intracellular TGF-β signaling pathway member to another intracellular protein such as a Co-Smad (e.g., Smad4 and Smad4β) as an indicator of TGF-β signaling pathway activation. In another embodiment, the cell is further contacted, in step (b), with a TGF-β ligand such as, for example, BMP-2, BMP-4, BMP-7, or GDF-5. Contacting the cell with DRAGON in step (b) may be performed either through the addition of exogenous DRAGON or by transfecting the cell with a nucleic acid capable of expressing DRAGON.

The invention yet further features a third method for identifying a compound that modulates a TGF-β signaling pathway, preferably a BMP/GDF pathway, by (a) providing a cell that expresses a reporter gene construct operably linked to a TGF-β ligand-dependent promoter, (b) contacting the cell with DRAGON protein and a candidate compound, and (c) assessing the level of expression of the reporter gene relative to the level of expression of the reporter gene in the absence of the candidate compound, wherein a candidate compound that modulates the level of expression of the reporter gene is identified as a compound that modulates a TGF-β signaling pathway. In preferred embodiments, the reporter construct is BMP-dependent. In other preferred embodiments, the reporter construct is the BRE-Luc reporter. In other embodiments, the cell is further contacted, in step (b), with a TGF-β ligand such as, for example, BMP-2, BMP-4, BMP-7, or GDF-5. In other embodiments, the cell further expresses recombinant DRAGON. Optionally, the cell also expresses, naturally or recombinantly, one or more BMP type I receptors (e.g., ALK2, ALK3, and ALK6) and/or one or more the type II BMP receptor (e.g., BMPRII; ActRIIA, and ActRIIB).

In another aspect, the invention features a method for identifying a compound that modulates cellular adhesion by (a) providing a sample containing a DRAGON protein and an adhesion-modulating protein, (b) contacting the sample with a candidate compound, and (c) assessing the binding of the DRAGON protein to the adhesion-modulating protein in the sample in the presence of the candidate compound relative to binding in the absence of the candidate compound, wherein a compound that modulates binding of the DRAGON protein to the an adhesion-modulating protein is identified as a compound that modulates cellular adhesion. In preferred embodiments, the adhesion-modulating protein is a cadherin (e.g., E-cadherin), a second DRAGON protein (a homophilic interaction), or a DRAGON-like protein (e.g., DL-N or DL-M). In other embodiments, the DRAGON protein and the adhesion-modulating protein are bound to microspheres or are present on the plasma membrane of a cell.

Compounds identified by any of the screening methods described herein find use in diagnosis and therapy of any DRAGON-related condition described herein, or as lead compounds for optimizing therapeutics for those conditions. Compounds identified by the present screens also find reproductive-related uses, such as treating infertility by increasing DRAGON activity or providing contraceptives by decreasing DRAGON activity.

In another aspect, the invention features a method for diagnosing cancer in a patient by assessing the amount of DRAGON is a biological sample. Suitable biological samples include, for example, blood samples, tissue biopsies, pleural fluid, and cerebrospinal fluid. This method is particularly useful for diagnosing colon cancer, breast cancer, testicular cancer, ovarian cancer, and neuronal and non-neuronal cancers of the nervous system (e.g., glioma, schwanoma, and neuroblastoma). The amount of DRAGON in a biological sample may be assessed by any technique known in the art including, for example, DRAGON-specific antibody-based assays (e.g., ELISA, Western blotting, and immunohistochemistry) and DRAGON-specific primer/probe-based molecular biological techniques using DRAGON-specific polynucleotides (e.g., in situ hybridization or PCR followed by Northern blotting). In preferred embodiments, a DRAGON protein or DRAGON RNA is visualized for its intracellular localization.

In another aspect, the invention features a method for assessing the likelihood of a patient to develop cancer by identifying a DRAGON mutation that correlates with a propensity to develop cancer. Such mutations may cause a change (i.e., increase or decrease) in DRAGON biological activity. Mutations in the GPI anchoring domain that are sufficient to disrupt the membrane anchoring of DRAGON are examples of mutations that reduce DRAGON biological activity and increase the likelihood of cancer. Other mutations may be located in the BMP ligand binding domain, the BMP receptor binding domain, or the cadherin binding domain. Such mutations may be polymorphic changes.

In yet another aspect, chimeric proteins consisting of a DRAGON protein or fragment or DRAGON-specific ligands, or an anti-DRAGON antibody, may be covalently linked to a cytotoxic moiety may be used to treat cancer. Useful cytotoxic moieties include, for example, saporin, *Pseudomonas* exotoxin, IL-12, TNF-α, and radioisotopes. Another useful moiety is boron which may be used to kill target cells using neutron capture therapy. The chimeric protein may be administered to the cancer cell from an exogenous source, or the chimeric protein may be expressed by the cancer cell following, for example, administration of a therapeutically effective amount of a nucleic acid encoding the chimeric protein, operably linked to a promoter that, when expressed in the cancer cells, is capable of expressing the chimeric protein.

The invention also features a method for treating a DRAGON-related condition in a patient by increasing the DRAGON activity in the patient. DRAGON activity may be increased by administering a compound capable of increasing DRAGON binding to a TGF-β signaling pathway member such as a TGF-β ligand (e.g., BMP-2, BMP-4, and GDF-5), or a compound capable of increasing DRAGON binding to a), a BMP type I receptor (e.g., ALK2, ALK4 and ALK6), or a BMP type II receptor (e.g., BMPRII, ActRIIA, and ActRIIB). Preferably, the compound has been previously identified by one of the foregoing screening methods. In preferred embodiments, the increased DRAGON activity causes increased signaling in the BMP/GDF pathway. In other embodiments, the method further comprises administering a biologically active BMP-2, BMP-4, or GDF-5 polypeptide. In another embodiment, the patient is administered a therapeutically effective amount of a nucleic acid encoding a DRAGON protein, operably linked to a promoter that, when expressed in the target cells, is capable of expressing the DRAGON protein. DRAGON-related conditions amenable to treatment using these methods include, for example, cancers characterized as having a defect in the BMP/GDF signaling pathway. Disorders of bone, cartilage, and joints may also be treated by increasing DRAGON activity. Such disorder include, for example, bone fractures, damage to the articular cartilage, arthritis, chondroplasia, and synostosis. Pulmonary hypertensions, particularly famililar primary pulmonary hypertension, kidney disorders (e.g., ischemic kidney disorders and renal fibrosis), male infertility, female infertility, and disorders of the thymus also can be treated by these methods.

The invention also features a method for treating a DRAGON-related condition in a patient by decreasing the DRAGON activity in the patient. DRAGON activity may be reduced by administering a soluble DRAGON protein (i.e., a DRAGON protein having a deletion or disruption of the GPI membrane anchoring domain) in order to sequester BMP ligands or bind (occupy) a membrane-bound DRAGON, an anti-DRAGON antibody or antibody fragment, a compound capable of inhibiting DRAGON binding to a TGF-β ligand (e.g., BMP-2, BMP-4, and GDF-5), a BMP type I receptor (e.g., ALK2, ALK4 and ALK6), or a BMP type II receptor (e.g., BMPRII, ActRIIA, and ActRIIB). Preferably, the compound has been previously identified by one of the foregoing screening methods. In another embodiment, the patient is administered a therapeutically effective amount of a DRAGON-specific RNAi sufficient to inhibit DRAGON expression. DRAGON activity may also be reduced by administering to the patient a nucleic acid encoding an antisense DRAGON nucleic acid or a soluble DRAGON protein. Certain types of cancers, such as breast cancer, colon cancer, non-small cell lung carcinoma, and neuronal and non-neuronal cancers of the nervous system (e.g., glioma, schwanoma, and neuroblastoma) are amenable to treatment by these methods. These methods may also be used to inhibit tumor metastasis in a patient diagnosed as having cancer. In other embodiments, the patient is further administered an inhibitor of a TGF-β ligand, a BMP type I receptor, or BMP type II receptor. Inhibitors of TGF-β ligands include ligand-specific antibodies and soluble BMP receptors and fragments. Inhibitors of the various BMP receptors also include receptor-specific antibodies, mutated TGF-β ligands that retain affinity and lack efficacy, and compounds that inhibit the kinase function of the receptor.

In another aspect, the invention features a method for inhibiting signaling by a BMP by administering a soluble DRAGON protein or a DRAGON-Fc fusion protein. In preferred embodiments, the BMP is BMP-2 or BMP-4.

By "DRAGON" is meant any naturally occurring DRAGON homolog and biologically active fragments thereof. The DRAGON protein has been identified in several species including the mouse, human, C. elegans, and zebrafish (SEQ ID NOs: 1-4, respectively). One particular example of a DRAGON homolog is RGMa (see FIG. 24A-H).

By "DRAGON nucleic acid" is meant a polynucleotide having a sequence which encodes a DRAGON protein, for example RGMa or RGMb. Preferably, a DRAGON nucleic acid is substantially identical or hybridizes under high stringency conditions to a DRAGON cDNA from, for example, the mouse, human, or zebrafish (SEQ ID NOs: 5-7, respectively).

By "mutation," when referring to a DRAGON nucleic acid is meant any alteration in the protein coding region which results in a change in the amino acid sequence encoded. Mutations include single point mutations and polymorphisms as well as deletions of one or more nucleic acids. Mutations may also occur in the untranslated region of a DRAGON nucleic acid such that the mutation affects biological activity. For example, a mutation in the promoter region of the DRAGON gene may have the effect of reducing DRAGON expression.

By "TGF-β signaling pathway member" is meant any protein involved in any TGF-β signal transduction pathway. These pathways include, for example, the BMP/GDF pathway and the TGF-β/Activin/Nodal pathways. The pathway members include the extracellular ligands (e.g., the BMPs), the transmembrane receptors (e.g., the BMP receptors and the TGF-β receptors), the intracellular substrates of the transmembrane receptors (e.g., the R-Smads), and the intracellular accessory proteins (e.g., the Co-Smads and SARA).

By "high stringency conditions" is meant any set of conditions that are characterized by high temperature and low ionic strength and allow hybridization comparable with those resulting from the use of a DNA probe of at least 40 nucleotides in length, in a buffer containing 0.5 M NaHPO$_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. See, e.g., Ausubel et al., *Current Protocols in Molecular Biology*, John Wiley & Sons, New York, N.Y., 2000, hereby incorporated by reference.

By "DRAGON antisense nucleic acid" is meant a nucleic acid complementary to a DRAGON coding, regulatory, or promoter sequence. Preferably, the antisense nucleic acid decreases DRAGON expression (e.g., transcription and/or translation) by at least 5%, 10%, 25%, 50%, 75%, 90%, 95%, or even 99%. Preferably, the DRAGON antisense nucleic acid comprises from about 8 to 30 nucleotides. A DRAGON antisense nucleic acid may also contain at least 40, 60, 85, 120, or more consecutive nucleotides that are complementary to a DRAGON mRNA or DNA, and may be as long as a full-length DRAGON gene or mRNA. The antisense nucleic acid may contain a modified backbone, for example, phosphorothioate, phosphorodithioate, or other modified backbones known in the art, or may contain non-natural internucleoside linkages.

A DRAGON antisense nucleic acid may also be encoded by a vector where the vector is capable of directing expression of the antisense nucleic acid. This vector may be inserted into a cell using methods known to those skilled in the art. For example, a full length DRAGON nucleic acid sequence, or portions thereof, can be cloned into a retroviral vector and driven from its endogenous promoter or from the retroviral long terminal repeat or from a promoter specific for the target cell type of interest. Other viral vectors which can be used include adenovirus, adeno-associated virus, vaccinia virus, bovine papilloma virus, or a herpes virus, such as Epstein-Ban Virus.

By "vector" is meant a DNA molecule, usually derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

By "substantially pure" is meant a nucleic acid, polypeptide, or other molecule that has been separated from the components that naturally accompany it. Typically, the polypeptide is substantially pure when it is at least 60%, 70%, 80%, 90% 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

By a "promoter" is meant a nucleic acid sequence sufficient to direct transcription of a gene. Also included in the invention are those promoter elements which are sufficient to render promoter-dependent gene expression controllable for cell type-specific, tissue-specific or inducible by external signals or agents (e.g. enhancers or repressors); such elements may be located in the 5' or 3' regions of the native gene, or within an intron.

By "operably linked" is meant that a nucleic acid molecule and one or more regulatory sequences (e.g., a promoter) are connected in such a way as to permit expression and/or secretion of the product (e.g., a protein) of the nucleic acid molecule when the appropriate molecules (e.g., transcriptional activator proteins) are bound to the regulatory sequences.

By "antibody that selectively binds" is meant an antibody capable of a high affinity interaction with a specific target molecule, having a dissociation constant of <1 μM, <100 nM, <10 nM, <1 nM, or even <100 pM. Preferably, the antibody has at least 10-fold, 100-fold, 1,000-fold, or even 10,000-fold lower affinity for other, non-target molecules. A "DRAGON-specific antibody" is, therefore, an antibody that selectively binds to a DRAGON protein.

By a "DRAGON-related condition" is meant any disease or disorder which is associated with the dysfunction or altered (increased or decreased) activity or expression of DRAGON. Alternatively, DRAGON-related conditions can also refer to any disease or disorder which, although not associated with DRAGON dysfunction, is amenable to treatment by modulating (increasing or decreasing) the activity or expression of a DRAGON protein or nucleic acid or by mimicking their actions. Typically, these DRAGON-related conditions are associated with a dysfunction in signal transduction in the BMP/GDF branch of the TGF-β signaling pathway. The dysfunction may be an inappropriate activation, in magnitude or duration, of the signaling pathway, requiring a reduction of DRAGON biological activity. Alternatively, the signaling pathway may be hypoactive and successful therapy requires increasing the level of pathway activation.

By a "therapeutically effective amount" is meant a quantity of compound (e.g., a DRAGON protein) delivered with sufficient frequency to provide a medical benefit to the patient. Thus, a therapeutically effective amount of a DRAGON protein is an amount sufficient to treat or ameliorate a DRAGON-related condition or symptoms.

By "treating" is meant administering a pharmaceutical composition for the purpose of improving the condition of a patient by reducing, alleviating, or reversing at least one adverse effect or symptom.

BRIEF DESCRIPTION OF DRAWINGS

FIG. 2A is a Western blot analysis of protein extract from untransfected HEK293 cells (−), or those transfected (+) with DRAGON expression vector. A distinct band having a molecular weight of about 50 KDa is recognized by the anti-DRAGON antibody in transfected, but not control, cells. ERK protein level was used as a loading control. FIG. 2B is a photomicrograph of an immunocytochemical study showing significant staining of DRAGON-expressing HEK cells (top). Pretreatment of DRAGON-expressing HEK cells with PI-PLC causes a significant reduction of anti-DRAGON staining (bottom). Non-transfected HEK cells show no anti-DRAGON staining (not shown). FIG. 2C is a photomicrograph of a Western blot analysis of samples of DRAGON-expressing HEK cell culture medium, with or without pretreatment using PI-PLC. A band corresponding to DRAGON is detected in PI-PLC treated medium samples. FIG. 2D is a series of photomicrographs from an anti-DRAGON immunohistochemical study of adult spinal cord and DRG at low (top) and high (middle) magnification. As a control, the anti-DRAGON antibody was pretreated with the immunogenic DRAGON fragment prior to immunohistochemical staining (bottom). Scale, 100 μM.

FIG. 5A is a photomicrograph of an in situ hybridization study showing that DRAGON and DRG11 mRNAs are both expressed in the dorsal root ganglion (DRG) and the spinal cord at E12.5. FIG. 5B is a bar graph showing the DRG11-dependent enhancer activity of the DRAGON promoter fragment. FIG. 5C shows the results of a pull-down experiment using either GST or GST-DBD (DBD=DRG11 DNA Binding Domain). The purified proteins (right panel) were incubated with the DRAGON promoter fragment, and "pulled down" using glutathione sepharose. Only GST-DBD fusion protein pulled down the promoter fragment as assessed by agarose gel electrophoresis.

FIG. 6 is a series of photomicrographs showing the distribution of DRAGON mRNA in the adult rat DRG by in situ hybridization.

FIG. 9A is a bar graph showing the effect of BMP-2 and DRAGON on BRE-Luc reporter gene activation. FIG. 9B is a bar graph showing the combined effects of BMP-2 and DRAGON on BRE-Luc reporter gene activation. FIG. 9C is a bar graph demonstrating that DRAGON does not affect TGF-β- or Activin-mediated signaling.

FIG. 20 is a photomicrograph showing the expression of DRAGON in the normal colon and in colon cancer tissue.

FIG. 24 A-H provides the amino acid (SEQ ID NOs.: 1, 2, and 4) and nucleic acid (SEQ ID NOs: 5-7) sequences of mouse, human, and zebrafish DRAGON, the amino acid sequences of *C. elegans* DRAGON (SEQ ID NO:3), the amino acid (SEQ ID NOs: 8-9) and nucleic acid (SEQ ID NOs: 10-11) sequences of human DL-M and DL-N, and the amino acid (SEQ ID NO:12) and nucleic acid (SEQ ID NO:13) sequences of RGMa.

FIGS. 26A-26D are images showing cellular localization of DRAGON in the mouse testis and epididymis during postnatal development by immunohistochemistry and in situ hybridization. For immunohistochemistry, all sections were stained with DAB and counterstained with hematoxylin. Images are shown at lower (40) or higher (100) magnification. FIG. 26A shows immunolocalization of DRAGON in testes at d1 (D1, a), d3 (D3, b), d9 (D9, c), d21 (D21, d), and d60 (D60, e and f). For negative control, sections were incubated with DRAGON antibody preincubated with competing immunizing peptide (g and h). DRAGON is highly expressed in gonocytes and spermatogonia in testes of newborn mice and spermatocytes and round spermatids in testes of adult mice. DRAGON is not expressed in spermatocytes of d21 testes. Spermatogonia are weakly stained in d21 testes but not stained in adult testes. FIG. 26B shows immunostaining of d21 testes with (b) and without (a) PMSG (5 IU) injection 2 d earlier. Immunostaining in spermatocytes is turned on by PMSG administration. FIG. 26C shows localization of DRAGON mRNA in mouse testes by in situ hybridization. Bright (left) and dark (right) field images are shown. FIG. 26D shows immunolocalization of DRAGON in d3 (D3, a-c) and d60 (D60, d-f) epididymis. Caput (a and d), corpus (b and e), and cauda (c and f) were dissected.

FIGS. 27A-27C are images showing cellular localization of DRAGON in the mouse ovary and uterus by immunohistochemistry and in situ hybridization. For immunohistochemistry, all sections were stained with DAB and counterstained with hematoxylin. Images are shown at lower (40) or higher (100) magnification. FIG. 27A shows DRAGON immunostaining in ovaries at d60 (D60, a-d) and d9 (D9, f). The staining in oocytes of secondary follicle (arrow) is stronger than that in oocytes of antral (arrowhead) and atretic (curved arrow) follicles (a and d). DRAGON is not expressed in oocytes of primordial (open arrow) and primary (triangle) follicles (b and c). For negative control, sections were incubated with DRAGON antibody preincubated with competing immunizing peptide (e). FIG. 27B shows localization of DRAGON mRNA in mouse adult ovaries by in situ hybridization. Dark (b and d) and bright (a and c) field images are shown. Signals are confined to oocytes, and signals are stronger in the secondary (arrow) than in antral (arrowhead) follicles (a and b). No signals are seen in primary follicles (triangle, c and d) and in corpus luteurii (CL). FIG. 27C shows immunohistochemistry of the mouse uterus showing protein expression of DRAGON (a and b), and negative control (c), incubation with DRAGON antibody preincubated with competing immunizing peptide. The solid arrow indicates luminal epithelial cells of endometrium, the arrowhead indicates glandular epithelial cells of endometrium, and the open arrow shows circular muscle.

FIGS. 28A and 28B are images showing immunolocalization of DRAGON in the pituitary and colocalization of DRAGON and FSH. FIG. 28A shows immunostaining for DRAGON in the mouse pituitary (paraffin sections). Sections were incubated with DRAGON antibody (a-c) or with DRAGON antibody preincubated with competing immunizing peptide (d-f), AL, Anterior lobe; IL, intermediate lobe; PL, posterior lobe. FIG. 28B shows colocalization of FSH and DRAGON in the mouse anterior pituitary (frozen sections). DRAGON and FSH were detected in the anterior pituitary. Double-labeled cells (arrows) indicate DRAGON expression in the mouse pituitary gonadotrope. Note that some FSH-positive cells are negative for DRAGON staining and some DRAGON-positive cells are negative for FSH staining.

FIG. 29A shows RT-PCR analyses of DRAGON mRNA in cell lines. β-Actin was used as a control for cDNA quality. FIG. 29B shows immunochemical localization of DRAGON in Ishikawa cells. The live unfixed cells were incubated with rabbit anti-DRAGON serum on ice and then fixed in 2% paraformaldehyde. The bound antibodies were detected by incubating with FITC-conjugated donkey antirabbit IgG. FIG. 29C shows localization of DRAGON in raft-enriched fractions prepared from Ishikawa cells. Cells were extracted using a buffer containing 1% Triton X-100. The lysate was mixed with 85% sucrose, sequentially layered with 35 and 5% sucrose, and centrifuged for 14 h at 150,000 g. Nine fractions were collected and analyzed for DRAGON, caveolin-1, and β-actin by Western blot. The bands specific for DRAGON are marked with asterisks.

FIG. 30A shows Ishikawa or KGN cells were transiently transfected with BRE-Luc reporter in combination with increasing doses of DRAGON cDNA and assayed for luciferase activity. Transfection with DRAGON increases BRE-Luc response in the absence of exogenous ligand. Values are ratios of BRE-Luc to pRL-TK and are mean±SE of triplicates from representative experiments. DRAGON protein is detectable by Western blot in Ishikawa cells after transfection with 100 ng cDNA. The membrane was stripped and reprobed with β-actin antibody as a control for loading (inset). FIG. 30B shows Ishikawa cells transfected with BRE-Luc reporter and DRAGON cDNA and treated with BMP2 alone or together with noggin. Values are ratios of BRE-Luc to pRL-TK and are mean±SE of triplicates from representative experiments. FIG. 30C shows control medium used in parallel with noggin-conditioned medium to demonstrate the specificity of the inhibitory activity of noggin-conditioned medium in BMP2 signaling. Although noggin inhibited BMP2 signaling, control conditioned medium had no inhibitory effect. FIG. 30D shows Ishikawa cells transiently transfected with BRE-Luc reporter and DRAGON (0 or 10 ng) in 24-well plates were incubated with increasing doses (0-2800 pM) of BMP2. Values are fold increases of luciferase activity in treated cells relative to untreated cells and are the means SE of six determinations from three independent experiments in duplicate. Asterisks indicate significant differences between transfected and untransfected cells at each BMP2 dose: **, P 0.01; *, P 0.05.

FIGS. 31A and 31B show LLC-PK1 cells transfected with the BMP-responsive firefly luciferase reporter (BRE-Luc, A) or the TGF-β-responsive firefly luciferase reporter (CAGA-Luc, B), in combination with pRL-TK Renilla luciferase vector, either alone (A, B bars 1, 2) or with 0.2 mg RGMa cDNA (A, B bar 3). Transfected cells were then incubated for 16 hrs in the absence (A, B bars 1, 3) or presence of 50 ng/ml BMP-2 (A, bar 2) or 20 ng/ml TGF-β1 (B, bar 2) followed by measurement of luciferase activity. FIG. 31C shows LLC-PK1 cells transfected with BRE-Luc and pRL-TK either alone or with increasing amounts of RGMa cDNA as indicated. Transfected cells were then incubated for 16 hrs in the absence (white bars) or presence of 50 ng/ml BMP-2 (black bars), followed by measurement of luciferase activity. Luciferase values were normalized for transfection efficiency relative to Renilla activity to generate relative luciferase units (R.L.U.). Results are reported as the mean+/−standard deviation.

FIGS. 32A and 32B show LLC-PK1 cells transfected with BRE-Luc and pRL-TK alone (A, B bars 1-2, 5-6) or in combination with 0.2 mg RGMa cDNA (A, B bars 3-4). RGMa transfected cells were then incubated alone (A, B bar 3) or with 1 mg/ml noggin protein (A, bar 4) or 20 mg/ml neutralizing antibody against BMP-2 and BMP-4 (α-BMP2/4, B, bar 4) for 48 hrs. As a control, cells without RGMa were incubated for 48 hrs in the absence (A, B, bars 1, 5) or presence of 1 mg/ml Noggin protein (A, bars 2, 6) or 20 mg/ml α-BMP2/4 (B, bars 2, 6), without (A, B, bars 1, 2) or with exogenous BMP-2 at 75 mg/ml (A, bars 5-6) or 25 mg/ml (B, bars 5-6) for 16 hrs.

Luciferase activity was measured from cell extracts and normalized for transfection efficiency relative. to Renilla activity to generate relative luciferase units (R.L.U.) Results are reported as the mean+/−standard deviation. FIG. 32C shows RT-PCR performed on total RNA from LLC-PK1 cells using primers for BMP-2 or BMP-4 as indicated (lane 3). Purified plasmid cDNAs containing BMP-2 or BMP-4 were used as positive controls (+, lane 1), and reactions without template were used as negative controls (−, lane 2).

FIG. 34A shows 400,000 counts $^{125}$I-BMP-2 was incubated overnight alone (background) or in combination with 25 ng RGMa.Fc, in the absence (total binding) or presence of excess unlabeled BMP-2, -4, -7, or TGF-β1 as indicated, followed by incubation on protein A coated plates and determination of radioactivity using a standard g counter. FIG. 34B shows buffer alone (C), 25 ng RGMa.Fc, or TGF-β type I receptor ALK5.Fc incubated with 400,000 counts $^{125}$I-BMP-4 with or without excess cold BMP-4 overnight at 4° C. This mixture was then incubated in the absence (−DSS) or presence of 2.5 mM DSS in DMSO (+DSS) as indicated for 2 hr at 4° C. After quenching of DSS activity, the mixture was incubated with Protein A beads at 4° C. for 2 hr, and the eluted protein complex analyzed by non-reducing SDS-PAGE, followed by autoradiography.

FIG. 35A shows, in the Left panel, LLC-PK1 cells transfected with BRE-Luc and pRL-TK either alone, (bar 1) or in combination with 0.2 mg RGMa cDNA (bars 2-4), in the absence (bar 2) or presence of 1 mg dominant negative type I receptors ALK3 (ALK3 DN, bar 3) or ALK6 (ALK6 DN, bar 4). In the Right panel, LLC-PK1 cells were transfected with BRE-Luc and pRL-TK either alone (bars 5, 6) or in combination with 1 mg ALK3 DN (bar 7) or ALK6 DN, (bar 8), followed by incubation in the absence (bar 5) or presence of 50 ng/ml BMP-2 (bars 6-8). Luciferase activity was measured from cell extracts and normalized for transfection efficiency relative to Renilla activity to generate relative luciferase units (R.L.U.). Results are expressed as the mean+/−standard deviation. FIG. 35B shows 200 ng RGMa.Fc, 200 ng ALK6.Fc, and/or 100 ng BMP-2 incubated in solution in various combinations as indicated with the crosslinker DSS. Complexes were pulled down with protein A beads, and the protein complex was analyzed by non-reducing SDS-PAGE followed by Western blot with RGMa antibody. Arrowheads indicate slower migrating bands containing RGMa.Fc complexes. FIG. 35C shows buffer alone (bar 1), 10 ng RGMa.Fc alone (bar 2), 10 ng ALK6.Fc alone (bar 3), or the combination of 10 ng each of RGMa.Fc and ALK6.Fc (bar 4) incubated with $^{125}$I-BMP-2, followed by incubation on protein A coated plates and determination of radioactivity using a standard g counter.

FIG. 36A shows LLC-PK1 cells transfected with BRE-Luc and pRL-TK either alone (lane 1, 7-8), or in combination with 1 mg wild-type Smad1 (Smad1 WT, bar 2, 9) or 1 mg dominant negative Smad1 (Smad1 DN, bar 3, 10). Transfected cells were then incubated in the absence (bar 1-3, 7) or presence of 50 ng/ml BMP-2 (bars 8-10). Alternatively, cells were co-transfected with BRE-Luc, pRL-TK, and 0.2 mg RGMa alone (bar 4), or in combination with Smad1 WT (bar 5) or Smad1 DN (bar 6). Luciferase activity was measured from cell extracts and normalized for transfection efficiency relative to Renilla activity to generate relative luciferase units (R.L.U.) Results are reported as the mean+/−standard deviation. FIG. 36B shows LLC-PK1 cells transiently transfected with 5 mg RGMa cDNA (middle 3 lanes) or empty vector (left and right 2 lanes). 24 hours after transfection, cells were incubated without (lanes 1-5) or with 50 ng/ml BMP-2 (right two lanes) for two hours. Cell lysates were analyzed by Western blot in succession with RGMa antibody (α-RGMa), phosphorylated Smad1/5/8 antibody (α-p-Smad1/5/8), Smad1 antibody (α-Smad1, as a loading control), Id1 antibody (α-Id1), and actin antibody (α-β-actin, as a loading control). FIGS. 36C and 36D show chemiluminescence from the Western blot in panel B quantitated by IPLab Spectrum software for phosphorylated Smad1/5/8 relative to Smad1 expression (FIG. 36C) and Id1 relative to β-actin expression (FIG. 36D). Results are reported as the mean+/−standard deviation of control cells (C), cells transfected with RGMa (RGMa), and cells treated with BMP-2 (BMP-2).

FIGS. 38A-38F are images of immunohistochimcal sections showing RGMa and nuclear phosphorylated Smad1/5/8 expressed in ventral horn motor neurons of adult rat spinal cord. Fixed adult rat spinal cord sections were co-immunostained with rabbit anti-RGMa antibody (α-RGMa, FIGS. 38A-38C) or rabbit anti-phosphorylated Smad1, 5, 8 antibody (α-p-Smad1/5/8; FIGS. 38D-38F) in combination with mouse anti-neuron-specific nuclear protein antibody to visualize neuronal cell bodies (α-NeuN, all panels), followed by Cy3-conjugated anti-rabbit and FITC-conjugated anti-mouse secondary antibodies. Shown are images of the ventral horn by fluorescence microscopy. Cy3 fluorescence is shown in the left column of panels (α-RGMa (FIG. 38A) or α-p-Smad1, 5, 8 (FIG. 38D)). FITC fluorescence is shown in the middle column of panels (α-NeuN (FIGS. 38B and 38E)). The corresponding superimposed images are shown in the right column of panels (Merge (FIGS. 38C and 38F)). Representative motor neurons are indicated (arrows).

FIG. 39B shows induction of phospho-Smad1 in cultured DRG neurons After BMP2 treatment (bottom) as compared to control (top).

FIG. 40B) and stained for β-tubulin III to assess neurite outgrowth. Note the increase in neurites after incubation with BMP2 indicating that BMP2 acts directly on sensory neurons to induce neurite outgrowth.

FIGS. 41A-41G are a schematic diagram and images showing results from an experiment similar to the one described in FIGS. 39 and 40, using the spinal cord slice paradigm (FIG. 41A) to show that spinal cord neurons also respond to BMP2 via the Classical Smad1, 5, 8 signaling pathway (FIGS. 41B-41G). After BMP2 treatment (100 ng/ml), the slices were analyzed by immunohistochemistry to assess levels of phosphorylated Smad1 (p-Smad1) as a marker for BMP signaling.

DETAILED DESCRIPTION

The TGF-β Signaling Pathway

Figure 1:
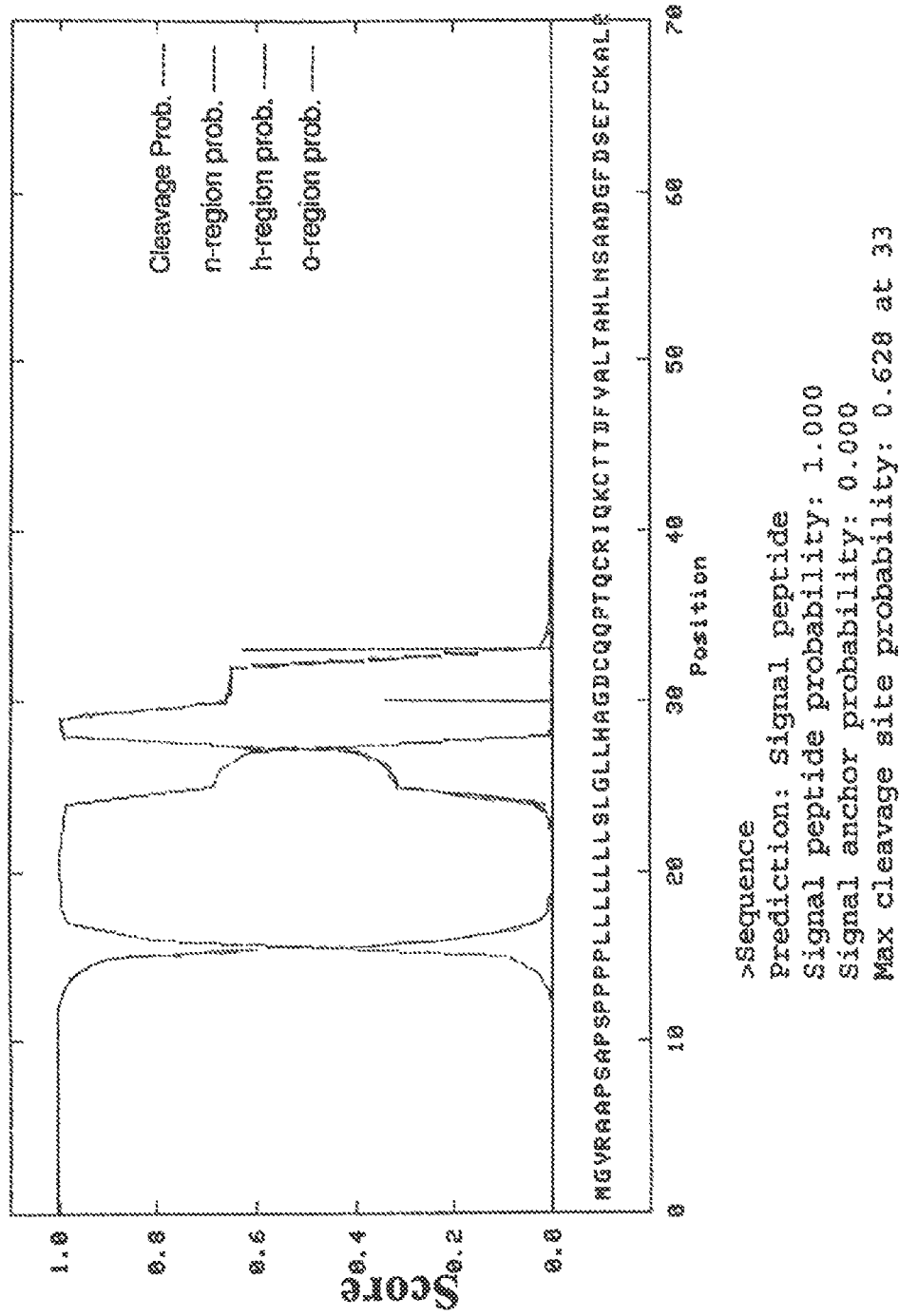
FIG. 1 is a graph illustrating the result of a computational structure-function analysis of mDRAGON, demonstrating the presence of a signal sequence which results in protein secretion.

Signaling through the TGF-β pathways influences the growth and differentiation of a variety of cell types by affecting gene transcription. TGF-β ligands, the extracellular signaling molecules, induce the formation of functional receptor complexes by combining members of two distinct families of serine/threonine kinases; the Type I and Type II TGF-β receptors. The Type II receptor activates, by phosphorylation, the Type I receptor which propagates the TGF-β signal by phosphorylating a member of the cytoplasmic receptor-activated Smad (R-Smad) protein family. Each TGF-β ligand has the capability to assemble several possible Type I/Type II receptor combinations and different combinations phosphorylate different intracellular R-Smad protein substrates. Signaling by an Activin/Nodal TGF-β ligand typically results in the phosphorylation of either Smad2 or Smad3; whereas BMP/GDF TGF-β ligand signals are frequently transduced through Smad1, Smad5, or Smad8. The R-Smads form heteromeric complexes with the Co-Smads and Smad4, and then translocate from the cytoplasm into the nucleus to regulate gene transcription.

The TGF-β ligands BMP2, BMP4, BMP7, and GDF5 activate the BMP/GDF branch of the TGF-β signaling pathway. Upon ligand binding, a functional TGF-β receptor is formed from BMP type I receptor (BMPRI) and a BMP type II receptor (BMPRII). The BMPRIs that mediate BMP2, BMP4, and BMP7 signaling include ALK2, ALK3, or ALK6. The group from which the BMPRII is selected includes the prototypical BMP type II receptor (BMPRII), the Activin type IIA receptor (ActRIIA), and the Activin type IIB receptor (ActRIIB).

Multiple extracellular and intracellular regulators enhance or reduce TGF-β and BMP signaling. Access of ligands to receptors is inhibited by soluble proteins that bind and sequester the ligand. These include LAP, decorin, and α2-macroglobulin, which bind to TGF-β. Soluble BMP antagonists include noggin, chordin, chordin-like, follistatin, FSRP, the DAN/Cerberus protein family, and sclerostin.

TGF-β ligand access to receptors is also controlled by membrane-bound co-receptors. The proteoglycan beta-glycan (TGF-β type III receptor) enhances TGF-β binding to the type II receptor while endoglin facilitates binding to Alk1. The connective tissue growth factor (CTGF) enhances TGF-β and inhibits BMP4 receptor binding. The CFC-EGF family regulates TGF-β signaling both as secreted factors and cell surface components. Cripto, a GPI-anchored membrane protein, increases binding of nodal, Vg1, and GDF1 to activin receptors but inhibits activin signaling by forming an "inert" complex with activin and ActRII. BAMBI acts as a decoy receptor that competes with the type I receptor for incorporation into ligand-induced receptor complexes.

So far only co-receptors that act on the TGF-β/activin/nodal signal transduction pathway have been identified. We have discovered that DRAGON, a membrane-associated GPI-anchored protein that is expressed early in vertebrate embryos, binds to BMP but not other TGF-β ligands, associates with BMP receptors, and activates BMP signaling in cell lines and *Xenopus* embryos. We conclude that DRAGON is the first identified co-receptor that enhances BMP signaling and may be used to modulate the BMP/GDF branch of the TGF-β signaling pathway.

Characterization of DRAGON

Murine DRAGON (SEQ ID NOs: 1 and 5) was identified, using a Genomic Binding Site (GBS) strategy, as a seminal member of a new family of DRG-11 responsive genes that are involved in embryogenesis. DRAGON homologs have been identified in the human (SEQ ID NOs: 2 and 6), Zebrafish (SEQ ID NOs: 4 and 7), and *C. elegans* (SEQ ID NO: 3).

Sequence analysis of the mDRAGON coding region identified conserved domains with homology to notch-3, phosphatidylinositol-4-phosphate-5-kinase type II beta), insulin-like growth factor binding protein-2, thrombospondin, ephrin type-B receptor 3 precursor, and Slit-2, all of which are known to influence axonal guidance, neurite outgrowth, and other neuronal developmental functions. The C-terminus of mDRAGON is also predicted to contain a hydrophobic domain indicative of a 21 amino acid extracellular GPI anchoring. A computational structure-function analysis of mDRAGON reveals the presence of a putative signal peptide sequence (FIG. 1), indicating that the gene product is a secreted protein, and further supporting an extracellular localization.

DRAGON Protein Expression

Figures 2A, 2B, 2C:
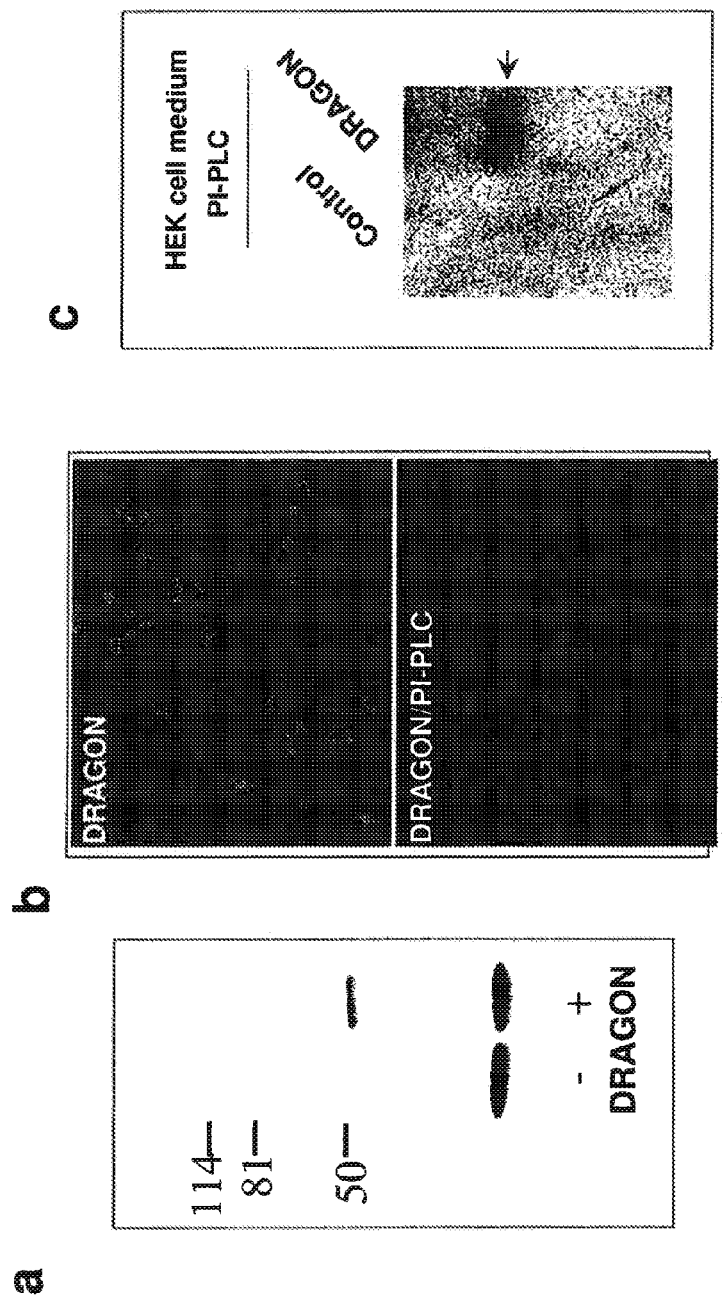
FIGS. 2A-2D provide experimental results using a novel anti-DRAGON rabbit polyclonal antibody.

A rabbit polyclonal antibody was raised against the peptide sequence TAAAHSALEDVEALHPRK (SEQ ID NO: 8; residues 388-405 of mDRAGON), present in the C-terminus of DRAGON, upstream of its hydrophobic tail. The antibody binds with high affinity to recombinant DRAGON expressed in HEK293T transfected cells, recognizing a band of 50 KDa in Western blots (FIG. 2a). Antibody specificity was confirmed by immunocytochemistry of DRAGON-expressing HED293T cells (FIG. 2b). Western blots of protein extracts from neonatal and adult DRG and DRG primary cultures show a similar band with an additional lower band of 40 KDa, indicating possible proteolytic cleavage of endogenous DRAGON. Treatment of HEK293T cells expressing DRAGON with PI-PLC results in the decrease of DRAGON detection on HEK cells and its release into the culture medium (FIG. 2c), indicating that DRAGON is GPI-anchored.

Figure 2D:
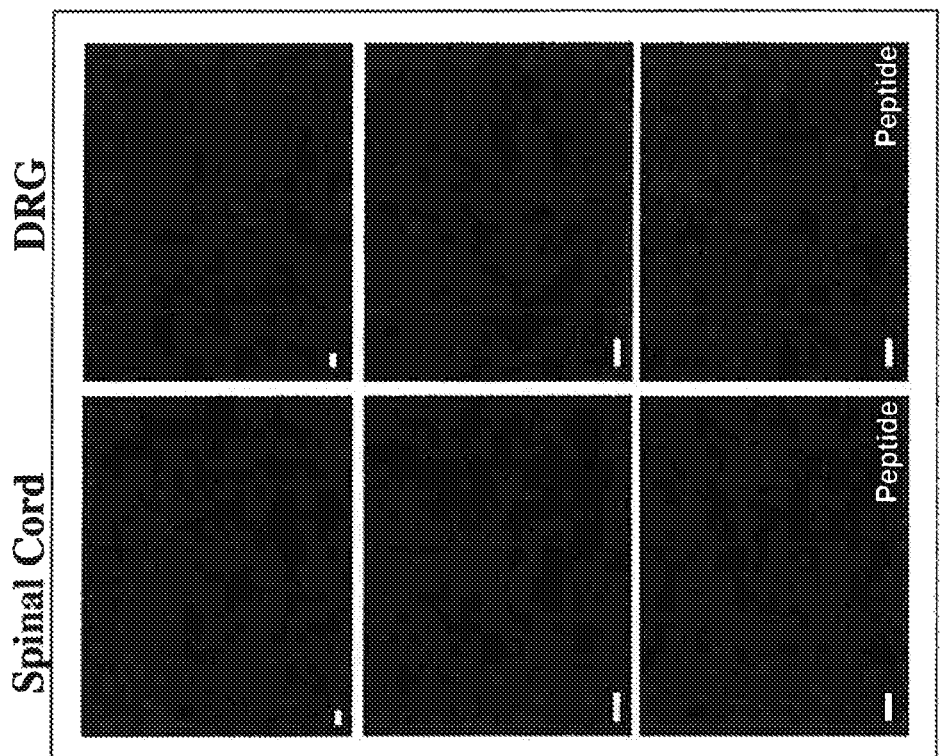
Figure 3:
FIG. 3 is a photomicrograph showing the distribution of DRAGON expression in the retina and optic nerve of a mouse embryo (E14.5) using immunohistochemistry.
Figure 4:
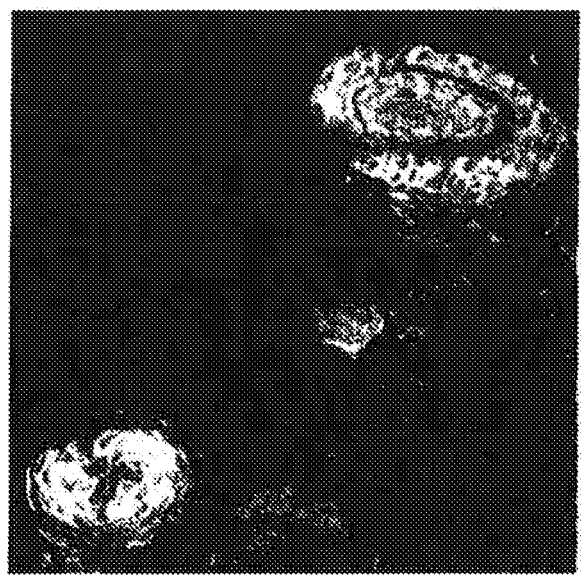
FIG. 4 is a photomicrograph showing the distribution of DRAGON expression in rat glaborous skin (base of the epidermis of the hindpaw) using immunohistochemistry. DRAGON expression is highest in the Merkel cells.

Immunohistochemistry confirms expression of DRAGON in the DRG, spinal cord and brain in the areas where DRAGON mRNA is found (FIG. 2d). In the adult DRG, DRAGON is more abundantly expressed in small neurons with unmyelinated axons than in medium and large myelinated neurons (Aδ and Aβ-fibers) (FIG. 2d). In the adult spinal cord, DRAGON expression is most prominent in the superficial laminae of the dorsal horn (FIG. 2d). Immunohistochemical studies also demonstrated that the DRAGON protein is expressed in the E14.5 mouse retina and optic nerve (FIG. 3) and skin (FIG. 4).

Tissue Localization of DRAGON Gene Expression

Figures 5D, 5E, 5F:
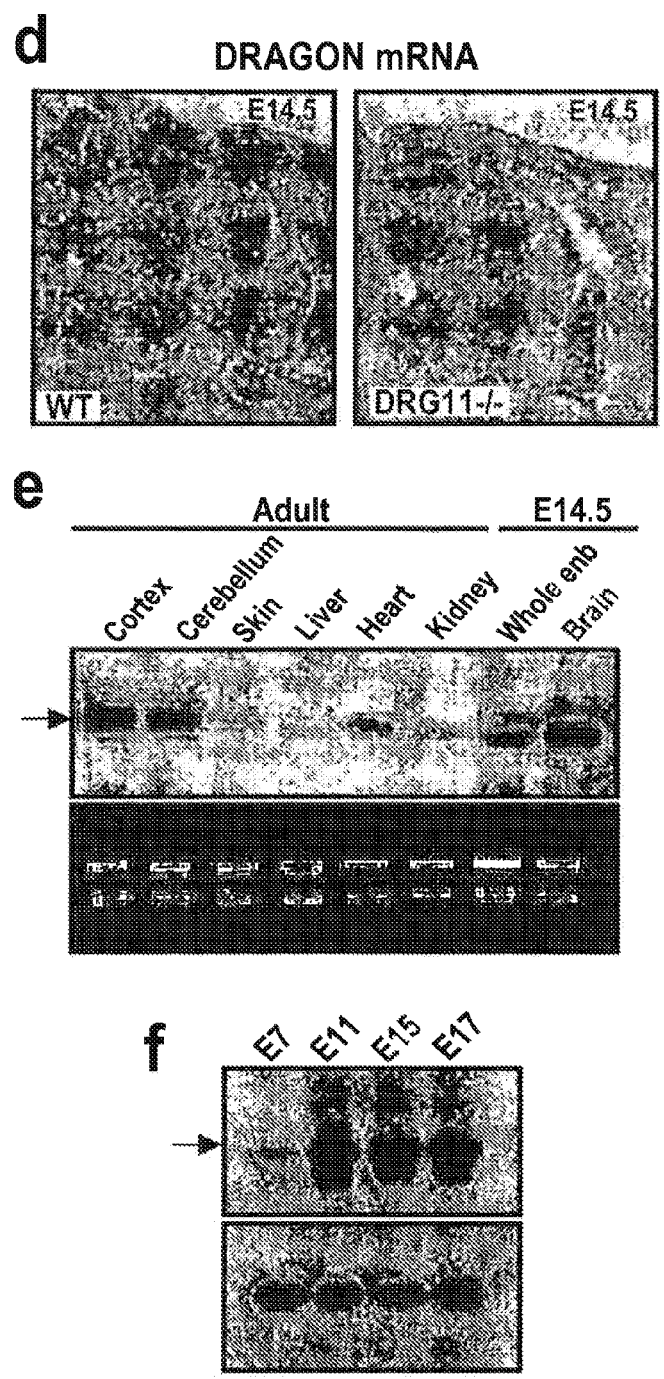
FIG. 5D is a photomicrograph of an in situ hybridization study demonstrating a decrease in DRAGON mRNA expression in the DRG and the spinal cord of DRG11−/− mouse at E14.5, compared to wildtype.
FIG. 5E shows the result of a Northern blot analysis of DRAGON mRNA expression in adult and embryonic E14.5 tissue.
FIG. 5F shows the result of a Northern blot analysis of DRAGON mRNA expression in whole mouse embryos during development. β-actin mRNA levels were used as a loading control.
Figure 7:
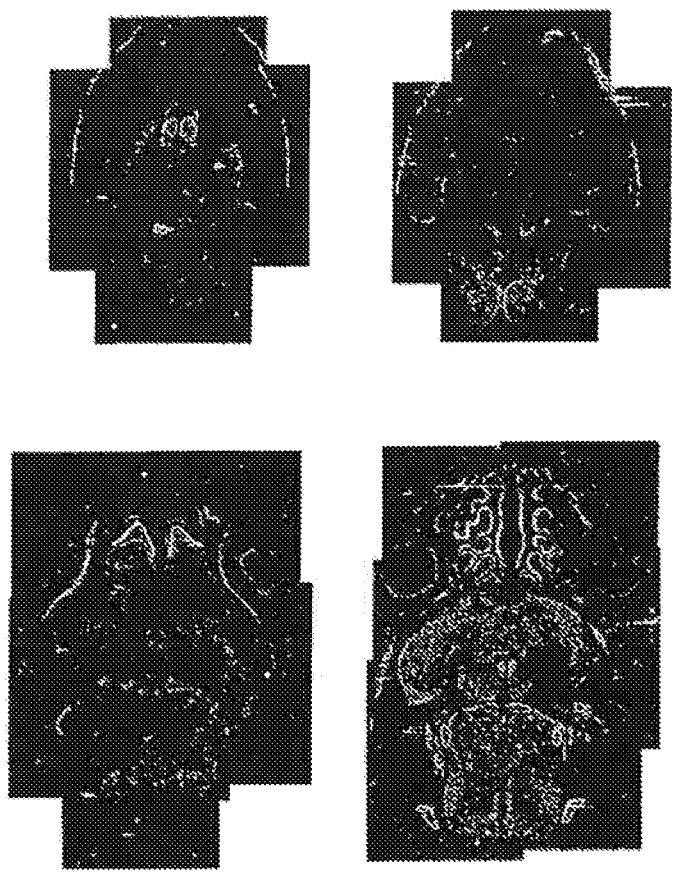
FIG. 7 is a series of photomicrographs showing the distribution of DRAGON mRNA in the brain of an E18 mouse by in situ hybridization.

Initial studies using in situ hybridization demonstrated that, at E12.5, DRG11 and DRAGON expression overlaps (FIG. 5a). In the DRG most neurons express both DRG11 and DRAGON; in the spinal cord DRG11 and DRAGON are expressed in the same medial region adjacent to the ventricular zone (FIG. 5a). A pull down assay was carried out to confirm interaction of DRG11 with the 363 bp promoter fragment of DRAGON obtained with the GBS screening. The promoter fragment was pulled down by a GST-DRG11-DBD fusion protein but not GST (FIG. 5c). Finally, DRAGON mRNA expression in DRG11 null mutant embryonic mice was examined. DRAGON expression in the spinal cord and DRG were significantly reduced in DRG11$^{-/-}$ mice compared to wildtype littermates (FIG. 5d). DRAGON mRNA is also expressed in embryonic and adult mouse DRGs, spinal cord, and brain, with little or no expression in the liver and kidney, and low levels in the heart (FIGS. 5e, 6, and 7).

Figures 8A, 8B, 8C:
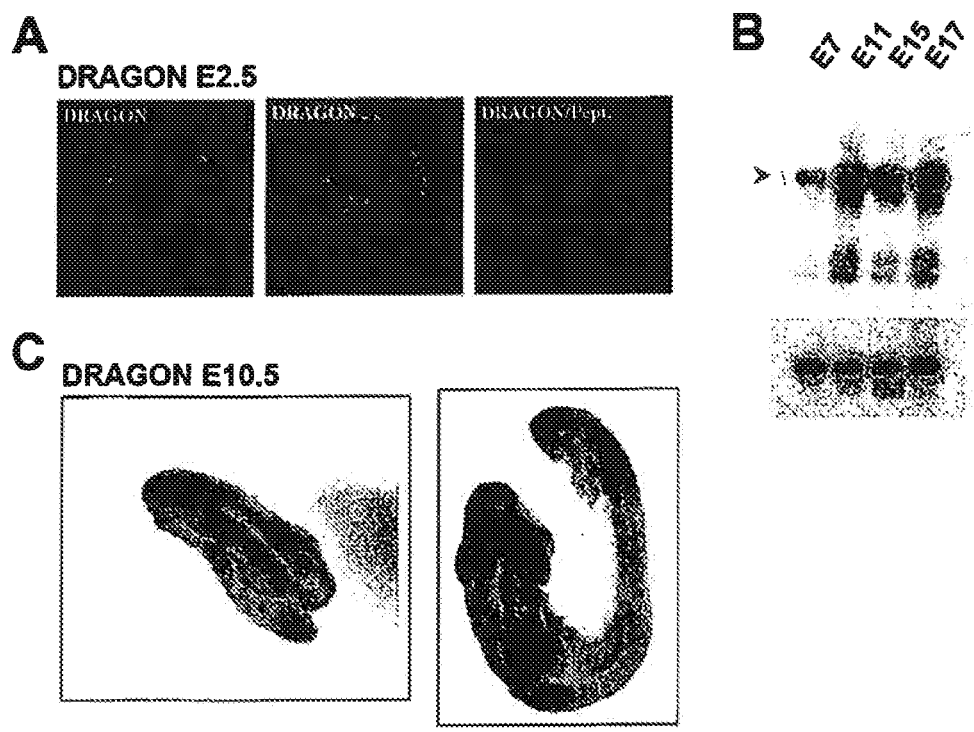
FIG. 8A is a series of photomicrographs showing the localization of DRAGON during mouse embryogenesis at E2.5, visualized using an anti-DRAGON antibody and FITC fluorescence (left panel). Nuclei of the cells are visualized by CY3 fluorescence (PI; middle panel). Pre-adsorption of the DRAGON antibody with the peptide antigen was used as a negative control (Pept.; right panel).
FIG. 8B is a Northern blot showing the developmental profile of DRAGON expression in the mouse embryo. Cyclophilin mRNA levels were measured as a loading control (lower panel).
FIG. 8C are photomicrographs of whole embryo (E10.5) DRAGON immunohistochemistry.
Figures 8D, 8E:
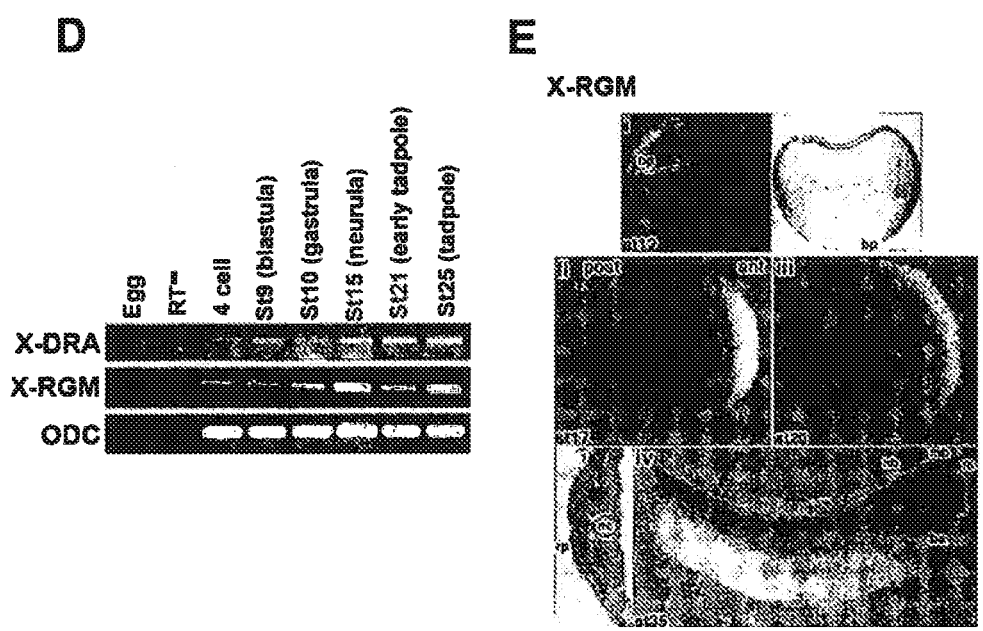
FIG. 8D is a Northern blot of embryonic Xenopus DRAGON expression, using RT-PCR. ODC levels were used as an internal control.
FIG. 8E is a series of photomicrographs of whole mounted Xenopus embryos following in situ hybridization of expression of RGMa at stages 12 (i), 17 (ii), 20 (iii), and 35 (iv). Transverse sections through stained st12 and st20 embryos are also shown. (bp=balstopore; post=posterior; ant=anterior; nc=notochord; rp=roof plate; hb=hindbrain; mb=midbrain; fb=forebrain; ba=brachial arches).

DRAGON is expressed throughout vertebrate embryonic development (FIG. 5f) but primarily in the developing peripheral and central nervous systems. It's expression begins in early embryogenesis, in ES cells and E2.5 embryos and in oocytes at the germinal vesicle stage indicates that DRAGON expression is maternal (FIG. 8). Post-implantation mouse embryos (>E7) also express DRAGON protein and mRNA (FIGS. 8A and 8B). In E10.5 mouse embryos, DRAGON expression is along the neural tube, in the dorsal root ganglia, and, at maximum levels, in the tips of the neural folds and the tail bud (FIG. 8C). The pattern of DRAGON expression is similar to that of the BMP receptors, particularly the type I receptors ALK3 and ALK6, and the type II receptor BMPRII (Dewulf et al., 1995; Soderstrom et al., 1996). The expression of the *Xenopus* orthologs of DRAGON and mRGM at different developmental stages of *Xenopus leavis* embryos shows a dorsal (e.g. roofplate) gradient-like pattern (FIGS. 8D and 8E) and is also consistent with that of members of the TGF-β superfamily signaling pathway. These observations prompted us to investigate if DRAGON contributes to or modulates TGF-β superfamily signal transduction.

DRAGON Enhances BMP but not TGF-fi Intracellular Signaling

In order to investigate the effect of DRAGON on BMP signaling, a BMP-responsive luciferase reporter construct (BRE-Luc; Korchynskyi et al., 2002) was transfected, with or without a DRAGON expression construct, into LLC-PK1 (kidney epithelial cell line), HepG2, or 10T1/2 cells. Stimulation of the LLC-PK1 cells with BMP2 (50 ng/ml) caused a 4-fold increase in luciferase activity compared to control (FIG. 9A). This effect was mimicked by the co-transfection and expression of DRAGON, in the absence of exogenous BMP-2.

The stimulatory effect of DRAGON was not observed for all TGF-β ligands. LLC-PK1 cells were transfected with a TGF-β-responsive luciferase reporter construct ((CAGA)12-MLP-Luc; Dennler et al., 1998). These cells demonstrated a 12-fold increase in luciferase activity upon stimulation with 10 ng/ml TGF-β1, but no effect was observed following the co-transfection of DRAGON without TGF-β1 stimulation (FIG. 9A). Expression of 'DRAGON in transfected LLC-PK1 cells was confirmed by Western blot (data not shown).

To assess whether DRAGON expression dynamically regulates BMP signaling, LLC-PK1 cells were co-transfected with the BRE-luc reporter construct and increasing amounts of a DRAGON cDNA expression vector (2 and 20 ng). Enhanced luciferase expression was measured following BMP2 stimulation of DRAGON-expressing cells compared to the untransfected controls. Specifically, 50 ng/ml BMP2 induced a 14-fold increase in luciferase activity in DRAGON co-transfected cells compared to a 6-fold increase in the absence of DRAGON (FIG. 9B).

In order to confirm the effect of DRAGON on BMP-dependent signaling, 10T1/2 and HepG2 cells were transfected with a luciferase reporter gene under the control of another BMP-responsive promoter, Msx2-Luc. Confirming the previous studies, co-expression of DRAGON induced a 4-fold increase in BMP-dependent signaling in the absence of an exogenously added BMP ligand (FIG. 9B). BMP signaling in DRAGON-expressing cells was increased 8-fold at a very low dose (50 pM) of exogenous BMP2 (FIG. 9B).

Results from the 10T1/2 and HepG2 cells also confirm that the effect of DRAGON is specific to BMP signaling. Co-transfection of DRAGON with luciferase constructs responsive to TGF-β, Activin, or GDF8-induced signaling did not induce reporter gene expression, alone or in a ligand-dependent manner (FIG. 9C and data not shown). These data demonstrate that DRAGON expression activates BMP but not TGF-β signaling and that DRAGON enhances ligand-mediated BMP signaling.

DRAGON Binds to BMP Type I and BMP Type H Receptors

The previous studies demonstrate that DRAGON enhances BMP-mediated signaling, but do not give an indication whether the effect occurs through a direct modulation of BMP receptors or thought an independent receptor pathway that converges on the Smad. To explore these possibilities we investigated first whether DRAGON interacts directly with BMP receptors, second, the mechanism by which DRAGON activates BMP signaling, and third, whether DRAGON binds to members of the TGF-β superfamily.

Figures 10A, 10B, 10C, 10D:
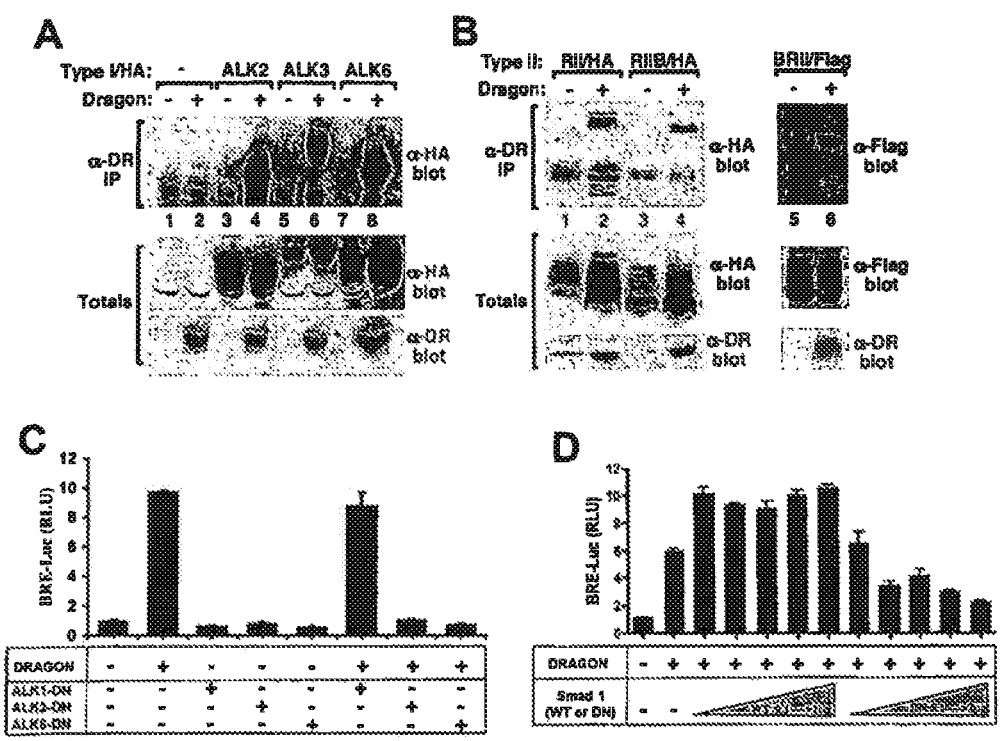
FIG. 10A is a series of Western blots following an anti-DRAGON immunoprecipitation, using an anti-HA antibody, that demonstrates that DRAGON physically binds to ALK2 (A2), ALK3 (A3), and ALK6 (A6).
FIG. 10B is a series of Western blots following an anti-DRAGON immunoprecipitation, using an anti-HA antibody, that demonstrates that DRAGON physically binds to BMPRIIA (RII), and BMPRIIB (RIIB)
FIG. 10C is a bar graph showing that DRAGON-induced signaling is mediated through ALK3 and ALK6. ALK3-DN, ALK6-DN, but not ALK1-DN expression reduces DRAGON-induced signaling.
FIG. 10D is a bar graph showing that DRAGON-induced signaling is mediated through a Smad1 dependent mechanism. BRE-Luc reporter gene activation is significantly reduced in the presence of increasing concentrations of a dominant negative Smad1.

To test whether DRAGON interacts with BMP receptors, DRAGON was co-transfected with type I or type II BMP receptors. The physical interaction between the receptors and DRAGON was studied by immunoprecipitation using an anti-DRAGON antibody and probing with anti-ALK receptor antibodies tagged with a detectable HA. Immunoprecipitates from doubly transfected HEK 293 cells demonstrate that DRAGON interacts with ALK2, ALK3 and ALK6 (FIG. 10A). BMPRIIA and BMPRIIB also interact with DRAGON when coexpressed in HEK cells (FIG. 10A). These data indicate that DRAGON has the ability to physically interact with both BMP type I and type II receptors.

Dominant negative isoforms of the BMP type I receptor ALK6 and the intracellular effector Smad1 were each cotransfected with DRAGON to confirm that DRAGON's action occurs via the classical BMP signaling pathway (FIGS. 10B and 10C). The dominant negative ALK6-KR mutant is deficient in kinase activity and unable to phosphorylate the Smads (Faber et al., 2002). Co-expression of DRAGON with ALK6-KR abolished the DRAGON-mediated induction of BMP-luciferase activity (FIG. 8B). Similarly, co-expression of DRAGON with a Smad1 dominant negative mutant that lacks the carboxy-terminal phospho-acceptor domain (Shi et al., 2003) reduced dose dependently DRAGON-induced signaling to baseline levels, whereas co-expression of wild type Smad1 enhanced this signaling (FIG. 10C). These data indicate that DRAGON binds to BMP receptors and utilizes the Smad effectors to activate and enhance the BMP-signal transduction pathway.

DRAGON Enhances BMP Signaling in a Ligand-Dependent Manner

The expression of DRAGON, in the absence of a BMP ligand, leads to activation of BMP signaling (FIG. 9A). Likewise, DRAGON enhances BMP-dependent gene expression in the presence of BMP ligand. To further study the contribution of DRAGON to the BMP signaling cascade, DRAGON-activated signaling was measured in the presence of the well documented BMP antagonist noggin (Balemans et al., Dev. Biol. 250: 231-250, 2002). When added to HepG2 cells, noggin inhibited DRAGON or BMP2 induced activation of the BRE-Luc reporter gene construct in a dose dependent manner (FIG. 11A), but had no effect on activin stimulation of the CAGA reporter construct (data not shown). Furthermore, equal doses of follistatin, sufficient to block activin activity, had no significant effect on DRAGON or BMP2 activity in the BRE-Luc-expressing cells (FIG. 11B), demonstrating that the noggin effect on DRAGON signaling is specific. These results also suggest a role for endogenous BMP type ligand(s) in this system.

Figures 11A, 11B, 11C, 11D:
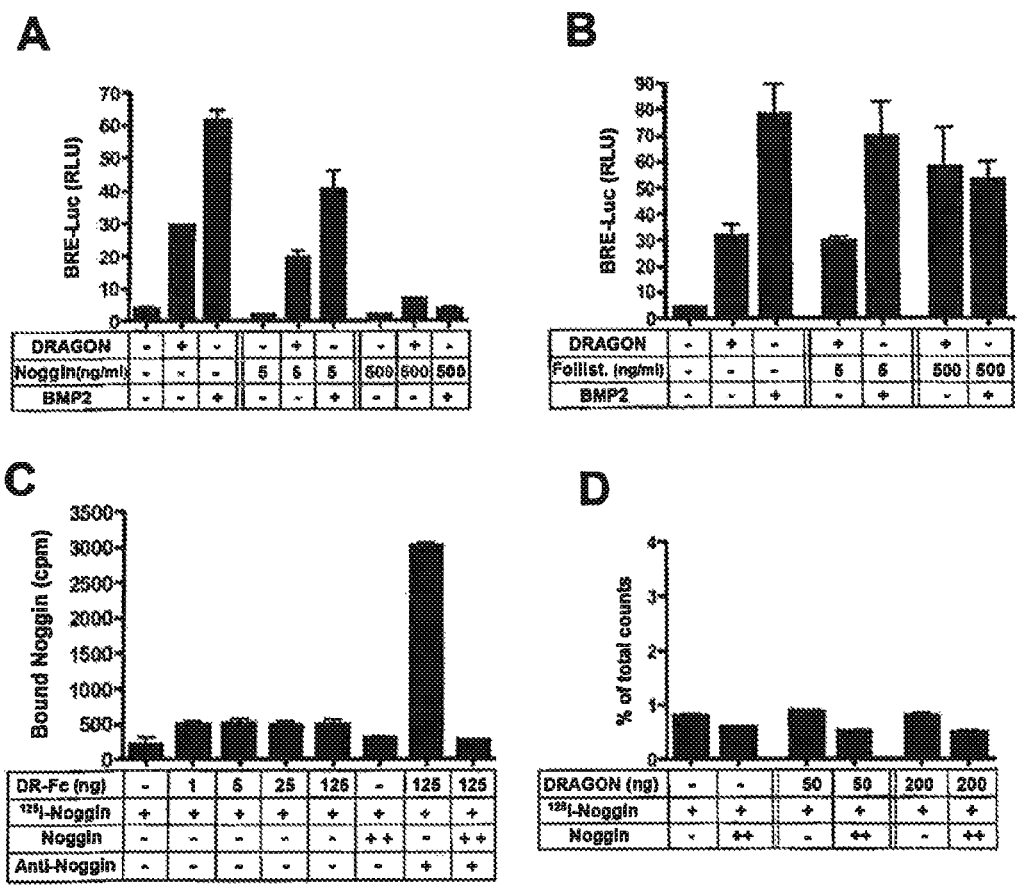
FIG. 11A is a bar graph demonstrating that noggin, a BMP antagonist, inhibits both BMP-2-dependent and DRAGON dependent BRE-Luc reporter gene activation.
FIG. 11B is a bar graph demonstrating that follistatin, an activin antagonist, has no effect on BMP-2-dependent and DRAGON dependent BRE-Luc reporter gene activation.
FIGS. 11C and 11D are bar graphs demonstrating the an anti-DRAGON-Fc antibody does not detect binding between DRAGON and [$^{125}$I]-noggin.

Noggin is known to exert its inhibitory effect on BMP signaling through a direct binding and neutralization of the BMP ligands. The possibility of a direct interaction between noggin and DRAGON was assessed in order to evaluate noggin's effect on DRAGON-enhanced signaling. Increasing amounts of the purified soluble fusion protein DRAGON-Fc (Samad et al., 2004) were incubated with a fixed amount of radio-labeled [$^{125}$I]-noggin followed by co-precipitation with protein A. No significant interaction between [$^{125}$I]-noggin and the DRAGON-Fc could be detected when compared to no-protein controls (FIG. 11C). An anti-noggin antibody, as a positive control, detected substantial quantities of [$^{125}$I]-noggin, demonstrating that the labeled noggin was intact (FIG. 11C). These results were confirmed in a similar assay using COS-7 cells in which no significant association between the two molecules was observed (FIG. 11D). These observations prove that noggin does not directly bind to DRAGON and that the DRAGON-mediated activation of BMP signaling is ligand dependent.

DRAGON Binds to BMP but not TGF-β Ligands

Figures 12A, 12B:
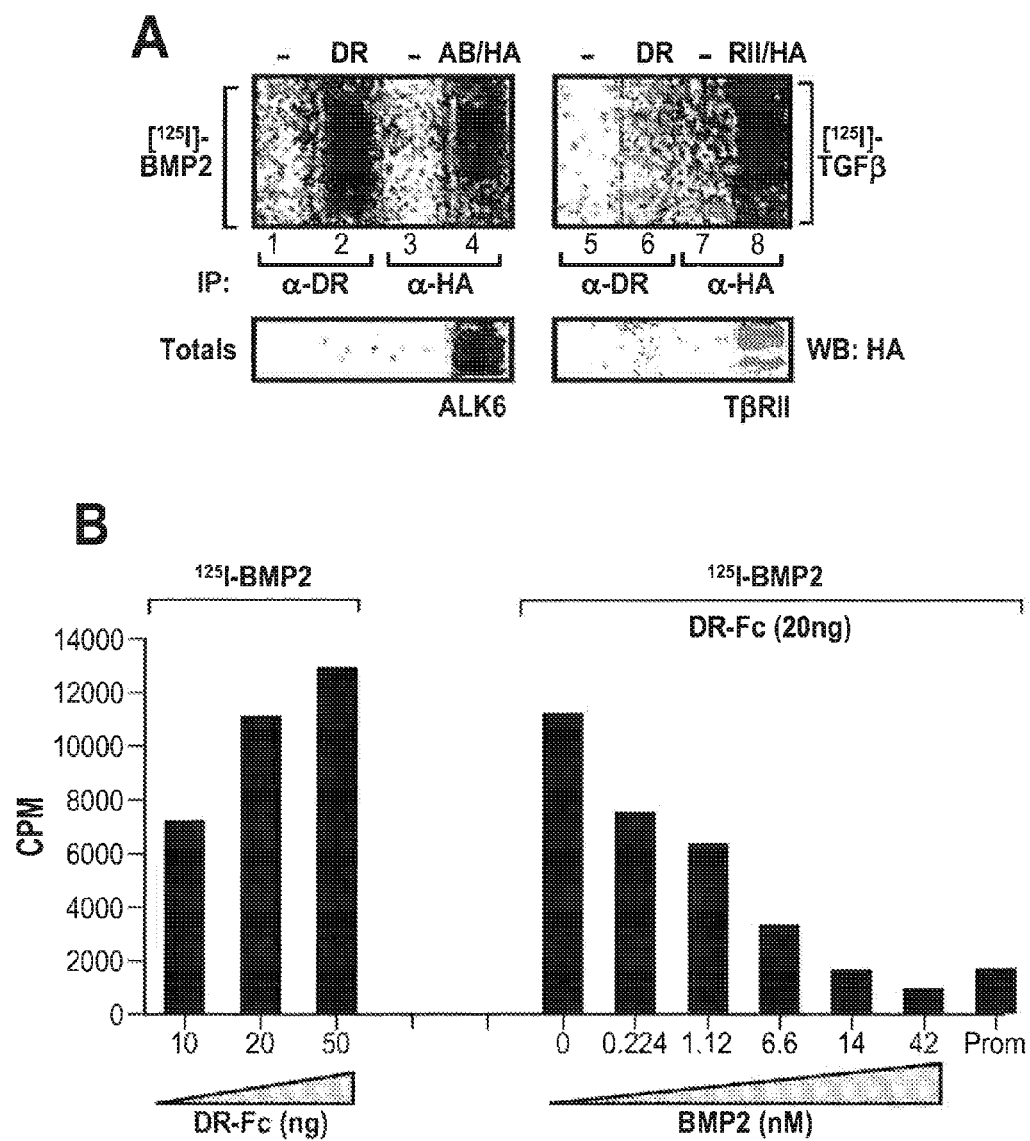
FIG. 12A is a series of phosphoimages demonstrating that DRAGON interacts directly with BMP2 and BMP4. COS-1 cells were transiently transfected with DRAGON, HA-tagged ALK6 or TβRII and affinity-labeled with [$^{125}$I]-BMP2 (left) or [$_{125}$I]-TGFβ (right) and immunoprecipitated using the indicated antibodies.
FIG. 12B is a bar graph quantifying the amount of DRAGON-Fc binding to [$^{125}$I]-BMP2. The DRAGON Fc/[$^{125}$I]-BMP2 complexes were captured on protein A coated plates and bound radioactivity was measured.

HEK 293 cells were transiently transfected with the DRAGON expression construct, and the binding of either [$^{125}$I]-BMP2 or [$^{125}$I]-TGF-β to the transfected cells was determined. As shown in FIG. 12A, [$^{125}$I]-BMP2 affinity-labeled the DRAGON-expressing cells, but [$^{125}$I]-TGF-β did not. Hemaglutinin-tagged ALK6 (a BMP type I receptor) and TGF-β receptor type II (TβRII) expression constructs were used as positive controls for [$^{125}$I]-BMP2 or [$^{125}$I]-TGF-β binding, respectively. Immunoprecipitation using an anti-HA antibody confirmed binding of BMP2 and TGF-β to ALK6 and TβRII respectively (FIG. 12A).

Figures 12C, 12D, 12E:
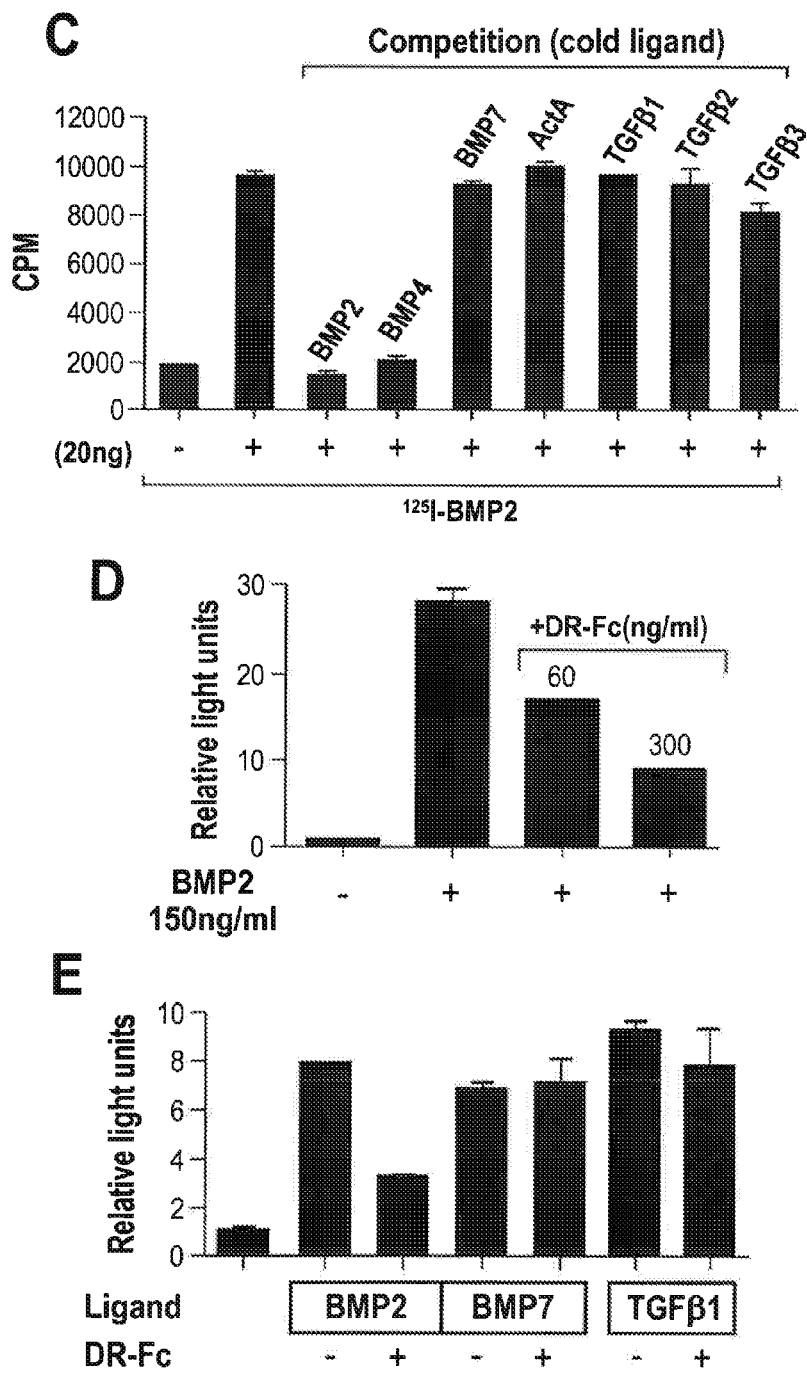
FIG. 12C is a bar graph quantifying the amount of DRAGON-Fc binding to [$^{125}$I]-BMP2 in the presence bf various TGF-β family receptors. DRAGON-Fc binding to [$^{125}$I]-BMP2 is effectively displaced by unlabeled BMP-2 and BMP-4, but not BMP-7, Activin A, TGF-β1, TGF-β2, or TGF-β3.
FIG. 12D is a bar graph showing the relative intensity of luciferase expression in LLC-PK1 cells transfected with the BRE-Luc reporter construct. Soluble DRAGON (DRAGON-Fc) reduces the BMP2-mediated signaling.
FIG. 12E is a bar graph showing the relative intensity of luciferase expression in LLC-PK1 cells transfected with the BRE-Luc reporter construct. Soluble DRAGON (DRAGON-Fc) reduces the BMP2-mediated signaling, but not BMP7- or TGF-β1-mediated signaling.

The binding affinity of the soluble DRAGON-Fc fusion protein (Samad et al., 2004; Del Re et al., 2004) to [$^{125}$I]-BMP2 was studied in the presence of increasing amounts of unlabeled BMP2 (FIG. 12B). DRAGON-Fc binds [$^{125}$I]-BMP2 with high affinity and an apparent dissociation rate constant (Kd) of 1.5 nM (FIG. 12B). The binding of [$^{125}$I]-BMP2 to DRAGON was inhibited by the addition of excess unlabeled BMP2 as well as unlabeled BMP4 (4 nM) (FIG. 12C). However, the BMP2-DRAGON interaction was not disrupted by 4 nM BMP7, or 1 nM Activin A, TGF-β1, TGF-β2, or TGF-β3 (FIG. 12C).

To further confirm the ability of DRAGON to bind to BMP2 and BMP4, we tested whether increasing amounts of exogenous DRAGON-Fc can competitively inhibit BMP-mediated signaling. Pretreatment of HEK 293 cells with increasing doses of DRAGON-Fc (60 and 300 ng/ml) leads, in a dose dependent manner, to a reduction of BMP2 mediated activation of BRE-Luc promoter as assessed by luciferase activity (FIG. 12D). However, as predicted from the binding experiments, DRAGON-Fc was not able to compete and inhibit BMP7 or TGF-β1 signaling (CAGA-Luc promoter was used to assess TGF-β signaling; FIG. 12E).

These data indicate that DRAGON interacts with members of the BMP ligand family and with BMP receptors to enhance intracellular BMP signaling. Because DRAGON binds both the BMP ligands and receptors, it is therefore a component of the BMP receptor complex.

DRAGON Enhances BMP Signaling when Expressed Only on the Cell Surface

Figures 13A, 13B:
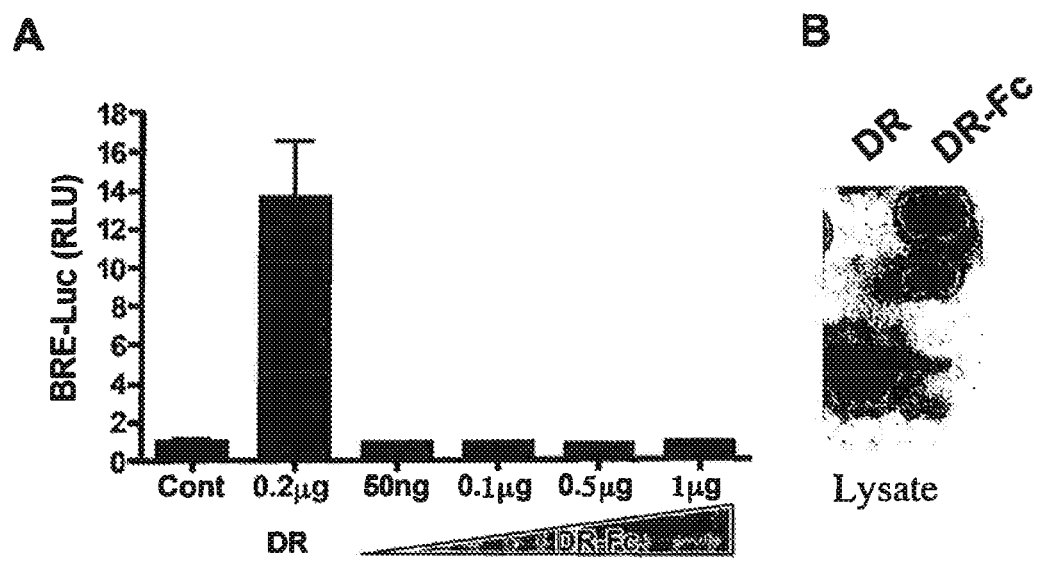
FIG. 13A is a bar graph demonstrating that membrane-bound DRAGON, but not soluble DRAGON, is capable of activating BRE-Luc reporter gene expression.
FIG. 13B is a western blot using an anti-DRAGON antibody to confirm the presence of both the membrane-bound and soluble form of DRAGON in the previous experiment.
Figure 14:
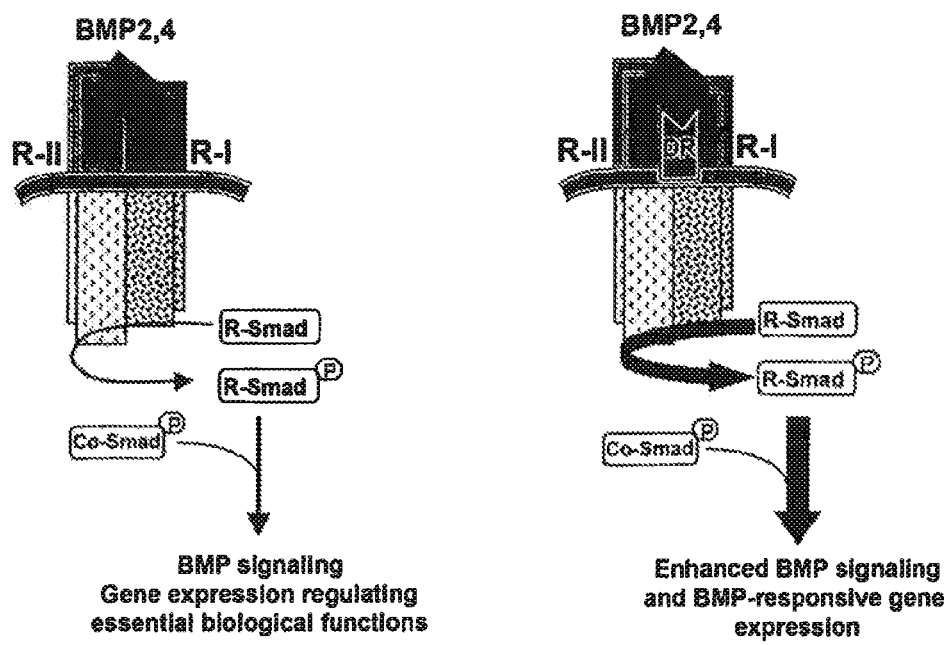
FIG. 14 is a schematic diagram of the interaction of DRAGON with the BMP signaling pathway.

As described above, DRAGON is normally a membrane bound protein. To test whether membrane anchoring is essential to its effect on BMP signaling, a DRAGON-Fc construct was created in which the C-terminal GPI anchor was deleted and replaced by the human Fc domain. When expressed, the DRAGON-Fc was secreted into the culture medium, whereas wild-type DRAGON is directed (at least in part) to the plasma membrane. The DRAGON-Fc, when co-transfected with the BRE-Luc reporter construct, failed to enhance BMP signaling (FIG. 13A). The expression of both DRAGON and DRAGON-Fc was confirmed by Western blot (FIG. 13B). Thus, these results demonstrate that, in order for DRAGON to function as a cell surface co-receptor for BMPs, it must be inserted into the plasma membrane. FIG. 14 conceptually outlines the location and function of DRAGON as a BMP co-receptor.

DRAGON Enhances BMP Signaling in Xenopus Embryos

Genetic evidence has shown that members of the BMP ligand family play pivotal roles in the gastrulation of mouse embryo, a process that lays down the future body plan (Lu et al. 2001). BMPs regulate the proliferation, survival, and patterning of the epiblast; the induction of primordial germ cell precursors; and formation of the mesoderm (Mishina et al. 1995; Winnier et al. 1995; Lawson et al. 1999). Mutant embryos deficient in BMP4 or BMPRIA are blocked at the beginning of gastrulation, and fail to form mesoderm (Ying and Zhao 2001). BMPs were also shown to be involved in endoderm formation (Kondoh et al., 2003). In order to investigate the contribution of DRAGON expression to BMP signaling and function in vivo, mDRAGON was expressed in Xenopus embryos and the expression of inesodermal and endodermal markers was assessed.

Figure 15:
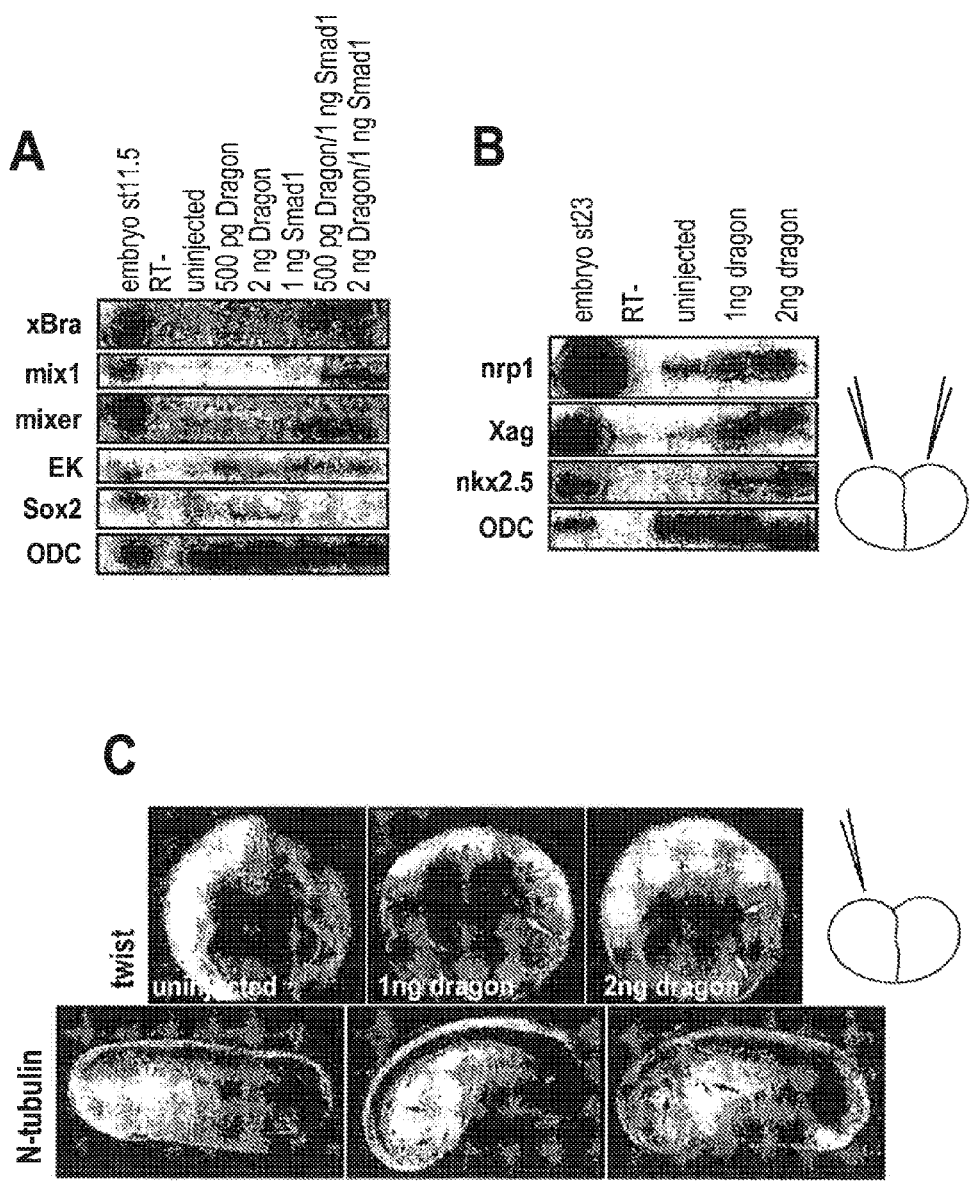
FIG. 15A is a series of RT-PCR Northern blots from *Xenopus* embryos microinjected with murine DRAGON mRNA.
FIG. 15B is a series of RT-PCR Northern blots from animal cap explants microinjected with DRAGON mRNA.
FIG. 15C is a series photomicrographs of whole mounted *Xenopus* embryos following injection of DRAGON mRNA into the animal pole of 1 out of 2 cells at the 2-cell stage. DRAGON induces inhibits twist RNA (a neural crest marker) and induces ectopic N-tubulin expression (a neural marker).

Mouse DRAGON mRNA was injected into Xenopus embryos at gastrula stages to investigate whether DRAGON alters BMP signaling, by measuring its interaction with Smad1. DRAGON co-expression with Smad1 led to induction of mRNA for the pan-mesodermal marker Xbra and two endodermal markers mix 1 and mixer mRNAs (FIG. 15A). At the doses used, DRAGON or Smad1 alone did not significantly induce expression of these markers (FIG. 15A). The reduction in the activity threshold of Smad1 by DRAGON is compatible with an enhancement in BMP signaling, as detected in the cell based assays.

DRAGON Regulates Neural Induction in Xenopus Embryos

In order to determine whether DRAGON affects cell differentiation and early embryonic development, DRAGON was injected into one cell at the animal pole of Xenopus embryos at the 2-cell stage. Embryos were allowed to develop until early tadpole stages. By injecting one out of two cells, a control side and an experimental side are present in the same embryo. A variety of markers were measured, including twist (expressed in anterior neural crest cells) and N-tubulin (a general neuronal differentiation marker), to determine whether DRAGON affects early neural patterning. Ectopic DRAGON caused a decrease in neural crest derivatives, as shown by loss of twist expression (FIG. 15C, top panels) and an increase in neuronal markers (FIG. 15C, bottom panels).

In ectodermal explant assays, DRAGON induced anterior neural markers (FIG. 15B). Nrp1 is a pan-neural marker, Otx2 is expressed within the forebrain and midbrain regions, and XAG is expressed in the cement gland (the most anterior structure in the tadpole). In addition, DRAGON induced nkx2.5, an early marker of cardiac development.

DRAGON Promotes Neuronal Survival

The anti-DRAGON polyclonal antibody was added to neonatal rat DRG neuronal cultures to investigate the contribution of DRAGON to neuronal survival. Neuronal cultures were treated with 0.25% anti-DRAGON serum, 0.25% pre-immune serum (negative control), or vehicle. A statistically significant 20-25% increase in neuronal cell death was measured following anti-DRAGON treatment compared to controls.

|  | 0.25% anti-DRAGON serum | 0.25% pre-immune serum | Vehicle Control (no serum) |
| --- | --- | --- | --- |
| % viable neurons (mean) | 41.8% | 55.3% | 51.8% |
| Standard Error (S.E.) | 1.7% | 2.3% | 2.5% |
| Number of isolated DRG cultures (n) | 12 | 12 | 11 |

Localization and Action of DRAGON (Repulsive Guidance Molecule b) in the Reproductive Axis The importance of DRAGON in reproduction is indicated by its pattern of expression in reproductive tissues. Mammalian reproduction is regulated by endocrine hormones such as pituitary FSH and LH as well as by locally produced growth factors, including TGF-β superfamily members activin, inhibin, and bone morphogenetic proteins (BMPs) (Welt et al., *Exp Biol Med (Maywood)* 227:724-752, 2002). BMPs were originally identified by their ability to induce bone and cartilage formation (Wozney et al., *Science* 242:1528-1534, 1988). However, numerous studies have revealed that BMPs have a wide variety of effects on many cell types, including monocytes and epithelial, mesenchymal, and neuronal cells, and play pivotal roles in cytodifferentiation, morphogenesis, and organogenesis (Kawabata et al., *Cytokine Growth Factor Rev* 9:49-61, 1998). Members of the TGF-superfamily, including BMPs, transduce their signals through binding to type I and II serine/threonine kinase receptors. BMP signaling is mediated intracellularly by the phosphorylation of receptor-activated Smads (R-Smads) 1, 5, and 8. Activated R-Smads complex with the common partner Smad 4 and translocate to the nucleus where they initiate BMP-stimulated alterations in target gene expression. Signaling of TGF-superfamily members including BMPs is also modulated by soluble extracellular proteins such as noggin, chordin, and gremlin. In addition, membrane-associated proteins, including betaglycan (TGF-type III receptor), endoglin, and crypto are also critical for assisting with ligand binding to receptor or for altering receptor specificity (reviewed in Massague et al., *Genes Dev* 14:627-644, 2000; Shi et al., *Cell* 113:685-700, 2003; Derynck, R. Zhang Y E, *Nature* 425:577-584, 2003).

The mRNAs encoding BMP2, 3, 3b, 4, 6, 7, and 15 have been identified in mammalian ovaries. Moreover, BMP receptors BMPRIA, IB, and II are widely expressed in the ovary, with the strongest expression in the granulosa cells and oocytes of developing follicles in normally cycling rats (Shimasaki et al., *Proc Natl Acad Sci USA* 96:7282-7287, 1999; Shimasaki et al., *Endocr Rev* 25:72-101, 2004). BMPs and their receptors are also expressed in uterine stroma and glandular epithelium (Erickson G F et al., *J Endocrinol* 182:203-217, 2004). In males, BMP2, BMP4, and BMP8A and BMP8B are expressed in germ cells, and BMP4, BMP7, and BMP8A are expressed in the epididymis (reviewed in Shimasaki et al., *Endocr Rev* 25:72-101, 2004). Moreover, mice deficient in BMP4, BMP8A, or BMP8B show germ cell degeneration in the testis and/or epithelial cell degeneration in the epididymis (Hu et al., *Dev Biol* 276:158-171, 2004; Zhao et al., *Genes Dev* 10:1657-1669, 1996; Zhao et al., *Development* 125:1103-1112, 1998). Together, these results suggest that BMPs may play important roles in regulating reproduction.

DRAGON was identified through a genomic screening strategy for genes regulated by DRG11, a homeobox transcription factor that is expressed in embryonic dorsal root ganglion (DRG) (Samad et al., *J Neurosci* 24:2027-2036 2004). Independently, this gene was also cloned as RGMb, one of three mouse homologues of the chicken repulsive guidance molecule (RGM) (Schmidtmer et al., *Gene Expr Patterns* 4:105-110 2004). The DRAGON gene encodes a 436-amino-acid glycosylphosphatidylinositol (GPI)-anchored protein, suggesting it may be associated with lipid rafts within the plasma membrane. Indeed, adhesion of DRG neurons to HEK293 cells was increased after transfection of HEK293 cells with DRAGON cDNA (Samad et al., *J Neurosci* 24:2027-2036 2004). DRAGON is expressed in a number of neural tissues including embryonic and adult mouse DRGs, spinal cord, and brain (Samad et al., *J Neurosci* 24:2027-2036 2004, Niederkofler et al., *J Neurosci* 24:808-818 2004; Oldekamp et al., *Gene Expr Patterns* 4:283-288; 2004). Interestingly, DRAGON is also involved in BMP signaling because 1) injection of DRAGON mRNA into *Xenopus* embryos induced expression of a number of BMP-regulated genes, 2) DRAGON binds directly to BMP2, BMP4, and BMP receptors, and 3) transfection of DRAGON cDNA into BMP-responsive cells enhances transcription of a BMP-responsive reporter (Samad et al., *J Biol Chem* 280:14122-14129, 2005). These observations indicate that DRAGON acts as a BMP coreceptor that regulates cellular response to BMP signals.

To understand the potential role of DRAGON in BMP signaling within the reproductive tissues, DRAGON expression in murine reproductive tissues and cell lines was examined. DRAGON is expressed and dynamically regulated in gonadal germ cells and in epithelial cells of the reproductive tract including epididymis and uterus. DRAGON is also expressed in the pituitary. As predicted from its being anchored to the cell membrane by a GPI anchor, DRAGON is indeed localized in lipid rafts where it enhances BMP2 and -4 signaling. The overlapping expression and function of BMPs in the reproductive system indicates that DRAGON plays an important role in reproduction through enhancement of BMP signaling.

Expression of DRAGON mRNA in Reproductive Organs

Figure 25:
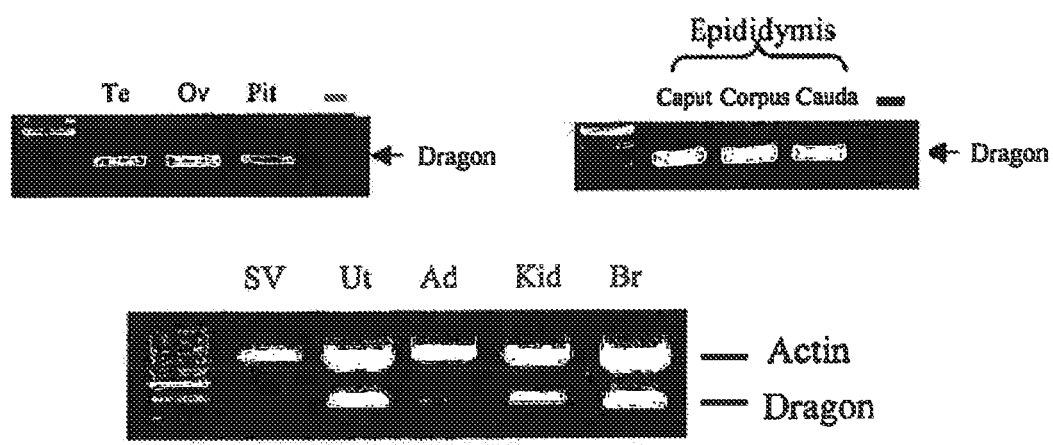
FIG. 25 is a set of images of gels showing DRAGON mRNA expression in mouse tissues. RNA extracted from various mouse tissues was examined for DRAGON mRNA expression by RT-PCR. In tissues where DRAGON expression was low, β-actin was used as a control for cDNA quality. DRAGON expression was strongly detected in testis (Te), ovary (Ov), pituitary (Pit), epididymis, uterus (Ut), kidney (Kid), and brain (Br). Weaker DRAGON signals were detected in seminal vesicles (SV) and adrenal (Ad).

DRAGON expression in mouse reproductive tract tissues was examined by RT-PCR (FIG. 25). DRAGON mRNA was detected in the testis, epididymis, and seminal vesicles in males and in the ovary, uterus, and pituitary in females.

Cellular Localization of DRAGON in the Testis and Epididymis

Immunohistochemical analyses of d1 and 3 mouse testes showed that DRAGON was localized to gonocytes both in the center and at the basement membrane of seminiferous tubules (FIGS. 26A, a and b). In testes from d9 mice, spermatogonia at the basement membrane were positive for DRAGON expression (FIG. 26A, c). However, DRAGON staining in spermatogonia became much weaker in testes from 21 d-old mice (FIG. 26A, d). Interestingly, a few gonocytes, which remain in the central region of the tubules from d21 testes, were strongly stained with DRAGON (FIG. 26A, d). Some interstitial cells showed weak staining in d1 testes (FIG. 26A, a), but no staining was observed in interstitial cells in older testes. In adult (d60) testis, DRAGON was expressed in spermatocytes and round spermatids, whereas spermatogonia and Sertoli cells did not appear to express DRAGON (FIGS. 26A, e and f). The staining in gonocytes, spermatogonia, and spermatocytes was completely abolished when the antiserum was preincubated with the competing immunizing peptide, demonstrating the specificity of the antiserum (FIG. 26A, g and h). DRAGON expression in spermatocytes and round spermatids from adult testes was confirmed by in situ hybridization (FIG. 26C).

Spermatocytes of d21 testes were not stained with DRAGON antibody, whereas those cells of adult testes were strongly stained (FIG. 26A, d and e). Interestingly, DRAGON was highly expressed in spermatocytes of testes collected after 2 d of PMSG administration to 19 d-old mice (FIG. 26B), suggesting that DRAGON expression levels are hormonally regulated.

In d3 epididymis, DRAGON protein was found on both the apical and basal sides of epithelial cells with staining in the apical side stronger compared with the basal side. DRAGON staining was stronger in caudal than in caput or corpus epididymis of 3 d-old mice (FIG. 26D, a-c). In contrast, DRAGON expression was primarily localized to the apical side of epithelial cells of adult epididymis, and it appeared that DRAGON was more highly expressed in caput or corpus, compared with caudal epididymis (FIG. 26D, d-f). These results suggest that DRAGON may be involved in regulation of spermatogenesis and epididymal epithelial function.

Cellular Localization of DRAGON in the Ovary and Uterus

Within the adult mouse ovary, DRAGON protein was detected exclusively within oocytes (FIG. 27A, a, b, and d) and was more intense in oocytes from secondary follicles compared with antral follicles (FIG. 27A, a). In contrast, no DRAGON staining was found in oocytes of primordial (FIG. 27A, b) or primary (FIG. 27A, c) follicles, nor in somatic cells of any follicles (FIG. 27A). In atretic follicles, oocytes showed weak DRAGON staining (FIG. 27A, d). There was no staining of the ovarian surface epithelium (FIG. 27A, b-d). Oocyte staining was completely blocked by preincubating antiserum with competing immunizing peptide (FIG. 27A, e). In d9 ovaries, DRAGON staining was detected only in the oocytes of secondary follicles but not in the primordial or primary follicles (FIG. 27A, f). PMSG treatment had no effect on DRAGON staining in oocytes (data not shown).

Consistent with immunostaining, DRAGON mRNA, as detected by in situ hybridization, was stronger in oocytes from secondary follicles (FIG. 27B, arrows) compared with antral (FIG. 27B, arrowheads) follicles and was undetectable in oocytes from primary follicles (FIG. 27B, triangle). DRAGON mRNA was not detectable in ovarian somatic cells. These results suggest that DRAGON regulates the development of oocytes and follicles by influencing the interaction between the oocyte and granulosa cells.

In the uterus, DRAGON protein was expressed in luminal and glandular epithelial cells of the endometrium (FIG. 27C, a and b). Weak staining was also found in circular muscle (FIG. 27C, a). Localization of DRAGON in the luminal and glandular epithelial cells indicate that DRAGON may also be required for normal endometrial function.

Cellular Localization of DRAGON in the Pituitary

Figure 29A:
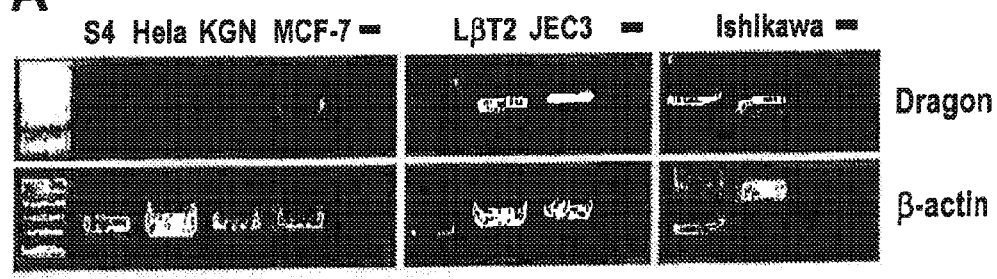
FIGS. 29A-29C are images showing expression of DRAGON in cell lines derived from reproductive tissues and localization of DRAGON into lipid rafts.

Sporadic staining was observed in both the anterior and posterior lobes of the pituitary, whereas no staining was detected in the intermediate lobe (FIG. 28A). BMPs and their receptors are expressed in mouse pituitary gonadotropes and in the LβT2 gonadotrope cell line (Paez-Pereda et al., *Proc Natl Acad Sci USA* 100:1034-1039, 2003; Otsuka et al., *J Biol Chem* 276:11387-11392, 2001), and BMPs can stimulate FSH biosynthesis (Huang et al., *Endocrinology* 142:2275-2283, 2001). To examine whether FSH-expressing gonadotropes also express DRAGON, frozen pituitary sections were dual labeled with DRAGON and FSH antibodies. FSH-expressing cells indeed overlapped extensively, albeit not completely, with DRAGON-expressing cells (FIG. 28B). Interestingly, LβT2 cells also express DRAGON (FIG. 29A). DRAGON may therefore influence BMP-mediated FSH biosynthesis in vivo and in vitro.

DRAGON Expression in Cell Lines of the Reproductive Axis

Screening cell lines originating from reproductive organs (FIG. 29A) indicated that DRAGON was expressed in Hela (cervical carcinoma), MCF-7 (breast carcinoma), LβT2 (pituitary carcinoma), JEG3 (placenta carcinoma), and Ishikawa (endometrium adenocarcinoma) cells. In contrast, DRAGON mRNA was undetectable in S4 spermatogonial cells (Feng et al., *Science* 297:392-395, 2002) or KGN granulosa tumor cells (Nishi et al., *Endocrinology* 142:437-445, 2001).

Lipid Raft Localization of DRAGON

Figure 29B:
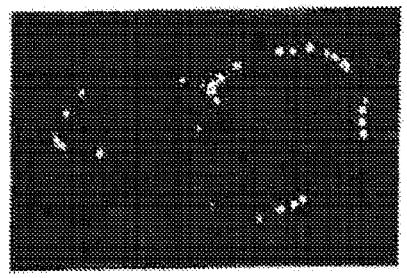
Figure 29C:
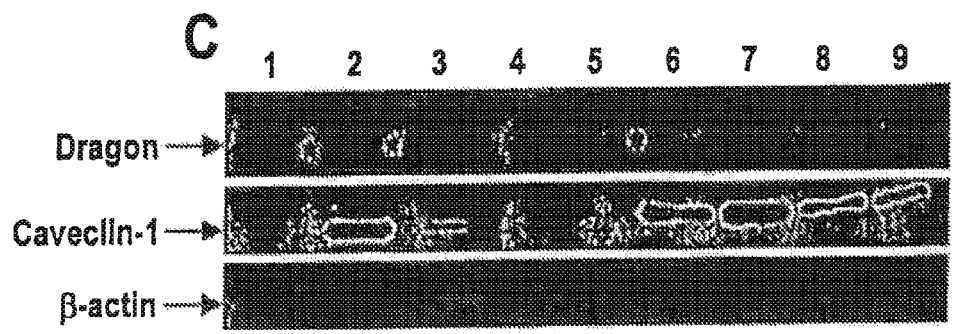

To explore the location of DRAGON on the cell surface using Ishikawa cells, live cells were incubated with DRAGON antibody at 4° C., fixed, and processed for immunocytochemistry. DRAGON has a punctate pattern on the cell membrane, typical of lipid raft proteins (FIG. 29B). DRAGON localization within membrane subdomains was then characterized by extracting cells on ice in the presence of 1% Triton X-100 and then subjecting the cells to sucrose gradient ultracentrifugation. As expected, DRAGON was detected primarily within the low-density fractions (FIG. 29C; fractions 2 and 3), along with caveolin-1, which is typically associated with lipid rafts. The high-density fractions, which include cellular and cytoskeletal proteins (fractions 6-9), contained β-actin, some caveolin-1, and a small amount of DRAGON. Thus, DRAGON is located within lipid rafts in Ishikawa cells.

DRAGON Enhances Signaling of BMP2 and BMP4

Figures 30A, 30B, 30C, 30D:
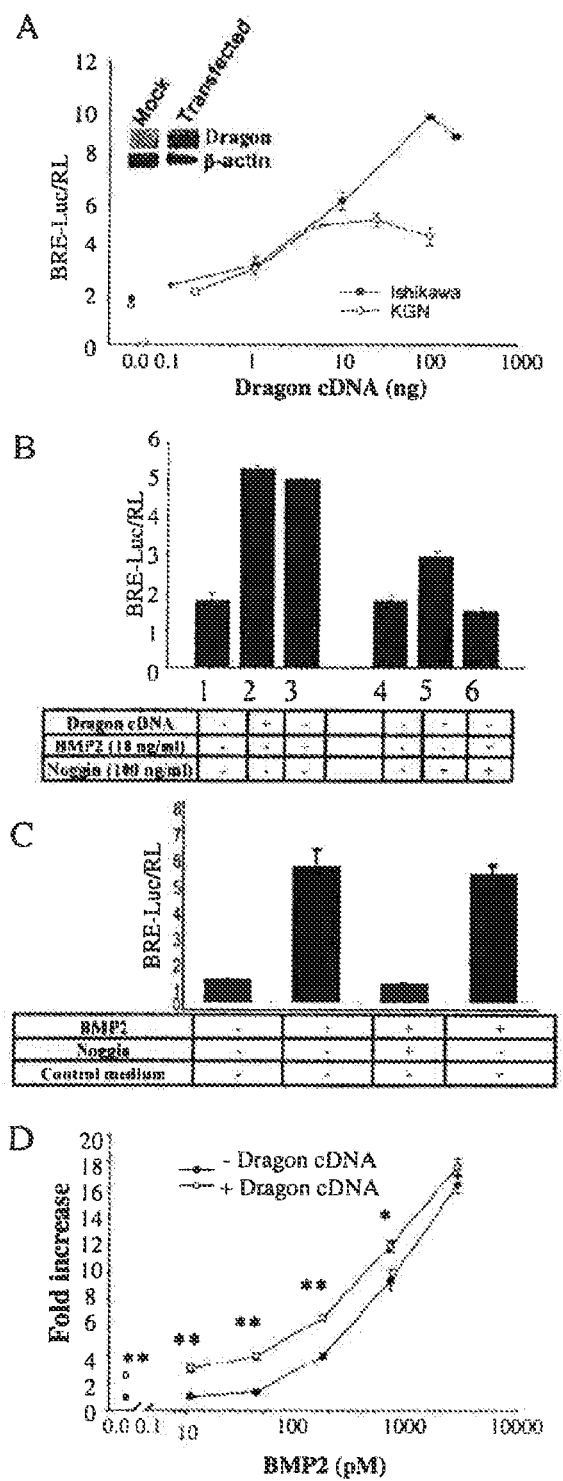
FIGS. 30A-30D are graphs showing that DRAGON enhances cellular response to BMPs in cell lines derived from reproductive tissues.

DRAGON is expressed in gonadal germ cells and in reproductive tract epithelial cells. Moreover, we have shown that DRAGON enhances the BMP2 response in the HepG2 liver cell and LLC-PK1 kidney cell lines (Samad et al., *J Biol Chem* 280:14122-14129, 2005). To examine whether DRAGON has a similar role in reproductive cells, Ishikawa and KGN cells were transfected with DRAGON cDNA together with BRE-Luc, a BMP-responsive luciferase reporter construct. DRAGON dose-dependently increased BRE luciferase activity in both Ishikawa and KGN cells in the absence of added BMPs (FIG. 30A). DRAGON induces similar reporter activity in both cell lines at lower doses (e.g., 0.1-10 ng), and a greater effect was seen in Ishikawa cells at higher doses. Although DRAGON protein was undetectable in Ishikawa cells before transfection, DRAGON was detectable after transfection with 100 ng cDNA (FIG. 30A, inset), indicating that the effects of transfected DRAGON are mediated by an increase in DRAGON protein. Treatment of Ishikawa cells with noggin-containing conditioned medium (100 ng/ml) resulted in partial inhibition of DRAGON-dependent BRE-Luc activity and completely inhibited signaling by BMP2 (10 ng/ml) (FIG. 30B). Conditioned medium from mock-transfected HEK293 cells had no inhibitory activity (FIG. 30C), indicating that the BMP-inhibiting activity in the noggin-conditioned medium was caused by noggin itself, also indicating that the effect of DRAGON on BMP reporter activity is dependent on endogenous ligand. The effect of DRAGON on BMP signaling in the presence of added BMP ligands was examined next. Ishikawa cells were transfected with DRAGON cDNA and treated with increasing doses of BMP ligands. DRAGON significantly increased BMP2 signaling at 11-700 pm BMP2 doses ($P<0.05$), but had no effect at 2800 pm (FIG. 30D). Thus, at lower BMP2 doses (i.e., 11 or 44 pm), DRAGON transfection resulted in detectable reporter activity that is not seen in the absence of DRAGON (FIG. 30D). Similar results were observed with BMP4 and in KGN cells (data not shown). DRAGON thus increases sensitivity of BMP-responsive cells to low concentrations of endogenous or exogenous BMP ligands.

DRAGON is also expressed in many specific cell types throughout the reproductive system. DRAGON is also expressed in numerous cell lines derived from reproductive tissues, and DRAGON expression enhances responsiveness of Ishikawa and KGN cells to BMP2 and BMP4. DRAGON therefore has important roles in mediating BMP signaling in reproduction. To define specific sites where DRAGON-mediated BMP signaling is important in reproduction, cell-specific expression in the male and female reproductive tracts were explored. In males, BMP8a and BMP8b are expressed in maturing spermatocytes, and BMP8b knockout males are infertile because of developmental arrest and degeneration of spermatocytes (Zhao et al., Genes Dev 10:1657-1669, 1996; Zhao et al., Development 125:1103-1112, 1998), suggesting that these BMPs are critical for normal spermatocyte development. BMP receptors ALK3 and BMPR-II are localized in postnatal spermatogonia, and BMP4 is produced by Sertoli cells very early in postnatal development, consistent with an ongoing requirement for BMP signaling in the testis (Pellegrini et al., J Cell Sci 116:3363-3372, 2003). In addition, BMP2 primarily stimulates spermatogonial proliferation, whereas BMP7 acts mainly on Sertoli cells in the testis from 7 d-old mice (Puglisi et al., Eur J Endocrinol 151:511-520, 2004). Our results extend these findings to a novel BMP coreceptor that enhances BMP signaling, because in 3 d-old male mice, DRAGON was highly expressed in gonocytes before and after they migrated from the tubule lumen to their basal position, with this immunoreactivity being maintained as spermatogonia in d9 animals. By d21, staining in spermatogonia was substantially diminished, but gonocytes remaining within the tubule lumen were still positive. In adults, DRAGON staining appeared in maturing spermatocytes but not in other testicular cell types. The shift in expression from gonocytes and spermatogonia in juvenile animals to spermatocytes in mature males suggests that the role of BMPs may change as the testes mature to produce active sperm. Taken together, these results indicate a critical role for BMPs in regulating testis development and spermatogenesis and indicate that DRAGON is an important mediator of these processes.

BMP4, BMP7, and BMP8A are expressed in the epididymis, and knockout of each gene by itself resulted in degeneration of the epididymal epithelium (Hu et al., Dev Biol 276:158-171, 2004; Zhao et al., Genes Dev 10:1657-1669, 1996; Zhao et al., Development 125:1103-1112, 1998), indicating that BMPs are involved in epididymal function. Interestingly, DRAGON was strongly expressed on the apical surface of polarized epididymal epithelium in immature and mature males consistent with a role for DRAGON in enhancing this essential BMP signaling.

In females, both BMPs and their receptors have been identified in numerous ovarian cell types, including oocytes and granulosa cells (Shimasaki et al., Endocr Rev 25:72-101, 2004). In vitro studies have demonstrated that BMP2, 4, 6, 7, and 15 regulate granulosa cell functions, and BMP4 and 7 promote the primordial-to-primary follicle transition during follicle maturation (reviewed in Shimasaki et al., Endocr Rev 25:72-101, 2004). The significance of BMP signaling in ovarian function is also underscored by the altered ovulation rates in Inverdale sheep with a natural point mutation in the BMP15 gene (Galloway et al., Nat Genet 25:279-283, 2000) and in Booroola sheep with a point mutation in the BMPRIB gene (Fabre et al., J Endocrinol 177:435-444, 2003). In the ovary, DRAGON is expressed exclusively in oocytes and most prominently in oocytes within secondary follicles. This is a time of oocyte growth and cytoplasmic maturation (Eppig et al., Reprod Fertil Dev 8:485-489, 1996), suggesting that BMP signaling in general, and DRAGON enhancement of this signaling in particular, is important for growth and maturation of oocytes.

BMP signaling components are expressed in a variety of cells within the rat uterus (Erickson et al., J Endocrinol 182: 203-217, 2004). BMP2 mRNA is restricted to periluminal stroma, and BMP7 is expressed in periluminal stroma and glandular epithelial cells, whereas BMP4 and BMP6 are expressed in blood vessels in the uterus. BMPRIA, BMPRIB, and BMPRII are expressed in a number of cell types in the uterus including luminal and glandular epithelial cells. DRAGON is expressed in luminal and glandular epithelial cells of the mouse endometrium, suggesting that DRAGON may enhance BMP signals involved in regulating uterine maturation in preparation for implantation.

BMP2, 4, 6, 7, and 15 are expressed in mouse pituitary, and BMP6, 7, and 15 have been shown to stimulate FSH synthesis and secretion (Paez-Pereda et al., Proc Natl Acad Sci USA 100:1034-1039, 2003; Huang et al., Endocrinology 142: 2275-2283, 2001; Otsuka et al., Endocrinology 143:4938-4941, 2002). BMP6 and BMP7 can also stimulate FSH mRNA biosynthesis in L$\beta$T2 mouse pituitary cells in culture (Huang et al., Endocrinology 142:2275-2283, 2001). DRAGON expression in L$\beta$T2 cells as well as in numerous cells within the mouse pituitary, some of which also stained for FSH, can be observed. BMPs may therefore act in an autocrine manner to modulate FSH biosynthesis and DRAGON may enhance this process.

In cell culture studies using cell lines from the reproductive tract, DRAGON expression enhanced the response to endogenous BMP ligand as well as low doses of exogenous BMP2 and BMP4, results that agree with our observations in nonreproductive cell lines (Samad et al., J Biol Chem 280:14122-14129, 2005). Immunocytochemical analysis indicates that DRAGON is located on the plasma membrane in discrete patches, consistent with its belonging to the class of GPI-anchored proteins that are known to localize in lipid rafts (Fullekrug et al., Ann NY Acad Sci 1014:164-169, 2004). Moreover, our work indicates that DRAGON can interact directly with BMPRII, ActRII, and the Alk3 and Alk6 type I receptors (Samad et al., J Biol Chem 280:14122-14129, 2005). Taken together, these results provide a model for enhanced BMP signaling in which DRAGON acts as a BMP coreceptor in collecting type II and type I receptors into lipid rafts where they are optimized to respond to low doses of BMP ligands. Because DRAGON can bind BMP2 and BMP4 directly, DRAGON may act to stabilize the ligand-receptor complex in lipid rafts, thereby facilitating endocytosis and signaling. Of course, these two possibilities are not mutually exclusive. Based on the localized expression of DRAGON in developing and maturing germ cells, as well as specific epithelial cells within the reproductive tract that are known to be BMP responsive, BMPs may therefore play an important role in regulating reproduction in mammals and that this role may be regulated by DRAGON.

Experiments related to DRAGON's role in reproduction were carried out as follows.

Animals

Mice [B6C3F1 (C57Bl/6×C$^3$H)] were maintained in the animal barrier facility and killed at different ages to collect tissues for immunohistochemistry and RNA extraction. In addition, mice at 19 d of age were injected with pregnant mare serum gonadotropin (PMSG; ip, 5 IU/mouse; Sigma Chemical Co., St. Louis, Mo.), and killed 48 h later to collect gonads for immunohistochemistry.

RT-PCR

Total RNA was extracted from tissues stored in RNAlater (Ambion, Austin, Tex.) or cells stored in Trizol (Life Technologies, Inc., Carlsbad, Calif.) according to the manufacturer's protocol. Total RNA (0.5-1.0 µg) was reverse transcribed as previously described (Sidis et al., *Biol Reprod* 59:807-812, 1998). Aliquots (2 µl) of first-strand cDNA mix were used in PCR (35 cycles) to amplify DRAGON and β-actin. The primers, which amplify both human and mouse DRAGON cDNA, were TGT TCC AAG GAT GGA CCC ACA TC (forward; SEQ ID NO:14) and GCA GGT CAT CTG TCA CAG CTT GG (reverse; SEQ ID NO:15).

Immunohistochemistry and Immunocytochemistry

A rabbit polyclonal antibody was raised against a peptide corresponding to the C terminus of DRAGON upstream of its GPI anchor. This antibody has been shown to specifically recognize DRAGON protein (Samad et al., *J Neurosci* 24:2027-2036 2004).

Immunohistochemistry on paraffin sections were performed as previously described (Xia et al., *Mol Endocrinol* 18:979-994, 2004). Briefly, ovaries were fixed in Bouin's solution, and other organs were fixed in 4% paraformaldehyde. Antigen retrieval was performed on paraffin sections in 0.01 m citrate buffer (pH 6.0). Tissue sections were incubated overnight with anti-DRAGON (1:4000), washed, incubated for 1 h with biotinylated goat antirabbit IgG and then 30 min with Vectastain Elite ABC (Vector Laboratories, Inc., Burlingame, Calif.), and developed with diaminobenzidine (DAB) for detection (ICN Biomedical, Inc., Aurora, Ohio). Sections were then counterstained with Harris' hematoxylin.

To colocalize DRAGON and FSH in the pituitary, mouse pituitaries were fixed in 4% paraformaldehyde at 4° C. overnight, cryoprotected in 30% sucrose overnight, and frozen in Tissue-Tek OCT embedding compound (Electron Microscopy Sciences, Fort Washington, Pa.). Sections (12 µm) were incubated with a mixture of rabbit anti-DRAGON serum (1:2000) and guinea pig antimouse FSH (1:1600, AFP-3080, National Institute of Diabetes and Digestive and Kidney Diseases, Bethesda, Md.) for 1 h, washed, and then with a mixture of fluorescein isothiocyanate (FITC)-conjugated donkey antirabbit IgG and tetramethyl rhodamine isothio-cyanate-conjugated donkey anti-guinea pig IgG (diluted 1:200; Jackson ImmunoResearch Laboratories, Inc., West Grove, Pa.).

For immunocytochemistry, Ishikawa cells were grown on glass coverslips. Live cells were incubated with anti-DRAGON serum (1:2000) for 1 h on ice. Cells were then fixed in 2% paraformaldehyde for 20 min. The bound antibodies were detected by incubating with FITC-conjugated donkey antirabbit IgG (diluted 1:200 in PBS) for 1 h. To demonstrate specificity, the DRAGON antibody was preincubated overnight with 10 mm immunization peptide before being applied to sections or cells.

In Situ Hybridization

Air-dried frozen sections (14-18 µm) were fixed in 4% paraformal-dehyde-PBS, digested with proteinase K, acetylated, washed, and dehydrated. Antisense and sense cRNA probes were prepared by means of in vitro transcription in the presence of [α-$^{35}$S]UTP, which were then hybridized in 50% deionized formamide, 10 mm Tris/HCl (pH 7.6), 600 mm NaCl, 0.25% SDS, 200 µg/ml yeast tRNA, 50 mm dithiothreitol, 1Denhardt's solution, and 10% dextran sulfate overnight at 55° C. in a humidified chamber. After hybridization, the sections were incubated with ribonuclease A and washed in 0.1 SSC containing 13-mercapto-ethanol (875 µl in 300 ml) and 0.5 mm EDTA at 65° C. for 1 h. After developing, the slides were counterstained with hematoxylin and mounted for photography.

Lipid Raft Protein Extraction

Lipid raft proteins were prepared after protocols previously described (20, 21). Briefly, Ishikawa cells were scraped and pelleted in ice-old PBS, resuspended in 2 ml ice-cold lysis buffer [10 mm Tris/HCl (pH 7.5), 150 mm NaCl, 1% Triton X-100, 2 mm EDTA, and proteinase inhibitors], and allowed to stand on ice for 30 min. The lysate was centrifuged for 5 min at 1300 g to remove nuclei and large cellular debris. The supernatant was mixed with an equal volume of 85% sucrose in TBS [10 mm Tris/HCl (pH 7.5), 150 mm NaCl], placed at the bottom of a 10-ml ultracentrifuge tube, and then overlaid with 5 ml of 35% sucrose and 1.4 ml of 5% sucrose. The sample was then centrifuged for 14 h at 150,000 g in a SW41Ti rotor so that rafts could float to the tip while cytoskeletal and cytoplasmic proteins remain at the bottom. Five fractions of 1 ml and four fractions of 1.35 ml were collected from the top of the tube. The light-scattering band, an indicator of the location of lipid rafts (Mukherjee et al., *J Biol Chem* 278:40806-40814, 2003), was located primarily in fraction 2. These fractions were analyzed by trichloroacetic acid precipitation of proteins from 100-0 aliquots followed by SDS-PAGE and Western blotting.

Western Blotting

Western blotting analyses were performed as previously described (Xia et al., *Mol Endocrinol* 18:979-994, 2004). Briefly, samples from sucrose gradient fractions were subjected to SDS-PAGE under reducing conditions, transferred to a polyvinylidene difluoride membrane (Millipore, Bedford, Mass.), blocked in 10% nonfat dry milk, and incubated overnight at 4° C. with rabbit anti-DRAGON (1:4000) or anti-caveolin-1 (1:2000; BD Biosciences, San Jose, Calif.) antibodies. The membranes were washed three times before being incubated for 2 h at room temperature with second antibody, which was detected with enhanced chemiluminescence (ECL) Reagent Plus (PerkinElmer Life Sciences, Boston, Mass.). After exposure, membranes were stripped for 30 min at 50° C. and reprobed with a monoclonal β-actin antibody (1:1000; Santa Cruz Biotechnology, Santa Cruz, Calif.).

Transfection and Luciferase Assay

Ishikawa and KGN cells were maintained in TT medium [1:1 mixture of DMEM and F-12, supplemented with 1% 1-glutamine, 100 IU/ml penicillin, 100 µg/ml streptomycin sulfate, and 10% fetal bovine serum (Life Technologies, Inc., Rockville, Md.)]. To examine the effect of DRAGON on BMP signaling, transfections were performed in 24-well trays using Lipofectamine 2000 (Invitrogen, Carlsbad, Calif.) with a total of 400 ng DNA [180 ng BRE-Luc, a BMP response element kindly provided by Dr. ten Dijke (Korchynskyi et al., *J Biol Chem* 277:4883-4891, 2002), 10 ng pRL-TK, and the indicated doses of DRAGON cDNA and pcDNA3]. Approximately 24 h after transfection, the medium was replaced with serum-free TT medium supplemented with 0.1% BSA, with or without BMP ligands (R&D Systems, Minneapolis, Minn.). After treating for 16 h, the cells were lysed and assayed for luciferase activity using the dual luciferase reporter assay kit (Promega, Madison, Wis.).

To obtain noggin protein for neutralization of endogenous BMPs, the human noggin cDNA (IMAGE clone 4737725 from American Type Culture Collection, Rockville, Md.) was subcloned into pcDNA3 (Invitrogen) and transfected into HEK-293-F suspension cultures in Freestyle serum-free medium (Invitrogen) as previously described (Keutmann et al., *Mol Endocrinol* 18:228-240, 2004). Concentrated conditioned medium was calibrated by two independent methods including 1) biological assay and 2) Western blotting. In the biological assay, increasing amounts of noggin-conditioned medium were mixed with 10 ng/ml BMP2 and used to treat HepG2 cells that were previously transfected with the BRE-Luc reporter. At the effective concentrations for half-maximal response (EC50), the amount of noggin in the culture medium was equal to that of the BMP2 concentration, assuming molar equivalent antagonism activity (Zimmerman et al., *The Spemann Cell* 86:599-606, 1996). For the Western blotting analysis, serial dilutions of noggin-conditioned medium were resolved by 12% PAGE under reducing conditions and visualized by staining with an antimouse noggin polyclonal antibody (R&D Systems). Noggin concentrations were estimated at the detection limit dose according to the manufacturer's information. Both methods gave similar results. As a control, concentrated conditioned medium from mock-transfected HEK293 cells was tested and determined to have no BMP-inhibitory activity.

To demonstrate that Ishikawa cells transfected with DRAGON cDNA actually produce DRAGON protein, transfected cells were extracted in RIPA buffer [150 mm NaCl, 50 mm Tris (pH 7.5), 1 mm EDTA, 50 mm NaF, 0.5% Nonidet P-40, 0.5% deoxycholic acid, and 0.1% SDS], and the lysates were then analyzed by Western blotting for DRAGON as described above.

Data Analysis

FIGS. 30A, 30C, and 30D depict the mean±SE of triplicates from representative experiments. In vitro bioassay experiments in the presence or absence of transfected DRAGON (FIG. 30D) represents the mean SE of six determinations from three independent experiments and were analyzed by two-way ANOVA. Differences between ligand doses or between presence and absence of DRAGON were identified by Student-Newman-Keuls post hoc test. Differences of $P<0.05$ were considered significant.

DRAGON Homolog RGMa

A DRAGON homolog, RGMa, has similar functionality to DRAGON, and may also be used in the methods of the invention.

Regulation of the signal transduction pathway occurs at many levels. One key regulatory mechanism for many TGF-β superfamily members is through accessory or co-receptors to promote or inhibit ligand binding (Shi and Massague, *Cell* 113:685-700, 2003; Lopez-Casillas et al., *Cell* 73:1435-1444, 1993; Shen and Schier, *Trends Genet.* 16:303-309, 2000; Cheng et al., *Genes Dev.* 17:31-36, 2003; Gray et al., *Proc. Natl. Acad. Sci. USA* 100:5193-5198, 2003; Samad et al., *J. Biol. Chem.* 280:14122-14129, 2005). For example, the TGF-β type III receptor (betaglycan) mediates binding of TGF-β2 to the type II receptor and is important for TGF-β2 signaling (Lopez-Casillas et al., *Cell* 73:1435-1444, 1993). Glycosylphosphatidylinositol (GPI)-linked proteins from the epidermal growth factor-Cripto-Criptic-FRL-1 family are co-receptors necessary for nodal, Vg1, and growth and differentiation factor 1 signaling (Shen and Schier, *Trends Genet.* 16:303-309, 2000; Cheng et al., *Genes Dev.* 17:31-36, 2003). Cripto also inhibits activin signaling by preventing binding of the activin/type II receptor complex to type I receptors (Gray et al., *Proc. Natl. Acad. Sci. USA* 100:5193-5198, 2003). We have recently identified the GPI-anchored protein DRAGON (RGMb) as the first co-receptor for BMP signaling (Samad et al., *J. Biol. Chem.* 280:14122-14129, 2005). DRAGON enhances cellular responses to BMP, but not TGF-β, signals in a ligand-dependent manner. DRAGON associates with BMP type I and type II receptors, and soluble DRAGON.Fc fusion protein binds selectively to BMP-2 and BMP-4, but not BMP-7 or other members of the TGF-β superfamily of ligands (Samad et al., *J. Biol. Chem.* 280:14122-14129, 2005).

DRAGON is a member of the repulsive guidance molecule (RGM) family of genes, which also includes RGMa and hemojuvelin (HJV/RGMc/HFE2). These family members share 50-60% amino acid identity and similar structural features, including an N-terminal signal sequence, conserved proteolytic cleavage site, partial von Willebrand factor type D domain, and GPI anchor (Monnier et al., *Nature* 419:392-395, 2002.; Papanikolaou et al., *Nat. Genet.* 36:77-82, 2004; Samad et al., *J. Neurosci.* 24:2027-2036, 2004; Niederkofler et al., *J. Neurosci.* 24:808-818, 2004; Schmidtmer and Engelkamp, *Gene Expr. Patterns* 4:105-110, 2004; Oldekamp et al., *Gene Expr Patterns* 4:283-288, 2004). Unlike DRAGON, RGMa and hemojuvelin also possess an RGD motif, which could be involved in cell attachment (Monnier et al., *Nature* 419:392-395, 2002). RGMa and DRAGON are expressed in a complementary manner in the central nervous system (Samad et al., *J. Neurosci.* 24:2027-2036, 2004; Niederkofler et al., *J. Neurosci.* 24:808-818, 2004; Schmidtmer and Engelkamp, *Gene Expr. Patterns* 4:105-110, 2004; Oldekamp et al., *Gene Expr Patterns* 4:283-288, 2004), where RGMa mediates repulsive axonal guidance (Monnier et al., *Nature* 419:392-395, 2002; Rajagopalan et al., *Nat. Cell Biol.* 6:756-762, 2004; Brinks et al., *J. Neurosci.* 24:3862-3869, 2004), and neural tube closure (Niederkofler et al., *J. Neurosci.* 24:808-818, 2004), while DRAGON contributes to neuronal cell adhesion through homophilic interactions (Samad et al., *J. Neurosci.* 24:2027-2036, 2004). RGMa also binds to the receptor neogenin (Rajagopalan et al., *Nat. Cell Biol.* 6:756-762, 2004) and functions as a cell survival factor (Matsunaga et al., *Nat. Cell Biol.* 6:749-755, 2004). Hemojuvelin is expressed most heavily in the liver, heart, and skeletal muscle, and is mutated in juvenile hemochromatosis, a disorder of iron overload (Papanikolaou et al., *Nat. Genet.* 36:77-82, 2004; Samad et al., *J. Neurosci.* 24:2027-2036, 2004; Niederkofler et al., *J. Neurosci.* 24:808-818, 2004; Schmidtmer and Engelkamp *Gene Expr. Patterns* 4:105-110, 2004; Oldekamp et al., *Gene Expr. Patterns* 4:283-288, 2004; Rodriguez Martinez et al., *Haematologica* 89:1441-1445, 2004).

RGMa is involved in the BMP signaling pathway. A reporter assay shows that transfection of RGMa cDNA into cells enhances BMP, but not TGF-β, signals in a ligand-dependent fashion. Binding and crosslinking studies in a cell-free system demonstrate that soluble RGMa.Fc fusion protein interacts with the BMP type I receptor ALK6 and binds directly to $^{125}$I-BMP-2 and $^{125}$I-BMP-4, but not other members of the TGF-β superfamily. Co-transfection of RGMa cDNA with dominant negative BMP type I receptors or with dominant negative Smad1 inhibits RGMa-mediated BMP signaling, suggesting that RGMa generates BMP signals via the classical BMP pathway. Transfection of RGMa cDNA into cells induces phosphotylation of endogenous Smad1/5/8 and upregulates endogenous Id1. Finally, immunofluorescence microscopy of adult rat spinal cord sections, reveals that RGMa is expressed in vivo in neurons which also show nuclear accumulation of p-Smad1/5/8. Taken together, these data indicate that RGMa functions as a BMP co-receptor.

RGMa Mediates BMP, but not TGF-β, Signaling

Figures 31A, 31B, 31C:
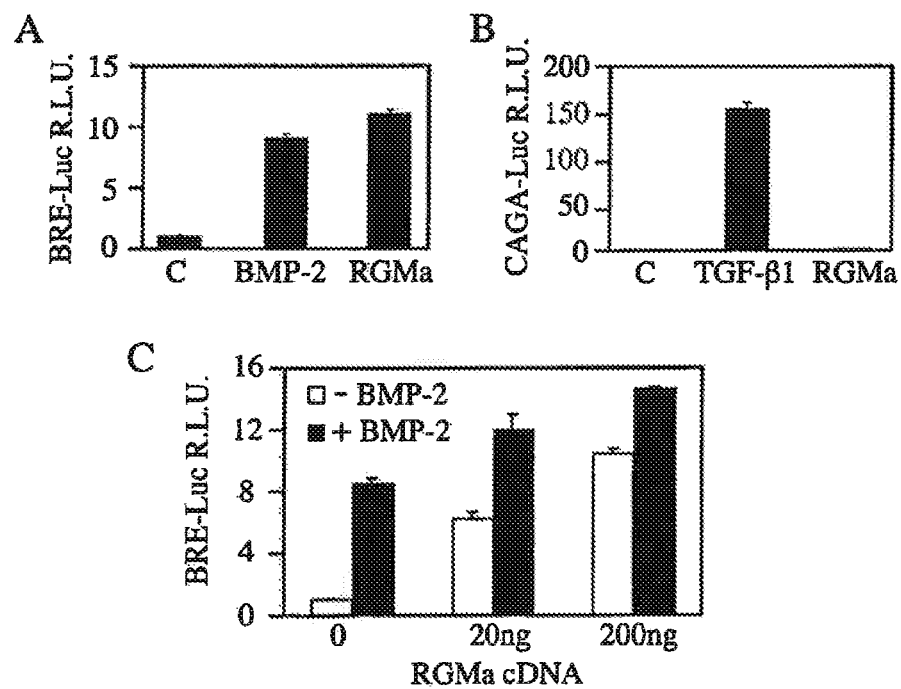
FIGS. 31A-31C are graphs showing RGMa signals via the BMP, but not the TGF-β, pathway.

As RGMa homolog DRAGON functions as a BMP co-receptor in LLC-PK1 porcine kidney epithelial cells (Samad et al *J. Biol. Chem.* 280:14122-14129, 2005), the ability of RGMa to mediate BMP signaling was tested in these cells. LLC-PK1 cells were transfected with a BMP-responsive luciferase reporter (BRE-Luc, Korchynskyi and ten Dijke *J. Biol. Chem* 277:4883-4891, 2002) (FIGS. 31A and 31C) or a TGF-β responsive luciferase reporter (CAGA-Luc, Dennler et al., *EMBO J.* 17:3091-3100, 1998) (FIG. 31B) either alone or in combination with cDNA encoding RGMa. Transfected cells were then incubated with or without BMP-2 or TGF-β1 for 16 hours followed by measurement of luciferase activity. In the absence of RGMa, stimulation with BMP-2 or TGF-β1 increased the relative luciferase activity for their respective reporters compared with unstimulated cells (FIGS. 31A and 31B, compare bars 2 to 1). Co-transfection with RGMa similarly increased BRE luciferase activity even in the absence of exogenous BMP ligand (FIG. 31A, bar 3). The RGMa-mediated BMP signaling was dose dependent (FIG. 31C, white bars), reaching a peak at about 200 ng cDNA per transfection. RGMa also augmented signaling produced by exogenous BMP-2 (FIG. 31C, black bars). In contrast, co-transfection with RGMa (up to 1 mg) did not increase the TGF-β responsive CAGA luciferase activity above baseline (FIG. 31B, bar 3). Similar results. were seen in another cell line (HepG2 cells, data not shown). Taken together, these results demonstrate that like DRAGON, RGMa mediates BMP, but not TGF-β, signaling.

RGMa-Mediated BMP Signaling is Ligand-Dependent

Figures 32A, 32B, 32C:
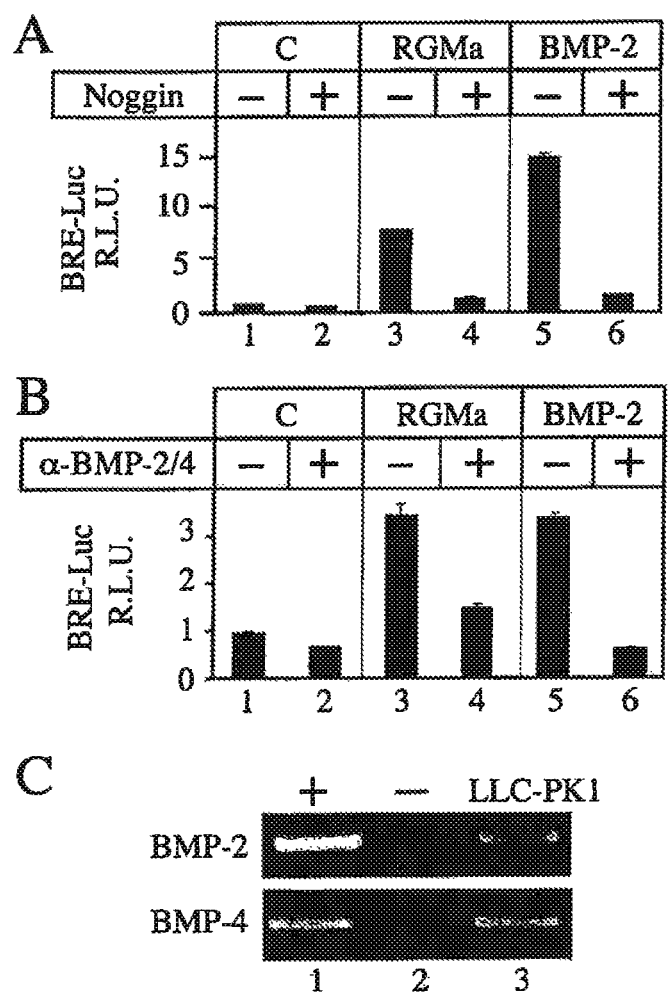
FIGS. 32A-32C are graphs and a gel image showing RGMa-mediated BMP signaling is ligand-dependent.

The ability of RGMa to generate BMP signals even in the absence of exogenous BMP ligand raises the question of whether RGMa acts in a ligand-independent manner, or whether it augments signaling by endogenous BMP ligands. To investigate this question, we examined whether RGMa-mediated signaling was inhibited by noggin, a soluble BMP inhibitor that binds and sequesters BMP ligands barring access to membrane receptors (Balemans and Van Hul *Dev. Biol.* 250:231-250, 2002; Groppe et al., *Nature* 420:636-642, 2002). The effects of noggin on exogenous BMP-2 and TGF-β1 stimulation were used as positive and negative controls respectively. Results were confirmed using a neutralizing antibody against BMP-2 and BMP-4 (α-BMP-2/4). In the absence of noggin, co-transfection with RGMa cDNA increased BRE luciferase activity 8-fold above baseline (FIG. 32A, compare bar 3 to 1). Similarly, exogenous BMP-2 increased BRE luciferase activity 15-fold over baseline (FIG. 32A, compare bar 5 to 1). This stimulation by either RGMa transfection or exogenous BMP-2 was blocked by noggin (FIG. 32A bars 4, 6). Noggin also decreased basal BMP signaling in cells neither transfected with RGMA nor stimulated with exogenous BMP-2 (FIG. 32A, compare bar 2 to 1). In contrast, noggin did not affect TGF-β1 induced CAGA luciferase activity (data not shown). Similar results were seen with a neutralizing antibody against BMP-2 and BMP-4 (FIG. 32B). Thus, RGMa generates BMP signals in a ligand-dependent manner, likely via endogenously expressed BMP ligands. The observation of mRNA for both BMP-2 and BMP-4 in these cells by RT-PCR further supports this possibility (FIG. 32C).

Production and Characterization of Soluble RGMa.Fc Fusion Protein

Figure 33:
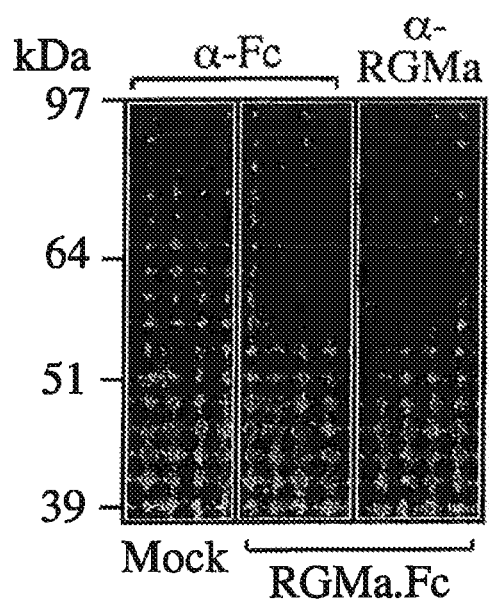
FIG. 33 is an image of a Western blot showing expression of soluble RGMa.Fc fusion protein. Soluble RGMa.Fc fusion protein was purified from the media of stably transfected HEK-293 cells via one-step Protein A affinity chromatography. Protein A purified media from cells transfected with empty vector was used as a negative control (Mock). Purified protein was analyzed by reducing SDS-PAGE followed by Western blot with anti-RGMa peptide antibody (α-RGMa, right lane) or anti-human Fc antibody (α-Fc, left 2 lanes) as indicated.

An RGMa.Fc fusion protein was produced by fusing the extracellular domain of RGMa to the Fc portion of human IgG. An affinity purified rabbit polyclonal antibody raised against a C-terminal peptide sequence of RGMa upstream of its GPI anchor (α-RGMa) was also generated. Purified RGMa.Fc was analyzed by reducing SDS-PAGE followed by Western blot using anti-human Fc antibody (α-Fc) and α-RGMa. Both antibodies recognized two bands of approximately 60 and 75 kDa not seen in mock transfected cells, confirming the presence of both the RGMa and Fc domains, and validating the RGMa antibody (FIG. 33). These bands were not seen when the RGMa antibody was pre-incubated with competing antigenic peptide (data not shown). The larger band is consistent with the predicted size of the full length RGMa.Fc fusion protein, and the smaller band is consistent with the predicted size of RGMa.Fc fusion protein which has been proteolytically cleaved as described for both the chick in Monnier et al. (*Nature* 419:392-395, 2002) and mouse homologues in Niederkofler et al. (*J. Neurosci.* 24:808-818, 2004) of RGMa.

RGMa.Fc Binds Selectively to BMP-2 and BMP-4, but not BMP-7 or TGF-β1

Figures 34A, 34B:
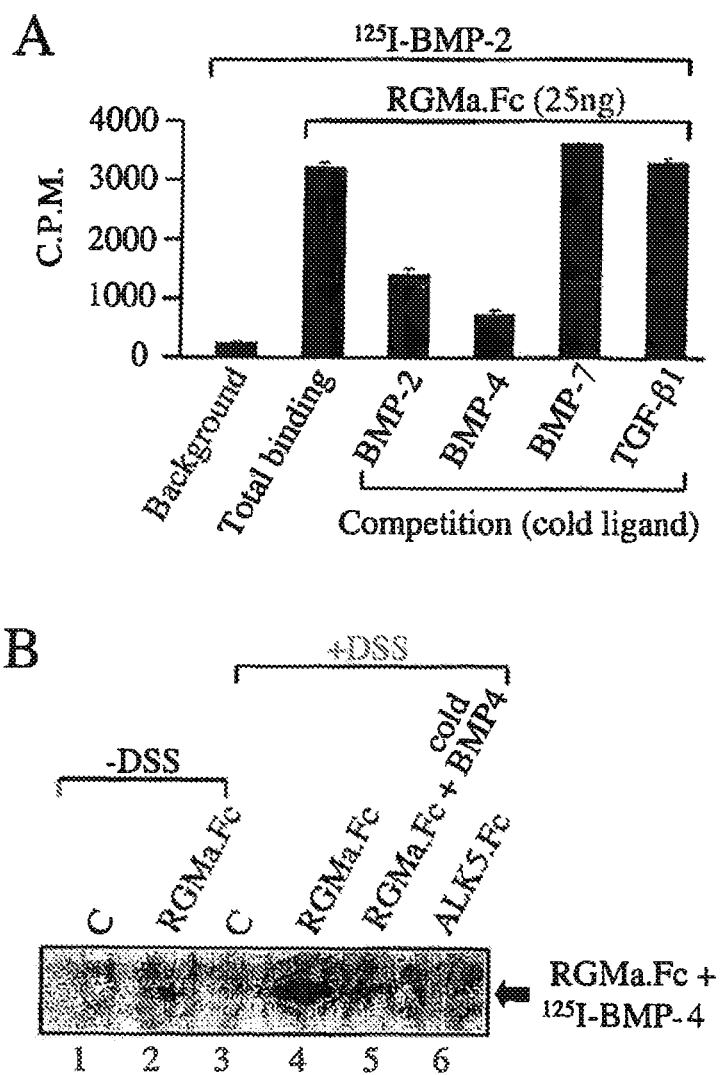
FIGS. 34A and 34B are a graph and an autoradiography gel image showing soluble RGMa.Fc binds BMP-2 and BMP-4 selectively.

Next, RGMa was tested for direct interactions with BMP ligands using soluble RGMa.Fc fusion protein in a cell free binding system. RGMa.Fc was incubated overnight with $^{125}$I-BMP-2 with or without excess cold BMP-2, -4, -7 or TGF-β1, followed by incubation on protein A coated plates and determination of radioactivity. RGMa.Fc bound to $^{125}$I-BMP-2 (FIG. 34A, compare bar 2 to 1). This binding was competitively inhibited by excess cold BMP-2 or BMP-4, but not by BMP-7 or TGF-β1. Similar findings were seen with $^{125}$I-BMP-4 (data not shown).

Chemical crosslinking experiments using DSS in a cell free system provided additional support for interaction between RGMa.Fc and BMP-2. $^{125}$I-BMP-4 was crosslinked with RGMa.Fc in the presence of DSS (FIG. 34B, bar 4), and this crosslinking was inhibited by excess cold BMP-4 (FIG. 34B, bar 5). No band was seen in the absence of DSS (FIG. 34B, bars 1-2) or when buffer alone (FIG. 34B, bar 3) or ALK5.Fc (a TGF-β type I receptor, FIG. 34B, bar 6) was used in place of RGMa.Fc. Similar results were seen for crosslinking with $^{125}$I-BMP-2 (data not shown). Taken together, these data indicate that RGMa.Fc binds directly and selectively to BMP-2 and BMP4, but not BMP-7 or TGF-β1.

RGMa Mediates BMP Signaling Via BMP Type I Receptors

Figures 35A, 35B, 35C:
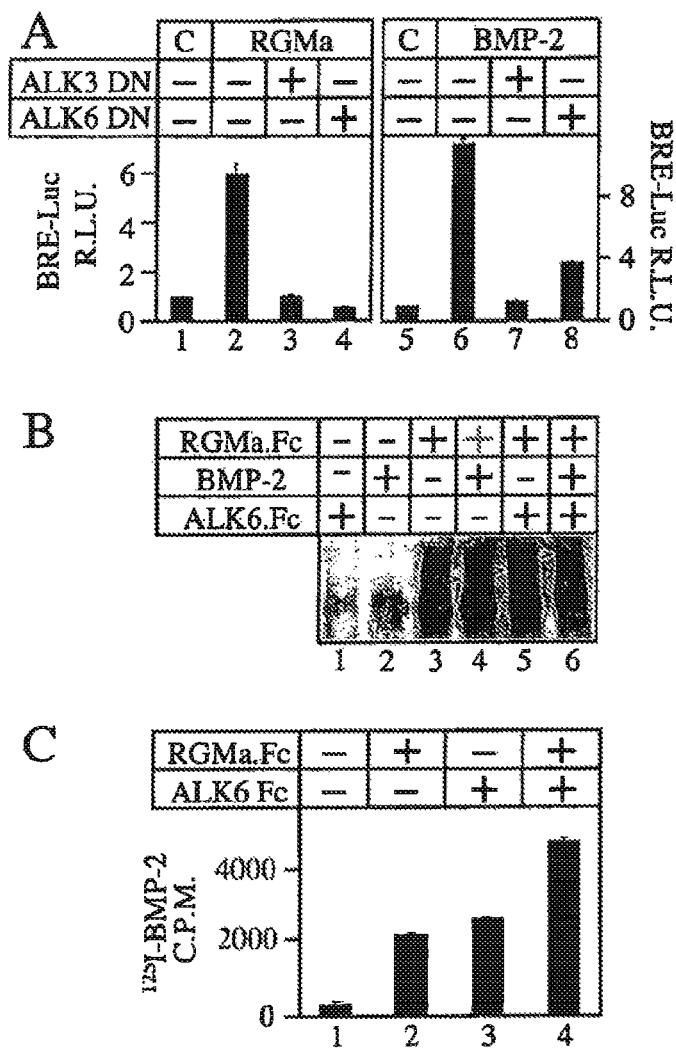
FIGS. 35A-35C are graphs and images of Western blots showing RGMa mediates BMP signaling through BMP receptors.

Determination of whether RGMa acts via the classical BMP signaling pathway through BMP receptors was made. Dominant negative mutants of BMP type I receptors ALK3 (ALK3 DN) and ALK6 (ALK6 DN), which are deficient in kinase activity and therefore unable to phosphorylate Smad1/5/8, have been described in Clarke et al. (*Mol. Endocrinol.* 15:946-959, 2001) and Chen et al. (*J. Cell Biol.* 142:295-305), 1998). The effects of co-transfection with dominant negative ALK3 and ALK6 mutants on RGMa-mediated BMP signaling were examined, and the effect of these mutants on exogenous BMP was used as a control. Transfection with RGMa or incubation of cells with exogenous BMP-2 increased BRE luciferase activity 6-10-fold above baseline (FIG. 35A, compare bar 2 to 1 and 6 to 5). This stimulation by either RGMa or exogenous BMP-2 was blocked by co-transfection with dominant negative ALK3 (FIG. 35A, bars 3, 7) or dominant negative ALK6 (FIG. 35A, bars 4, 8).

To determine whether RGMa interacted directly with BMP type I receptors, purified RGMa.Fc, ALK6.Fc, and/or BMP-2 were incubated in solution either individually or in various combinations, in the presence of the crosslinker DSS. Complexes were pulled down with protein A beads and analyzed by non-reducing SDS-PAGE, followed by Western blot with α-RGMa. RGMa.Fc formed a complex in solution with BMP-2, demonstrated by a more slowly migrating band under non-reducing conditions compared with RGMa.Fc alone (FIG. 35B, compare arrowhead in lane 4 to lane 3). RGMa.Fc also formed a complex with ALK6.Fc, even in the absence of BMP-2 (FIG. 35B, compare arrowhead in lane 5 to lane 3). In the presence of BMP-2, an even larger shift was seen, indicating that a complex containing RGMa.Fc, ALK6.Fc, and BMP-2 had formed (FIG. 35B, lane 6, arrowhead). No bands were seen for ALK6.Fc or BMP-2 in the absence of RGMa.Fc (FIG. 35B, lanes 1 and 2). BMP ligands exhibit high affinity for BMP type I receptors and low affinity for BMP type II receptors (Shi and Massague, *Cell* 113:685-700, 2003). The combination of RGMa and BMP type I receptors increased binding of BMP ligands compared with BMP type I receptors alone was thus tested. Purified RGMa.Fc and ALK6.Fc were incubated overnight in solution with $^{125}$I-BMP-2, followed by incubation on protein A coated plates and determination of radioactivity. RGMa.Fc and $^{125}$I-ALK6.Fc alone each significantly bound BMP-2 (FIG. 35C, compare bars 2 and 3 to 1). As a negative control, BMP type II receptor was unable to bind (data not shown). The combination of RGMa.Fc and ALK6.Fc increased binding to $^{125}$I-BMP-2 compared with ALK6.Fc alone (FIG. 35C, compare bar 4 to 3).

Figures 36A, 36B, 36C, 36D:
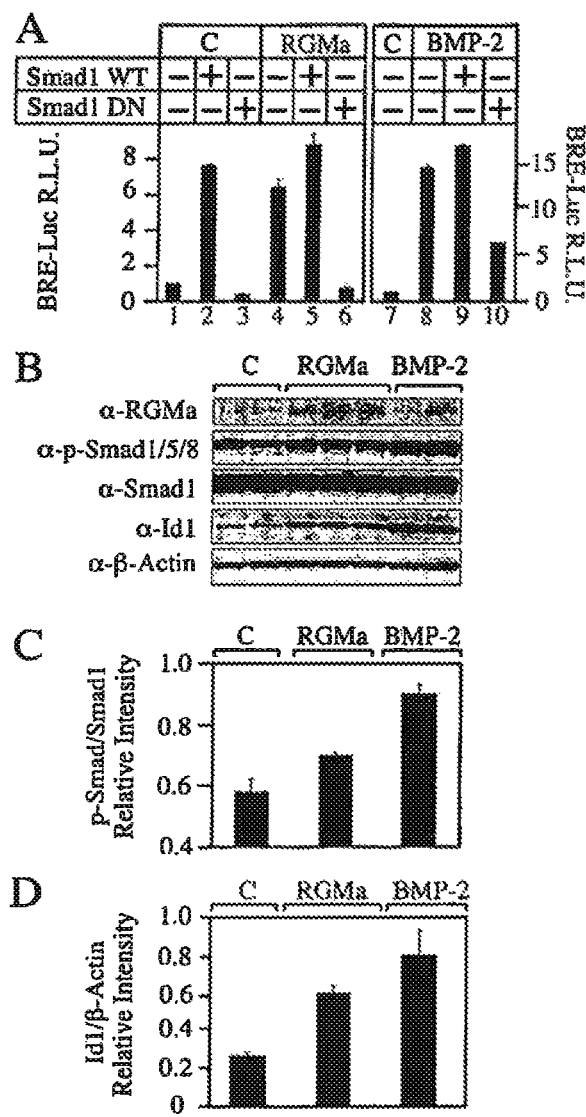
FIGS. 36A-36D show RGMa mediates BMP signaling through Smad1/5/8 and upregulates Id1.

RGMa Mediates BMP Signaling Via Smad1/5/8, and Upregulates Endogenous Id1 Expression The role of RGMa in the classical BMP signaling pathway was studied using the effects of wildtype Smad1 (WT Smad1) versus dominant negative Smad1 (DN Smad1), a dominant negative mutant of Smad1 with deleted carboxy terminal phosphoacceptor residues (Samad et al., *J. Biol. Chem.* 280: 14122-14129, 2005; Macias-Silva et al., *J. Biol. Chem.* 273: 25628-25636, 1998, Piscione et al., *Am. J. Physiol. Renal Physiol.* 280:F19-33, 2001), on RGMa-mediated BMP signaling. Results were compared with their effects on exogenous BMP-2 signaling as a control. Consistent with other studies (Samad et al., *J. Biol. Chem.* 280:14122-14129, 2005; Hoodless et al., *Cell* 85:489-500, 1996; Macias-Silva et al., *Cell* 87:1215-1224, 1996), transfection with WT Smad1 alone increased BRE luciferase activity 8-fold above baseline (FIG. 36A, compare bar 2 to 1), while transfection with DN Smad1 alone decreased BRE luciferase activity below baseline (FIG. 36A, compare bar 3 to 1). Transfection with RGMa increased BRE luciferase activity 7-fold above baseline (FIG. 36A, bar 4). Co-transfection of WT Smad1 with RGMa further augmented the signaling induced by either WT Smad1 or RGMa alone (FIG. 36A, compare bar 5 to 2, 4). Co-transfection of DN Smad1 with RGMa blocked the increase in signal seen with RGMa alone (FIG. 36A, compare bar 6 to 4). Similar results were seen for the effects of WT Smad1 and DN Smad1 on exogenous BMP-2 stimulation (FIG. 36A, bars 7-10).

To demonstrate that RGMa mediates BMP signaling through the Smad signaling pathway, the effect of RGMa expression on phosphorylation of endogenous Smad1/5/8 was studied. LLC-PK1 cells were transiently transfected with RGMa cDNA and cell lysates were assayed for p-Smad1/5/8 by Western blot (FIG. 36B, α-p-Smad1/5/8). Blots were stripped and reprobed for total Smad1 as a loading control (FIG. 36B, α-Smad1). Results were compared to mock transfected cells as a negative control, and cells stimulated for 2 hours with 50 ng/ml exogenous BMP-2 as a positive control. Expression of p-Smad1/5/8 relative to Smad1 was quantitated using IPLab Spectrum software (FIG. 36C). Consistent with our other data supporting the notion of endogenous BMP signaling in these cells, mock transfected cells (without RGMa or exogenous BMP-2 stimulation) did have some basal level of p-Smad1/5/8 (FIG. 36B, left two lanes). Transfection with RGMa cDNA increased p-Smad1/5/8 levels compared with mock transfected cells (FIG. 36B, compare middle three lanes to left two lanes; FIG. 36C, compare bar 2 to 1). As a positive control, stimulation with exogenous BMP-2 also increased p-Smad1/5/8 levels (FIG. 36B, right two lanes; FIG. 36C, bar 3).

We then demonstrated that RGMa affects expression of endogenous Id1, an important downstream target of BMP signals (Hollnagel et al., *J. Biol. Chem.* 274:19838-19845, 1999; Korchynskyi and ten Dijke *J. Biol. Chem* 277:4883-4891, 2002; Lopez-Rovira et al., *J. Biol. Chem.* 277:3176-3185, 2002; Miyazono and Miyazawa, *Sci STKE.* 2002:PE40, 2002; ten Dijke et al., *Mol. Cell. Endocrinol.* 211:105-113, 2003). Western blots used in the p-Smad1/5/8 assay above were stripped and re-probed with anti-Id1 antibody (FIG. 36B, α-Id1). Blots were stripped again and re-probed with actin antibody (FIG. 36B, α-β-actin) as a loading control, and the ratio of Id1 to β-actin expression was quantitated using IPLab Spectrum software (FIG. 36D). Transfection with RGMa increased expression of Id1 protein about 2.3-fold compared with mock transfected cells (FIG. 36B compare middle three lanes to left two lanes; FIG. 36D compare bar 2 to 1). As a positive control, stimulation with exogenous BMP-2 also increased Id1 expression (FIG. 36B, right two lanes; FIG. 36D, bar 3). Thus, RGMa mediates BMP signaling via the classical BMP pathway involving Smad1/5/8, and RGMa increases expression of endogenous Id1 protein, a downstream target of BMP signals.

RGMa is Widely Expressed

Figure 37:
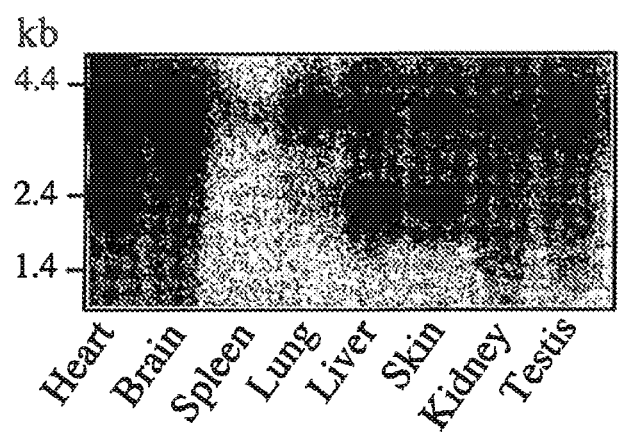
FIG. 37 is a Northern blot of RGMa expression in adult rat tissues. 10 mg total RNA was loaded per tissue per lane and probed for RGMa. Tissues are indicated by name.
Figure 39A:
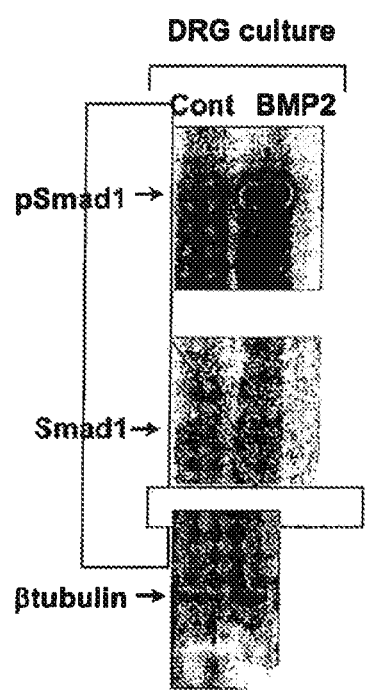
FIGS. 39A and 39B are a Western blot and an immunocytochemical analysis showing increase in levels of phosphorylated-Smad1 (pSmad1) in cultured DRG treated with BMP2. Note that levels of Smad1 are unchanged. β-tubulin levels were used as loading Control. Immunocytochemical analysis
Figure 39B:
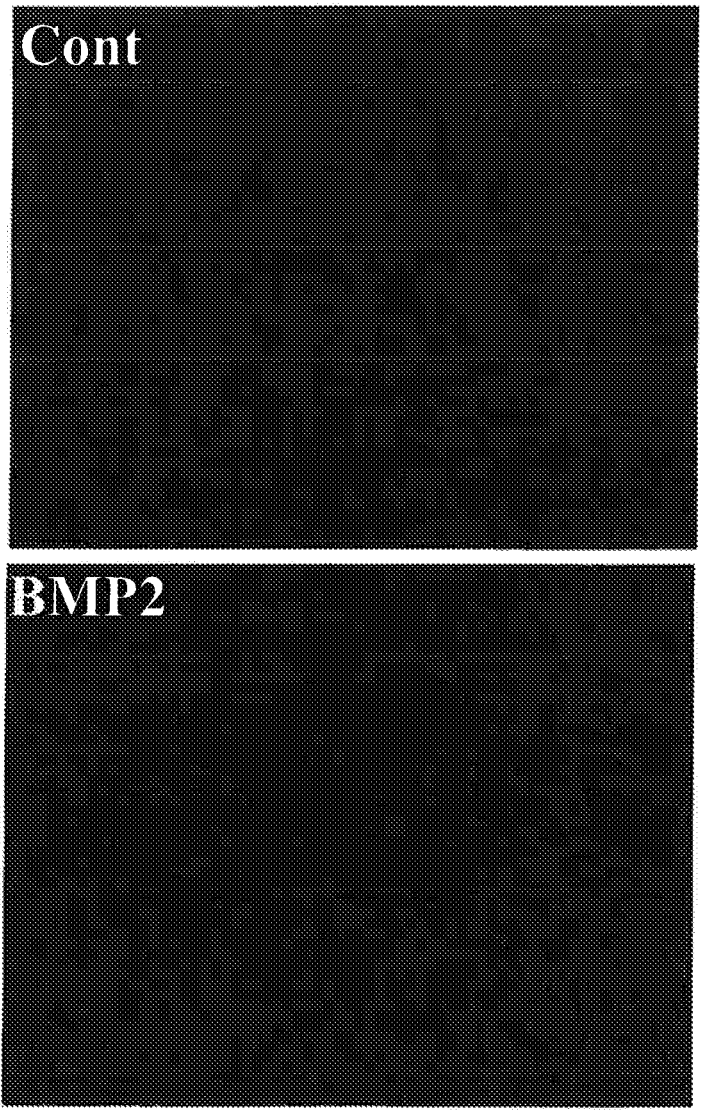
Figure 40A:
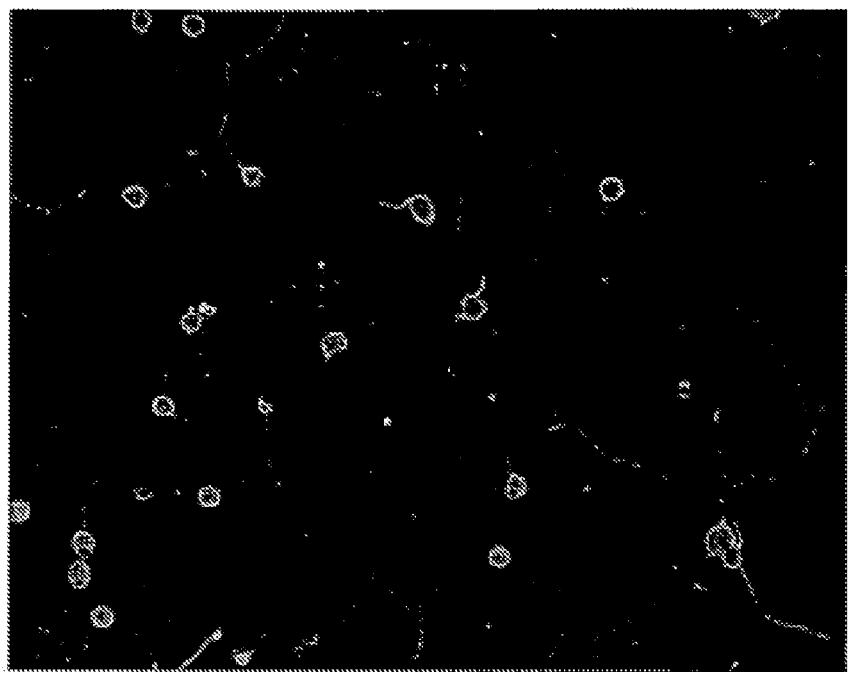
FIGS. 40A and 40B are images showing DRG neurons cultured (48 hrs) in the absence (FIG. 40A; Cont) or presence of BMP2 (100 ng/ml.
Figure 40B:
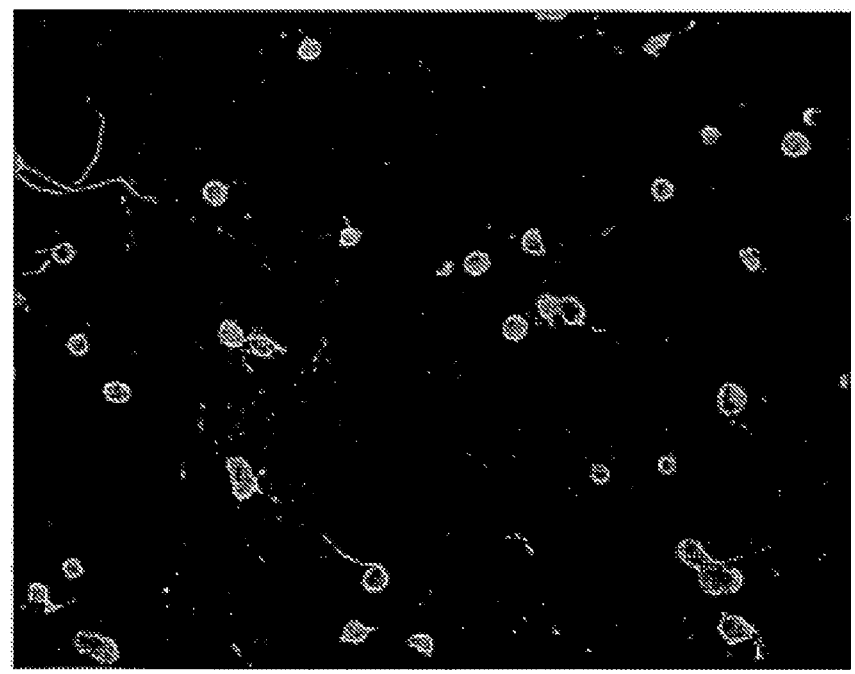
Figure 41A:
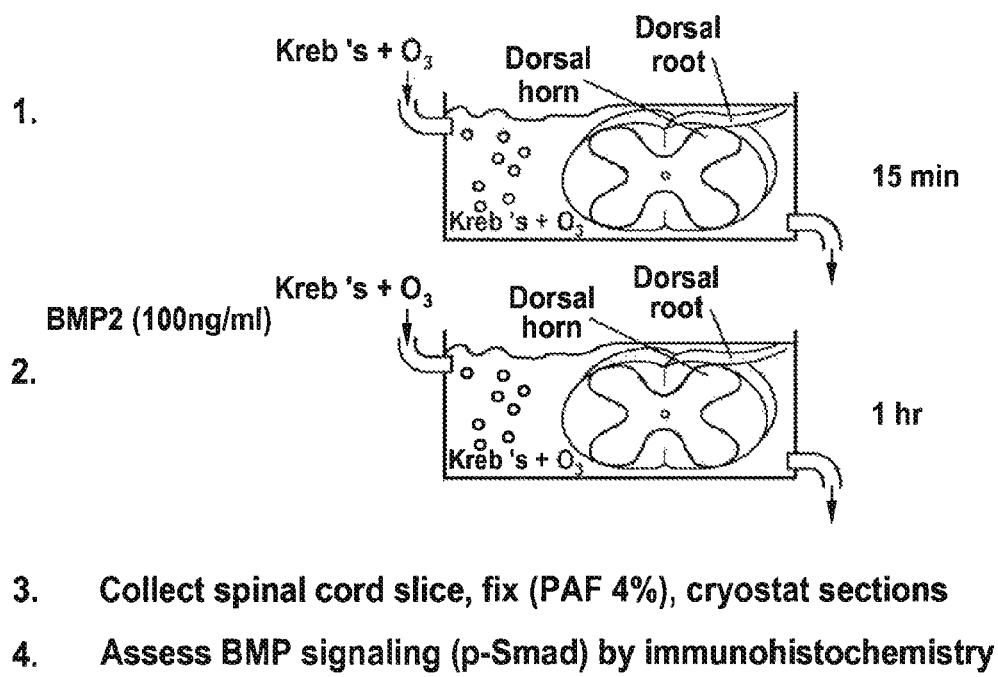
Figures 41B, 41C:
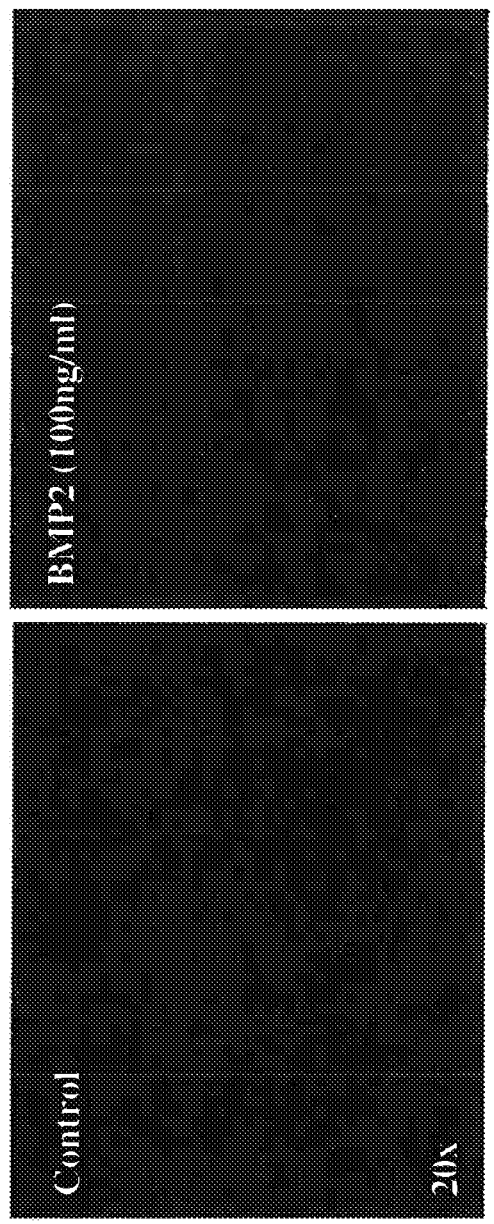
Figure 42:
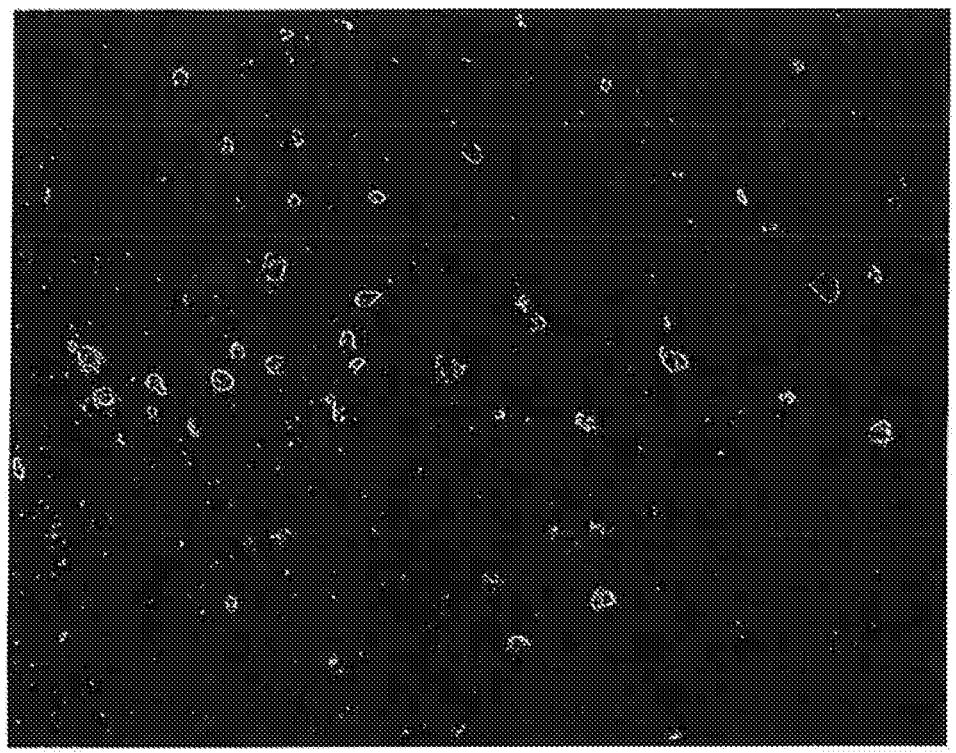
FIG. 42 is an image showing the slices co-stained with anti-NeuN (an antibody that labels neurons) to show that the detected increase of BMP signaling (phospho-Smad1) observed in the spinal cord is also neuronal.

Our studies are the first to examine expression of RGMa in a wide variety of tissues. Other studies have focused on detailing the expression pattern of endogenous RGMa in the central nervous system and during development (Samad et al., *J. Neurosci.* 24:2027-2036, 2004; Niederkofler et al., *J. Neurosci.* 24:808-818, 2004; Schmidtmer and Engelkamp *Gene Expr. Patterns* 4:105-110, 2004; Oldekamp et al., *Gene Expr Patterns* 4:283-288, 2004). To begin to elucidate the role of RGMa in vivo, we performed Northern blot analysis of endogenous RGMa expression in a variety of adult rat tissues. RGMa message is widely expressed in many of the tissues tested, including heart, brain, lung, liver, skin, kidney, and testis (FIG. 37). Two distinct bands were seen in some tissues, possibly representing alternative transcription initiation or alternative splicing.

BMP Signaling Occurs in Neurons of the Adult Spinal Cord which Express RGMa

Next, we demonstrated that RGMa expression in vivo correlates with its hypothesized role as a co-receptor for BMP signaling. RGMa mRNA has been is widely expressed in a complementary fashion to DRAGON in the central nervous system (Samad et al., *J. Neurosci.* 24:2027-2036, 2004; Niederkofler et al., *J. Neurosci.* 24:808-818, 2004; Schmidtmer and Engelkamp *Gene Expr. Patterns* 4:105-110, 2004; Oldekamp et al., *Gene Expr Patterns* 4:283-288, 2004), including ventral horn neurons of the spinal cord (Samad et al., *J. Neurosci.* 24:2027-2036, 2004). We therefore determined whether RGMa protein was expressed in ventral horn neurons, and we examined whether these neurons also showed evidence of BMP signaling, i.e., nuclear accumulation of p-Smad1/5/8. Adult rat spinal cord sections were analyzed by immunofluorescence microscopy with α-RGMa, α-p-Smad1/5/8, and/or anti-neuron-specific nuclear protein antibody (α-NeuN) to visualize neuronal cell bodies (Samad et al., *J. Neurosci.* 24:2027-2036, 2004). RGMa staining colocalized with NeuN staining in ventral horn motor neurons (FIGS. 38A-38C). Ventral horn motor neurons were also positive for nuclear p-Smad1/5/8 (FIGS. 38D-38F), suggesting that there is basal signal transduction via the BMP pathway in these cells. Thus, endogenous RGMa is expressed in ventral horn motor neurons which also generate BMP signals, indicating a role for RGMa as a BMP co-receptor in vivo.

BMPs are members of the TGF-β superfamily of ligands which play a pleitropic role in vertebrate development and adult tissues (Hogan, *Genes Dev.* 10:1580-1594, 1996; Zhao, *Genesis* 35:43-56, 2003; Balemans and Van Hul *Dev. Biol.* 250:231-250, 2002). These functions require tight spatiotemporal regulation and specific activation via receptor complexes of particular intracellular signaling pathways. In order to generate specificity and to finely tune these signals, regulation occurs at multiple levels extracellularly, at the membrane surface, and intracellularly (Shi and Massague, *Cell* 113:685-700, 2003; Balemans and Van Hul *Dev. Biol.* 250: 231-250, 2002; von Bubnoff and Cho *Dev. Biol.* 239:1-14, 2001).

For the BMP pathway, most regulatory mechanisms identified to date are inhibitory. Soluble BMP antagonists such as noggin, chordin, chordin-like, follistatin, FSRP, DAN, cerebrus, and gremlin bind BMPs in the extracellular space and mask receptor binding interfaces for BMP type I and type II receptors (Balemans and Van Hul *Dev. Biol.* 250:231-250, 2002; Groppe et al., *Nature* 420:636-642, 2002). At the membrane surface, BAMBI (BMP and activin receptor membrane bound inhibitor), which is structurally related to type I receptors in the extracellular domain but lacks the intracellular serine/threonine kinase domain, inhibits BMP signals by stably associating with type II receptors and preventing formation of the active receptor complexes (Onichtchouk et al., *Nature* 401:480-485, 1999). Inhibin, in concert with its co-receptor betaglycan (also known as the TGF-β type III receptor), competes with BMPs for access to BMP type II receptors (Wiater and Vale, *J. Biol. Chem.* 278:7934-7941, 2003). Inside the cell, inhibitory Smads (Smad 6 and Smad 7) inhibit signaling by either interacting with phosphorylated type I receptors to prevent activation of receptor-activated Smads (Imamura et al., *Nature* 389:622-626, 1997; Nakao et al., *Nature* 389:631-635, 1997; Souchelnytskyi et al., *J. Biol. Chem.* 273:25364-25370, 1998), or through competition to prevent formation of the receptor-activated Smad/Co-Smad complex (Hata et al., *Genes Dev.* 12:186-197, 1998). Other intracellular molecules Smurf1 and Smurf2 (Smad ubiquitination regulatory factors), selectively target activated type I receptors and Smad proteins for degradation (Zhu et al., *Nature* 400:687-693, 1999; Kaysak et al., *Mol. Cell* 6:1365-1375, 2000; Zhang et al., *Proc. Natl. Acad. Sci. USA.* 98:974-979, 2001).

For other TGF-β superfamily members, accessory or co-receptors also play an important regulatory role to promote or inhibit ligand binding (Shi and Massague, *Cell* 113:685-700, 2003; Lopez-Casillas et al., *Cell* 73:1435-1444, 1993; Shen and Schier, *Trends Genet.* 16:303-309, 2000; Cheng et al., *Genes Dev.* 17:31-36, 2003; Gray et al., *Proc. Natl. Acad. Sci. USA* 100:5193-5198, 2003). Recently, we identified DRAGON (RGMb) as the first known co-receptor for BMP signaling (Samad et al., *J. Biol. Chem.* 280:14122-14129, 2005). We therefore investigated whether another RGM family member, RGMa, was similarly involved in the BMP signaling pathway. Here, we have demonstrated that RGMa is a BMP co-receptor which enhances cellular responses to BMP, but not TGF-β.

Although transfection of RGMa into LLC-PK1 cells enhanced BMP signal transduction without exogenously added ligand, our results indicate that this process is ligand-dependent, which is supported by the fact that RGMa-mediated BMP signaling was inhibited by noggin, a soluble BMP inhibitor which binds and sequesters BMP ligands, preventing access to BMP receptors (Balemans and Van Hul *Dev. Biol.* 250:231-250, 2002; Groppe et al., *Nature* 420:636-642, 2002). However, this does not pinpoint the endogenous ligand (s) responsible for RGMa-mediated BMP signaling in these cells, since noggin has been shown to bind and antagonize several BMPs, including BMP-2, BMP-4, and BMP-7, as well as some other TGF-β superfamily members, including growth and differentiation factor 5 (Balemans and Van Hul *Dev. Biol.* 250:231-250, 2002; Groppe et al., *Nature* 420:636-642, 2002; Zimmerman et al., *Cell* 86:599-606, 1996; Merino et al., *Dev. Biol.* 206:33-45, 1999). Our findings that a neutralizing antibody to BMP-2 and BMP-4 also inhibited RGMa-mediated BMP signaling suggest that the major endogenous ligand(s) in these cells may be BMP-2 and/or BMP-4. Indeed, RT-PCR confirmed that these cells do endogenously express both BMP-2 and BMP-4. However, this does not preclude the possibility that some portion of the signaling is related to other BMP ligands. Indeed, the manufacturer of this neutralizing antibody does report some minimal cross-reactivity to other BMP ligands. Additionally, this antibody did not completely inhibit RGMa-mediated BMP signaling to baseline levels. Further evidence for the role of RGMa as a co-receptor for BMP-2 and/or BMP-4 is provided by binding and crosslinking studies of purified RGMa.Fc in solution. These assays allow the determination of the binding properties of single types of receptors and combinations of receptors in isolation, avoiding the presence of any confounding co-expressed accessory proteins that may also be present at the cell surface (del Re et al., *J. Biol. Chem.* 279:22765-22772, 2004). Here, RGMa.Fc bound directly and specifically to $^{125}$I-BMP-2 and $^{125}$I-BMP-4, and binding was competitively inhibited by excess cold BMP-2 and BMP-4, but not BMP-7 or TGFb1. RGMa.Fc also formed a complex with the BMP type I receptor ALK6.Fc, and the presence of RGMa.Fc in combination with ALK6.Fc increased binding to $^{125}$I-BMP-2 compared with ALK6.Fc alone. No further increase in binding was seen with the addition of the BMP type II receptor.Fc (data not shown). Although this increased binding was additive, not synergistic, the fact that RGMa.Fc formed a complex with ALK6.Fc indicates that RGMa associates with BMP type I receptors that on the cell surface, thereby increasing overall binding of BMP ligands to the receptor complex and enhancing BMP signal transduction. While the binding and crosslinking experiments were performed using RGMa.Fc and BMP receptor.Fc fusion proteins in solution, support for the role of GPI-anchored, cell-surface RGMa in the BMP signaling pathway is provided by our findings that RGMa-mediated BMP signaling was inhibited by dominant negative BMP type I receptors and by dominant negative Smad1, using a BMP-responsive luciferase reporter assay in cell culture. Additionally, transfection of RGMa into LLC-PK1 cells increased phosphorylation of endogenous Smad1/5/8, and increased expression of endogenous Id1 protein, an important target gene of BMP signaling in many tissues (Hollnagel et al., *J. Biol. Chem.* 274:19838-19845, 1999; Korchynskyi and ten Dijke *J. Biol. Chem* 277:4883-4891, 2002; Lopez-Rovira et al., *J. Biol. Chem.* 277:3176-3185, 2002; Miyazono and Miyazawa, *Sci STKE.* 2002:PE40, 2002; ten Dijke et al., *Mol. Cell. Endocrinol.* 211:105-113, 2003). The physiologic role of endogenous RGMa as a BMP co-receptor in vivo is indicated by RGMa expression in spinal cord neurons along with nuclear accumulation of p-Smad1/5/8, indicative of BMP signal transduction in these cells. Interestingly, RGMa also acts as a cell survival factor by binding to the receptor neogenin and inhibiting neogenin's pro-apoptotic activity (Rajagopalan et al., *Nat. Cell Biol.* 6:756-762, 2004; Matsunaga et al., *Nat. Cell Biol.* 6:749-755, 2004). RGMa and DRAGON are members of the RGM family of proteins, which also includes the juvenile hemochromatosis gene HJV. RGM family members are highly conserved across vertebrates and invertebrates and share significant sequence homology as well as similar structural features (Monnier et al., *Nature* 419:392-395, 2002; Papanikolaou et al., *Nat. Genet.* 36:77-82, 2004; Samad et al., *J. Neurosci.* 24:2027-2036, 2004; Niederkofler et al., *J. Neurosci.* 24:808-818, 2004; Schmidtmer and Engelkamp, *Gene Expr. Patterns* 4:105-110, 2004; Oldekamp et al., *Gene Expr Patterns* 4:283-288, 2004). HJV also mediates BMP signaling (J. L. Babitt, unpublished data), indicating that these family members all share the ability to act as co-receptors to enhance BMP signals. Our results do not reveal any differences between RGMa and DRAGON in regard to their function as BMP co-receptors. Both bind to BMP-2 and BMP-4, but not BMP-7 or other members of the TGF-β superfamily. Both signal via the BMP type I receptors ALK3 and ALK6 and Smad1. A secreted protein, Kielin/chordin-like protein, has recently been described as a paracrine enhancer of BMP-7 signaling (Lin et al., *Nat. Med.* 11:387-393, 2005). Thus, multiple enhancing regulatory mechanisms may exist for BMP signaling to complement the inhibitory regulatory mechanisms which have been described (Shi and Massague, *Cell* 113:685-700, 2003; Balemans and Van Hul *Dev. Biol.* 250:231-250, 2002; von Bubnoff and Cho *Dev. Biol.* 239:1-14, 2001).

The role of RGM family members may be to differentially increase the sensitivity of cells in which they are expressed to low levels of BMP ligands, thus contributing to the tight spatiotemporal regulation of BMP signal transduction. Northern blot analysis of adult rat tissues revealed that endogenous RGMa is expressed in a variety of organs, including heart, brain, lung, liver, skin, kidney, and testis. While some studies have reported a more limited distribution, they were largely focused on expression in the central nervous system and during development (Samad et al., *J. Neurosci.* 24:2027-2036, 2004; Niederkofler et al., *J. Neurosci.* 24:808-818, 2004; Schmidtmer and Engelkamp, *Gene Expr. Patterns* 4:105-110, 2004; Oldekamp et al., *Gene Expr Patterns* 4:283-288; 2004). Additionally, the one previously published Northern blot of RGMa expression in a variety of tissues was limited by under-exposure (Niederkofler et al., *J. Neurosci.* 24:808-818, 2004), also a possible explanation for their finding only the larger of the two bands seen in our study. Recent work has also demonstrated a broader tissue distribution for DRAGON, including many tissues throughout the reproductive axis (Xia et al., *Endocrinology* [Epub ahead of print], 2005). We have also found DRAGON expression in the adult rat heart, liver, and kidney by Northern blot (data not shown). While HJV expression has been described predominantly in the liver, cardiac muscle, and skeletal muscle (Papanikolaou et al., *Nat. Genet.* 36:77-82, 2004; Samad et al., *J. Neurosci.* 24:2027-2036, 2004; Niederkofler et al., *J. Neurosci.* 24:808-818, 2004; Schmidtmer and Engelkamp, *Gene Expr. Patterns* 4:105-110, 2004; Oldekamp et al., *Gene Expr Patterns* 4:283-288, 2004), one recent study suggested that HJV is also expressed in the adult mouse brain, lung, spleen, kidney, testis, blood, stomach, and intestine (Rodriguez Martinez et al., *Haematologica* 89:1441-1445, 2004). Thus, RGM family member expression overlaps in a variety of tissues. However, it is possible that the distribution within those tissues is different. For example, in the central nervous system, where RGMa and DRAGON expression have been best characterized, they are predominantly expressed in a non-overlapping areas (Samad et al., *J. Neurosci.* 24:2027-2036, 2004; Niederkofler et al., *J. Neurosci.* 24:808-818, 2004; Schmidtmer and Engelkamp, *Gene Expr. Patterns* 4:105-110, 2004; Oldekamp et al., *Gene Expr Patterns* 4:283-288, 2004).

Our results define the first family of proteins which function as BMP co-receptors. RGM family members increase the sensitivity of cells in which they are expressed to BMP stimulation, and allow these cells to respond earlier or more robustly to a low level of BMP ligand. RGM family members thus represent an important addition to the complex array of regulatory molecules which help to generate specificity and tightly coordinate cellular responses to BMP ligands.

Experiments relating to RGMa were carried out as follows.

cDNA Subcloning cDNA encoding murine RGMa was subcloned into the expression vector pCDNA4/HisB (Promega, Madison, Wis.). cDNA encoding the extracellular domain of murine RGMa was amplified by polymerase chain reaction (PCR) and subcloned into the mammalian expression vector pIgplus (R & D Systems, Minneapolis, Minn.) into the restriction sites BamHI and HindIII in-frame with the Fc portion of human immunoglobulin (IgG) to generate soluble RGMa.Fc fusion protein.

Cell Culture and Transfection

HEK 293 cells and LLC-PK1 cells were obtained from the American Type Culture Collection (ATCC #CRL1573 and CL-101 respectively) and cultured in Dulbecco's modification of Eagle's medium (DMEM; Cellgro Mediatech, Herndon, Va.) containing 10% fetal bovine serum (FBS; Atlanta Biologicals, Lawrenceville, Ga.). All plasmid transfections were performed with Lipofectamine 2000 (Invitrogen, Carlsbad, Calif.) according to manufacturer instructions. Stably transfected cells were selected and cultured in 2 mg/ml G418 (Cellgro Mediatech).

Luciferase Assay

LLC-PK1 cells were transiently transfected with a TGF-β responsive firefly luciferase reporter, (CAGA)12MLP-Luc (CAGA-Luc, Dennler et al., *EMBO J.* 17:3091-3100, 1998), or a BMP responsive firefly luciferase reporter (BRE-Luc, Korchynskyi, and ten Dijke, *J. Biol. Chem* 277:4883-4891, 2002) (both kindly provided by Peter ten Dijke, Netherlands Cancer Institute), in combination with pRL-TK Renilla luciferase vector (Promega) in a ratio of 10:1 to control for transfection efficiency, with or without co-transfection with RGMa cDNA. Forty-eight hours after transfection, cells were serum starved in DMEM supplemented with 1% FBS for 6 hours and treated with varying amounts of TGF-β, BMP-2, BMP-4, or BMP-7 ligands (R&D Systems) for 16 hours, in the absence or presence of noggin (R&D Systems) or anti-BMP-2/4 antibody (R&D Systems). Cells were lysed, and luciferase activity was determined with the Dual Reporter Assay (Promega) according to the manufacturer's instructions. Experiments were performed in duplicate or triplicate wells. Relative luciferase units (R.L.U.) were calculated as the ratio of firefly (reporter) and Renilla (transfection control) luciferase values.

Reverse Transcription Polymerase Chain Reaction (RT-PCR)

LLC-PK1 cells were grown to confluence on 6-cm tissue culture plates. Total RNA was isolated using the RNeasy Mini Kit (QIAGEN Inc., Valencia, Calif.) including DNase digestion with the RNase-Free DNase Set (QIAGEN) according to the manufacturer's instructions. First strand cDNA synthesis was performed using iScript cDNA Synthesis Kit (Bio-Rad, Hercules, Calif.) according to the manufacturer's instructions. Transcripts of BMP-2 were amplified using the forward primer 5'-CGTGACCAGACTTTTGGACAC-3' (SEQ ID NO:16) and reverse primer 5'-GGCATGATTAGTGGAGT-TCAG-3' (SEQ ID NO:17). Transcripts of BMP-4 were amplified using the forward primer 5'-AGCAGCCAAAC-TATGGGCTA-3' (SEQ ID NO:18) and reverse primer 5'-TG-GTTGAGTTGAGGTGGTCA-3' (SEQ ID NO:19).

Purification and Characterization of RGMa.Fc

HEK 293 cells stably expressing RGMa.Fc were cultured in DMEM supplemented with 5% FBS using 175-cm$^2$ multifloor flasks (Denville Scientific, Southplainfield, N.J.). RGMa.Fc was purified from the media of stably transfected cells via one-step Protein A affinity chromatography using HiTrap rProtein A FF columns (Amersham Biosciences, Piscataway, N.J.) as described in del Re et al., (*J. Biol. Chem.*

279:22765-22772, 2004). Purified protein was eluted with 100 mM glycine-HCl, pH 3.2 and neutralized with 0.3 M Tris-HCl pH 9 as described in del Re et al, supra).

Purified human RGMa.Fc was subjected to reducing sodium dodecylsulfate-polyacrylamide gel electrophoresis (SDS-PAGE) using pre-cast NuPAGE Novex 4-12% Bis-Tris gels (Invitrogen), and gels were stained with Bio-safe Coomassie blue (Bio-Rad) to determine the purity of RGMa.Fc and quantify protein concentration. For Western blot analysis, gels were electroblotted to polyvinylidene difluoride filter (PDVF) membranes (Bio-Rad). Membranes were blocked with TBS-T (Tris buffered saline, 0.2% Tween 20) containing 6% milk powder for 1 hour and washed three times with TBS-T for 10 minutes. Membranes were then probed with an affinity purified rabbit polyclonal anti-mouse RGMa antibody (α-RGMa) raised against the peptide RMDEEVVNAVEDRDSQGLYLC (SEQ ID NO:20; amino acids 296-316 in the C terminus of mouse RGMa upstream of its hydrophobic tail; GenBank Accession Number NM 177740) (1:2,000) at 4° C. overnight, or with anti-Fc antibody (Jackson ImmunoResearch, West Grove, Pa.) (1:2000) at room temperature for 1 hr in blocking solution. Membranes were washed with TBS-T and incubated with donkey anti-rabbit or anti-goat horseradish peroxidase (HRP)-linked secondary antibody (1:10,000) (Santa Cruz Biotechnology, Santa Cruz, Calif.). Antibody binding was detected with chemiluminescence reagent (PerkinElmer Life Sciences, Boston, Mass.) and exposed to BioMax XAR film (Kodak, Rochester, N.Y.).

Ligand Iodination

Two mg of carrier free human BMP-2 and BMP-4 ligand (R & D Systems) per reaction was iodinated with [$^{125}$I] by the modified chloramine-T method as described in Frolik et al., *J. Biol. Chem.* 259:10995-11000, 1984).

Binding Assay 25 ng purified RGMa.Fc in 1× Tris buffered saline/Casein blocking buffer (BioFX, Owings Mills, Md.) or buffer alone was incubated with $^{125}$I-BMP-2 or $^{125}$I-BMP-4 in a total volume of 200 ml overnight at 4° C., either alone or in the presence of 80 ng cold BMP-2, BMP-4, BMP-7 or TGF-β1 for competition assays. For mixing studies, buffer alone, 10 ng purified RGMa.Fc alone, 10 ng ALK6.Fc alone (R & D Systems), or 10 ng each of RGMa.Fc and ALK6.Fc together were incubated in 1× Tris buffered saline/Casein blocking buffer with $^{125}$I-BMP-2 in a total volume of 200 ml. The reaction mix was then incubated for 1.5 hrs at 4° C. on protein A coated plates (Pierce, Rockford, Ill.), plates were washed with wash solution (KPL, Gaithersberg, Md.), and individual wells were counted with a standard g counter.

DSS Crosslinking in Solution 100 ml $^{125}$I-BMP-2 or $^{125}$I-BMP-4 (400,000 C.P.M) was incubated overnight at 4° C. with an equal volume of 20 mM HEPES (pH 7.8), 0.1% bovine serum albumin, and protease inhibitors (Roche Diagnostics, Mannheim, Germany) alone, or containing 25 ng RGMa.Fc or ALK5.Fc (R & D Systems), in the absence or presence of 80 ng cold BMP-2 or BMP-4. This mixture was incubated in the absence or presence of 2.5 mM disuccinimidyl suberate (DSS, Sigma, St. Louis, Mo.) in dimethyl sulfoxide for 2 hr on ice, followed by quenching of DSS activity with 40 mM Tris (pH 7.5) for 15 minutes. The mixture was then centrifuged and the supernatant incubated with Protein A Sepharose beads (Amersham) at 4° C. for 2 hr to precipitate hot BMP-2 or -4 bound to RGMa.Fc. Beads were washed with phosphate buffered saline (PBS) and protein eluted by non-reducing Laemmli sample buffer (Bio-Rad). Eluted protein was separated by SDS-PAGE and analyzed by autoradiography.

For receptor crosslinking studies, 200 ng RGMa.Fc, 200 ng ALK6.Fc; and/or 100 ng BMP2 were incubated in 100 ml 20 mM HEPES (pH 7.8), 0.1% bovine serum albumin, and protease inhibitors at 4° C. overnight. The mixtures were then crosslinked with DSS, incubated with protein A beads, and eluted with non-reducing Laemmli sample buffer as described above. The protein complex was then separated by non-reducing SDS-PAGE, electroblotted to PVDF membranes, and analyzed by Western blot using RGMa antibody (1:2000) as described above for RGMa.Fc.

Measurement of Smad1/5/8 Phosphorylation and Id1 Expression

LLC-PK1 cells plated to 70% confluence were transiently transfected with 5 mg RGMa cDNA or empty vector. Twenty-four hours after transfection cells were incubated in DMEM supplemented with 1% FBS in the absence or presence of 50 ng/ml BMP2 for 2 hours at 37° C. Cells were sonicated and lysed in 200 mM Tris-Hcl, pH 8.0, 100 mM NaCl, 1 mM EDTA, 0.5% NP-40, and 10% glycerol containing a mixture of protease inhibitors (Roche Diagnostics) for twenty minutes on ice. After centrifugation for 20 minutes at 4° C., the supernatant was assayed for protein concentration by colorimetric assay (BCA kit, Pierce). 30 mg protein was separated by SDS-PAGE and transferred to PVDF membranes. Membranes were probed with α-RGMa (1:2000) as described above for RGMa.Fc. Membranes were stripped in 0.2 M glycine, pH 2.5, 0.5% Tween 20 for 1 hour, and re-probed in succession with rabbit polyclonal anti-p-Smad1/5/8 antibody (α-p-Smad1/5/8, Cell Signaling, Beverly, Ma) (1:1000) at 4° C. overnight according to the manufacturer's instructions, rabbit polyclonal anti-Smad1 antibody (α-Smad1, Upstate Biotechnology, Lake Placid, N.Y.) (1:250) at 4° C. overnight, mouse monoclonal anti-β-actin antibody (α-β-actin, clone AC 15, Sigma) (1:5000) at room temperature for 1 hour, and rabbit polyclonal anti-Id1 antibody (α-Id1, C 20, Santa Cruz Biotechnology) (1:200) at 4° C. overnight followed by the appropriate HRP-conjugated secondary antibody and chemiluminescence detection after each as described above. Chemiluminescence was quantitated using IPLab Spectrum software (Scanalytics, Vienna, Va.).

Northern Blot

Adult rat total RNA was separated on a 1.5% formaldehyde agarose gel and blotted onto GeneScreen Plus membrane (NEN, Boston, Mass.) as described in Costigan et al. (*J. Neurosci.* 18:5891-5900, 1998).

Immunohistochemistry

Freshly dissected adult rat lumbar spinal cord was embedded in OCT (Sakura, Tokyo, Japan), frozen on dry ice, cut by cryostat in 16 mm sections, and stored at −80° C. Spinal sections were fixed in 4% paraformaldehyde, washed 3 times in PBS and incubated for 1 hr at room temperature in blocking buffer (1% bovine serum albumin, 0.5% Triton X in PBS). Fixed sections were incubated overnight at 4° C. in blocking buffer with rabbit polyclonal α-RGMa (1/500) or rabbit polyclonal α-p-Smad1/5/8 (1/100), in combination with mouse monoclonal anti-neuron-specific nuclear protein antibody (α-NeuN, 1/1000) (Chemicon, Temecula, Calif.) to visualize neuronal cell bodies. Sections were then washed 3 times in PBS and incubated with cyanin 3 (Cy3)-conjugated anti-rabbit and fluorescein isothiocyanate (FITC)-conjugated anti-mouse secondary antibodies (1/200 each, Jackson ImmunoResearch) for 1 hr at room temperature. Finally, sections were washed 3 times in PBS and visualized by fluorescence microscopy.

Enhancing DRAGON Activity for the Treatment or Prevention of a DRAGON-Related Condition Both the BMP/GDF and the TGF-β/Activin/Nodal branches of the TGF-β signaling pathway regulate cell proliferation. Normally, TGF-β can induce an antiproliferative gene response, arresting the cell cycle during G1. Dysfunction of these pathways has been documented in a variety of cancers. Dysregulation of the TGF-β pathway can occur at almost any level. The binding of the TGF-β ligands to the various TGF-β receptors is influenced by soluble protein inhibitors including, for example, noggin, chordin, caronte, and cerberus. Likewise, the downstream effects of TGF-β ligand binding are transduced by a protein cascade that includes the R-Smads, Co-Smads, and other co-factors. The antiproliferative gene responses may involve altering the expression of a variety of cell cycle regulators (e.g., the cyclin-dependent kinases) or proto-oncogenes (e.g., c-Myc and the retinoblastoma gene). Thus, an intervention that enhances the activity associated with a TGF-β receptor-ligand binding is a potential point for antiproliferative therapy.

Based on DRAGON's role as an enhancer of BMP-dependent intracellular signaling, compounds or therapies which enhance or mimic the biological activity of DRAGON may be therapeutically useful as an antiproliferative agent. Such candidate compounds include the wild-type DRAGON protein and any compound identified by one of the screening methods described herein.

DRAGON-enhancing therapy is effective for treating or preventing cancers such as pancreatic cancer which have mutations that disable a component of the TGF-β signaling pathway (Goggins et al., *Cancer Res.* 58: 5329-5332, 1998; Grady et al., *Cancer Res.* 59: 320-324, 1999; Villanueva et al., *Oncogene* 17: 1969-1978, 1998). Cancer-associated mutations have been identified in the TGF-β receptors, Smad4, and Smad2. Increased hepatocyte proliferation, reduced lung and liver apoptosis (Tang et al. *Nat. Med.* 4: 802-807, 1998), and increased mammary epithelial proliferation and ductal outgrowth in response to hormones (Barcellos-Hoff et al., *Breast Cancer Res.* 2: 92-99, 2000) has been observed in TGF-β1 heterozygous null mice. These studies suggest that a normal and functioning TGF-β signaling pathway has antiproliferative action in these cell types. Thus, DRAGON therapy is useful for treating cancers of these tissues.

Prostate cancer may also be successfully treated by increasing DRAGON biological activity. Recently, Masuda et al. (*Prostate*, 59: 101-106, 2004) reported that BMP7 expression is highest in the normal prostate glandular tissue and that levels trended lower during the development and progression of prostate cancer. These findings implicate dysfunctional TGF-β signaling along the BMP/GDF pathway. Although DRAGON does not directly interact with BMP7, both BMP7 and BMP4 (also expressed in normal prostate) signal through common combinations of BMP type I and type II receptors and intracellular R-Smads. Thus, enhancing BMP4 signaling may functionally reverse the deficit in BMP-7 during prostate cancer progression. BMP4 signaling is enhanced by increasing the biological activity of DRAGON either through administration of a DRAGON protein, a compound that mimics DRAGON's biological activity, or through gene therapy techniques. Thus, DRAGON therapy represents an important avenue for treatment of prostate cancer.

Pulmonary hypertension is another disorder that may be treated by enhancing DRAGON activity. Familial primary pulmonary hypertension is an autosomal dominant disorder caused by a mutation in the BMPRII. This disease, however, has a low (10-20%) penetrance into the affected population, suggesting that other endogenous mechanism may compensate for the genetic defect. The histopathologic changes observed in this autosomal disorder include smooth muscle cell proliferation and in situ thrombosis. Similar changes are observed in epigenetic forms of pulmonary hypertension.

The commonality among all of the diseases described above is a defect in the BMP/GDF branch of the TGF-β signaling pathway. In view of the promiscuity of the various BMP type I and type II receptors and the convergence of several signaling pathways on common intracellular effectors (e.g., the R-Smads), the common mechanism of increasing DRAGON activity and enhancing signaling through the remaining and functional BMP receptors and pathways can effectively treat the genetic and epigenetic forms of each disease.

Figure 16:
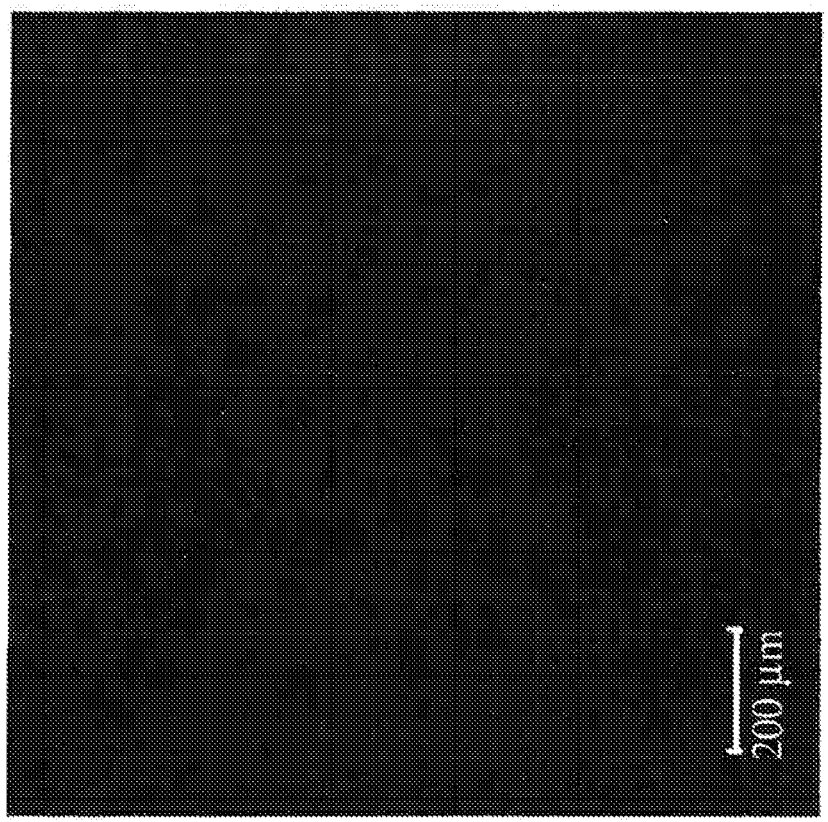
FIG. 16 is a photomicrograph showing the expression of DRAGON in the mouse knee joint.

Recent studies have demonstrated that the addition of BMPs to damaged joints promotes healing (Edwards, et al., *Semin. Arthritis Rheum.* 31: 33-42, 2001). We have discovered high levels of DRAGON expression in the knee joint of mice (FIG. 16). In view of DRAGON's role as a BMP co-receptor, these findings together indicate that enhanced DRAGON activity is also be useful for treating disorders of cartilage and bone. The BMPs and the BMP-related factor, GDF5/CDMP1, regulate early cartilage condensation and developmental joint formation (Storm et al., *Development* 122: 3969-3979, 1996; *Dev. Biol.* 209: 11-27, 1999). Enhancing DRAGON biological activity therefore is useful for promoting chondrogenesis and aiding in healing and repair. This is supported by molecular epidemiological studies which demonstrate that heterozygous missense mutations in noggin, an upstream inhibitor of BMP and GDF5, results in two autosomal dominant disorders; proximal symphalangism and multiple synostoses syndrome (Gong et al. *Nat. Genet.* 21: 302-304, 1999). Furthermore, noggin$^{-/-}$ mice die at or prior to birth with extreme mesenchymal malformations including excessive cartilage and bony fusions of the appendicular skeleton (Brunet et al. *Science* 280: 1455-1457, 1998; McMahon et al. *Genes Dev.* 12: 1438-1452, 1998). Mutations in CDMP1 are also associated with human hereditary disease that may be treatable with DRAGON therapy. Loss-of-function mutations in CDMP1 have been linked to chondrodysplasias (Hunter-Thompson type acromesomelic chondrodysplasia), autosomal dominant brachydactyly type C, and Grebe type chondrodysplasia. Thus, a variety of genetic and epigenetic disorders of the bone, cartilage, and joint are amenable to treatment by increasing DRAGON activity.

Figure 17:
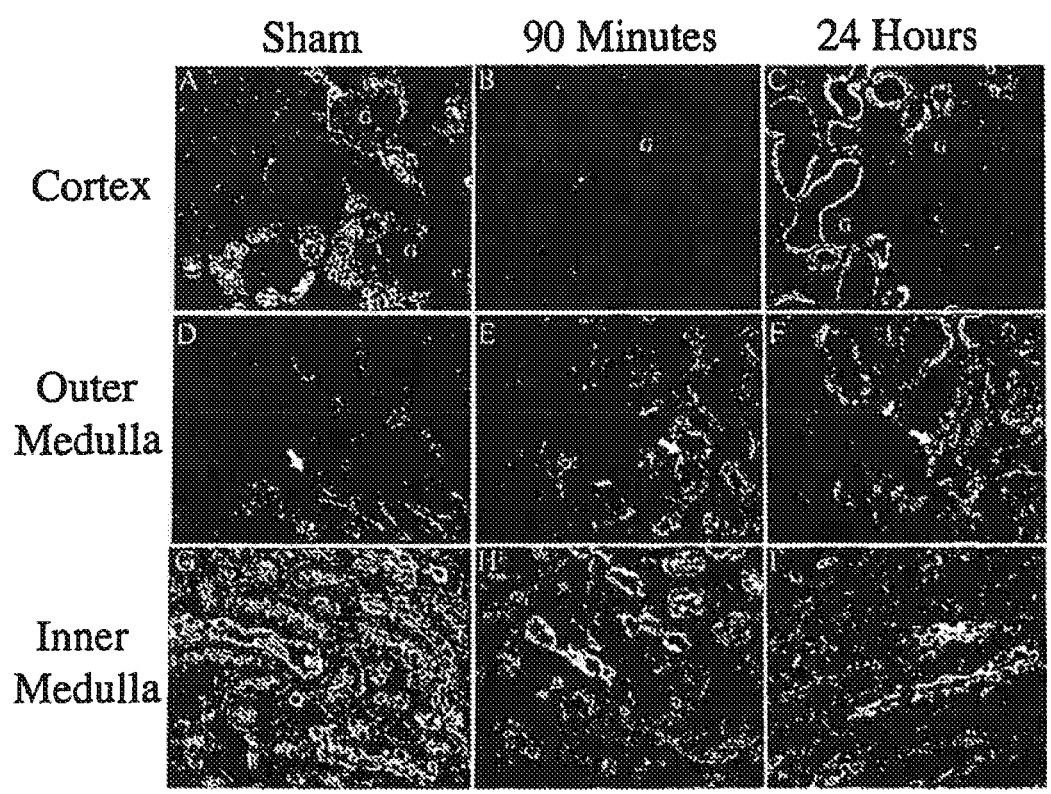
FIG. 17 is a series of photomicrographs showing the elevated expression of DRAGON in the ischemic kidney.

BMP-7 has been shown to reduce renal injury and fibrosis and act as a renotrophic factor. These effects of BMP-7 have been documented in models of acute and chronic renal failure and under conditions for prevention as well as therapy. The renotrophic effects of BMP-7 indicate that renal disorders and diseases may be treated by increasing DRAGON activity. Although DRAGON does not appear to directly interact with BMP-7, DRAGON expression is increased following an ischemic kidney injury (FIG. 17) it is known that signaling through BMP-2 and BMP-4, known DRAGON targets, converge on common intracellular R-Smads. Thus, it is possible to replicate the therapeutic effects of BMP-7 by increasing DRAGON-enhanced signaling through other BMP members. Renal diseases amenable to such treatment include ischemic kidney disease and renal fibrosis.

Figure 18:
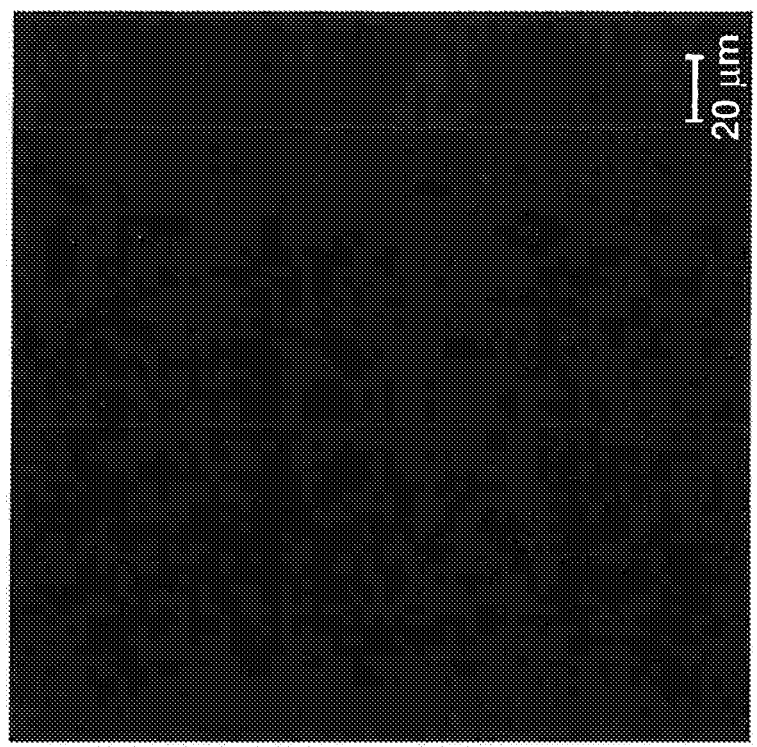
FIG. 18 is a photomicrograph showing the expression of DRAGON in the mouse testis.

DRAGON is also highly expressed in normal mouse testis (FIG. 18) and ova. Thus, male and female infertility that is associated with reduced levels of DRAGON expression may be treated by increasing DRAGON activity using any of the methods described here.

Inhibiting DRAGON Activity for the Treatment or Prevention of a DRAGON-Related Condition Certain pathological conditions are characterized by overactivation of the BMP/GDF branch of the TGF-β signaling pathway and, as such, are amenable to treatment by reducing DRAGON biological activity.

Figure 19:
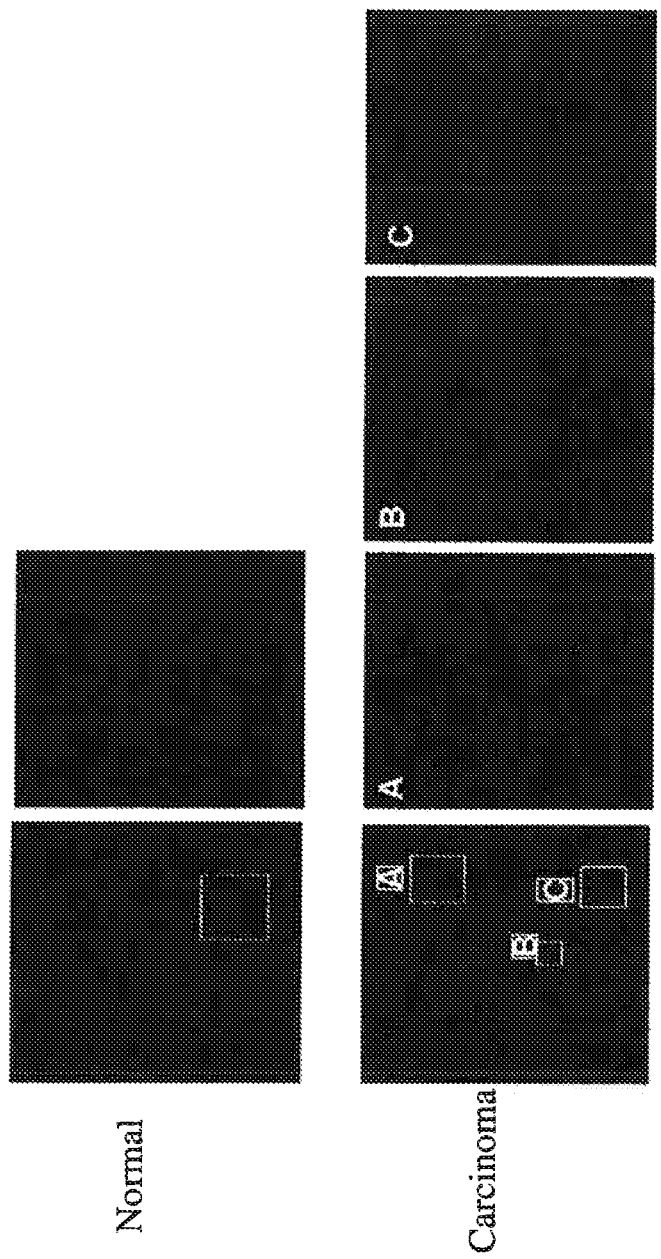
FIG. 19 is a photomicrograph showing the expression of DRAGON in normal breast tissue and breast cancer tissue.
Figures 21A, 21B, 21C, 21D:
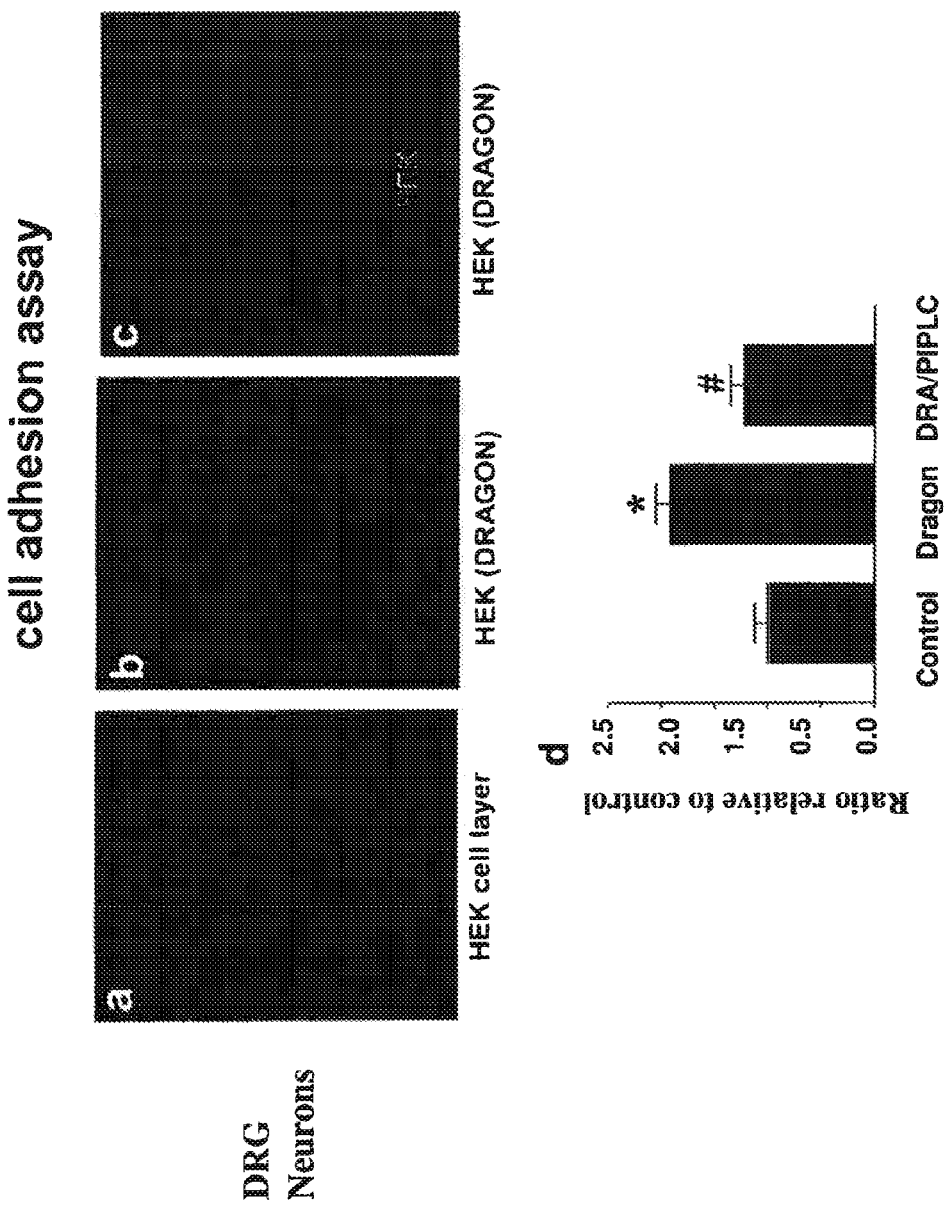
FIGS. 21A-21C are a series of photomicrographs that demonstrate the adhesion of DRG neurons to DRAGON-expressing HEK 293 cells. P14 neonatal DRG neurons were plated on a monolayer of confluent HEK cells and DRAGON transfected HEK cells. The culture slides were washed, fixed, and immunostained for DRG neurons using anti-NeuN (neuronal marker). Double immuno-labeling using anti-NeuN and anti-DRAGON indicates a direct interaction between DRAGON expressing HEK cells and DRG neurons (FIG. 21C).
FIG. 21D is a bar graph quantifying the adhesion experiment results. A 1.9-fold increase in the number of adherent DRG neurons was observed when plated on DRAGON-expressing HEK 293 cells, compared to control HEK 293 cells. Pretreatment of the DRAGON-expressing HEK cells with PI-PLC significantly reduced the adherence of DRG neurons.

We have discovered that DRAGON is present in abnormally high levels in breast cancer (FIG. 19) and colon cancer (FIG. 20). This finding indicates that breast and colon cancer may be treated or prevented by inhibiting the DRAGON activity. As discussed below, another benefit of inhibiting DRAGON activity in these forms of cancer is the reduction or prevention in tumor metastasis. Many metastases lodge in the bone, a tissue high in endogenous BMP activity. Thus, preventing metastases is an effective method for controlling the spread of secondary tumors which are often more invasive than the primary ones.

BMP2 is overexpressed in non-small cell lung carcinoma but has little or no expression in normal lung tissue (Langenfeld et al., *Carcinogenesis* 24: 1445-1454, 2003). It appears that BMP2 in lung tissue may act as a morphogen and also stimulate proliferation, differentiation, and migration, similar to its effects during embryogenesis. Thus, in view of DRAGON's enhancing effects on BMP2 signaling, non-small cell lung carcinoma may be treated, or at least prevented from metastasizing, by administration of a compound that inhibits DRAGON activity. Such compounds include, for example, a soluble DRAGON protein fragment (i.e., a DRAGON protein having a deletion of the GPI anchoring domain), or a candidate compound identified by any of the screening methods described herein. Therapy may be administered systemically (i.e., by intravenous, intramuscular, or subcutaneous injection) or by inhalation. Alternatively, DRAGON biological activity may be inhibited using antisense gene therapy or RNAi technology according to previously published methods.

DRAGON Analysis for Cancer Diagnosis

DRAGON expression is altered in may forms of cancer. Accordingly, alterations in DRAGON can be used as a cancer diagnostic or to identify patients with an increased likelihood of developing cancer. For example, the DRAGON gene of a patient not diagnosed as having cancer may be assessed to determine whether the gene contains an activating or an inactivating mutation. Mutations that result in inappropriately elevated DRAGON activity indicate an increased likelihood for developing, for example, a cancer of the breast, colon, testicles, or ovaries. Mutations that result in reduced DRAGON activity (e.g., inactivating mutations) indicate an increased likelihood for developing, for example, non-small cell lung cancer. Assessing the DRAGON gene of a patient can be done by any suitable means known in the art including, for example, sequencing the gene, or assessing restriction fragment length polymorphisms, single nucleotide polymorphisms, RT-PCR, and in situ hybridization.

DRAGON expression can also be used to diagnose cancer. For example, the presence of an altered DRAGON gene (i.e., one with an inactivating mutation or one that causes constitutive activity) may be assessed in a biological sample used for diagnosis. Such samples include, for example, tissue biopsies. Alternatively, for cancers characterized by altered DRAGON protein expression, the level of soluble DRAGON expression may be measured in a biological fluid such as blood, seminal fluid, or saliva, and compared to the DRAGON levels in healthy individuals. DRAGON may be measured at either the RNA or protein level. DRAGON protein levels may be measured by any appropriate technique known in the art including, for example, antibody-based assays such as ELISA or Western blotting. DRAGON RNA levels may be measured using any techniques known in the art including, for example, RT-PCR or Northern blotting. Biopsy samples may also be used to diagnose a cancerous or precancerous condition based on the DRAGON expression levels. In this case, the diagnosis can be based on the assessment of the DRAGON protein or RNA levels measured in the biopsy tissue.

DRAGON Promotes Cellular Adhesion

Cell surface GPI-anchored proteins, including the ephrins and tenascin, act as neuronal and non-neuronal cell adhesion molecules, binding to molecules expressed on neighboring cells or in the extracellular matrix. To examine whether DRAGON has a cell adhesion role, we measured the amount of adhesion between DRG neurons and HEK293 cells expressing recombinant DRAGON. DRAGON expression caused nearly a two-fold increase in the number of cultured DRG neurons that adhered to a monolayer of DRAGON-expressing HEK cells, compared to control HEK cells (FIGS. 21a-21d). Moreover, pretreatment of DRAGON-expressing HEK cells with PI-PLC resulted in only basal levels of DRG adhesion (FIGS. 21a-21d).

We also compared the cellular adhesive effects of DRAGON to other adhesion substrates. Tissue culture plates were coated with laminin, poly-D-lysine, laminin/polylysine, or DRAGON-Fc. DRG neurons were found to adhere most to the DRAGON-Fc plates, compared to any other adhesion substrate tested. Neuronal adhesion to each of the tested substrates was significantly greater than that measured in untreated plates.

To test whether DRAGON promotes adhesion in a homophilic manner, we assessed the interaction between native DRAGON and an AP-tagged DRAGON (DRAGON-AP) that is not detected using the anti-DRAGON antibody. Coexpression of both constructs followed by immunoprecipitation demonstrated a significant physical interaction between the two proteins, confirming that DRAGON is capable of homophilic interactions. This finding was confirmed by the addition of DRAGON-GST, also undetectable using the anti-DRAGON antibody, to HEK cells expressing recombinant native DRAGON. Using confocal microscopy, DRAGON-GST colocalized with the native DRAGON on the cell surface, further proving the homophilic DRAGON interaction.

To determine whether the DRAGON homophilic binding requires other molecules, we have used the previously described bead aggregation assay, commonly used for the analysis of cell adhesion molecules using purified proteins (Chappuis-Flament et al., 2001; De Angelis et al., 2001). This assay provides an in vitro cell free mimic of cell aggregation experiments. Green fluorescence and red fluorescence beads coated with DRAGON-Fc were dissociated by sonication before incubation in the presence of 1 mM calcium at 37° C. and observed microscopically. DRAGON-coated beads aggregated after 2 and 4 hours; whereas, Fc-coated beads (negative control) did not. DRAGON, therefore, shares a common mechanistic feature with the cadherins—both proteins mediate homophilic adhesive interaction in a calcium-dependent manner.

In order to assess the interaction between DRAGON and E-Cadherin, lysates of cultured primary DRG neurons were used for immunoprecipitation and Western blotting with anti-DRAGON and anti-Cadherin antibodies. These studies demonstrated that DRAGON and E-Cadherin physically interact, suggesting a common cellular function. Additional immunoprecipitation studies indicate that DRAGON facilitates the interaction between E-Cadherin and β-Catenin.

Figure 22:
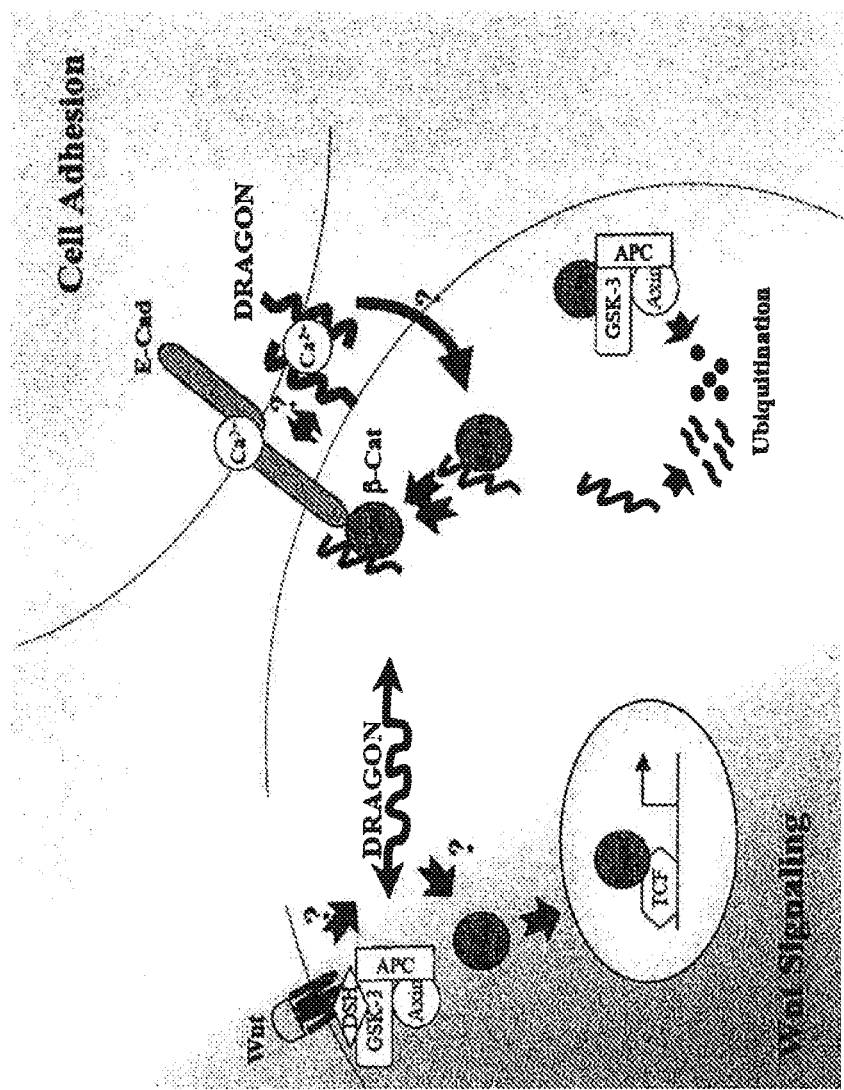
FIG. 22 is a schematic diagram of the role of DRAGON in cell adhesion.

It is likely that the DRAGON-dependent adhesive contacts are facilitated by an interaction of DRAGON with e-cadherin and β-catenin to increase their association (FIG. 22). In view of the pro-adhesion properties of DRAGON, therapies that increase DRAGON activity are useful for inhibiting tumor metastasis. Likewise, patient screening for DRAGON status of a malignant tumor can be used as an index of the likelihood of metastasis. Additionally, DRAGON-enhancing therapy can also treat lesions of epithelial cells by facilitating wound closure through epithelial cell adhesion across the lesion site. This therapy is useful for treating dermal lesions.

RNA Interference

RNAi is a method for decreasing the cellular expression of specific proteins of interest (reviewed in Tuschl, *Chembiochem* 2:239-245, 2001; Sharp, *Genes & Devel.* 15:485-490, 2000; Hutvagner et al., *Curr. Opin. Genet. Devel.* 12:225-232, 2002; and Hannon, *Nature* 418:244-251, 2002). In RNAi, gene silencing is typically triggered post-transcriptionally by the presence of double-stranded RNA (dsRNA) in a cell. This dsRNA is processed intracellularly into shorter pieces called small interfering RNAs (siRNAs). The introduction of siRNAs into cells either by transfection of dsRNAs or through expression of siRNAs using a plasmid-based expression system is increasingly being used to create loss-of-function phenotypes in mammalian cells. Based on the nucleotide sequence of the DRAGON genes; various RNAi molecules may be designed to inhibit DRAGON expression in vivo.

Double-stranded RNA (dsRNA) molecules contain distinct strands of RNA that have formed a complex, or a single RNA strand that has formed a duplex (small hairpin (sh) RNA). Typically, dsRNAs are about 21 or 22 base pairs, but may be shorter or longer if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. *Science* 296:550-553, 2002; Paddison et al: *Genes & Devel.* 16:948-958, 2002. Paul et al. *Nature Biotechnol.* 20:505-508, 2002; Sui et al. *Proc. Natl. Acad. Sci. USA* 99:5515-5520, 2002; Yu et al. *Proc. Natl. Acad. Sci. USA* 99:6047-6052, 2002; Miyagishi et al. *Nature Biotechnol.* 20:497-500, 2002; and Lee et al. *Nature Biotechnol.* 20:500-505 2002, each of which is hereby incorporated by reference.

Small hairpin RNAs consist of a stem-loop structure with optional 3' UU-overhangs. While there may be variation, stems can range from 21 to 31 base pairs (desirably 25 to 29 bp), and the loops can range from 4 to 30 base pairs (desirably 4 to 23 base pairs). For expression of shRNAs within cells, plasmid vectors containing, for example, either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Figures 23A, 23B:
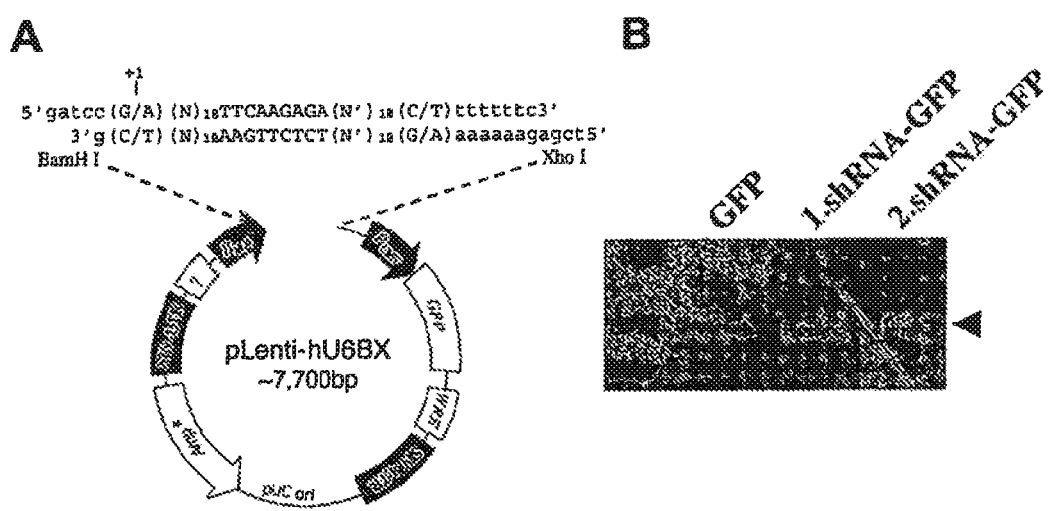
FIG. 23A is a vector map of the pLenti-hU6BX expression vector designed to express double stranded shRNA to silence DRAGON gene expression. The GFP cassette is used to check transfection and expression and the ampicillin resistance gene is used to select for positive clones.
FIG. 23B is a Western blot on extracts from SHSYSY neuroblastoma cells expressing two different shRNA vectors or a negative control. Each of the shRNA vectors is directed to a different region of the DRAGON cDNA.

We have designed, developed, and used a lentiviral expression vector to express shRNA from the human U6 snRNA promoter (Cellogenetics, Inc.) as shown in FIG. 23. These data demonstrate that the DRAGON gene may be silenced using shRNA technology.

siRNA

Short twenty-one to twenty-five nucleotide double stranded RNAs are effective at down-regulating gene expression in vitro, for example, in mammalian tissue culture cell lines (Elbashir et al., *Nature* 411: 494-498, 2001). Alternatively, siRNAs can be injected into an animal, for example, into the blood stream as described by McCaffrey et al., (*Nature* 418: 38-9, 2002).

siRNAs have been shown to effectively downregulate viral gene expression (Coburn et al. *J. Virol.* 76: 9225-31, 2002; Bitko et al. *BMC Microbiol.* 1:34, 2001; Ge et al., *Proc. Natl. Acad. Sci. USA* 100: 2718-23, 2003; Gitlin et al., *Nature* 418: 430-4, 2002).

siRNAs and antisense oligonucleotides have also been used effectively in vivo (U.S. Patent Publication 20030153519, McCaffrey et al., *Nature* 418: 38-39, 2002; McCaffrey et al., *Hepatology.* 38:503-8, 2003).

Methods for producing siRNAs are standard in the art. For example, the siRNA can be chemically synthesized or recombinantly produced. For example, short sense and antisense RNA oligomers can be synthesized and annealed to form double-stranded RNA structures with 2-nucleotide overhangs at each end (Caplen, et al. *Proc. Natl. Acad. Sci. USA,* 98:9742-9747, 2001; Elbashir, et al. *EMBO J.,* 20:6877-88, 2001). These double-stranded siRNA structures can then be directly introduced to cells, either by passive uptake or a delivery system of choice, such as described below.

In some embodiments, siRNAs are generated by processing longer double-stranded RNAs, for example, in the presence of the enzyme dicer under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In preferred embodiments, at least one strand of the siRNA molecules has a 3' overhang from about 1 to about 6 nucleotides in length, though it may be from 2 to 4 nucleotides in length. More preferably, the 3' overhangs are 1-3 nucleotides in length. In other embodiments, one strand has a 3' overhang and the other strand is blunt-ended or also has an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In some embodiments, the RNAi construct is in the form of a hairpin structure. The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev,* 2002, 16:948-58; McCaffrey et al., *Nature,* 2002, 418: 38-9; McManus et al., *RNA,* 2002, 8:842-50; Yu et al., *Proc Natl. Acad. Sci. USA,* 2002, 99:6047-52). Preferably, hairpin RNAs are engineered in cells or in animals to ensure continuous and stable suppression of a desired gene. It is known in the art that siRNAs can be produced by processing a hairpin RNA in the cell.

In other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA. PCT application WO01/77350 describes an exemplary vector for bi-directional transcription of a transgene to yield both sense and antisense RNA transcripts of the same transgene in a eukaryotic cell.

Methods for the production and therapeutic administration of siRNAs for in vivo therapies are described in U.S. Patent Publications: 20030180756, 2003/0157030, and 20030170891. Methods describing the successful in vivo use of siRNAs are described by Sang et al. (*Nature Medicine* 9: 347-351, 2003).

Gene Therapy

Gene therapy is another therapeutic approach for modulating DRAGON activity in a patient. Heterologous nucleic acid molecules, encoding for example a DRAGON anti-sense nucleic acid, a biologically active DRAGON protein, a soluble DRAGON protein, or a DRAGON fusion protein, can be delivered to the target cell of interest. The nucleic acid molecules must be delivered to those cells in a form in which they can be taken up by the cells and so that sufficient levels of protein can be produced to provide a therapeutic benefit.

Transducing viral (e.g., retroviral, adenoviral, and adeno-associated viral) vectors can be used for somatic cell gene therapy, especially because of their high efficiency of infection and stable integration and expression (see, e.g., Cayouette et al., *Human Gene Therapy* 8:423-430, 1997; Kido et al., *Current Eye Research* 15:833-844, 1996; Bloomer et al., *J. Virology* 71:6641-6649, 1997; Naldini et al., *Science* 272: 263-267, 1996; and Miyoshi et al., *Proc. Natl. Acad. Sci. USA* 94:10319, 1997). For example, a full length gene, or a portion thereof, can be cloned into a retroviral vector and expression can be driven from its endogenous promoter, from the retroviral long terminal repeat, or from a promoter specifically expressed in a target cell type of interest (e.g., a neoplastic cell). Other viral vectors that can be used include, for example, a vaccinia virus, a bovine papilloma virus, or a herpes virus, such as Epstein-Barr Virus (also see, for example, the vectors of Miller, *Human Gene Therapy* 15-14, 1990; Friedman, *Science* 244:1275-1281, 1989; Eglitis et al., *BioTechniques* 6:608-614, 1988; Tolstoshev et al., *Curr. Opin. Biotechnol.* 1:55-61, 1990; Sharp, *Lancet* 337:1277-1278, 1991; Cornetta et al., *Nuc. Acid Res. Mol. Biol.* 36:311-322, 1987; Anderson, *Science* 226:401-409, 1984; Moen, *Blood Cells* 17:407-416, 1991; Miller et al., *Biotechnology* 7:980-990, 1989; Le Gal La Salle et al., *Science* 259:988-990, 1993; and Johnson, *Chest* 107:77S-83S, 1995). Retroviral vectors are particularly well developed and have been used in clinical settings (Rosenberg et al., *N. Engl. J. Med.* 323:370, 1990; U.S. Pat. No. 5,399,346).

Non-viral approaches can also be employed for the introduction of therapeutic nucleic acids to target cells of a patient. For example, a nucleic acid molecule can be introduced into a cell by administering the nucleic acid in the presence of lipofection (Felgner et al., *Proc. Natl. Acad. Sci. USA* 84:7413, 1987; Ono et al., *Neurosci. Lett.* 17:259, 1990; Brigham et al., *Am. J. Med. Sci.* 298:278, 1989; Staubinger et al., *Meth. Enzymol.* 101:512, 1983), asialoorosomucoid-polylysine conjugation (Wu et al., *J. Biol. Chem.* 263:14621, 1988; Wu et al, *J. Biol. Chem.* 264:16985, 1989), or by microinjection under surgical conditions (Wolff et al., *Science* 247: 1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in gene therapy methods can be directed from any suitable promoter (e.g., an endocan promoter, Flt-1 promoter, or other tumor endothelial promoter identified using the methods described herein), and regulated by any appropriate mammalian regulatory element. For example, if desired, an enhancers known to preferentially direct gene expression in a tumor endothelial cell, (e.g., the 300 base pair Tie-2 intronic enhancer element described herein) can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant nuclear encoded mitochondrial metabolism or proteasomal polypeptide, either directly to the site of a potential or actual disease-affected tissue (for example, by injection into the ventricles of the brain or into the cerebrospinal fluid) or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions. Generally, between 0.1 mg and 100 mg, is administered per day to an adult in any pharmaceutically acceptable formulation.

A desired mode of gene therapy is to provide the polynucleotide in such a way that it will replicate inside the cell, enhancing and prolonging the desired effect. Thus, the polynucleotide is operably linked to a suitable promoter, such as the natural promoter of the corresponding gene, a heterologous promoter that is intrinsically active in target cell, or a heterologous promoter that can be induced by a suitable agent.

Identification of Candidate Compounds for Treatment of DRAGON-Related Conditions A candidate compound that is beneficial in the treatment, stabilization, or prevention of a DRAGON-related condition can be identified by the methods of the present invention. A candidate compound can be identified for its ability to affect (increase or decrease) the biological activity of a DRAGON protein or the expression of a DRAGON gene or to modulate its action. Compounds that are identified by the methods of the present invention that increase the biological activity or expression levels of a DRAGON protein or that compensate for the loss of DRAGON protein activity or gene expression, for example, due to loss of the DRAGON gene due to a genetic lesion, can be used in the treatment or prevention of a DRAGON-related condition. Compound that are identified by these methods that reduce DRAGON biological activity or expression levels may also be used as therapeutics for DRAGON-related conditions characterized by inappropriately high levels of DRAGON biological activity. Elevated DRAGON biological activity in a disease state may result from over-expression a DRAGON gene, elevated levels of an activating post-translational modification of a DRAGON protein, or through interactions of other molecules or cellular components with the DRAGON protein. A candidate compound identified by the present invention can mimic, activate, or inhibit the biological activity of a DRAGON protein, bind a DRAGON protein, modulate (e.g., increase or decrease) transcription of a DRAGON gene, or modulate translation of a DRAGON mRNA.

One method for evaluating the ability of candidate compounds to modulate DRAGON biological activity is by measuring the binding between DRAGON and a TGF-$\beta$ signaling pathway member (e.g., a BMP ligand or a type I or type II BMP receptor). Compounds that modulate this binding interaction are expected to modulate DRAGON biological activity. Such screening methods may be performed in cell-based or cell-free assay systems.

Another method for evaluating the ability of candidate compounds to modulate DRAGON biological activity, in a cell-based assay, is to provide cells that express DRAGON and a TGF-$\beta$ signaling pathway member (e.g., a type I or type II BMP receptor, or another intracellular pathway member), and contact the cell with a candidate compound. Compounds that modulate (increase or decrease) the level of TGF-$\beta$ pathway activation may be useful for treating DRAGON-related conditions. TGF-$\beta$ pathway activation may be measured in cells expressing a heterologous reporter gene construct, as described below, or may be measured by any other appropriate technique including, for example, measuring the phosphorylation levels of intracellular TGF-$\beta$ signaling pathway members such as the Smads.

Any number of methods are available for carrying out screening assays to identify new candidate compounds that promote or inhibit the expression of a DRAGON gene. In one working example, candidate compounds are added at varying concentrations to the culture medium of cultured cells expressing one of the DRAGON nucleic acid sequences of the invention. Gene expression is then measured, for example, by microarray analysis, Northern blot analysis (Ausubel et al., supra), or RT-PCR, using any appropriate fragment prepared from the nucleic acid molecule as a hybridization probe. The level of DRAGON gene expression in the presence of the candidate compound is compared to the level measured in a control culture medium lacking the candidate compound. A compound which promotes a change (increase or decrease) in the expression of a DRAGON gene is considered useful in the invention and may be used as a therapeutic to treat a human patient.

In another working example, the effect of candidate compounds may be measured at the level of DRAGON protein production using the same general approach and standard immunological techniques, such as Western blotting or immunoprecipitation with an antibody specific for a DRAGON protein. For example, immunoassays may be used to detect or monitor the expression of at least one of the polypeptides of the invention in an organism. Polyclonal or monoclonal antibodies that are capable of binding to a DRAGON protein may be used in any standard immunoassay format (e.g., ELISA, Western blot, or RIA assay) to measure the level of the protein. In some embodiments, a compound that promotes a change (increase or decrease) in DRAGON expression or biological activity is considered particularly useful.

Expression of a reporter gene that is operably linked to the promoter of a TGF-$\beta$ signaling pathway member, (e.g., a promoter from a DRAGON gene, a BMP ligand gene, or a BMP type I or type II receptor gene) can also be used to identify a candidate compound for treating or preventing a DRAGON-related condition. Assays employing the detection of reporter gene products are extremely sensitive and readily amenable to automation, hence making them ideal for the design of high-throughput screens. Assays for reporter genes may employ, for example, colorimetric, chemiluminescent, or fluorometric detection of reporter gene products. Many varieties of plasmid and viral vectors containing reporter gene cassettes are easily obtained. Such vectors contain cassettes encoding reporter genes such as lacZ/$\beta$-galactosidase, green fluorescent protein, and luciferase, among others. A genomic DNA fragment carrying a TGF-$\beta$ signaling pathway member-specific (e.g., DRAGON-specific) transcriptional control region (e.g., a promoter and/or enhancer) is first cloned using standard approaches (such as those described by Ausubel et al. (supra). The DNA carrying the TGF-$\beta$ signaling pathway member transcriptional control region is then inserted, by DNA subcloning, into a reporter vector, thereby placing a vector-encoded reporter gene under the control of that transcriptional control region. The activity of the TGF-$\beta$ signaling pathway member transcriptional control region operably linked to the reporter gene can then be directly observed and quantified as a function of reporter gene activity in a reporter gene assay.

In one embodiment, for example, the DRAGON transcriptional control region could be cloned upstream from a luciferase reporter gene within a reporter vector. This could be introduced into the test cells, along with an internal control reporter vector (e.g., a lacZ gene under the transcriptional regulation of the ($\beta$-actin promoter). After the cells are exposed to the test compounds, reporter gene activity is measured and DRAGON reporter gene activity is normalized to internal control reporter gene activity.

In addition, candidate compounds may be identified using any of the DRAGON fusion proteins described above (e.g., as compounds that bind to those fusion proteins), or by any of the two-hybrid or three-hybrid assays described above.

A candidate compound identified by the methods of the present invention can be from natural as well as synthetic sources. Those skilled in the field of drug discovery and development will understand that the precise source of test extracts or compounds is not critical to the methods of the invention. Examples of such extracts or compounds include, but are not limited to, plant-, fungal-, prokaryotic-, or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

Synthesis of DRAGON Proteins

Nucleic acids that encode a DRAGON protein or fragment thereof may be introduced into various cell types or cell-free systems for expression, thereby allowing purification of the DRAGON protein for biochemical characterization, large-scale production, antibody production, and patient therapy.

Eukaryotic and prokaryotic DRAGON expression systems may be generated in which a DRAGON gene sequence is introduced into a plasmid or other vector, which is then used to transform living cells. Constructs in which the DRAGON cDNA contains the entire open reading frame inserted in the correct orientation into an expression plasmid may be used for protein expression. Alternatively, portions of the DRAGON gene sequence, including wild-type or mutant DRAGON sequences, may be inserted. Prokaryotic and eukaryotic expression systems allow various important functional domains of the DRAGON protein to be recovered, if desired, as fusion proteins, and then used for binding, structural, and functional studies and also for the generation of appropriate antibodies. Typical expression vectors contain promoters that direct the synthesis of large amounts of mRNA corresponding to the inserted DRAGON nucleic acid in the plasmid-bearing cells. They may also include a eukaryotic or prokaryotic origin of replication sequence allowing for their autonomous replication within the host organism, sequences that encode genetic traits that allow vector-containing cells to be selected for in the presence of otherwise toxic drugs, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Expression of foreign sequences in bacteria, such as *Escherichia coli*, requires the insertion of the DRAGON nucleic acid sequence into a bacterial expression vector. Such plasmid vectors contain several elements required for the propagation of the plasmid in bacteria, and for expression of the DNA inserted into the plasmid. Propagation of only plasmid-bearing bacteria is achieved by introducing, into the plasmid, selectable marker-encoding sequences that allow plasmid-bearing bacteria to grow in the presence of otherwise toxic drugs. The plasmid also contains a transcriptional promoter capable of producing large amounts of mRNA from the cloned gene. Such promoters may be (but are not necessarily) inducible promoters that initiate transcription upon induction. The plasmid also preferably contains a polylinker to simplify insertion of the gene in the correct orientation within the vector.

Mammalian cells can also be used to express a DRAGON protein. Stable or transient cell line clones can be made using DRAGON expression vectors to produce DRAGON proteins in a soluble (truncated and tagged) or membrane anchored (native) form. Appropriate cell lines include, for example, COS, HEK293T, CHO, or NIH cell lines.

Once the appropriate expression vectors containing a DRAGON gene, fragment, fusion, or mutant are constructed, they are introduced into an appropriate host cell by transformation techniques, such as, but not limited to, calcium phosphate transfection, DEAE-dextran transfection, electroporation, microinjection, protoplast fusion, or liposome-mediated transfection. The host cells that are transfected with the vectors of this invention may include (but are not limited to) *E. coli* or other bacteria, yeast, fungi, insect cells (using, for example, baculoviral vectors for expression in SF9 insect cells), or cells derived from mice, humans, or other animals. In vitro expression of a DRAGON protein, fusion, polypeptide fragment, or mutant encoded by cloned DNA may also be used. Those skilled in the art of molecular biology will understand that a wide variety of expression systems and purification systems may be used to produce recombinant DRAGON proteins and fragments thereof. Some of these systems are described, for example, in Ausubel et al. (supra).

Once a recombinant protein is expressed, it can be isolated from cell lysates using protein purification techniques such as affinity chromatography. Once isolated, the recombinant protein can, if desired, be purified further by e.g., by high performance liquid chromatography (HPLC; e.g., see Fisher, Laboratory Techniques In Biochemistry And Molecular Biology, Work and Burdon, Eds., Elsevier, 1980).

Polypeptides of the invention, particularly short DRAGON fragments can also be produced by chemical synthesis (e.g., by the methods described in Solid Phase Peptide Synthesis, 2nd ed., 1984, The Pierce Chemical Co., Rockford, Ill.).

Chimeric DRAGON Proteins

Also included in the invention are DRAGON proteins fused to heterologous sequences, such as cytotoxic moieties (e.g., saporin) and detectable markers (for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides. These fusion proteins may be produced by any standard method. For production of stable cell lines expressing a DRAGON fusion protein, PCR-amplified DRAGON nucleic acids may be cloned into the restriction site of a derivative of a mammalian expression vector. For example, KA, which is a derivative of pcDNA3 (Invitrogen, Carlsbad, Calif.) contains a DNA fragment encoding an influenza virus hemagglutinin (HA). Alternatively, vector derivatives encoding other tags, such as c-myc or poly Histidine tags, can be used.

The DRAGON expression construct may be co-transfected, with a marker plasmid, into an appropriate mammalian cell line (e.g. COS, HEK293T, or NIH 3T3 cells) using, for example, Lipofectamine™ (Gibco-BRL, Gaithersburg, Md.) according to the manufacturer's instructions, or any other suitable transfection technique known in the art. Suitable transfection markers include, for example, β-galactosidase or green fluorescent protein (GFP) expression plasmids or any plasmid that does not contain the same detectable marker as the DRAGON fusion protein. The DRAGON-expressing cells can be sorted and further cultured, or the tagged DRAGON can be purified.

In one particular example, a DRAGON open reading frame (ORF) was amplified by polymerase chain reaction (PCR) using standard techniques and primers containing restriction sites (e.g. Sal I sites). The top strand primer consisted of the sequence 5'-ATA AGC TTA TGG GCG TGA GAG CAG CAC CTT CC-3' (SEQ ID NO:21) and the bottom strand primer consisted of the sequence 5'-GAA GTC GAC GAA ACA ACT CCT ACA AAA AC-3' (SEQ ID NO:22). DRAGON cDNA was also amplified without the signal peptide and subcloned into a vector (pSecTagHis) having a strong secretion signal peptide. The same bottom strand primer was used (SEQ ID NO:22); however, the top strand primer was substituted for one having the sequence 5'-CTC AAG CTT CAG CCT ACT CAA TGC CGA ATC-3' (SEQ ID NO:23).

In another example, DRAGON-Fc was generated by subcloning DRAGON cDNA without its GPI anchor into the mammalian expression vector pIgplus (R&D Systems, Minneapolis, Minn.) in frame with the Fc portion of the human IgG. This allowed expression of a soluble DRAGON-Fc fusion protein. DRAGON-Fc collected in the media of stably transfected HEK293 cells was purified using HiTrap Protein A Affinity Columns (Amersham Biosciences) and eluted with 100 mM glycine-HCl, pH 3.0. The elution fraction was neutralized with 0.3 mM Tris-HCl, pH 9. Purified DRAGON-Fc was identified following electrophoretic separation on an SDS-PAGE gel and immunoblotting with anti-DRAGON antibody and an anti-Fc antibody.

In another example, we generated DRAGON-alkaline phosphatase (AP) fusion protein using the mammalian expression vector, pAPtag-5' (Flanagan et al., Meth. Enzymol. 327:198-210, 2000). When expressed in mammalian cells (e.g. HEK 293), the DRAGON-AP fusion protein is secreted at high levels into the culture medium and is easily detected by the AP activity assay. The resulting DRAGON-AP fusion protein can be used to screen expression libraries to identify, clone, sequence, and characterize molecules which interact with DRAGON, such as cell surface receptors or endogenous DRAGON ligands. Of course, this method is broadly applicable to any number of suitable tags known in the art.

A fusion protein (chimera) of DRAGON protein or fragment and a cytotoxic moiety may be used for the treatment of cancer. A particularly useful cytotoxic moiety is saporin, a protein isolated from *Saponaria officinalis* (common soapwort) which function as ribosomal inactivating proteins. Several such saporins are described, for example, Barthelemy et al. (*J. Biol. Chem.* 268: 6541-6548, 1993). One particularly useful saporin is represented by Genbank Accession No. CAA48885. When using a proteinaceous cytotoxic moiety, such as saporin, the polynucleotide coding sequence may be directly linked, in frame, to either the 5' or the 3' terminus of the DRAGON coding sequence. Preferably, the cytotoxic moiety is linked to the 5' (N-terminus) of the DRAGON sequence in order to preserve the naturally-occurring GPI anchoring domain at the DRAGON C-terminus. Optionally, a polynucleotide encoding a linker peptide may be inserted between the two sequences.

Fusion proteins containing a DRAGON protein or fragment and a cytotoxic moiety (e.g., saporin) may be administered to a patient, for the treatment of cancer, using any appropriate technique. For example, a vector encoding the fusion protein may be administered such that the fusion protein is expressed in the targeted cancer cells or in non-cancerous cells. The DRAGON moiety is used to target the fusion protein to cancerous cells expressing a high level of a TGF-β signaling pathway member (e.g., a type I or type II BMP receptor) and allow the cytotoxic moiety to affect cell killing. Alternatively, the fusion protein may be administered systemically or by an intra-tumor injection.

Generation of Anti-DRAGON Antibodies

In order to prepare polyclonal antibodies, DRAGON proteins, fragments, or fusion proteins containing defined portions of a DRAGON protein may be synthesized in bacterial, fungal, or mammalian cells by expression of corresponding DNA sequences in a suitable cloning vehicle. The protein can be purified, coupled to a carrier protein, mixed with Freund's adjuvant (to enhance stimulation of the antigenic response in an innoculated animal), and injected into rabbits or other laboratory animals. Following booster injections at bi-weekly intervals, the rabbits or other laboratory animals are then bled and the sera isolated. The sera can be used directly or can be purified prior to use by various methods, including affinity chromatography employing reagents such as Protein A-Sepharose, antigen-Sepharose, and anti-mouse-Ig-Sepharose. The sera can then be used to probe protein extracts from DRAGON-expressing tissue electrophoretically fractionated on a polyacrylamide gel to identify DRAGON proteins. Alternatively, synthetic peptides can be made that correspond to the antigenic portions of the protein and used to innoculate the animals. As described above, a polyclonal antibody against mDRAGON was created using, as the immunogenic DRAGON fragment, a polypeptide corresponding to residues 388-405 of SEQ ID NO: 5. Suitable immunogens for creating anti-hDRAGON antibodies include, for example, the polypeptide sequences encoded by residues 54-72, 277-294, or 385-408 of SEQ ID NO: 2.

Alternatively, monoclonal antibodies may be prepared using DRAGON proteins described above and standard hybridoma technology (see, e.g., Kohler et al., Nature 256: 495, 1975; Kohler et al., Eur. J. Immunol. 6:511; 1976; Kohler et al., Eur. J. Immunol. 6:292, 1976; Hammerling et al., In Monoclonal Antibodies and T Cell Hybridomas, Elsevier, New York, N.Y., 1981). Once produced, monoclonal antibodies are also tested for specific DRAGON protein recognition by Western blot or immunoprecipitation analysis.

Antibodies of the invention may also be produced using DRAGON amino acid sequences that do not reside within highly conserved regions, and that appear likely to be antigenic, as analyzed by criteria such as those provided by the Peptide Structure Program (Genetics Computer Group Sequence Analysis Package, Program Manual for the GCG Package, Version 7, 1991) using the algorithm of Jameson and Wolf (CABIOS 4:181, 1988).

In Situ Hybridization

The in situ hybridization methods used herein have been described previously (Karchewski et al., J. Comp. Neurol. 413:327, 1999). Hybridization was performed on fresh frozen, mounted tissue sections from mouse embryo and adult rat dorsal root ganglia (DRG) using terminally-labeled oligonucleotide probes. Probes had approximately 50% G-C content and were complementary and selective for mDRAGON mRNAs. Probes were 3'-end labeled with $^{35}$S-dATP using a terminal transferase reaction and purified through a spin column (Qiagen). Hybridization was done under very high stringency conditions such that probe annealing required at least 90% sequence identity (Dagerlind et al., Histochemistry 98:39, 1992).

Briefly, slides were brought to room-temperature and covered with a hybridization solution (50% formamide, 1×Denhardt's solution, 1% sarcosyl, 10% dextran sulphate, 0.02M phosphate buffer, 4×SSC, 200 nM DTT, 500 mg/ml salmon sperm DNA) containing $10^7$ cpm/ml of labeled probe. Slides were incubated in a humidified chamber at 43° C. for 14-18 hours, then washed 4×15 min in 1×SSC at 55° C. In the final rinse, slides were brought to room temperature, washed in dH$_2$O, dehydrated in ethanol, and air dried.

Autoradiograms were generated by dipping slides in NTB2 nuclear track emulsion and storing in the dark at 4° C. Prior to conventional developing and fixation, sections were allowed to expose for 1-3 weeks, depending on the abundance of transcript. Unstained tissue was viewed under darkfield conditions using a fiber-optic darkfield stage adapter (MVI), while stained tissue was examined under brightfield conditions. Control experiments using sense probes were conducted to confirm the specificity of hybridization. The antisense oligonucleotide probe is:

mDRAGON-specific for nucleotides
831-879 of SEQ ID NO: 5:

(SEQ ID NO: 24)
5'-TCG CAC AAA CAC TGT GGT GCC TAT GTA GCG GGC ATG

CAT CTC TAC GTA-3'.

Pharmaceutical Compositions for Increasing DRAGON Biological Activity

The present invention includes the administration of DRAGON for the treatment or prevention of a DRAGON-related condition. The administration of biologically active DRAGON, regardless of its method of manufacture, restores DRAGON biological activity in a patient lacking endogenous activity of a DRAGON protein due to a loss or reduction of expression or biological activity, e.g., by mutation or loss of DRAGON gene or cells that normally express DRAGON.

Peptide agents of the invention, such as DRAGON, can be administered to a subject, e.g., a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in Remington's Pharmaceutical Sciences, (19th edition), ed. A. Gennaro, 1995, Mack Publishing Company, Easton, Pa.

Pharmaceutical formulations of a therapeutically effective amount of a peptide agent or candidate compound of the invention, or pharmaceutically acceptable salt-thereof, can be administered orally, parenterally (e.g. intramuscular, intraperitoneal, intravenous, or subcutaneous injection), or by intrathecal or intracerebroventricular injection in an admixture with a pharmaceutically acceptable carrier adapted for the route of administration.

Methods well known in the art for making formulations are found, for example, in Remington's Pharmaceutical Sciences (19th edition), ed. A. Gennaro, 1995, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents.

Biocompatible, biodegradable lactide polymer, lactide/glycolide copolymer, or polyoxyethylene-polyoxypropylene copolymers may be used to control the release of the compounds. Other potentially useful parenteral delivery systems for the proteins of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

The amount of active ingredient in the compositions of the invention can be varied. One skilled in the art will appreciate that the exact individual dosages may be adjusted somewhat depending upon a variety of factors, including the protein being administered, the time of administration, the route of administration, the nature of the formulation, the rate of excretion, the nature of the subject's conditions, and the age, weight, health, and gender of the patient. Generally, dosage levels of between 0.1 μg/kg to 100 mg/kg of body weight are administered daily as a single dose or divided into multiple doses. Desirably, the general dosage range is between 250 μg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The protein or therapeutic compound of the invention can be administered in a sustained release composition, such as those described in, for example, U.S. Pat. No. 5,672,659 and U.S. Pat. No. 5,595,760. The use of immediate or sustained release compositions depends on the type of condition being treated. If the condition consists of an acute or subacute disorder, a treatment with an immediate release form will be preferred over a prolonged release composition. Alternatively, for preventative or long-term treatments, a sustained released composition will generally be preferred.

The protein or therapeutic compound of the present invention can be prepared in any suitable manner. The protein or therapeutic compound can be isolated from naturally occurring sources, recombinantly produced, or produced synthetically, or produced by a combination of these methods. The synthesis of short peptides is well known in the art. See e.g. Stewart et al., Solid Phase Peptide Synthesis (Pierce Chemical Co., 2d ed., 1984).

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Other embodiments are within the claims.

The invention claimed is:

1. A method for identifying a compound that modulates a BMP/GDF signaling pathway, said method comprising the steps of:
   a) providing a sample comprising a DRAGON (DRG11-Responsive Axonal Guidance and Outgrowth of Neurite) protein and a BMP/GDF signaling pathway member, wherein the DRAGON protein is selected from the group consisting of RGMa, RGMb and HJV and wherein the BMP/GDF signaling pathway member is selected from the group consisting of a BMP, a type I BMP receptor and a type II BMP receptor;
   b) contacting said sample with a candidate compound; and
   c) assessing the binding of said DRAGON protein to said BMP/GDF signaling pathway member in said sample in the presence of said candidate compound relative to binding in the absence of said candidate compound, wherein a compound that modulates binding of said DRAGON protein to said BMP/GDF signaling pathway member is identified as a compound that modulates a BMP/GDF signaling pathway.

2. The method of claim 1, wherein said BMP is BMP-2 or BMP-4.

3. The method of claim 1, wherein the assessing step (c) comprises the use of a DRAGON-specific antibody or the use of an antibody specific for the BMP/GDF signaling pathway member.

4. A method for identifying a compound that modulates a BMP/GDF signaling pathway, said method comprising the steps of:
   a) providing a cell that expresses a type I BMP receptor, a type II BMP receptor, and an intracellular BMP/GDF signaling pathway member;
   b) contacting said cell with a DRAGON (DRG11-Responsive Axonal Guidance and Outgrowth of Neurite) protein and a candidate compound, wherein the DRAGON protein is selected from the group consisting of RGMa, RGMb and HJV; and
   c) assessing the level of activation of the BMP/GDF signaling pathway by assessing the activation of said intracellular BMP/GDF signaling pathway member relative to the level of activation in the absence of said candidate compound, wherein a compound that modulates the activation of said intracellular BMP/GDF signaling pathway member is identified as a compound that modulates a BMP/GDF signaling pathway.

5. The method of claim 4, wherein said type I BMP receptor is ALK2, ALK3, or ALK6.

6. The method of claim 4, wherein said type II BMP receptor is BMPRII, ActRIIA, or ActRIIB.

7. The method of claim 4, wherein said contacting step (b) further comprises contacting said cell with a TGF-β ligand.

8. The method of claim 7, wherein said TGF-β ligand is BMP-2, BMP-4, BMP-7, or GDF-5.

9. A method for identifying a compound that modulates a BMP/GDF signaling pathway, said method comprising the steps of:
   a) providing a cell that expresses a reporter gene construct operably linked to a TGF-β ligand-dependent promoter;
   b) contacting said cell with a DRAGON (DRG11-Responsive Axonal Guidance and Outgrowth of Neurite) protein and a candidate compound, wherein the DRAGON protein is selected from the group consisting of RGMa, RGMb and HJV; and
   c) assessing the level of expression of said reporter gene relative to the level of expression of said reporter gene in the absence of said candidate compound, wherein a candidate compound that modulates the level of expression of said reporter gene is identified as a compound that modulates a BMP/GDF signaling pathway.

10. The method of claim 9, wherein said reporter gene construct is the BRE-Luc construct.

11. The method of claim 9, wherein the contacting step (b) further comprises contacting said cell with a TGF-β ligand.

12. The method of claim 9, wherein said TGF-β ligand is BMP-2, BMP-4, BMP-7, or GDF-5.

13. The method of claim 9, wherein said cell further expresses a BMP type I receptor.

14. The method of claim 9, wherein said cell further expresses a BMP type II receptor.

* * * * *

```
                          SEQUENCE LISTING

<160> NUMBER OF SEQ ID NOS: 24

<210> SEQ ID NO 1
<211> LENGTH: 436
<212> TYPE: PRT
<213> ORGANISM: Mus musculus

<400> SEQUENCE: 1

Met Gly Val Arg Ala Ala Pro Ser Cys Ala Ala Pro Ala Ala Ala
1               5                  10                  15

Gly Ala Glu Gln Ser Arg Arg Pro Gly Leu Trp Pro Pro Ser Pro Pro
                20                  25                  30

Pro Pro Leu Leu Leu Leu Leu Leu Ser Leu Gly Leu Leu His Ala
            35                  40                  45

Gly Asp Cys Gln Gln Pro Thr Gln Cys Arg Ile Gln Lys Cys Thr Thr
50                  55                  60

Asp Phe Val Ala Leu Thr Ala His Leu Asn Ser Ala Ala Asp Gly Phe
65                  70                  75                  80

Asp Ser Glu Phe Cys Lys Ala Leu Arg Ala Tyr Ala Gly Cys Thr Gln
                85                  90                  95

Arg Thr Ser Lys Ala Cys Arg Gly Asn Leu Val Tyr His Ser Ala Val
                100                 105                 110

Leu Gly Ile Ser Asp Leu Met Ser Gln Arg Asn Cys Ser Lys Asp Gly
            115                 120                 125

Pro Thr Ser Ser Thr Asn Pro Glu Val Thr His Asp Pro Cys Asn Tyr
130                 135                 140

His Ser His Gly Gly Val Arg Glu His Gly Gly Asp Gln Arg Pro
145                 150                 155                 160

Pro Asn Tyr Leu Phe Cys Gly Leu Phe Gly Asp Pro His Leu Arg Thr
                165                 170                 175

Phe Lys Asp His Phe Gln Thr Cys Lys Val Glu Gly Ala Trp Pro Leu
                180                 185                 190

Ile Asp Asn Asn Tyr Leu Ser Val Gln Val Thr Asn Val Pro Val Val
            195                 200                 205

Pro Gly Ser Ser Ala Thr Ala Thr Asn Lys Val Thr Ile Ile Phe Lys
210                 215                 220

Ala Gln His Glu Cys Thr Asp Gln Lys Val Tyr Gln Ala Val Thr Asp
225                 230                 235                 240

Asp Leu Pro Ala Ala Phe Val Asp Gly Thr Thr Ser Gly Gly Asp Gly
                245                 250                 255

Asp Val Lys Ser Leu His Ile Val Glu Lys Glu Ser Gly Arg Tyr Val
                260                 265                 270

Glu Met His Ala Arg Tyr Ile Gly Thr Thr Val Phe Val Arg Gln Leu
            275                 280                 285

Gly Arg Tyr Leu Thr Leu Ala Ile Arg Met Pro Glu Asp Leu Ala Met
            290                 295                 300

Ser Tyr Glu Glu Ser Gln Asp Leu Gln Leu Cys Val Asn Gly Cys Pro
305                 310                 315                 320

Met Ser Glu Cys Ile Asp Asp Gly Gln Gly Gln Val Ser Ala Ile Leu
                325                 330                 335
```

```
Gly His Ser Leu Pro His Thr Thr Ser Val Gln Ala Trp Pro Gly Tyr
            340                 345                 350

Thr Leu Glu Thr Ala Ser Thr Gln Cys His Glu Lys Met Pro Val Lys
            355                 360                 365

Asp Ile Tyr Phe Gln Ser Cys Val Phe Asp Leu Leu Thr Thr Gly Asp
            370                 375                 380

Ala Asn Phe Thr Ala Ala His Ser Ala Leu Glu Asp Val Glu Ala
385                 390                 395                 400

Leu His Pro Arg Lys Glu Arg Trp His Ile Phe Pro Ser Ser Cys Gly
                405                 410                 415

Gly Cys Arg Asp Leu Pro Val Gly Leu Gly Leu Thr Cys Leu Ile Leu
            420                 425                 430

Ile Met Phe Leu
        435

<210> SEQ ID NO 2
<211> LENGTH: 437
<212> TYPE: PRT
<213> ORGANISM: Homo sapiens

<400> SEQUENCE: 2

Met Gly Leu Arg Ala Ala Pro Ser Ser Ala Ala Ala Ala Ala Ala Glu
1               5                   10                  15

Val Glu Gln Arg Arg Pro Gly Leu Cys Pro Pro Leu Glu Leu
            20                  25                  30

Leu Leu Leu Leu Leu Phe Ser Leu Gly Leu Leu His Ala Gly Asp Cys
            35                  40                  45

Gln Gln Pro Ala Gln Cys Arg Ile Gln Lys Cys Thr Thr Asp Phe Val
50                  55                  60

Ser Leu Thr Ser His Leu Asn Ser Ala Val Asp Gly Phe Asp Ser Glu
65                  70                  75                  80

Phe Cys Lys Ala Leu Arg Ala Tyr Ala Gly Cys Thr Gln Arg Thr Ser
                85                  90                  95

Lys Ala Cys Arg Gly Asn Leu Val Tyr His Ser Ala Val Leu Gly Ile
            100                 105                 110

Ser Asp Leu Met Ser Gln Arg Asn Cys Ser Lys Asp Gly Pro Thr Ser
            115                 120                 125

Ser Thr Asn Pro Glu Val Thr His Asp Pro Cys Asn Tyr His Ser His
            130                 135                 140

Ala Gly Ala Arg Glu His Arg Arg Gly Asp Gln Asn Pro Pro Ser Tyr
145                 150                 155                 160

Leu Phe Cys Gly Leu Phe Gly Asp Pro His Leu Arg Thr Phe Lys Asp
                165                 170                 175

Asn Phe Gln Thr Cys Lys Val Glu Gly Ala Trp Pro Leu Ile Asp Asn
            180                 185                 190

Asn Tyr Leu Ser Val Gln Val Thr Asn Val Pro Val Val Pro Gly Ser
            195                 200                 205

Ser Ala Thr Ala Thr Asn Lys Ile Thr Ile Phe Lys Ala His His
            210                 215                 220

Glu Cys Thr Asp Gln Lys Val Tyr Gln Ala Val Thr Asp Asp Leu Pro
225                 230                 235                 240

Ala Ala Phe Val Asp Gly Thr Thr Ser Gly Gly Asp Ser Asp Ala Lys
                245                 250                 255

Ser Leu Arg Ile Val Glu Arg Glu Ser Gly His Tyr Val Glu Met His
            260                 265                 270
```

```
Ala Arg Tyr Ile Gly Thr Thr Val Phe Val Arg Gln Val Gly Arg Tyr
        275                 280                 285

Leu Thr Leu Ala Ile Arg Met Pro Glu Asp Leu Ala Met Ser Tyr Glu
290                 295                 300

Glu Ser Gln Asp Leu Gln Leu Cys Val Asn Gly Cys Pro Leu Ser Glu
305                 310                 315                 320

Arg Ile Asp Asp Gly Gln Gly Gln Val Ser Ala Ile Leu Gly His Ser
                325                 330                 335

Leu Pro Arg Thr Ser Leu Val Gln Ala Trp Pro Gly Tyr Thr Leu Glu
                340                 345                 350

Thr Ala Asn Thr Gln Cys His Glu Lys Met Pro Val Lys Asp Ile Tyr
                355                 360                 365

Phe Gln Ser Cys Val Phe Asp Leu Leu Thr Thr Gly Asp Ala Asn Phe
                370                 375                 380

Thr Ala Ala Ala His Ser Ala Leu Glu Asp Val Glu Ala Leu His Pro
385                 390                 395                 400

Arg Lys Glu Arg Trp His Ile Phe Pro Ser Ser Gly Asn Gly Thr Pro
                405                 410                 415

Arg Gly Gly Ser Asp Leu Ser Val Ser Leu Gly Leu Thr Cys Leu Ile
                420                 425                 430

Leu Ile Val Phe Leu
            435

<210> SEQ ID NO 3
<211> LENGTH: 420
<212> TYPE: PRT
<213> ORGANISM: C. elegans

<400> SEQUENCE: 3

Met Arg Arg His Trp Lys Glu Phe Glu Cys Glu Lys Trp Glu Ser Cys
1               5                   10                  15

Asn Asp Asn Ser His Val Lys Arg Lys His Val Asn Thr Gly His Ile
                20                  25                  30

Cys Gly Gly Lys Phe Glu Leu Ser Glu Lys Asn Leu Ala Ala Lys Phe
            35                  40                  45

Lys Tyr Ser Gly Asp Thr Val Trp Arg Gly Arg Pro Asn Phe Leu Lys
50                  55                  60

Ser Leu Cys Tyr Phe Asn Pro Pro Ser Asn Arg Lys Leu Lys Tyr
65                  70                  75                  80

Cys Ser Leu Phe Gly Asp Pro His Leu Ile Met Phe Asn Gly Ser Val
                85                  90                  95

Gln Thr Cys Ser Glu Glu Gly Ala Arg Pro Leu Val Asp Asn Arg Tyr
            100                 105                 110

Phe Leu Val Gln Val Thr Asn Arg Asn Val Arg Gly Glu Ala Leu Thr
        115                 120                 125

Thr Thr Val Thr Lys Val Thr Val Leu Val Arg Lys His Asn Cys Thr
130                 135                 140

Ala Ser Leu Arg Tyr Glu Ala Ser Ser Asp Glu Glu Gly Leu Pro Arg
145                 150                 155                 160

Gly Phe Val Asp Gly Thr Thr Phe Gln Met Thr Ser Lys His Ser Val
                165                 170                 175

Glu Val Leu Trp Gln Asp Asp Asn Tyr Val Glu Ile Ala Leu His Phe
            180                 185                 190

Ile His Ser Ser Ile His Ile Arg Arg Gln Gly Pro Tyr Leu Ser Val
```

```
              195                 200                 205
Ser Val Arg Ala Pro Thr Ile Val Leu Glu Thr Gly Gly Asp Val Ala
210                 215                 220

Arg Glu Leu Cys Trp Ser Gly Cys Arg Lys Ser Ser Arg Ile Pro Ala
225                 230                 235                 240

Glu Leu Ala Val Glu Met Thr Lys Lys Phe Ala Glu Cys Tyr Arg Arg
                245                 250                 255

Arg Val His Val Pro Lys Lys Val Ala Glu Thr Thr Phe Leu Ser
                260                 265                 270

Glu Gln Lys Val Leu Pro Ile Tyr Asp Arg Cys Lys Asp Ile Gly Asn
            275                 280                 285

Ile Gly Val Phe Phe Asp Ala Ser Ala Arg Lys Ile Leu Asn Phe Arg
290                 295                 300

Val Ser Gly Ser Gln Val Thr Ser Leu Gln Asn Cys Lys Ala Arg Arg
305                 310                 315                 320

Gly Leu Arg Arg Gly Gln Ala Ile Ile Leu Glu Arg Tyr Phe Ser Ala
                325                 330                 335

Pro Lys Pro Lys Lys Phe His Leu Cys Thr Ala Thr Gly Gly Gln Val
            340                 345                 350

Thr Ala Leu Gln Ser Phe Glu Ala Arg Arg Gly Leu Arg Arg Gly Gln
        355                 360                 365

Ala Thr Thr Val Glu Arg Cys Ile Ser Ala Pro Arg Asp Pro Thr Asp
370                 375                 380

Leu Lys Ile Phe Ala Leu Thr Asp Asn Cys Glu Glu Thr Lys Lys Tyr
385                 390                 395                 400

Trp Asn Phe Phe Arg Tyr Asp Ile Leu Cys Asp Thr His Ser Gln Asn
                405                 410                 415

Phe Leu Leu Pro
            420

<210> SEQ ID NO 4
<211> LENGTH: 436
<212> TYPE: PRT
<213> ORGANISM: Danio rerio

<400> SEQUENCE: 4

Met Gly Met Gly Arg Ala Gly Ser Tyr Tyr Pro Gly Ala Glu Arg Leu
1               5                   10                  15

Ile Ser Pro Val Leu His Leu Leu Val Leu Cys Thr Leu Ser Ser Leu
                20                  25                  30

Thr Pro Ile Gly Glu Ser Gln Val Gln Thr Pro Gln Cys Arg Ile Gln
            35                  40                  45

Lys Cys Thr Thr Asp Phe Val Ser Leu Thr Ser His Leu Asn Pro Ser
50                  55                  60

Leu Asp Gly Phe Asp Thr Glu Phe Cys Lys Ala Leu Arg Ala Tyr Ser
65                  70                  75                  80

Ala Cys Thr Gln Arg Thr Ala Lys Ser Cys Arg Gly Asn Leu Val Phe
                85                  90                  95

His Ser Ala Met Leu Gly Ile Thr Asp Leu Met Ser Gln Arg Asn Cys
            100                 105                 110

Ser Lys Asp Gly Pro Thr Ser Ser Thr His Pro Val Ile Pro Ile Glu
        115                 120                 125

Pro Cys Asn Tyr His Ser Arg His His His Val Ser Arg Phe Gly
130                 135                 140
```

Thr Gly Val Pro Glu His Pro Arg Leu Met Tyr Leu Phe Cys Gly Leu
145                 150                 155                 160

Phe Gly Asp Pro His Leu Arg Thr Phe Lys Asp Gln Phe Gln Thr Cys
            165                 170                 175

Lys Val Glu Gly Ala Trp Pro Leu Ile Asp Asn Asn Tyr Leu Ser Val
            180                 185                 190

Gln Val Thr Asn Val Pro Val Val Tyr Gly Ser Ser Ala Thr Ala Thr
            195                 200                 205

Asn Lys Ile Thr Ile Ile Phe Lys Pro Tyr Gln Glu Cys Thr Asp Gln
210                 215                 220

Lys Val Tyr Gln Ala Val Thr Asp Asp Leu Pro Ala Ala Phe Val Asp
225                 230                 235                 240

Gly Thr Ile Ser Gly Gly Asp Ser Glu Thr Arg Ser Ile Trp Ile Leu
            245                 250                 255

Glu Lys Ser Pro Gly Arg His Val Glu Ile His Ala Ala Tyr Ile Gly
            260                 265                 270

Val Thr Ile Ile Ile Arg Gln Gln Gly Arg Tyr Leu Thr Leu Ala Val
            275                 280                 285

Arg Met Pro Glu Glu Leu Ala Met Ala Phe Asp Glu Thr Gln Asp Leu
290                 295                 300

Gln Leu Cys Met Asn Gly Cys Pro Thr Ser Glu Arg Ile Asp Gln Glu
305                 310                 315                 320

Gly His Leu Gln Leu Pro Val Leu Gly Leu Gln Ala Gly Phe Gln
            325                 330                 335

Gln Gln Gln Gln Pro Arg Val Glu Ala Gln Arg Gly Val Phe Thr Leu
            340                 345                 350

Glu Ser Ala Ser Arg Arg Cys Arg Asp Gln Leu Glu Val Lys Asp Ile
            355                 360                 365

Tyr Phe His Ser Cys Val Phe Asp Leu Leu Thr Thr Gly Asp Ala Asn
            370                 375                 380

Phe Thr Thr Ala Ala Tyr Asn Ala Leu Lys Asp Met Glu Thr Leu His
385                 390                 395                 400

Pro Lys Lys Glu Arg Trp Gln Ile Phe Pro Asn Ser Ala Ser Arg Leu
            405                 410                 415

Ser Pro Phe Ser Leu Leu Thr Ala Leu Leu Ser Ser Phe Leu Ile
            420                 425                 430

Ala Val Leu Leu
        435

<210> SEQ ID NO 5
<211> LENGTH: 1332
<212> TYPE: DNA
<213> ORGANISM: Mus musculus

<400> SEQUENCE: 5
acgagacctg catggacggg catgggcgtg agagcagcac cttcctgcgc cgccgccccc      60
gccgccgccg gggctgagca gtcccgccgc cccgggctct ggccgccgtc gccccgccg     120 ccgctgttgc tgctgctgct gctcagcctt gggctgctcc acgcaggtga ttgccaacag     180
cctactcaat gccgaatcca gaaatgtacc acagacttcg tggccctgac tgcacacctg     240
aactctgccg ctgatgggtt tgactctgag ttttgcaagg cacttcgcgc ctatgctggc     300
tgcacccagc gaacttcaaa ggcctgccga ggcaacctgg tgtaccattc tgctgtgtta     360
ggcatcagtg atctcatgag ccagaggaac tgttccaagg atggacccac atcttccacc     420

| | |
|---|---|
| aatccggaag tgacccatga ccctgtaac taccacagcc acgggggagt cagagaacat | 480 |
| gggggagggg accagagacc tcccaattac ctttctgtg gcttgtttgg agaccctcac | 540 |
| cttcgaactt tcaaggatca cttccagaca tgcaaagtgg aaggggcctg gccactcata | 600 |
| gacaacaatt acctttcggt tcaagtgacg aacgtgcctg tggtccccgg gtccagtgca | 660 |
| actgctacaa acaaggtcac gattatcttc aaagcacagc acgagtgcac ggatcagaag | 720 |
| gtgtaccaag ctgtgacaga tgacctgccg gccgcctttg tagatggcac caccagtggg | 780 |
| ggggacggtg acgtgaagag tcttcacatc gtggagaagg agagtggccg ctacgtagag | 840 |
| atgcatgccc gctacatagg caccacagtg tttgtgcgac agctgggtcg ctacctaacc | 900 |
| ctcgctatcc ggatgcccga agacttggcc atgtcctatg aggaaagcca ggacttgcag | 960 |
| ctgtgtgtga atggctgccc catgagtgaa tgcattgatg atggacaagg ccaggtgtct | 1020 |
| gctatcctgg ggcacagcct gcctcacacc acctcagtgc aggcctggcc tggctacaca | 1080 |
| ctggagactg ccagcaccca atgccacgag aagatgccgg tgaaggacat ctatttccaa | 1140 |
| tcgtgtgtct tcgacctgct caccactggt gatgccaact ttactgctgc agcccacagt | 1200 |
| gccttggagg atgtggaagc gctgcaccca agaaaggaac gctggcacat cttccccagc | 1260 |
| agctgtgggg gatgtaggga tttgcctgtt ggtcttggac tcacatgctt gatccttatt | 1320 |
| atgttttgt ag | 1332 |

<210> SEQ ID NO 6
<211> LENGTH: 3946
<212> TYPE: DNA
<213> ORGANISM: Homo sapiens

<400> SEQUENCE: 6

| | |
|---|---|
| acgacacctg catggacggg catgggcttg agagcagcac cttccagcgc cgccgctgcc | 60 |
| gccgccgagg ttgagcagcg ccgccgcccc gggctctgcc cccgccgct ggagctgctg | 120 |
| ctgctgctgc tgttcagcct cgggctgctc acgcaggtg actgccaaca gccagcccaa | 180 |
| tgtcgaatcc agaaatgcac cacggacttc gtgtccctga cttctcacct gaactctgcc | 240 |
| gttgacggct ttgactctga gttttgcaag gccttgcgtg cctatgctgg ctgcacccag | 300 |
| cgaacttcaa aagcctgccg tggcaacctg gtataccatt ctgccgtgtt gggtatcagt | 360 |
| gacctcatga gccagaggaa ttgttccaag atggaccca catcctctac caaccccgaa | 420 |
| gtgacccatg atccttgcaa ctatcacagc cacgctggag ccagggaaca caggagaggg | 480 |
| gaccagaacc ctcccagtta cctttttgt ggcttgtttg gagatcctca cctcagaact | 540 |
| ttcaaggata acttccaaac atgcaaagta gaaggggcct ggccactcat agataataat | 600 |
| tatctttcag ttcaagtgac aaacgtacct gtggtccctg gatccagtgc tactgctaca | 660 |
| aataaggtca ctattatctt caaagcccac catgagtgta cagatcagaa agtctaccaa | 720 |
| gctgtgacag atgacctgcc ggccgccttt gtggatggca ccaccagtgg tggggacagc | 780 |
| gatgccaaga gcctgcgtat cgtggaaagg agagtggcc actatgtgga gatgcacgcc | 840 |
| cgctatatag ggaccacagt gtttgtgcgg caggtgggtc gctacctgac ccttgccatc | 900 |
| cgtatgcctg aagacctggc catgtcctac aggagagcc aggacctgca gctgtgcgtg | 960 |
| aacggctgcc ccctgagtga acgcatcgat gacgggcagg ccaggtgtc tgccatcctg | 1020 |
| ggacacagcc tgcctcgcac ctccttggtg caggcctggc ctggctacac actggagact | 1080 |
| gccaacactc aatgccatga aagatgccag tgaaggaca tctatttcca gtcctgtgtc | 1140 |
| ttcgacctgc tcaccactgg tgatgccaac tttactgccg cagcccacag tgccttggag | 1200 |

-continued

```
gatgtggagg ccctgcaccc aaggaaggaa cgctggcaca ttttccccag cagtggcaat    1260
gggactcccc gtggaggcag tgatttgtct gtcagtctag gactcacctg cttgatcctt    1320
atcgtgtttt tgtaggggtt gtcttttgtt ttggttttt atttttttgtc tataacaaaa    1380 ttttaaaata tatattgtca taatatattg agtaaaagag tatatatgta tataccatgt    1440
atatgacagg atgtttgtcc tgggacaccc accagattgt acatactgtg tttggctgtt    1500
ttcacatatg ttggatgtag tgttctttga ttgtatcaat tttgtttttgc agttctgtga    1560 aatgttttat aatgtccctg cccagggacc tgttagaaag cactttattt tttatatatt    1620
aaatatttat gtgtgtgctt ggttgatatg tatagtacat atacacagac atccatatgc    1680
agcgtttcct ttgaaggtga ccagttgttt gtagctattc ttggctgtac cttcctgccc    1740
tttcccattg ctactgattt gccacggtgt gcagctttta ctcgccacct tccggtggag    1800
ctgcctcgtt cctttgaact atgccctcac ccttctgccc tcacttgatt tgaaagggtc    1860
gttaactctc ccttacaggt gctttgactc ttaaacgctg atcttaagaa gctctcttca    1920
tctaagagct gttacttttt cagaaggggg ggtattattg gtattctgat tactctcaat    1980
tctaattgtt atatatttga gcccatacag tgtattaggt tgaaccatag aaactgctat    2040
tctcgtaggt caaaagggtc tagtgatgga agttttgtag ataagtacca ggcatctcag    2100
taactcctag acttttttctc atcccatgcc ccgttttaaa ttgtcagttt tccctctgac    2160
tcttctgtgt taaaacatga aactataaat ttagtaatta tcatgccttg ctcttttaa     2220 tctatatgac tgatgcaagc ccctcttctt aaccgtttct tggctttgag cccagaaaca    2280
cagctctccc tgtctccaac tccagtaagc cctcctcagc ctcaccttac gaatccaaag    2340
aactggggtt tgttaggttc tttctctaat gtagaggccc agatcccatc acaaagtttt    2400
tcattcttcc ttgtccacca tgatcttcat cacagtcttt gatatgtctg catgcaaagt    2460
ggaacagagt tgggcggcaa tgacagaaga gcttccttgg cctgactcgg tgtgcggcca    2520
cttcggcact gcttaatcca gatattcttg ttaactaagc attgtgcttc ccaggtggtc    2580
tgaagtcagg tactctctct ctcaacacct gtagttgaat atgatttggt cagttgctcg    2640
ttgtaacttg gagaaattcc tataaagtaa gatctccttg cctcttccat ccattgttgg    2700 caccccccttg caaaaggaaa agaacagcaa aagtcaggag cagtaatctg agaaagttaa    2760
ctccaggata ggtaggtttc tattgttata gctagatgta aatctttagt tccaagaagt    2820
gatagagttt ctgctttaat aatttgttga taagtttaca taaacagaaa taaaagatac    2880
tatctttacc gtagtagttc aggccaagat tatgcttagt tttagttctc caggtagtta    2940
cttttgccat gtcctattga tcagtgacac tgccagaggc ccataccggc aagaggaaga    3000
ggacgtcatt ttgtaaagtt taacttctta gcgaactgat gtgccaccca gtcacagagt    3060
ggagttgtga attcatgtag aggtggcaaa cctctacctt gtgttgatga gagaataatc    3120
ttgggcagtc tgggaaaata aggaaggcat ctccttctta ctccatggaga ttcaactata    3180 gagagttgaa acctaaaccc gccttccttt tatagaagct ggactagaga cggactgacc    3240
atcagctctg aactgtggct tttttttgttc acctatgatg ccatgtacca aattcagaag    3300
ctatcgttaa taatttgttt tataattgag tagtacaagc gaggaaaaaa tacgaggat     3360 aaccactatt tttgtgcaaa tagtatgaaa gtgaagtaaa agcaatagaa gaaatttcta    3420
taggatctgg gttagagtg tgtatcatta ataaatatac ctttgctctt ttcagggaaa     3480
ataacaacca cccttactga tagttgggaa aagaagattg ggttatttg ccatatcatt      3540
```

| | |
|---|---|
| tagctggaag tgacatttaa aagcaccctg catcactagt aatagtgtat tttgctattc | 3600 |
| tgcccttgta atcggtgtcc ctgtaaaaca atccccacag attactttca gaaatagatg | 3660 |
| tatttctcta cgtaagggcc aggtttattt tctccttttt tgagatttct agaaaaaatg | 3720 |
| ctgcttgcac atgttggttc ttgaaacctt agctagaaga atttcaggtc ataccaacat | 3780 |
| gtggataggc tatagctgtt cagaggtctc ctggggagc ttaaaacggg ggaaacactg | 3840 |
| gttttcacag atgctccaca tggctgtctt taaaagactc aaaacttttt tttgtcctct | 3900 |
| ttgttatgct tggaagctcc cccccccca acagtgtgtc gagtct | 3946 |

<210> SEQ ID NO 7
<211> LENGTH: 1311
<212> TYPE: DNA
<213> ORGANISM: Danio rerio

<400> SEQUENCE: 7

| | |
|---|---|
| atgggtatgg ggagagcagg atcttactac cccggggctg agcgcctcat ctctccggta | 60 |
| ctacatctac tagtgctgtg caccctctcc tccctcactc ccataggtga gagtcaggtt | 120 |
| cagactcctc agtgccgcat ccagaagtgc actaccgact tcgtttctct gacgtcccat | 180 |
| ctgaacccat cactggatgg cttttgatacg gagttctgca aggcgctgcg agcctattcg | 240 |
| gcctgtacgc agcgtacagc caagagctgc aggggggaacc tggtcttcca ctccgccatg | 300 |
| ctgggcatca ctgaccttat gagccagagg aactgctcca agacgggcc cacgtcctcc | 360 |
| acccatcccg tcatccctat cgagccttgc aactatcaca gccggcatca ccaccacgtg | 420 |
| tcgcggttcg ggacgggggt gcccgaacac cctcgtctga tgtacctgtt ctgtggcctg | 480 |
| ttcggggacc ctcatcttag gacttttaaa gaccagtttc aaacgtgtaa agttgaaggg | 540 |
| gcttggcctc tcattgataa caactacctg tcagtgcagg tcactaatgt tccagtggtt | 600 |
| tatggatcca gtgccacagc taccaataag atcacaataa tcttcaaacc ataccaagaa | 660 |
| tgcacagacc agaaggtcta ccaggccgtg acagacgacc ttccagccgc cttcgtagac | 720 |
| ggcaccatca gcggaggtga cagtgagacc cgcagcatct ggatcctgga gaaatctccc | 780 |
| ggtcggcatg tagaaatcca cgctgcgtac atcggggtca ccatcatcat acgccagcag | 840 |
| ggccgttacc tgacactagc tgtgcgaatg cctgaggaac tggccatggc ctttgatgaa | 900 |
| acgcaggacc tgcagctgtg catgaacggc tgccccacat cagagcgcat tgaccaggag | 960 |
| ggacacctcc agctgcccgt gcttggcctc cagcaggctg gctttcagca gcagcagcag | 1020 |
| cccagggtgg aagcccagag aggcgtcttc actcttgaaa gtgcctccag gaggtgcagg | 1080 |
| gaccaactgg aggtgaagga catctatttc cactcctgtg tgtttgacct gctcactaca | 1140 |
| ggagatgcca acttcaccac tgccgcctac aatgccctga agacatgga gacactgcat | 1200 |
| cccaaaaagg agcgctggca gattttcccc aactcggctt ccaggctgag tccttttttca | 1260 |
| ttgcttctca ctgcactgct gagcagcttc cttatcgctg tgctttata a | 1311 |

<210> SEQ ID NO 8
<211> LENGTH: 450
<212> TYPE: PRT
<213> ORGANISM: Homo sapiens

<400> SEQUENCE: 8

Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Phe Trp Pro
            20                  25                  30

```
Thr Leu Ala Phe Leu Leu Cys Ser Phe Pro Ala Ala Thr Ser Pro Cys
         35                  40                  45

Lys Ile Leu Lys Cys Asn Ser Glu Phe Trp Ser Ala Thr Ser Gly Ser
 50                  55                  60

His Ala Pro Ala Ser Asp Asp Thr Pro Glu Phe Cys Ala Ala Leu Arg
 65                  70                  75                  80

Ser Tyr Ala Leu Cys Thr Arg Arg Thr Ala Arg Thr Cys Arg Gly Asp
                 85                  90                  95

Leu Ala Tyr His Ser Ala Val His Gly Ile Glu Asp Leu Met Ser Gln
                100                 105                 110

His Asn Cys Ser Lys Asp Gly Pro Thr Ser Gln Pro Arg Leu Arg Thr
                115                 120                 125

Leu Pro Pro Ala Gly Asp Ser Gln Glu Arg Ser Asp Ser Pro Glu Ile
130                 135                 140

Cys His Tyr Glu Lys Ser Phe His Lys His Ser Ala Thr Pro Asn Tyr
145                 150                 155                 160

Thr His Cys Gly Leu Phe Gly Asp Pro His Leu Arg Thr Phe Thr Asp
                165                 170                 175

Arg Phe Gln Thr Cys Lys Val Gln Gly Ala Trp Pro Leu Ile Asp Asn
                180                 185                 190

Asn Tyr Leu Asn Val Gln Val Thr Asn Thr Pro Val Leu Pro Gly Ser
                195                 200                 205

Ala Ala Thr Ala Thr Ser Lys Leu Thr Ile Ile Phe Lys Asn Phe Gln
210                 215                 220

Glu Cys Val Asp Gln Lys Val Tyr Gln Ala Glu Met Asp Glu Leu Pro
225                 230                 235                 240

Ala Ala Phe Val Asp Gly Ser Lys Asn Gly Gly Asp Lys His Gly Ala
                245                 250                 255

Asn Ser Leu Lys Ile Thr Glu Lys Val Ser Gly Gln His Val Glu Ile
                260                 265                 270

Gln Ala Lys Tyr Ile Gly Thr Thr Ile Val Val Arg Gln Val Gly Arg
                275                 280                 285

Tyr Leu Thr Phe Ala Val Arg Met Pro Glu Glu Val Val Asn Ala Val
                290                 295                 300

Glu Asp Trp Asp Ser Gln Gly Leu Tyr Leu Cys Leu Arg Gly Cys Pro
305                 310                 315                 320

Leu Asn Gln Gln Ile Asp Phe Gln Ala Phe His Thr Asn Ala Glu Gly
                325                 330                 335

Thr Gly Ala Arg Arg Leu Ala Ala Ala Ser Pro Ala Pro Thr Ala Pro
                340                 345                 350

Glu Thr Phe Pro Tyr Glu Thr Ala Val Ala Lys Cys Lys Glu Lys Leu
                355                 360                 365

Pro Val Glu Asp Leu Tyr Tyr Gln Ala Cys Val Phe Asp Leu Leu Thr
370                 375                 380

Thr Gly Asp Val Asn Phe Thr Leu Ala Ala Tyr Tyr Ala Leu Glu Asp
385                 390                 395                 400

Val Lys Met Leu His Ser Asn Lys Asp Lys Leu His Leu Tyr Glu Arg
                405                 410                 415

Thr Arg Asp Leu Pro Gly Arg Ala Ala Ala Gly Leu Pro Leu Ala Pro
                420                 425                 430

Arg Pro Leu Leu Gly Ala Leu Val Pro Leu Leu Ala Leu Leu Pro Val
                435                 440                 445
```

Phe Cys
    450

<210> SEQ ID NO 9
<211> LENGTH: 426
<212> TYPE: PRT
<213> ORGANISM: Homo sapiens

<400> SEQUENCE: 9

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Cys Gly Leu
            20                  25                  30

Ala His Ser Gln Cys Lys Ile Leu Arg Cys Asn Ala Glu Tyr Val Ser
            35                  40                  45

Ser Thr Leu Ser Leu Arg Gly Gly Gly Ser Gly Ala Leu Arg Gly
        50                  55                  60

Gly Gly Gly Gly Arg Gly Gly Val Gly Ser Gly Gly Leu Cys
65                  70                  75                  80

Arg Ala Leu Arg Ser Tyr Ala Leu Cys Thr Arg Arg Thr Ala Arg Thr
                85                  90                  95

Cys Arg Gly Asp Leu Ala Phe His Ser Ala Val His Gly Ile Glu Asp
            100                 105                 110

Leu Met Ile Gln His Asn Cys Ser Arg Gln Gly Pro Thr Ala Pro Pro
            115                 120                 125

Pro Pro Arg Gly Pro Ala Leu Pro Gly Ala Gly Ser Gly Leu Pro Ala
        130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
            195                 200                 205

Ala Leu Gly Ala Asn Ala Thr Ala Thr Arg Lys Leu Thr Ile Ile Phe
        210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Arg
            275                 280                 285

Gln Thr Ala Gly Gln Leu Ser Phe Ser Ile Lys Val Ala Glu Asp Val
        290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
            355                 360                 365

Gly Asp Pro Asn Phe Thr Val Ala Ala Gln Ala Ala Leu Glu Asp Ala
        370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
                405                 410                 415

Gly Leu Phe Val Leu Trp Leu Cys Ile Gln
            420                 425

<210> SEQ ID NO 10
<211> LENGTH: 2145
<212> TYPE: DNA
<213> ORGANISM: Homo sapiens

<400> SEQUENCE: 10

| | | | | | |
|---|---|---|---|---|---|
| attgcagcca | gtccggggga | tcggggacag | acatggagaa | ggagatggag | gaccccctgg | 60 |
| ctggagcaga | ccaacagaat | aggcaactat | ggctggagaa | ccgggtatca | gagtaatgct | 120 |
| tgacctcggg | aaacaccaaa | tttcttcttc | cgatcgcaga | agtagtactc | ggcgaaattc | 180 |
| actaggtagg | aggctcctca | tctgggaaga | accggtgcct | gggggaccct | ggctggatag | 240 |
| gtatggggga | tcgaggccgg | tccctagtc | tccggtcccc | ccatggcagt | cctccaactc | 300 |
| taagcaccct | cactctcctg | ctgctcctct | gtggacaggc | tcactcccag | tgcaagatcc | 360 |
| tccgctgcaa | tgccgagtac | gtctcgttca | ctctgagcct | tcggggaggg | ggctcaccgg | 420 |
| acacgccacg | tggaggcggc | cgtggtgggc | cggcctcagg | tggcttgtgt | cgcgccctgc | 480 |
| gctcctacgc | tctctgcacg | cggcgcaccg | cccgcacctg | ccgcggggac | ctcgctttcc | 540 |
| actccgcggt | gcatggcata | gaggacctga | tgatccagca | caactgctca | cgccagggtc | 600 |
| ccacggcctc | gcccccggcc | cggggtcctg | ccctgcccgg | ggccggccca | gcgcccctga | 660 |
| ccccagatcc | ctgtgactat | gaagcccggt | tttccaggct | gcacggtcga | accccgggtt | 720 |
| tcttgcattg | tgcttccttt | ggagaccccc | atgtgcgcag | cttccacaat | cactttcaca | 780 |
| catgccgcgt | ccaaggagct | tggccccctac | tagataacga | cttcctcttt | gtccaagcca | 840 |
| ccagctcccc | ggtagcatcg | ggagccaacg | ctaccaccat | ccggaagatc | actatcatat | 900 |
| ttaaaaacat | gcaggaatgc | attgaccaga | aagtctacca | ggctgaggta | gacaatcttc | 960 |
| ctgcagcctt | tgaagatggt | tctgtcaatg | ggggcgaccg | acctggggc | tcgagtttgt | 1020 |
| ccattcaaac | tgctaacctt | gggagccacg | tggagattcg | agctgcctac | attggaacaa | 1080 |
| ctataatcgt | tcgtcagaca | gctggacagc | tctccttctc | catcagggta | gcggaggatg | 1140 |
| tggcacgggc | cttctctgct | gagcaggatc | tacagctgtg | tgttggggga | tgccctccga | 1200 |
| gccagcgact | ctctcgctca | gagcgcaatc | gccgtgggc | gatagccata | gatactgcca | 1260 |
| gaaggttgtg | taaggaaggg | cttccggttg | aagatgccta | cttccaatcc | tgcgtctttg | 1320 |
| atgtttcagt | ctccggtgac | cccaactta | ctgtggcagc | tcagtcagct | ctggacgatg | 1380 |
| cccgagtctt | cttgaccgat | ttggagaact | tgcaccttt | cccagtagat | gcggggcctc | 1440 |
| ccctctctcc | agccacctgc | ctagtccggc | ttctttcggt | cctctttgtt | ctgtggtttt | 1500 |
| gcattcagta | agtaggccag | caacccgtga | ctagtttgga | aacggtttga | ggagagaggt | 1560 |
| tgatgtgaga | aaacacaaag | atgtgccaaa | ggaaacagtg | gggacaggag | acaacgacct | 1620 |
| tactcaatca | cacgaggttg | cagtccaggg | ctgaaatgac | cctagaataa | agattctgag | 1680 |
| acagggtttt | gcactccaga | ccttggtatg | ggctccccat | gtatttcccc | attagtgatt | 1740 |

```
tcccacttgt agtgaaattc tactctctgt acacctgata tcactcctgc aaggctagag    1800
attgtgagag cgctaagggc cagcaaaaca ttaaagggct gagatatctt aaaggcagaa    1860
actagaaaag gggaaaccat gattatctat aagaaaatca aaagaggggt ttgggaattt    1920
agctcagtgg tagagcactt gcctagcaag cgcaaggccc tgggttcggt ccccagctcc    1980
taaaaaagaa aaaaaaatc aaaagagaaa aaactaatta aggcaagctt tttggttcag    2040
aaatgaagtg ggcattgtct ggcagaggaa gtcagctttt ggagactggc accaacatct    2100
ccacccttcc tactctgtta ttaaagtgac gaattcccca tcctg                    2145

<210> SEQ ID NO 11
<211> LENGTH: 3216
<212> TYPE: DNA
<213> ORGANISM: Homo sapiens

<400> SEQUENCE: 11
agttgtctcc cgagcgctgg ctgcgccgcc cgagccgctg ggccggggaa gcactggccg      60
ttcgctcccg ggccggcccc gccaggcgct cgcaggcatg cagcccggga gcaggaggcg     120 ctcccccggggc cgctgctgag ccggccgggg cggcggggac cagcgccagc ggagcccctc    180
ccaccttgcc ccggggcaga cgagcggcgc cccgacaccc cctcttctcc cgcagccccg     240
ccagcgccac ccccgcgggg ccgcagggggc tcatgcagcc gccaagggag aggctagtgg    300
taacaggccg agctggatgg atgggtatgg ggagagggggc aggacgttca gccctgggat   360
tctggccgac cctcgccttc cttctctgca gcttccccgc agccacctcc ccgtgcaaga    420
tcctcaagtg caactctgag ttctggagcg ccacgtcggg cagccacgcc ccagcctcag    480
acgacacccc cgagttctgt gcagccttgc gcagctacgc cctgtgcacg cggcggacgg    540
cccgcacctg ccggggtgac ctggcctacc actcggccgt ccatggcata gaggacctca    600
tgagccagca caactgctcc aaggatggcc ccacctcgca gccacgcctg cgcacgctcc    660
caccggccgg agacagccag gagcgctcgg acagccccga gatctgccat tacgagaaga    720
gctttcacaa gcactcggcc acccccaact acacgcactg tggcctcttc ggggacccac    780
acctcaggac ttttcaccgac cgcttccaga cctgcaaggt gcagggcgcc tggccgctca    840
tcgacaataa ttacctgaac gtgcaggcca ccaacacgcc tgtgctgccc ggctcagcgg    900
ccactgccac cagcaagctc accatcatct tcaagaactt ccaggagtgt gtggaccaga    960
aggtgtacca ggctgagatg gacgagctcc cggccgcctt cgtggatggc tctaagaacg    1020
gtggggacaa gcacgggggcc aacagcctga agatcactga aaggtgtca ggccagcacg    1080 tggagatcca ggccaagtac atcggcacca ccatcgtggt gcgccaggtg ggccgctacc    1140
tgacctttgc cgtccgcatg ccagaggaag tggtcaatgc tgtggaggac tgggacagcc    1200
agggtctcta cctctgcctg cggggctgcc ccctcaacca gcagatcgac ttccaggcct    1260
tccacaccaa tgctgagggc accggtgccc gcaggctggc agccgccagc cctgcaccca    1320
cagcccccga gaccttccca tacgagacag ccgtggccaa gtgcaaggag aagctgccgg    1380
tggaggacct gtactaccag gcctgcgtct tcgacctcct caccacgggc gacgtgaact    1440
tcacactggc cgcctactac gcgttggagg atgtcaagat gctccactcc aacaaagaca    1500
aactgcacct gtatgagagg actcgggacc tgccaggcag ggcggctgcg gggctgcccc    1560 tggcccccg gccctcctg ggccctctcg tcccgctcct ggccctgctc cctgtgttct     1620
gctagacgcg tagatgtgga gggaggcgcg ggctccgtcc tctcggcttc cccatgtgtg    1680
ggctgggacc gcccacgggg tgcagatctc ctggcgtgtc caccatggcc ccgcagaacg    1740
```

```
ccagggaccg cctgctgcca agggctcagg catggacccc tcccttcta gtgcacgtga    1800
caaggttgtg gtgactggtg ccgtgatgtt tgacagtaga gctgtgtgag agggagagca    1860
gctcccctcg ccccgcccct gcagtgtgaa tgtgtgaaac atcccctcag gctgaagccc    1920
cccaccccca ccagagacac actgggaacc gtcagagtca gctccttccc cctcgcaatg    1980
cactgaaagg cccggccgac tgctgctcgc tgatccgtgg ggcccccctgt gcccgccaca    2040
cgcacgcaca cactcttaca cgagagcaca ctcgatcccc ctaggccagc ggggacaccc    2100
cagccacaca gggaggcatc cttggggctt ggccccaggc agggcaaccc cggggcgctg    2160
cttggcacct tagcagactg ctggaacctt ttggccagta ggtcgtgccc gcctggtgcc    2220
ttctggcctg tggcctccct gcccatgttc acctggctgc tgtgggtacc agtgcaggtc    2280
ccggttttca ggcacctgct cagctgcccg tctctggcct gggcccctgc ccttccacc    2340
ctgtgcttag aaagtcgaag tgcttggttc taaatgtcta aacagagaag agatccttga    2400
cttctgttcc tctccctcct gcagatgcaa gagctcctgg gcaggggtgc ctgggccca    2460
gggtgtggca ggagacccag tggatggggc cagctggcct gccctgatcc tctgcttcct    2520
cctcacaacc ccaagagccc ccagcccggt ccatccacgt ctggagtctg ggagaggag    2580
cagggtctta ggactctcag ctctgagcat ccctggcagg gtcttcaacc tctaatctct    2640
tcccttaagc cctgtggcca cacagccagg agagacttgc cgctggctcc cgcctcattt    2700
cagcccaggg tgctcatcca ggggcccaga acagtccac ctgtgctgct atgcccacag    2760
cacaaagcca ggcttcactc ccaaaagtgc agccaggccc tggagggtga tcctgccagc    2820
agccctacag ctccacaccc tacccaccca tcggcagcct ctctgctgtt ccccagggac    2880
ctctcataca ctggccagga ggctgcagaa cgtgtgtctc cccctccctc caagaggtcc    2940
tgctccctct gccagaaccg tgtgtgggcg ggtgggaggg cgctcggggc ccggcccctc    3000
cctctccctg ctggttttag ttggtcccta tgttggaagt aaaaagtgaa gcactttatt    3060
ttggttgtgt ttgctcacgt tctgcttgga agtggggacc cctcactgcg tccacgtgtc    3120
tgcgacctgt gtggagtgtc accgcgtgta catactgtaa attatttatt aatggctaaa    3180
tgcaagtaaa gtttggtttt tttgttattt tctttt                             3216
```

<210> SEQ ID NO 12
<211> LENGTH: 450
<212> TYPE: PRT
<213> ORGANISM: Homo sapiens

<400> SEQUENCE: 12

```
Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Phe Trp Pro
            20                  25                  30

Thr Leu Ala Phe Leu Leu Cys Ser Phe Pro Ala Ala Thr Ser Pro Cys
        35                  40                  45

Lys Ile Leu Lys Cys Asn Ser Glu Phe Trp Ser Ala Thr Ser Gly Ser
    50                  55                  60

His Ala Pro Ala Ser Asp Asp Thr Pro Glu Phe Cys Ala Ala Leu Arg
65                  70                  75                  80

Ser Tyr Ala Leu Cys Thr Arg Arg Thr Ala Arg Thr Cys Arg Gly Asp
                85                  90                  95

Leu Ala Tyr His Ser Ala Val His Gly Ile Glu Asp Leu Met Ser Gln
            100                 105                 110
```

His Asn Cys Ser Lys Asp Gly Pro Thr Ser Gln Pro Arg Leu Arg Thr
            115                 120                 125
Leu Pro Pro Ala Gly Asp Ser Gln Glu Arg Ser Asp Ser Pro Glu Ile
130                 135                 140
Cys His Tyr Glu Lys Ser Phe His Lys His Ser Ala Thr Pro Asn Tyr
145                 150                 155                 160
Thr His Cys Gly Leu Phe Gly Asp Pro His Leu Arg Thr Phe Thr Asp
                165                 170                 175
Arg Phe Gln Thr Cys Lys Val Gln Gly Ala Trp Pro Leu Ile Asp Asn
            180                 185                 190
Asn Tyr Leu Asn Val Gln Ala Thr Asn Thr Pro Val Leu Pro Gly Ser
        195                 200                 205
Ala Ala Thr Ala Thr Ser Lys Leu Thr Ile Ile Phe Lys Asn Phe Gln
    210                 215                 220
Glu Cys Val Asp Gln Lys Val Tyr Gln Ala Glu Met Asp Glu Leu Pro
225                 230                 235                 240
Ala Ala Phe Val Asp Gly Ser Lys Asn Gly Gly Asp Lys His Gly Ala
                245                 250                 255
Asn Ser Leu Lys Ile Thr Glu Lys Val Ser Gly Gln His Val Glu Ile
            260                 265                 270
Gln Ala Lys Tyr Ile Gly Thr Thr Ile Val Val Arg Gln Val Gly Arg
        275                 280                 285
Tyr Leu Thr Phe Ala Val Arg Met Pro Glu Glu Val Val Asn Ala Val
    290                 295                 300
Glu Asp Trp Asp Ser Gln Gly Leu Tyr Leu Cys Leu Arg Gly Cys Pro
305                 310                 315                 320
Leu Asn Gln Gln Ile Asp Phe Gln Ala Phe His Thr Asn Ala Glu Gly
                325                 330                 335
Thr Gly Ala Arg Arg Leu Ala Ala Ala Ser Pro Ala Pro Thr Ala Pro
            340                 345                 350
Glu Thr Phe Pro Tyr Glu Thr Ala Val Ala Lys Cys Lys Glu Lys Leu
        355                 360                 365
Pro Val Glu Asp Leu Tyr Tyr Gln Ala Cys Val Phe Asp Leu Leu Thr
    370                 375                 380
Thr Gly Asp Val Asn Phe Thr Leu Ala Ala Tyr Tyr Ala Leu Glu Asp
385                 390                 395                 400
Val Lys Met Leu His Ser Asn Lys Asp Lys Leu His Leu Tyr Glu Arg
                405                 410                 415
Thr Arg Asp Leu Pro Gly Arg Ala Ala Ala Gly Leu Pro Leu Ala Pro
            420                 425                 430
Arg Pro Leu Leu Gly Ala Leu Val Pro Leu Leu Ala Leu Leu Pro Val
        435                 440                 445
Phe Cys
    450

<210> SEQ ID NO 13
<211> LENGTH: 3216
<212> TYPE: DNA
<213> ORGANISM: Homo sapiens

<400> SEQUENCE: 13
agttgtctcc cgagcgctgg ctgcgccgcc cgagccgctg ggccggggaa gcactggccg    60
ttcgctcccg ggccggcccc gccaggcgct cgcaggcatg cagcccggga gcaggaggcg   120

| | | | | |
|---|---|---|---|---|
| ctccccgggc | cgctgctgag | ccggccgggg | cggcggggac | cagcgccagc ggagcccctc | 180 |
| ccaccttgcc | ccggggcaga | cgagcggcgc | cccgacaccc | cctcttctcc cgcagccccg | 240 |
| ccagcgccac | ccccgcggg | ccgcaggggc | tcatgcagcc | gccaagggag aggctagtgg | 300 |
| taacaggccg | agctggatgg | atgggtatgg | ggagaggggc | aggacgttca gccctgggat | 360 |
| tctggccgac | cctcgccttc | cttctctgca | gcttccccgc | agccacctcc ccgtgcaaga | 420 |
| tcctcaagtg | caactctgag | ttctggagcg | ccacgtcggg | cagccacgcc ccagcctcag | 480 |
| acgacacccc | cgagttctgt | gcagccttgc | gcagctacgc | cctgtgcacg cggcggacgg | 540 |
| cccgcacctg | ccggggtgac | ctggcctacc | actcggccgt | ccatggcata gaggacctca | 600 |
| tgagccagca | caactgctcc | aaggatggcc | ccacctcgca | gccacgcctg cgcacgctcc | 660 |
| caccggccgg | agacagccag | gagcgctcgg | acagccccga | gatctgccat tacgagaaga | 720 |
| gctttcacaa | gcactcggcc | accccaact | acacgcactg | tggcctcttc ggggacccac | 780 |
| acctcaggac | tttcaccgac | cgcttccaga | cctgcaaggt | gcagggcgcc tggccgctca | 840 |
| tcgacaataa | ttacctgaac | gtgcaggcca | ccaacacgcc | tgtgctgccc ggctcagcgg | 900 |
| ccactgccac | cagcaagctc | accatcatct | tcaagaactt | ccaggagtgt gtggaccaga | 960 |
| aggtgtacca | ggctgagatg | gacgagctcc | cggccgcctt | cgtggatggc tctaagaacg | 1020 |
| gtggggacaa | gcacggggcc | aacagcctga | agatcactga | gaaggtgtca ggccagcacg | 1080 |
| tggagatcca | ggccaagtac | atcggcacca | ccatcgtggt | cgccaggtg ggccgctacc | 1140 |
| tgacctttgc | cgtccgcatg | ccagaggaag | tggtcaatgc | tgtggaggac tgggacagcc | 1200 |
| agggtctcta | cctctgcctg | cggggctgcc | ccctcaacca | gcagatcgac ttccaggcct | 1260 |
| tccacaccaa | tgctgagggc | accggtgccc | gcaggctggc | agccgccagc cctgcaccca | 1320 |
| cagcccccga | gaccttccca | tacgagacag | ccgtggccaa | gtgcaaggag aagctgccgg | 1380 |
| tggaggacct | gtactaccag | gcctgcgtct | tcgacctcct | caccacgggc gacgtgaact | 1440 |
| tcacactggc | cgcctactac | gcgttggagg | atgtcaagat | gctccactcc aacaaagaca | 1500 |
| aactgcacct | gtatgagagg | actcgggacc | tgccaggcag | ggcggctgcg gggctgcccc | 1560 |
| tggccccccg | gcccctcctg | ggcgcccctcg | tcccgctcct | ggccctgctc cctgtgttct | 1620 |
| gctagacgcg | tagatgtgga | gggaggcgcg | ggctccgtcc | tctcggcttc cccatgtgtg | 1680 |
| ggctgggacc | gcccacgggg | tgcagatctc | ctggcgtgtc | caccatggcc ccgcagaacg | 1740 |
| ccagggaccc | cctgctgcca | agggctcagg | catggacccc | tccccttcta gtgcacgtga | 1800 |
| caaggttgtg | gtgactggtg | ccgtgatgtt | tgacagtaga | gctgtgtgag agggagagca | 1860 |
| gctcccctcg | ccccgcccct | gcagtgtgaa | tgtgtgaaac | atcccctcag gctgaagccc | 1920 |
| cccacccca | ccagagacac | actgggaacc | gtcagagtca | gctccttccc cctcgcaatg | 1980 |
| cactgaaagg | cccggccgac | tgctgctcgc | tgatccgtgg | ggcccctgt gcccgccaca | 2040 |
| cgcacgcaca | cactcttaca | cgagagcaca | ctcgatcccc | ctaggccagc ggggacaccc | 2100 |
| cagccacaca | gggaggcatc | cttggggctt | ggcccaggc | agggcaaccc cggggcgctg | 2160 |
| cttggcacct | tagcagactg | ctggaacctt | ttggccagta | ggtcgtgccc gcctggtgcc | 2220 |
| ttctggcctg | tggcctccct | gcccatgttc | acctggctgc | tgtgggtacc agtgcaggtc | 2280 |

```
ccggttttca ggcacctgct cagctgcccg tctctggcct gggcccctgc cccttccacc    2340
ctgtgcttag aaagtcgaag tgcttggttc taaatgtcta aacagagaag agatccttga    2400
cttctgttcc tctccctcct gcagatgcaa gagctcctgg gcagggtgc ctgggcccca     2460 gggtgtggca ggagacccag tggatggggc cagctggcct gccctgatcc tctgcttcct    2520
cctcacaacc ccaagagccc ccagcccggt ccatccacgt ctggagtctg gggagaggag    2580
cagggtctta ggactctcag ctctgagcat ccctggcagg gtcttcaacc tctaatctct    2640
tcccttaagc cctgtggcca cacagccagg agagacttgc cgctggctcc cgcctcattt    2700
cagcccaggg tgctcatcca ggggcccaga acagtcccac ctgtgctgct atgcccacag    2760
cacaaagcca ggcttcactc ccaaaagtgc agccaggccc tggagggtga tcctgccagc    2820
agccctacag ctccacaccc tacccaccca tcggcagcct ctctgctgtt ccccagggac    2880
ctctcataca ctggccagga ggctgcagaa cgtgtgtctc cccctccctc caagaggtcc    2940
tgctccctct gccagaaccg tgtgtgggcg gtgtgggagg gcgctcgggg ccggcccctc    3000
cctctccctg ctggttttag ttggtcccta tgttggaagt aaaaagtgaa gcactttatt    3060
ttggttgtgt ttgctcacgt tctgcttgga agtggggacc cctcactgcg tccacgtgtc    3120
tgcgacctgt gtggagtgtc accgcgtgta catactgtaa attatttatt aatggctaaa    3180
tgcaagtaaa gtttggtttt tttgttattt tctttt                              3216
```

<210> SEQ ID NO 14
<211> LENGTH: 23
<212> TYPE: DNA
<213> ORGANISM: artificial sequence
<220> FEATURE:
<223> OTHER INFORMATION: primer

<400> SEQUENCE: 14
tgttccaagg atggacccac atc                                             23

<210> SEQ ID NO 15
<211> LENGTH: 23
<212> TYPE: DNA
<213> ORGANISM: artificial sequence
<220> FEATURE:
<223> OTHER INFORMATION: primer

<400> SEQUENCE: 15
gcaggtcatc tgtcacagct tgg                                             23

<210> SEQ ID NO 16
<211> LENGTH: 21
<212> TYPE: DNA
<213> ORGANISM: artificial sequence
<220> FEATURE:
<223> OTHER INFORMATION: primer

<400> SEQUENCE: 16
cgtgaccaga cttttggaca c                                               21

<210> SEQ ID NO 17
<211> LENGTH: 21
<212> TYPE: DNA
<213> ORGANISM: artificial sequence
<220> FEATURE:
<223> OTHER INFORMATION: primer

<400> SEQUENCE: 17
ggcatgatta gtggagttca g                                               21

<210> SEQ ID NO 18
<211> LENGTH: 20
<212> TYPE: DNA
<213> ORGANISM: artificial sequence
<220> FEATURE:
<223> OTHER INFORMATION: primer

<400> SEQUENCE: 18
agcagccaaa ctatgggcta                                           20

<210> SEQ ID NO 19
<211> LENGTH: 20
<212> TYPE: DNA
<213> ORGANISM: artificial sequence
<220> FEATURE:
<223> OTHER INFORMATION: primer

<400> SEQUENCE: 19
tggttgagtt gaggtggtca                                           20

<210> SEQ ID NO 20
<211> LENGTH: 21
<212> TYPE: PRT
<213> ORGANISM: Mus musculus

<400> SEQUENCE: 20

Arg Met Asp Glu Glu Val Val Asn Ala Val Glu Asp Arg Asp Ser Gln
1               5                   10                  15

Gly Leu Tyr Leu Cys
            20

<210> SEQ ID NO 21
<211> LENGTH: 32
<212> TYPE: DNA
<213> ORGANISM: artificial sequence
<220> FEATURE:
<223> OTHER INFORMATION: primer

<400> SEQUENCE: 21
ataagcttat gggcgtgaga gcagcacctt cc                             32

<210> SEQ ID NO 22
<211> LENGTH: 29
<212> TYPE: DNA
<213> ORGANISM: artificial sequence
<220> FEATURE:
<223> OTHER INFORMATION: primer

<400> SEQUENCE: 22
gaagtcgacg aaacaactcc tacaaaaac                                 29

<210> SEQ ID NO 23
<211> LENGTH: 30
<212> TYPE: DNA
<213> ORGANISM: artificial sequence
<220> FEATURE:
<223> OTHER INFORMATION: primer

<400> SEQUENCE: 23
ctcaagcttc agcctactca atgccgaatc                                30

<210> SEQ ID NO 24
<211> LENGTH: 48
<212> TYPE: DNA

```
<213> ORGANISM: artificial sequence
<220> FEATURE:
<223> OTHER INFORMATION: primer

<400> SEQUENCE: 24
tcgcacaaac actgtggtgc ctatgtagcg ggcatgcatc tctacgta                    48
```